US012128069B2

(12) United States Patent
Albelda

(10) Patent No.: US 12,128,069 B2
(45) Date of Patent: Oct. 29, 2024

(54) TREATMENT OF CANCER USING CHIMERIC ANTIGEN RECEPTOR AND PROTEIN KINASE A BLOCKER

(71) Applicants: Novartis AG, Basel (CH); The Trustees of the University of Pennsylvania, Philadelphia, PA (US)

(72) Inventor: Steven M. Albelda, Philadelphia, PA (US)

(73) Assignees: The Trustees of the University of Pennsylvania, Philadelphia, PA (US); Novartis AG, Basel (CH)

(*) Notice: Subject to any disclaimer, the term of this patent is extended or adjusted under 35 U.S.C. 154(b) by 70 days.

(21) Appl. No.: 15/568,683

(22) PCT Filed: Apr. 22, 2016

(86) PCT No.: PCT/US2016/028986
§ 371 (c)(1),
(2) Date: Oct. 23, 2017

(87) PCT Pub. No.: WO2016/172583
PCT Pub. Date: Oct. 27, 2016

(65) Prior Publication Data

US 2018/0298068 A1 Oct. 18, 2018

Related U.S. Application Data

(60) Provisional application No. 62/151,707, filed on Apr. 23, 2015.

(51) Int. Cl.

| | |
|---|---|
| ***A61K 35/17*** | (2015.01) |
| ***A61K 9/00*** | (2006.01) |
| ***A61K 38/17*** | (2006.01) |
| ***A61K 39/00*** | (2006.01) |
| ***A61K 39/395*** | (2006.01) |
| ***C07K 14/47*** | (2006.01) |
| ***C07K 14/705*** | (2006.01) |
| ***C07K 14/725*** | (2006.01) |
| ***C07K 16/32*** | (2006.01) |
| ***C12N 5/0783*** | (2010.01) |
| ***C12N 15/85*** | (2006.01) |

(Continued)

(52) U.S. Cl.
CPC ............ *A61K 35/17* (2013.01); *A61K 9/0019* (2013.01); *A61K 38/1709* (2013.01); *A61K 38/177* (2013.01); *A61K 38/1774* (2013.01); *A61K 39/0011* (2013.01); *A61K 39/001102* (2018.08); *A61K 39/001104* (2018.08); *A61K 39/001111* (2018.08); *A61K 39/001112* (2018.08); *A61K 39/001117* (2018.08); *A61K 39/001124* (2018.08); *A61K 39/001156* (2018.08); *A61K 39/001157* (2018.08); *A61K 39/00117* (2018.08); *A61K 39/00118* (2018.08); *A61K 39/001182* (2018.08); *A61K 39/001184* (2018.08); *A61K 39/00119* (2018.08); *A61K 39/001193* (2018.08); *A61K 39/39558* (2013.01); *C07K 14/47* (2013.01); *C07K 14/7051* (2013.01); *C07K 14/70521* (2013.01); *C07K 16/32* (2013.01); *C12N 15/85* (2013.01); *A61K 2039/5154* (2013.01); *A61K 2039/54* (2013.01); *A61K 2039/572* (2013.01); *A61K 45/06* (2013.01); *C07K 14/70578* (2013.01); *C07K 2317/622* (2013.01); *C07K 2317/732* (2013.01); *C07K 2319/02* (2013.01); *C07K 2319/03* (2013.01); *C07K 2319/035* (2013.01); *C12N 5/0637* (2013.01); *C12N 7/00* (2013.01); *C12N 2510/00* (2013.01); *C12N 2740/15043* (2013.01)

(58) Field of Classification Search
CPC .. A61K 35/17; A61K 9/0019; A61K 38/1709; A61K 38/177; A61K 38/1774; A61K 39/0011; A61K 39/39558; C07K 14/47; C07K 14/7051; C12N 15/85
USPC ...... 424/93.21, 174.1; 435/320.1, 328, 372.3
See application file for complete search history.

(56) References Cited

U.S. PATENT DOCUMENTS 5,359,046 A 10/1994 Capon et al.
5,686,281 A 11/1997 Roberts
5,712,149 A 1/1998 Roberts (Continued)

FOREIGN PATENT DOCUMENTS

EP 0574512 A1 12/1993
EP 0871495 A1 10/1998

(Continued)

OTHER PUBLICATIONS

Jarnaess et al. (2008) J. Biol., Chem., vol. 283(48), 33708-33718.*

(Continued)

*Primary Examiner* — Anne Marie S Wehbe
(74) *Attorney, Agent, or Firm* — Saul Ewing LLP; Kathryn Doyle

(57) ABSTRACT

The invention provides compositions and methods for treating diseases associated with expression of a cancer associated antigen as described herein. The invention also relates to chimeric antigen receptor (CAR) specific to a cancer associated antigen as described herein, vectors encoding the same, and recombinant T cells comprising the CARs of the present invention. The invention also includes methods of administering a genetically modified T cell expressing a CAR that comprises an antigen binding domain that binds to a cancer associated antigen as described herein.

46 Claims, 36 Drawing Sheets

Specification includes a Sequence Listing.

(51) Int. Cl.
*A61K 45/06* (2006.01)
*C12N 7/00* (2006.01)

(56) References Cited

U.S. PATENT DOCUMENTS

| | | | |
|---|---|---|---|
| 5,874,240 | A | 2/1999 | Ni et al. |
| 5,906,936 | A | 5/1999 | Eshhar et al. |
| 6,103,521 | A | 8/2000 | Capon et al. |
| 6,319,494 | B1 | 11/2001 | Capon et al. |
| 6,355,779 | B1 | 3/2002 | Goodwin et al. |
| 6,410,319 | B1 | 6/2002 | Raubitschek et al. |
| 6,569,997 | B1 | 5/2003 | Kwon |
| 7,049,136 | B2 | 5/2006 | Seed et al. |
| 7,052,906 | B1 | 5/2006 | Lawson et al. |
| 7,070,995 | B2 | 7/2006 | Jensen |
| 7,265,209 | B2 | 9/2007 | Jensen |
| 7,319,143 | B2 | 1/2008 | Gross et al. |
| 7,320,787 | B2 | 1/2008 | Seed et al. |
| 7,446,190 | B2 | 11/2008 | Sadelain et al. |
| 7,446,191 | B2 | 11/2008 | Jensen |
| 7,514,537 | B2 | 4/2009 | Jensen |
| 7,638,326 | B2 | 12/2009 | June et al. |
| 7,741,465 | B1 | 6/2010 | Eshhar et al. |
| 7,745,140 | B2 | 6/2010 | June et al. |
| 7,754,482 | B2 | 7/2010 | Riley et al. |
| 7,994,298 | B2 | 8/2011 | Zhang et al. |
| 8,211,422 | B2 | 7/2012 | Eshhar et al. |
| 8,252,914 | B2 | 8/2012 | Zhang et al. |
| 8,389,282 | B2 | 3/2013 | Sadelain et al. |
| 8,399,645 | B2 | 3/2013 | Campana et al. |
| 8,465,743 | B2 | 6/2013 | Rosenberg et al. |
| 8,637,307 | B2 | 1/2014 | June et al. |
| 8,722,400 | B2 | 5/2014 | Riley et al. |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 9,394,368 | B2 | 7/2016 | Brogdon et al. |
| 9,573,988 | B2 | 2/2017 | Brogdon et al. |
| 9,745,368 | B2 | 8/2017 | Milone et al. |
| 9,777,061 | B2 | 10/2017 | Ebersbach et al. |
| 9,815,901 | B2 | 11/2017 | Brogdon et al. |
| 2003/0060444 | A1 | 3/2003 | Finney et al. |
| 2003/0077249 | A1 | 4/2003 | Bebbington et al. |
| 2003/0148982 | A1 | 8/2003 | Brenner et al. |
| 2003/0224520 | A1 | 12/2003 | June et al. |
| 2004/0038886 | A1 | 2/2004 | Finney et al. |
| 2004/0043401 | A1 | 3/2004 | Sadelain et al. |
| 2005/0113564 | A1 | 5/2005 | Campana et al. |
| 2005/0129671 | A1 | 6/2005 | Cooper et al. |
| 2007/0036773 | A1 | 2/2007 | Cooper et al. |
| 2008/0131415 | A1 | 6/2008 | Riddell et al. |
| 2008/0248008 | A1 | 10/2008 | Carlson et al. |
| 2009/0104177 | A1 | 4/2009 | Klussmann |
| 2009/0202487 | A1 | 8/2009 | Chang |
| 2009/0257994 | A1 | 10/2009 | Jensen |
| 2010/0119533 | A1 | 5/2010 | Clancy |
| 2011/0052554 | A1 | 3/2011 | Zakrzewski et al. |
| 2012/0148552 | A1 | 6/2012 | Jensen |
| 2012/0321667 | A1 | 12/2012 | Sentman |
| 2013/0071409 | A1 | 3/2013 | Riley et al. |
| 2013/0071414 | A1 | 3/2013 | Dotti et al. |
| 2013/0149337 | A1 | 6/2013 | Cooper et al. |
| 2013/0155909 | A1 | 6/2013 | Jackson et al. |
| 2013/0287748 | A1 | 10/2013 | June et al. |
| 2014/0050708 | A1 | 2/2014 | Powell et al. |
| 2014/0099309 | A1 | 4/2014 | Powell, Jr. et al. |
| 2014/0099340 | A1 | 4/2014 | June et al. |
| 2014/0106449 | A1 | 4/2014 | June et al. |
| 2014/0186947 | A1 | 7/2014 | June et al. |
| 2014/0212446 | A1 | 7/2014 | Riley et al. |
| 2014/0219975 | A1 | 8/2014 | June et al. |
| 2014/0227237 | A1 | 8/2014 | June et al. |
| 2014/0271635 | A1 | 9/2014 | Brogdon et al. |
| 2014/0322169 | A1 | 10/2014 | Harper et al. |
| 2014/0322183 | A1 | 10/2014 | Milone et al. |
| 2014/0322212 | A1* | 10/2014 | Brogdon .......... C07K 14/70517 424/134.1 |
| 2014/0322275 | A1 | 10/2014 | Brogdon et al. |
| 2014/0370045 | A1 | 12/2014 | June et al. |
| 2015/0017141 | A1 | 1/2015 | June et al. |
| 2015/0140019 | A1 | 5/2015 | June et al. |
| 2015/0190428 | A1 | 7/2015 | June et al. |
| 2015/0202286 | A1 | 7/2015 | June et al. |
| 2015/0283178 | A1 | 10/2015 | June et al. |
| 2015/0290244 | A1 | 10/2015 | June et al. |
| 2015/0342994 | A1 | 12/2015 | Riley et al. |
| 2016/0046724 | A1 | 2/2016 | Brogdon et al. |
| 2016/0051651 | A1 | 2/2016 | Brogdon et al. |
| 2016/0068601 | A1 | 3/2016 | Brogdon et al. |
| 2016/0096892 | A1 | 4/2016 | Brogdon et al. |
| 2016/0185861 | A1 | 6/2016 | Bedoya et al. |
| 2016/0311907 | A1 | 10/2016 | Brogdon et al. |
| 2016/0311917 | A1 | 10/2016 | Beatty et al. |
| 2016/0340406 | A1 | 11/2016 | Zhao et al. |
| 2016/0362472 | A1 | 12/2016 | Bitter et al. |
| 2017/0008963 | A1 | 1/2017 | Brogdon et al. |
| 2017/0081411 | A1 | 3/2017 | Engels et al. |
| 2017/0137783 | A1 | 5/2017 | Bedoya et al. |
| 2017/0183415 | A1 | 6/2017 | Brogdon et al. |
| 2017/0209492 | A1 | 7/2017 | June et al. |
| 2017/0211055 | A1 | 7/2017 | Brogdon et al. |
| 2017/0226495 | A1 | 8/2017 | Guimaraes |
| 2017/0239294 | A1 | 8/2017 | Thomas-Tikhonenko et al. |
| 2017/0260268 | A1 | 9/2017 | Beatty et al. |
| 2017/0274014 | A1 | 9/2017 | Brogdon et al. |
| 2017/0306416 | A1 | 10/2017 | Bedoya et al. |
| 2017/0335281 | A1 | 11/2017 | Loew et al. |
| 2018/0022795 | A1 | 1/2018 | Milone et al. |
| 2018/0044423 | A1 | 2/2018 | Ebersbach et al. |
| 2018/0044424 | A1 | 2/2018 | June et al. |
| 2018/0118834 | A1 | 5/2018 | Brogdon et al. |
| 2018/0125892 | A1 | 5/2018 | Brannetti et al. |
| 2018/0133296 | A1 | 5/2018 | Barrett et al. |
| 2018/0140602 | A1 | 5/2018 | Angst et al. |
| 2018/0230193 | A1 | 8/2018 | Loew et al. |
| 2018/0252727 | A1 | 9/2018 | Garfall et al. |
| 2018/0258149 | A1 | 9/2018 | Motz et al. |
| 2018/0312595 | A1 | 11/2018 | Brogdon et al. |
| 2019/0000880 | A1 | 1/2019 | Motz et al. |
| 2019/0000944 | A1 | 1/2019 | Brogdon et al. |
| 2019/0135940 | A1 | 5/2019 | Brogdon et al. |
| 2019/0151365 | A1 | 5/2019 | Anak et al. |
| 2019/0153061 | A1 | 5/2019 | Brogdon et al. |
| 2019/0161542 | A1 | 5/2019 | Gill et al. |
| 2019/0263914 | A1 | 8/2019 | Brogdon et al. |
| 2019/0292238 | A1 | 9/2019 | Bitter et al. |
| 2019/0292257 | A1 | 9/2019 | Bedoya et al. |
| 2019/0298715 | A1 | 10/2019 | Motz et al. |
| 2019/0330356 | A1 | 10/2019 | Brogdon et al. |
| 2019/0336504 | A1 | 11/2019 | Gill et al. |
| 2019/0375815 | A1 | 12/2019 | Engels et al. |
| 2019/0382500 | A1 | 12/2019 | Abujoub et al. |
| 2019/0388471 | A1 | 12/2019 | June et al. |
| 2019/0389928 | A1 | 12/2019 | Posey et al. |
| 2020/0048359 | A1 | 2/2020 | Albelda et al. |
| 2020/0055948 | A1 | 2/2020 | Daley et al. |
| 2020/0061113 | A1 | 2/2020 | Kassim et al. |
| 2020/0085869 | A1 | 3/2020 | Schuster et al. |
| 2020/0087376 | A1 | 3/2020 | Fraietta et al. |

FOREIGN PATENT DOCUMENTS

| | | | |
|---|---|---|---|
| EP | 1226244 | A2 | 7/2002 |
| WO | 1992015322 | A1 | 9/1992 |
| WO | 199530014 | A1 | 11/1995 |
| WO | 9623814 | A1 | 8/1996 |
| WO | 9624671 | A1 | 8/1996 |
| WO | 1997015669 | A1 | 5/1997 |
| WO | 9723613 | A2 | 7/1997 |
| WO | 9818809 | A1 | 5/1998 |

(56) References Cited

FOREIGN PATENT DOCUMENTS

| | | | |
|---|---|---|---|
| WO | 9900494 | A2 | 1/1999 |
| WO | 9957268 | A1 | 11/1999 |
| WO | 0014257 | A1 | 3/2000 |
| WO | 2002033101 | A1 | 4/2002 |
| WO | 02077029 | A2 | 10/2002 |
| WO | 02088334 | A1 | 11/2002 |
| WO | 2003057171 | A2 | 7/2003 |
| WO | 2005019429 | A2 | 3/2005 |
| WO | 2005044996 | A2 | 5/2005 |
| WO | 2005060996 | A2 | 7/2005 |
| WO | 2005/118788 | A2 | 12/2005 |
| WO | WO 2006/032923 | * | 3/2006 |
| WO | 2006060878 | A1 | 6/2006 |
| WO | 2008032923 | A2 | 3/2008 |
| WO | 2008045437 | A2 | 4/2008 |
| WO | 2010085660 | A2 | 7/2010 |
| WO | 2011059836 | A2 | 5/2011 |
| WO | 2011097477 | A1 | 8/2011 |
| WO | 2012058460 | A2 | 5/2012 |
| WO | 2012079000 | A1 | 6/2012 |
| WO | 2012082841 | A2 | 6/2012 |
| WO | 2012/099973 | A2 | 7/2012 |
| WO | 2012127464 | A2 | 9/2012 |
| WO | 2012129514 | A1 | 9/2012 |
| WO | 2012135854 | A2 | 10/2012 |
| WO | 2012138858 | A1 | 10/2012 |
| WO | 2013019615 | A2 | 2/2013 |
| WO | 2013033626 | A2 | 3/2013 |
| WO | 2013040371 | A2 | 3/2013 |
| WO | 2013040557 | A2 | 3/2013 |
| WO | 2013059593 | A1 | 4/2013 |
| WO | 2013/126712 | A1 | 8/2013 |
| WO | 2013126726 | A1 | 8/2013 |
| WO | 2013126729 | A1 | 8/2013 |
| WO | 2013126733 | A1 | 8/2013 |
| WO | 2013128726 | A1 | 9/2013 |
| WO | 2014/011984 | A1 | 1/2014 |
| WO | 2014/011987 | A1 | 1/2014 |
| WO | 2014/011993 | A2 | 1/2014 |
| WO | 2014/012001 | A2 | 1/2014 |
| WO | 2014011988 | A2 | 1/2014 |
| WO | 2014011996 | A1 | 1/2014 |
| WO | 2014031687 | A1 | 2/2014 |
| WO | 2014039513 | A2 | 3/2014 |
| WO | 2014/055442 | A2 | 4/2014 |
| WO | 2014055657 | A1 | 4/2014 |
| WO | 2014130635 | A1 | 8/2014 |
| WO | 2014/145252 | A2 | 9/2014 |
| WO | 2015010048 | A1 | 1/2015 |
| WO | 2015090229 | A1 | 6/2015 |
| WO | 2015090230 | A1 | 6/2015 |
| WO | 2015112626 | A1 | 7/2015 |
| WO | 2015/142661 | A1 | 9/2015 |
| WO | 2015142675 | A2 | 9/2015 |
| WO | WO 2015/142675 | * | 9/2015 |
| WO | 2015157252 | A1 | 10/2015 |
| WO | 2016014501 | A1 | 1/2016 |
| WO | 2016014530 | A1 | 1/2016 |
| WO | 2016014535 | A1 | 1/2016 |
| WO | 2016014553 | A1 | 1/2016 |
| WO | 2016014565 | A2 | 1/2016 |
| WO | 2016014576 | A1 | 1/2016 |
| WO | 2016019300 | A1 | 2/2016 |
| WO | 2016025880 | A1 | 2/2016 |
| WO | 2016028896 | A1 | 2/2016 |
| WO | 2016044605 | A1 | 3/2016 |

OTHER PUBLICATIONS

Bridgeman et al. (2013) Clin. Experiment. Immunol., vol. 175, 258-267.*

Goedhart et al. (2011) PLoS ONE, vol. 6(11): e27321. doi:10.1371/journal.pone. 0027321.*

Jones et al. (2009) Human Gene Therapy, vol. 20, 630-640.*

Torres et al. (2010) J. Biotech., vol. 146, 138-142.*

Kuras et al. (2012) Am. J. Physiol. Cell Physiol., vol. 302, C1504-C1512.*

Gulati et al. (2013) J. Immunother., vol. 1(Suppl 1):P12.*

Kim et al. (2011) PloS ONE, vol. 6(4), e18556, doi:10.1371/journal.pone. 0018556, pp. 1-8.*

Kochenderfer et al. "Construction and Pre-clinical Evaluation of an Anti-CD19 Chimeric Antigen Receptor", J Immunother (2009) vol. 32, No. 7, pp. 689-702.

Kochenderfer et al., "Eradication of B-lineage cells and regression of lymphoma in a patient treated with autologous T cells genetically-engineered to recognize CD19," Blood 116: 4099-4102 (2010).

Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.

Kwon et al., "cDNA sequences of two inducible T-cell genes". Proc. Natl. Acad. Sci. U.S.A. 86(6): 1963-1967 (1989).

Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.

Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).

Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.

Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.

Lee et al., "The Future is Now: Chimeric Antigen Receptors as New Targeted Therapies for Childhood Cancer," Clin. Cancer Res. 18: 2780-2790 (2012).

Letourneur et al., "T-cell and basophil activation through the cytoplasmic tail of T-cell-receptor zeta family proteins," Proc. Natl. Acad. Sci. U.S.A 88: 8905-8909 (1991).

Levine et al., "Gene transfer in humans using a conditionally replicating lentiviral vector" PNAS (2006) vol. 103 No. 46 pp. 17372-17377.

MaCallan et al., "Measurement and modeling of human T cell kinetics" European Journal of Immunology (2003) vol. 33 pp. 2316-2326.

Maher et al., "Human T lymphocyte cytotoxicity and proliferation directed by a single chimeric TCRzeta/CD28 receptor," Nat. Biotechnol. 20: 70-75 (2002).

McGuinness et al., "Anti-tumor activity of human T cells expressing the CC49-zeta chimeric immune receptor," Hum. Gene Ther. 10: 165-173 (1999).

Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.

Molina, "A Decade of Rituximab: Improving Survival Outcomes in Non-Hodgkin's Lymphoma" Annu. Rev. Med. (2008) vol. 59 pp. 237-250.

Moon et al. "Expression of a Functional CCR2 Receptor Enhances Turnor Localization and Tumor Eradication by Retargeted Human T cells Expressing a Mesothelin-Specific Chimeric Antibody Receptor" Clinical Cancer Research (2011) vol. 17, pp. 4719-4730.

Morgan et al., "Case Report of a Serious Adverse Event Following the Administration of T Cells Transduced With a Chimeric Anitgen Receptor Recognizing ErbB2," Mol. Ther. 18(4): 843-851 (2010).

Moritz and Groner, "A spacer region between the single chain antibody- and the CD3 zeta-chain domain of chimeric T cell receptor components is required for efficient ligand binding and signaling activity," Gene Therapy 2(8): 539-546 (1995).

Moritz et al., "Cytotoxic T lymphocytes with a grafted recognition specificity for ERBB2-expressing tumor cells" Proc. Natl. Acad. Sci (1994) vol. 91 pp. 4318-4322.

(56) References Cited

OTHER PUBLICATIONS

Mosenden et al. "Mice with Disrupted Type I Protein Kinase A Anchoring in T Cells Resist Retrovirus-Induced Immunodeficiency" The Journal of Immunology (2011) vol. 186, pp. 5119-5130.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Newick et al. "Augmentation of CAR T-cell Trafficking and Antitumor Efficacy by Blocking Protein Kinase A Localization" Cancer Immunology Research (2016) vol. 4, No. 6, pp. 541-551.
Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.
Willemsen et al., "Genetic Engineering of T Cell Specificity for Immunotherapy of Cancer" Human Immunology (2003) vol. 64 pp. 56-68.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Baeksgaard & Sorensen, "Acute tumor lysis syndrome in solid tumors—a case report and review of the literature" Cancer Chemotherapy Pharmacology (2003) vol. 51 pp. 187-192.
Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone Are Insufficient to Prime Resting T Lymphocytes" J. Exp. Med. (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Carpenito et al. "Control of large, established tumor xenografts with genetically retargeted human T cells containing CD28 and CD137 domains", Proc Natl Acad Sci USA (2009) vol. 106 pp. 3360-3365.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al, "A Third-Generation Lentivirus Vector with a Conditional Packaging System" Journal of Virology (1998) vol. 72 No. 11 pp. 8463-8471.
Eshhar et al., "Specific activation and targeting of cytotoxic lymphocytes through chimeric single chains consisting of antibody-

(56) References Cited

OTHER PUBLICATIONS binding domains and the gamma or zeta subunits of the immunoglobulin and T-cell receptors," PNAS USA 90: 720-724 (1993).
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
GENESEQ Database "A-kinase anchoring protein (AKAP) antagonist peptide RIAD, SEQ ID 93" Database Accession No. BBP22048 (2014).
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Han et al. "Chimeric antigen receptor-engineered T cells for cancer immunotherapy: progress and challenges" Journal of Hematology & Oncology (2013) vol. 6, No. 47, pp. 1-7.
Hekele et al., "Growth Retardation of Tumors by Adoptive Transfer of Cytotoxic T Lymphocytes Reprogrammed by CD44V6-Specific SCFV:~-Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Search Report and Written Opinion for International Application No. PCT/US2016/028986 dated Aug. 3, 2016.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH); Orlando, FL, USA; Dec. 4-7, 2010 abstract.
Carlson et al. "Delineation of Type I Protein Kinase A-selective Signaling Events Using an RI Anchoring Disruptor" The Journal of Biological Chemistry (2006) vol. 281, No. 30, pp. 21535-21545.
Agata, et al., "Expression of the PD-1 antigen on the surface of stimulated mouse T and B lymphocytes", Int Immunol. 8(5), May 1996, 765-772.
Alves, et al., "Common gamma chain cytokines: dissidence in the details", Immunol Lett. 108(2), Feb. 2007, 113-120 (abstract only).
Barrett, et al., "Treatment of Advanced Leukemia in Mice with mRNA Engineered T Cells", Human Gene Therapy 22:1575-1586 (Dec. 2011).
Carpenito , et al., "Control of large, established tumor xenografts with genetically retargeted human T cells containing CD28 and CD137 domains", Proc Natl Acad Sci USA. 106(9)' Mar. 2009, 3360-3385.
Carter , et al,, "PD-1 :PD-L inhibitory pathway affects both CD4+ and CD8+ T cells and is overcome by IL-2", Eur. J. Immunol. 32, 2002, 634-643.
Carter, et al., "Humanization of an anti-p185HER2 antibody for human cancer therapy", Proc. Natl. Acad. Sci. 89, 1992, 4285-4289.
Cheever, et al., "The Prioritization of Cancer Antigens: A National Cancer Institute Pilot Project for the Acceleration of Translational Research", Clin Cancer Res. 15(17), Sep. 2009, 5323-5337.
Chmielewski, et al., "CD28 cosignalling does not affect the activation threshold in a chimeric antigen receptor-edirected T-cell attack", Gene Ther. 18(1), Jan. 2011, 62-72.
Dong , et al., "B7-H1 pathway and its role in the evasion of tumor immunity", J Mol Med (Berl). 81(5), May 2003, 281-287 (abstract).
Freeman , et al., "Engagement of the PD-1 immunoinhibitory receptor by a novel B7 family member leads to negative regulation of lymphocyte activation", 2000, J Exp Med 192(7) 1027-1034.

(56) References Cited

OTHER PUBLICATIONS

Heitner , et al., "Selection of cell binding and internalizing epidermal growth factor receptor antibodies from a phage Display library", J Immunol Methods. 248(1-2), Feb. 2001, 17-30 (abstract only).
Hudecek , et al., "Receptor affinity and extracellular domain modifications affect tumor recognition by ROR1-specific chimeric antigen receptor Tcells", Clin Cancer Res, 19(12), Jun. 2013, 3153-3164.
International Search Report and Written Opinion for PCT International Application No. PCT/US2016/028925 issued Aug. 18, 2016.
Konishi, et al., "B7-H1 Expression on Non-Small Cell Lung Cancer Cells and Its Relationship with Tumor-Infiltrating Lymphocytes and Their PD-1 Expression", Clin Cancer Res. 10(15), Aug. 2004, 5094-5100.
Latchman, et al., "PD-L2 is a second ligand for PD-1 and inhibits T cell activation.", 2001, Nat Immunol 2:261-268; (Abstract).
Lenardo, et al., "Mature T lymphocyte apoptosis-immune regulation in a dynamic and unpredictable antigenic environment", Annu Rev Immunol. 17, 1999, 221-253.
Liao, et al., "Interleukin-2 at the crossroads of effector responses, tolerance, and immunotherapy", Immunity 38(1), Jan. 2013, 13-25.
Linette, et al., "Cardiovascular toxicity and titin cross-reactivity of affinity-enhanced T cells in myeloma and melanoma", Blood. 122(6), Aug. 2013, 863-871.
Liu, et al., "A-kinase anchoring protein (AKAP) antagonist peptide RIAD, SEQ ID 93", Database Geneseq XP002760000 retrieved from EBI accession No. GSP: BBP22048, Database accession No. BBP22048 sequence, 2014.
Malek, et al., "Interleukin-2 receptor signaling: at the interface between tolerance and immunity", Immunity. 33(2), Aug. 2010, 153-165.
Moon, et al., "Multifactorial T-cell hypofunction that is reversible can limit the efficacy of chimeric antigen receptor-ransduced human T cells in solid tumors", Clin Cancer Res. 20(16), Aug. 2014,4262-4273.
Morgan, et al., "Cancer regression and neurologic toxicity following anti-MAGEA3 TCR gene therapy", J Immunother. 36(2), Feb. 2013,133-151.
Parkhurst, et al., "T Cells Targeting Carcinoembryonic Antigen Can Mediate Regression of Metastatic Colorectal Cancer but Induce Severe Transient Colitis", Mol Ther. 19(3), Mar. 2011, 620-626.
Perez-Soler, et al., "Cutaneous adverse effects with HER1/EGFR-targeted agents: is there a silver lining?", J Clin Oncol. 23(22), Aug. 2005, 5235-5246.
Riese, et al., "Enhanced effector responses in activated CD8+ T cells deficient in diacylglycerol kinases", Cancer Res 73, Jun. 2013, 3566-3577.
Riether et al, "Stimulation of ß2-Adrenergic Receptors inhibits Calcineurin Activity in CD4(+) T Cells via PKA-AKAP interaction", Brain Behav Immun. 25(1), Jan. 2011, 59-88 (Jan. 2011).
Robertson, et al., Clinical and biological effects of recombinant human interleukin-18 administered by intravenous infusion to patients with advanced cancer, Clin Cancer Res. 12(14 Pt 1), Jul. 2006,4265-4273.
Schmid, et al., "Evidence for a TCR affinity threshold delimiting maximal CD8 T cell function", J Immunol. 184(9), May 2010, 4936-4946.
Srivastava, et al., "Interleukin-18: biology and role in the immunotherapy of cancer", Curr Med Chem. 17(29), Oct. 2010, 3353-3357 (abstract only).
Wang, et al., "Targeting Fibroblast Activation Protein in Tumor Stroma with Chimeric Antigen Receptor T Cells Can Inhibit Tumor Growth and Augment Host Immunity Without Severe Toxicity", Cancer Immunol Res. 2(2), Feb. 2014, 154-166.
Xu, et al., "Efficacy and safety of adoptive immunotherapy using anti-CD19 chimeric antigen receptor transduced T-cells: a systematic review of phase I clinical trials", Leuk Lymphoma 54(2), Feb. 2013,255-260 (abstract only).
Zhao et al., "Multiple injections of electroporated autologous T cells expressing a chimeric antigen receptor mediate regression of human disseminated tumor", Cancer Research, 2010, 70, 9053-9061.
Zhong, et al., "T-cell receptor affinity and avidity defines antitumor response and autoimmunity in T-cell Immunotherapy", Proc Natl Acad Sci USA. 110(17), Apr. 2013, 6973-6978.
Zhou, et al., "Impact of single chain Fv antibody fragment affinity on nanoparticle targeting of epidermal growth factor receptor expressing tumor cells", J Mol Biol. 371(4), Aug. 2007, 934-947.

* cited by examiner riad = RISR-RIAD riad = RISR-RIAD riad = RISR-RIAD

RIAD = RISR-RIAD

RIAD = RISR-RIAD riad = RISR-RIAD

RIAD = RISR-RIAD

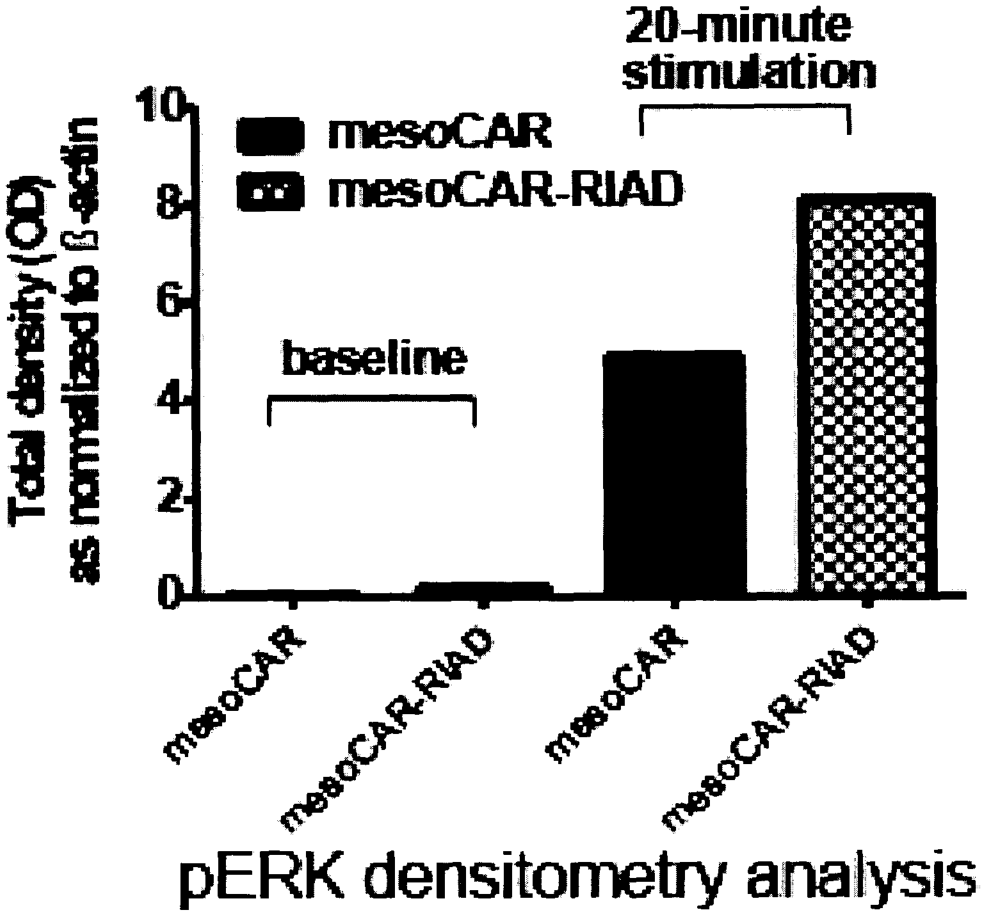
RIAD = RISR-RIAD
Fig. 13A, continued

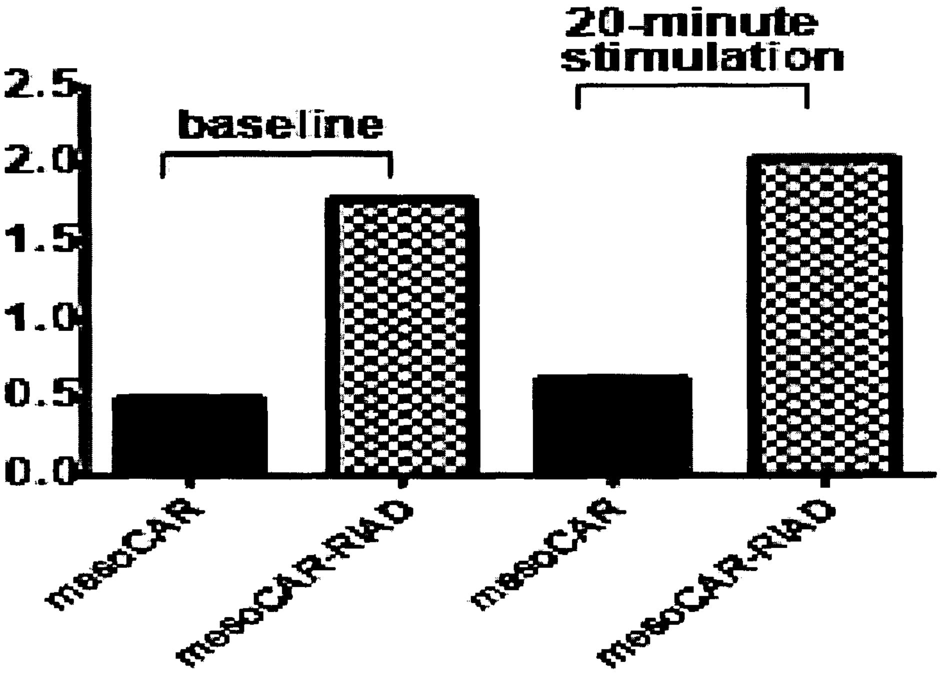
pLck densitometry analysis
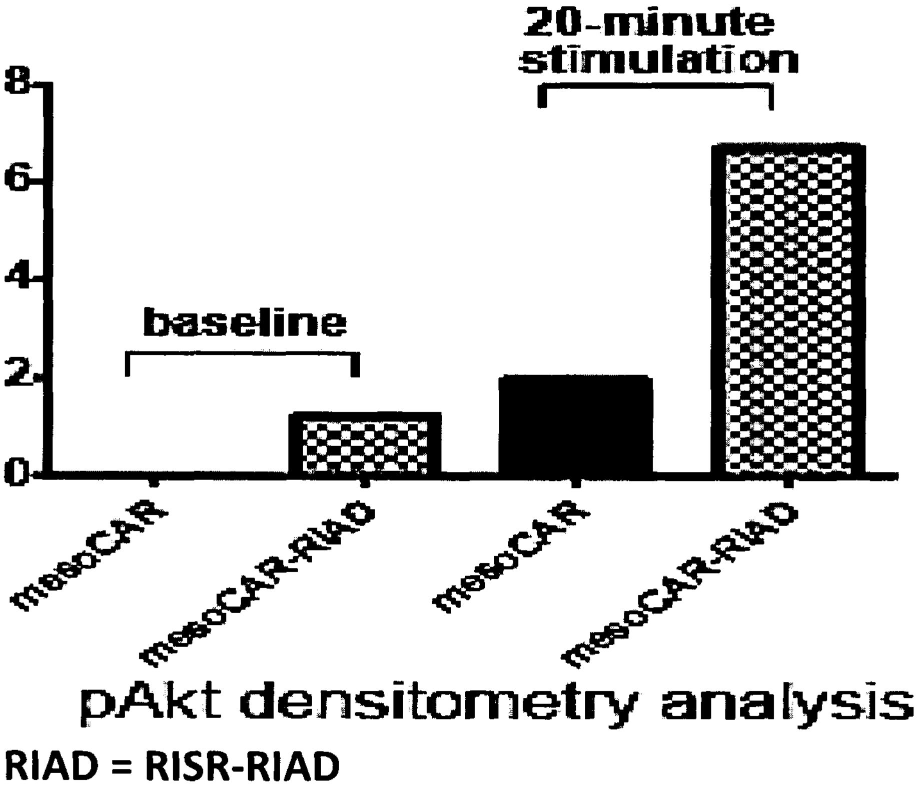
pAkt densitometry analysis
RIAD = RISR-RIAD
Fig. 13A, continued

RIAD = RISR-RIAD

TREATMENT OF CANCER USING CHIMERIC ANTIGEN RECEPTOR AND PROTEIN KINASE A BLOCKER

This application is a U.S. National Stage Application under 35 U.S.C. § 371 of International Application No. PCT/US2016/028986, filed Apr. 22, 2016, which claims priority to U.S. Ser. No. 62/151,707 filed Apr. 23, 2015, the contents of each of which are incorporated herein by reference in their entirety.

STATEMENT REGARDING FEDERALLY SPONSORED RESEARCH OR DEVELOPMENT

This invention was made with government support under grant number CA066726 awarded by the National Institutes of Health. The government has certain rights in the invention.

FIELD OF THE INVENTION

The present invention relates generally to the use of immune effector cells (e.g., T cells, NK cells) engineered to express a Chimeric Antigen Receptor (CAR) and a RIAD polypeptide to treat a disease associated with expression of a tumor antigen.

BACKGROUND OF THE INVENTION

Adoptive cell transfer (ACT) therapy with autologous T-cells, especially with T-cells transduced with Chimeric Antigen Receptors (CARs), has shown promise in hematologic cancer trials.

SUMMARY OF THE INVENTION

The present invention pertains, at least in part, to the use of immune effector cells (e.g., T cells, NK cells) engineered to express a CAR polypeptide that binds to a tumor antigen as described herein to treat cancer associated with expression of said tumor antigen. In particular, the invention features such cells also including a RIAD or Ezrin polypeptide as described herein.

CAR-Encoding Nucleic Acids

Accordingly, in one aspect, the invention pertains to an isolated nucleic acid molecule encoding a chimeric antigen receptor (CAR) and/or RIAD or Ezrin polypeptide, wherein the CAR comprises an antigen binding domain (e.g., antibody or antibody fragment, TCR or TCR fragment) that binds to a tumor antigen as described herein, a transmembrane domain (e.g., a transmembrane domain described herein), and an intracellular signaling domain (e.g., an intracellular signaling domain described herein) (e.g., an intracellular signaling domain comprising a costimulatory domain (e.g., a costimulatory domain described herein) and/or a primary signaling domain (e.g., a primary signaling domain described herein). In some embodiments, the tumor antigen is chosen from one or more of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1

(ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2 M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, tumor antigen bound by the encoded CAR molecule is chosen from one or more of: TSHR, CD171, CS-1, CLL-1, GD3, Tn Ag, FLT3, CD38, CD44v6, B7H3, KIT, IL-13Ra2, IL-11Ra, PSCA, PRSS21, VEGFR2, LewisY, CD24, PDGFR-beta, SSEA-4, MUC1, EGFR, NCAM, CAIX, LMP2, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, ETV6-AML, sperm protein 17, XAGE1, Tie 2, MAD-CT-1, MAD-CT-2, Fos-related antigen 1, p53 mutant, hTERT, sarcoma translocation breakpoints, ML-IAP, ERG (TMPRSS2 ETS fusion gene), NA17, PAX3, Androgen receptor, Cyclin B1, MYCN, RhoC, CYP1B1, BORIS, SART3, PAX5, OY-TES1, LCK, AKAP-4, SSX2, CD79a, CD79b, CD72, LAIR1, FCAR, LILRA2, CD300LF, CLEC12A, BST2, EMR2, LY75, GPC3, FCRL5, and IGLL1.

In certain embodiments, the tumor antigen bound by the encoded CAR molecule is chosen from one or more of: TSHR, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, and OR51E2.

In some embodiments, the antigen binding domain of the encoded CAR molecule comprises an antibody, an antibody fragment, an scFv, a Fv, a Fab, a (Fab')2, a single domain antibody (SDAB), a VH or VL domain, or a camelid VHH domain.

In some embodiments, the transmembrane domain of the encoded CAR molecule comprises a transmembrane domain chosen from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R $\alpha$, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In certain embodiments, the encoded transmembrane domain comprises an amino acid sequence of a CD8 transmembrane domain having at least one, two or three modifications but not more than 20, 10 or 5 modifications of an amino acid sequence of SEQ ID NO: 12, or a sequence with 95-99% identity to an amino acid sequence of SEQ ID NO: 12. In one embodiment, the encoded transmembrane domain comprises the sequence of SEQ ID NO: 12.

In other embodiments, the nucleic acid molecule comprises a nucleotide sequence of a CD8 transmembrane domain, e.g., comprising the sequence of SEQ ID NO: 13, or a sequence with 95-99% identity thereof.

In certain embodiments, the encoded antigen binding domain is connected to the transmembrane domain by a hinge region. In one embodiment, the encoded hinge region comprises the amino acid sequence of a CD8 hinge, e.g., SEQ ID NO: 2; or the amino acid sequence of an IgG4 hinge, e.g., SEQ ID NO: 6, or a sequence with 95-99% identity to SEQ ID NO:2 or 6. In other embodiments, the nucleic acid sequence encoding the hinge region comprises a sequence of SEQ ID NO: 3 or SEQ ID NO: 7, corresponding to a CD8 hinge or an IgG4 hinge, respectively, or a sequence with 95-99% identity to SEQ ID NO:3 or 7. In certain embodiments, the chimeric antigen receptor comprises a leader region, wherein said leader region encodes an amino acid sequence comprising SEQ ID NO: 2, or a sequence with 95-99% identity thereof; or said leader region comprises the nucleotide sequence of SEQ ID NO: 3, or a nucleotide sequence with 95-99% identity thereof.

In other embodiments, the nucleic acid molecule encodes an intracellular signaling domain comprising a sequence encoding a primary signaling domain and/or a sequence encoding a costimulatory signaling domain. In some embodiments, the intracellular signaling domain comprises a sequence encoding a primary signaling domain. In some embodiments, the intracellular signaling domain comprises a sequence encoding a costimulatory signaling domain. In some embodiments, the intracellular signaling domain comprises a sequence encoding a primary signaling domain and a sequence encoding a costimulatory signaling domain.

In certain embodiments, the encoded primary signaling domain comprises a functional signaling domain of a protein selected from the group consisting of CD3 zeta, CD3 gamma, CD3 delta, CD3 epsilon, common FcR gamma (FCER1G), FcR beta (Fc Epsilon R1b), CD79a, CD79b, Fcgamma RIIa, DAP10, and DAP12.

In one embodiment, the encoded primary signaling domain comprises a functional signaling domain of CD3 zeta. The encoded CD3 zeta primary signaling domain can comprise an amino acid sequence having at least one, two or three modifications but not more than 20, 10 or 5 modifications of an amino acid sequence of SEQ ID NO: 18 or SEQ ID NO: 20, or a sequence with 95-99% identity to an amino acid sequence of SEQ ID NO:18 or SEQ ID NO: 20. In some embodiments, the encoded primary signaling domain comprises a sequence of SEQ ID NO:18 or SEQ ID NO: 20. In other embodiments, the nucleic acid sequence encoding the primary signaling domain comprises a sequence of SEQ ID NO:19 or SEQ ID NO: 21, or a sequence with 95-99% identity thereof.

In some embodiments, the encoded intracellular signaling domain comprises a sequence encoding a costimulatory signaling domain. For example, the intracellular signaling domain can comprise a sequence encoding a primary signaling domain and a sequence encoding a costimulatory signaling domain. In some embodiments, the encoded costimulatory signaling domain comprises a functional signaling domain of a protein chosen from one or more of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

In certain embodiments, the encoded costimulatory signaling domain comprises an amino acid sequence having at least one, two or three modifications but not more than 20, 10 or 5 modifications of an amino acid sequence of SEQ ID NO:14 or SEQ ID NO: 16, or a sequence with 95-99% identity to an amino acid sequence of SEQ ID NO:14 or SEQ ID NO: 16. In one embodiment, the encoded costimulatory signaling domain comprises a sequence of SEQ ID NO: 14 or SEQ ID NO: 16. In other embodiments, the nucleic acid sequence encoding the costimulatory signaling domain comprises a sequence of SEQ ID NO:15 or SEQ ID NO: 17, or a sequence with 95-99% identity thereof.

In other embodiments, the encoded intracellular domain comprises the sequence of SEQ ID NO: 14 or SEQ ID NO: 16, and the sequence of SEQ ID NO: 18 or SEQ ID NO: 20, wherein the sequences comprising the intracellular signaling domain are expressed in the same frame and as a single polypeptide chain.

In certain embodiments, the nucleic acid sequence encoding the intracellular signaling domain comprises a sequence of SEQ ID NO:15 or SEQ ID NO: 17, or a sequence with 95-99% identity thereof, and a sequence of SEQ ID NO:19 or SEQ ID NO:21, or a sequence with 95-99% identity thereof.

In some embodiments, the nucleic acid molecule further comprises a leader sequence. In one embodiment, the leader sequence comprises the sequence of SEQ ID NO: 2.

In certain embodiments, the encoded antigen binding domain has a binding affinity KD of $10^{-4}$ M to $10^{-8}$ M.

In one embodiment, the encoded antigen binding domain is an antigen binding domain described herein, e.g., an antigen binding domain described herein for a target provided above.

In one embodiment, the encoded CAR molecule comprises an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In one embodiment, the antigen binding domain has a binding affinity that is at least five-fold, 10-fold, 20-fold, 30-fold, 50-fold, 100-fold or 1,000-fold less than a reference antibody, e.g., an antibody described herein. In one embodiment, the encoded antigen binding domain has a binding affinity at least 5-fold less than a reference antibody (e.g., an antibody from which the antigen binding domain is derived).

In one aspect, the invention pertains to an isolated nucleic acid molecule encoding a chimeric antigen receptor (CAR), wherein the CAR comprises an antigen binding domain (e.g., antibody or antibody fragment, TCR or TCR fragment) that binds to a tumor-supporting antigen (e.g., a tumor-supporting antigen as described herein), a transmembrane domain (e.g., a transmembrane domain described herein), and an intracellular signaling domain (e.g., an intracellular signaling domain described herein) (e.g., an intracellular signaling domain comprising a costimulatory domain (e.g., a costimulatory domain described herein) and/or a primary signaling domain (e.g., a primary signaling domain described herein). In some embodiments, the tumor-supporting antigen is an antigen present on a stromal cell or a myeloid-derived suppressor cell (MDSC).

Vectors

In another aspect, the invention pertains to a vector comprising a nucleic acid sequence encoding a CAR and/or RIAD or Ezrin polypeptide described herein. In one embodiment, the vector is chosen from a DNA vector, an RNA vector, a plasmid, a lentivirus vector, adenoviral vector, or a retrovirus vector. In one embodiment, the vector is a lentivirus vector.

In an embodiment, the vector comprises a nucleic acid sequence that encodes a CAR, e.g., a CAR described herein, and a nucleic acid sequence that encodes an inhibitory molecule comprising: an inhKIR cytoplasmic domain; a transmembrane domain, e.g., a KIR transmembrane domain; and an inhibitor cytoplasmic domain, e.g., an ITIM domain, e.g., an inhKIR ITIM domain. In an embodiment the inhibitory molecule is a naturally occurring inhKIR, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring inhKIR.

In an embodiment, the nucleic acid sequence that encodes an inhibitory molecule comprises: a SLAM family cytoplasmic domain; a transmembrane domain, e.g., a SLAM family transmembrane domain; and an inhibitor cytoplasmic domain, e.g., a SLAM family domain, e.g., an SLAM family ITIM domain. In an embodiment the inhibitory molecule is a naturally occurring SLAM family member, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring SLAM family member.

In one embodiment, the vector further comprises a promoter. In some embodiments, the promoter is chosen from an EF-1 promoter, a CMV IE gene promoter, an EF-1α promoter, an ubiquitin C promoter, or a phosphoglycerate kinase (PGK) promoter. In one embodiment, the promoter is an EF-1 promoter. In one embodiment, the EF-1 promoter comprises a sequence of SEQ ID NO: 1.

In one embodiment, the vector is an in vitro transcribed vector, e.g., a vector that transcribes RNA of a nucleic acid molecule described herein. In one embodiment, the nucleic acid sequence in the vector further comprises a poly(A) tail, e.g., a poly A tail described herein, e.g., comprising about 150 adenosine bases (SEQ ID NO:33). In one embodiment, the nucleic acid sequence in the vector further comprises a 3'UTR, e.g., a 3' UTR described herein, e.g., comprising at least one repeat of a 3'UTR derived from human beta-globulin. In one embodiment, the nucleic acid sequence in the vector further comprises promoter, e.g., a T2A promoter.

CAR Polypeptides

In another aspect, the invention features an isolated CAR polypeptide molecule comprising an antigen binding domain, a transmembrane domain, and an intracellular signaling domain, wherein said antigen binding domain binds to a tumor antigen chosen from one or more of: CD19, CD123, CD22, CD30, CD171, CS-1, CLL-1 (CLECL1), CD33, EGFRvIII, GD2, GD3, BCMA, Tn Ag, PSMA, ROR1, FLT3, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2 M, Ephrin B2, FAP, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, legumain, HPV E6, E7, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In some embodiments, the antigen binding domain of the CAR polypeptide molecule binds to a tumor antigen chosen from one or more of: TSHR, CD171, CS-1, CLL-1, GD3, Tn Ag, FLT3, CD38, CD44v6, B7H3, KIT, IL-13Ra2, IL-11Ra, PSCA, PRSS21, VEGFR2, LewisY, CD24, PDGFR-beta, SSEA-4, MUC1, EGFR, NCAM, CAIX, LMP2, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, ETV6-AML, sperm protein 17, XAGE1, Tie 2, MAD-CT-1, MAD-CT-2, Fos-related antigen 1, p53 mutant, hTERT, sarcoma translocation breakpoints, ML-IAP, ERG (TMPRSS2 ETS fusion gene), NA17, PAX3, Androgen receptor, Cyclin B1, MYCN, RhoC, CYP1B1, BORIS, SART3, PAX5, OY-TES1, LCK, AKAP-4, SSX2, CD79a, CD79b, CD72, LAIR1, FCAR, LILRA2, CD300LF, CLEC12A, BST2, EMR2, LY75, GPC3, FCRL5, and IGLL1.

In some embodiments, the antigen binding domain of the CAR polypeptide molecule binds to a tumor antigen chosen from one or more of: TSHR, CLDN6, GPRC5D, CXORF61, CD97, CD179a, ALK, polysialic acid, PLAC1, GloboH, NY-BR-1, UPK2, HAVCR1, ADRB3, PANX3, GPR20, LY6K, and OR51E2.

In some embodiments, the antigen binding domain of the CAR polypeptide molecule comprises an antibody, an antibody fragment, an scFv, a Fv, a Fab, a (Fab')2, a single domain antibody (SDAB), a VH or VL domain, or a camelid VHH domain.

In some embodiments, the antigen binding domain of the CAR polypeptide molecule comprises a transmembrane domain of a protein chosen from an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In other embodiments, the transmembrane domain of the CAR polypeptide molecule comprises an amino acid sequence having at least one, two or three modifications but not more than 20, 10 or 5 modifications of an amino acid sequence of a CD8 transmembrane domain, e.g., SEQ ID NO: 12, or a sequence with 95-99% identity to an amino acid sequence of SEQ ID NO: 12. In one embodiment, the transmembrane domain comprises a sequence of SEQ ID NO: 12.

In other embodiments, the antigen binding domain of the CAR polypeptide molecule is connected to the transmembrane domain by a hinge region. In one embodiment, the encoded hinge region comprises the amino acid sequence of a CD8 hinge, e.g., SEQ ID NO: 2, or the amino acid sequence of an IgG4 hinge, e.g., SEQ ID NO: 6, or a sequence with 95-99% identity thereof.

In other embodiments, the intracellular signaling domain of the CAR polypeptide molecule comprises a primary signaling domain and/or a costimulatory signaling domain. In other embodiments, the intracellular signaling domain of the CAR polypeptide molecule comprises a primary signaling domain. In other embodiments, the intracellular signaling domain of the CAR polypeptide molecule comprises a costimulatory signaling domain. In yet other embodiments, the intracellular signaling domain of the CAR polypeptide molecule comprises a primary signaling domain and a costimulatory signaling domain.

In other embodiments, the primary signaling domain of the CAR polypeptide molecule comprises a functional signaling domain of a protein selected from the group consisting of CD3 zeta, CD3 gamma, CD3 delta, CD3 epsilon, common FcR gamma (FCER1G), FcR beta (Fc Epsilon R1b), CD79a, CD79b, Fcgamma RIIa, DAP10, and DAP12. In one embodiment, the primary signaling domain comprises a functional signaling domain of CD3 zeta. The CD3 zeta primary signaling domain can comprise an amino acid sequence having at least one, two or three modifications but not more than 20, 10 or 5 modifications of an amino acid sequence of SEQ ID NO: 18 or SEQ ID NO: 20, or a sequence with 95-99% identity to an amino acid sequence of SEQ ID NO:18 or SEQ ID NO: 20. In some embodiments, the primary signaling domain of the CAR polypeptide molecule comprises a sequence of SEQ ID NO:18 or SEQ ID NO: 20.

In some embodiments, the intracellular signaling domain of the CAR polypeptide molecule comprises a sequence encoding a costimulatory signaling domain. For example, the intracellular signaling domain can comprise a sequence encoding a primary signaling domain and a sequence encoding a costimulatory signaling domain. In some embodiments, the encoded costimulatory signaling domain comprises a functional signaling domain of a protein chosen from one or more of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

In certain embodiments, the costimulatory signaling domain of the CAR polypeptide molecule comprises an amino acid sequence having at least one, two or three modifications but not more than 20, 10 or 5 modifications of an amino acid sequence of SEQ ID NO:14 or SEQ ID NO: 16, or a sequence with 95-99% identity to an amino acid sequence of SEQ ID NO:14 or SEQ ID NO: 16. In one embodiment, the encoded costimulatory signaling domain comprises a sequence of SEQ ID NO: 14 or SEQ ID NO: 16. In other embodiments, the intracellular domain of the CAR polypeptide molecule comprises the sequence of SEQ ID NO: 14 or SEQ ID NO: 16, and the sequence of SEQ ID NO: 18 or SEQ ID NO: 20, wherein the sequences comprising the intracellular signaling domain are expressed in the same frame and as a single polypeptide chain.

In some embodiments, the CAR polypeptide molecule further comprises a leader sequence. In one embodiment, the leader sequence comprises the sequence of SEQ ID NO: 2.

In certain embodiments, the antigen binding domain of the CAR polypeptide molecule has a binding affinity KD of $10^{-4}$ M to $10^{-8}$ M. In one embodiment, the antigen binding domain is an antigen binding domain described herein, e.g., an antigen binding domain described herein for a target provided above. In one embodiment, the CAR molecule comprises an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In one embodiment, the antigen binding domain has a binding affinity that is at least five-fold, 10-fold, 20-fold, 30-fold, 50-fold, 100-fold or 1,000-fold less than a reference antibody, e.g., an antibody described herein. In one embodiment, the encoded antigen binding domain has a binding affinity at least 5-fold less than a reference antibody (e.g., an antibody from which the antigen binding domain is derived).

In another aspect, the invention features an isolated CAR polypeptide molecule comprising an antigen binding domain, a transmembrane domain, and an intracellular signaling domain, wherein said antigen binding domain binds to a tumor-supporting antigen (e.g., a tumor-supporting antigen as described herein). In some embodiments, the tumor-supporting antigen is an antigen present on a stromal cell or a myeloid-derived suppressor cell (MDSC).

CAR-Expressing Cells

In another aspect, the invention pertains to a cell, e.g., an immune effector cell, (e.g., a population of cells, e.g., a population of immune effector cells) comprising a nucleic acid molecule, a CAR polypeptide molecule, or a vector as described herein.

In one embodiment, the cell is a human T cell. In one embodiment, the cell is a cell described herein, e.g., a human T cell, e.g., a human T cell described herein; or a human NK cell, e.g., a human NK cell described herein. In one embodiment, the human T cell is a CD8+ T cell. In one embodiment, the cell is a T cell and the T cell is diacylglycerol kinase (DGK) deficient. In one embodiment, the cell is a T cell and the T cell is Ikaros deficient. In one embodiment, the cell is a T cell and the T cell is both DGK and Ikaros deficient.

In another embodiment, a CAR-expressing immune effector cell described herein can further express another agent, e.g., an agent which enhances the activity of a CAR-expressing cell. For example, in one embodiment, the agent can be an agent which inhibits an inhibitory molecule. Examples of inhibitory molecules include PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGFR beta, e.g., as described herein. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 or TGFR beta, or a fragment of any of these, and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD-1 or a fragment thereof, and a second polypeptide of an intracellular signaling domain described herein (e.g., a CD28, CD27, OX40 or 4-IBB signaling domain described herein and/or a CD3 zeta signaling domain described herein).

In one embodiment, the CAR-expressing immune effector cell described herein can further comprise a second CAR, e.g., a second CAR that includes a different antigen binding domain, e.g., to the same target (e.g., a target described above) or a different target. In one embodiment, the second CAR includes an antigen binding domain to a target expressed on the same cancer cell type as the target of the first CAR. In one embodiment, the CAR-expressing immune effector cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain.

While not wishing to be bound by theory, placement of a costimulatory signaling domain, e.g., 4-1BB, CD28, CD27 or OX-40, onto the first CAR, and the primary signaling domain, e.g., CD3 zeta, on the second CAR can limit the CAR activity to cells where both targets are expressed. In one embodiment, the CAR expressing immune effector cell comprises a first CAR that includes an antigen binding domain that targets, e.g., a target described above, a transmembrane domain and a costimulatory domain and a second CAR that targets an antigen other than antigen targeted by the first CAR (e.g., an antigen expressed on the same cancer cell type as the first target) and includes an antigen binding domain, a transmembrane domain and a primary signaling domain. In another embodiment, the CAR expressing immune effector cell comprises a first CAR that includes an antigen binding domain that targets, e.g., a target described above, a transmembrane domain and a primary signaling domain and a second CAR that targets an antigen other than antigen targeted by the first CAR (e.g., an antigen expressed on the same cancer cell type as the first target) and includes an antigen binding domain to the antigen, a transmembrane domain and a costimulatory signaling domain.

In one embodiment, the CAR-expressing immune effector cell comprises a CAR described herein, e.g., a CAR to a target described above, an inhibitory CAR, and/or a RIAD or Ezrin polypeptide. In one embodiment, the inhibitory CAR comprises an antigen binding domain that binds an antigen found on normal cells but not cancer cells, e.g., normal cells that also express the target. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 or TGFR beta.

In one embodiment, an immune effector cell (e.g., T cell, NK cell) comprises a first CAR comprising an antigen binding domain that binds to a tumor antigen as described herein, and a second CAR comprising a PD1 extracellular domain or a fragment thereof.

In one embodiment, the cell further comprises an inhibitory molecule comprising: an inhKIR cytoplasmic domain; a transmembrane domain, e.g., a KIR transmembrane domain; and an inhibitor cytoplasmic domain, e.g., an ITIM domain, e.g., an inhKIR ITIM domain. In an embodiment the inhibitory molecule is a naturally occurring inhKIR, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring inhKIR.

In one embodiment, the cell further comprises an inhibitory molecule comprising: a SLAM family cytoplasmic domain; a transmembrane domain, e.g., a SLAM family transmembrane domain; and an inhibitor cytoplasmic domain, e.g., a SLAM family domain, e.g., an SLAM family ITIM domain. In an embodiment the inhibitory molecule is a naturally occurring SLAM family member, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring SLAM family member.

In one embodiment, the second CAR in the cell is an inhibitory CAR, wherein the inhibitory CAR comprises an antigen binding domain, a transmembrane domain, and an intracellular domain of an inhibitory molecule. The inhibitory molecule can be chosen from one or more of: PD1, PD-L1, CTLA-4, TIM-3, LAG-3, VISTA, BTLA, TIGIT, LAIR1, CD160, 2B4, TGFR beta, CEACAM-1, CEACAM-3, and CEACAM-5. In one embodiment, the second CAR molecule comprises the extracellular domain of PD1 or a fragment thereof.

In embodiments, the second CAR molecule in the cell further comprises an intracellular signaling domain comprising a primary signaling domain and/or an intracellular signaling domain.

In other embodiments, the intracellular signaling domain in the cell comprises a primary signaling domain comprising the functional domain of CD3 zeta and a costimulatory signaling domain comprising the functional domain of 4-1BB.

In one embodiment, the second CAR molecule in the cell comprises the amino acid sequence of SEQ ID NO: 26.

In certain embodiments, the antigen binding domain of the first CAR molecule comprises a scFv and the antigen binding domain of the second CAR molecule does not comprise a scFv. For example, the antigen binding domain of the first CAR molecule comprises a scFv and the antigen binding domain of the second CAR molecule comprises a camelid VHH domain.

Methods of Treatment/Combination Therapies

In another aspect, the present invention provides a method comprising administering a CAR molecule and/or RIAD or Ezrin polypeptide, e.g., as described herein, or a cell comprising one or more nucleic acids encoding a CAR molecule and/or RIAD or Ezrin polypeptide, e.g., as described herein. In one embodiment, the subject has a disorder described herein, e.g., the subject has cancer, e.g., the subject has a cancer which expresses a target antigen described herein. In one embodiment, the subject is a human.

In another aspect, the invention pertains to a method of treating a subject having a disease associated with expression of a cancer associated antigen as described herein comprising administering to the subject an effective amount of a cell comprising a CAR molecule and/or RIAD or Ezrin polypeptide, e.g., as described herein.

In yet another aspect, the invention features a method of treating a subject having a disease associated with expression of a tumor antigen, comprising administering to the subject an effective amount of a cell, e.g., an immune effector cell (e.g., a population of immune effector cells) comprising a CAR molecule, wherein the CAR molecule comprises an antigen binding domain, a transmembrane domain, and an intracellular domain, said intracellular domain comprises a costimulatory domain and/or a primary signaling domain, wherein said antigen binding domain binds to the tumor antigen associated with the disease, e.g. a tumor antigen as described herein.

In a related aspect, the invention features a method of treating a subject having a disease associated with expression of a tumor antigen. The method comprises administering to the subject an effective amount of a cell, e.g., an immune effector cell (e.g., a population of immune effector cells) comprising a CAR molecule, in combination with an agent that increases the efficacy of the immune cell, wherein:

the CAR molecule comprises an antigen binding domain, a transmembrane domain, and an intracellular domain comprising a costimulatory domain and/or a primary signaling domain, wherein said antigen binding domain binds to the tumor antigen associated with the disease, e.g. a tumor antigen as disclosed herein; and the agent that increases the efficacy of the immune cell is chosen from one or more of:

a protein phosphatase inhibitor;

a kinase inhibitor;

a cytokine;

an inhibitor of an immune inhibitory molecule; or an agent that decreases the level or activity of a $T_{REG}$ cell.

In a related aspect, the invention features a method of treating a subject having a disease associated with expression of a tumor antigen, comprising administering to the subject an effective amount of a cell, e.g., an immune effector cell (e.g., a population of immune effector cells) comprising a CAR molecule, wherein:

the CAR molecule comprises an antigen binding domain, a transmembrane domain, and an intracellular domain comprising a costimulatory domain and/or a primary signaling domain, wherein said antigen binding domain binds to the tumor antigen associated with the disease, e.g., a tumor antigen as disclosed herein; and the antigen binding domain of the CAR molecule has a binding affinity at least 5-fold less than an antibody from which the antigen binding domain is derived.

In another aspect, the invention features a composition comprising an immune effector cell (e.g., a population of immune effector cells) comprising a CAR molecule and/or RIAD or Ezrin polypeptide, e.g., as described herein for use in the treatment of a subject having a disease associated with expression of a tumor antigen, e.g., a disorder as described herein.

In certain embodiments of any of the aforesaid methods or uses, the disease associated with a tumor antigen, e.g., a tumor antigen described herein, is selected from a proliferative disease such as a cancer or malignancy or a precancerous condition such as a myelodysplasia, a myelodysplastic syndrome or a preleukemia, or is a non-cancer related indication associated with expression of a tumor antigen described herein. In one embodiment, the disease is a cancer described herein, e.g., a cancer described herein as being associated with a target described herein. In one embodiment, the disease is a hematologic cancer. In one embodiment, the hematologic cancer is leukemia. In one embodiment, the cancer is selected from the group consisting of one or more acute leukemias including but not limited to B-cell acute lymphoid leukemia ("BALL"), T-cell acute lymphoid leukemia ("TALL"), acute lymphoid leukemia (ALL); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and to disease associated with expression of a tumor antigen described herein include, but not limited to, atypical and/or non-classical cancers, malignancies, precancerous conditions or proliferative diseases expressing a tumor antigen as described herein; and any combination thereof. In another embodiment, the disease associated with a tumor antigen described herein is a solid tumor.

In certain embodiments of any of the aforesaid methods or uses, the tumor antigen associated with the disease is chosen from one or more of: CD19, CD123, CD22, CD30, CD171, CS-1, CLL-1 (CLECL1), CD33, EGFRvIII, GD2, GD3, BCMA, Tn Ag, PSMA, ROR1, FLT3, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2 M, Ephrin B2, FAP, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, legumain, HPV E6, E7, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In other embodiments of any of the aforesaid methods or uses, the tumor antigen associated with the disease is chosen from one or more of: TSHR, TSHR, CD171, CS-1, CLL-1, GD3, Tn Ag, FLT3, CD38, CD44v6, B7H3, KIT, IL-13Ra2, IL-11Ra, PSCA, PRSS21, VEGFR2, LewisY, CD24, PDGFR-beta, SSEA-4, MUC1, EGFR, NCAM, CAIX, LMP2, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, ETV6-AML, sperm protein 17, XAGE1, Tie 2, MAD-CT-1, MAD-CT-2, Fos-related antigen 1, p53 mutant, hTERT, sarcoma translocation breakpoints, ML-IAP, ERG (TMPRSS2 ETS fusion gene), NA17, PAX3, Androgen receptor, Cyclin B1, MYCN, RhoC, CYP1B1, BORIS, SART3, PAX5, OY-TES1, LCK, AKAP-4, SSX2, CD79a, CD79b, CD72, LAIR1, FCAR, LILRA2, CD300LF, CLEC12A, BST2, EMR2, LY75, GPC3, FCRL5, and IGLL1.

In other embodiments of any of the aforesaid methods or uses, the tumor antigen associated with the disease is chosen from one or more of: TSHR, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, and OR51E2.

In certain embodiments, the methods or uses are carried out in combination with an agent that increases the efficacy of the immune effector cell, e.g., an agent as described herein.

In any of the aforesaid methods or uses, the disease associated with expression of the tumor antigen is selected from the group consisting of a proliferative disease, a precancerous condition, a cancer, and a non-cancer related indication associated with expression of the tumor antigen.

The cancer can be a hematologic cancer, e.g., a cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or preleukemia.

The cancer can also be chosen from colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

In certain embodiments of the methods or uses described herein, the CAR molecule is administered in combination with an agent that increases the efficacy of the immune effector cell, e.g., one or more of a protein phosphatase inhibitor, a kinase inhibitor, a cytokine, an inhibitor of an immune inhibitory molecule; or an agent that decreases the level or activity of a $T_{REG}$ cell.

In certain embodiments of the methods or uses described herein, the protein phosphatase inhibitor is a SHP-1 inhibitor and/or an SHP-2 inhibitor.

In other embodiments of the methods or uses described herein, kinase inhibitor is chosen from one or more of a CDK4 inhibitor, a CDK4/6 inhibitor (e.g., palbociclib), a BTK inhibitor (e.g., ibrutinib or RN-486), an mTOR inhibitor (e.g., rapamycin or everolimus (RAD001)), an MNK inhibitor, or a dual P13K/mTOR inhibitor. In one embodiment, the BTK inhibitor does not reduce or inhibit the kinase activity of interleukin-2-inducible kinase (ITK).

In other embodiments of the methods or uses described herein, the agent that inhibits the immune inhibitory molecule comprises an antibody or antibody fragment, an inhibitory nucleic acid, a clustered regularly interspaced short palindromic repeats (CRISPR), a transcription-activator like effector nuclease (TALEN), or a zinc finger endonuclease (ZFN) that inhibits the expression of the inhibitory molecule.

In other embodiments of the methods or uses described herein, the agent that decreases the level or activity of the $T_{REG}$ cells is chosen from cyclophosphamide, anti-GITR antibody, CD25-depletion, or a combination thereof.

In certain embodiments of the methods or uses described herein, the immune inhibitory molecule is selected from the group consisting of PD1, PD-L1, CTLA-4, TIM-3, LAG-3, VISTA, BTLA, TIGIT, LAIR1, CD160, 2B4, TGFR beta, CEACAM-1, CEACAM-3, and CEACAM-5.

In other embodiments, the agent that inhibits the inhibitory molecule comprises a first polypeptide comprising an inhibitory molecule or a fragment thereof and a second polypeptide that provides a positive signal to the cell, and wherein the first and second polypeptides are expressed on the CAR-containing immune cells, wherein (i) the first polypeptide comprises PD1, PD-L1, CTLA-4, TIM-3, LAG3, VISTA, BTLA, TIGIT, LAIR1, CD160, 2B4, TGFR beta, CEACAM-1, CEACAM-3, and CEACAM-5 or a fragment thereof; and/or (ii) the second polypeptide comprises an intracellular signaling domain comprising a primary signaling domain and/or a costimulatory signaling domain. In one embodiment, the primary signaling domain comprises a functional domain of CD3 zeta; and/or the costimulatory signaling domain comprises a functional domain of a protein selected from 41BB, CD27 and CD28.

In other embodiments, cytokine is chosen from IL-7, IL-15 or IL-21, or both.

In other embodiments, the immune effector cell comprising the CAR molecule and a second, e.g., any of the combination therapies disclosed herein (e.g., the agent that that increases the efficacy of the immune effector cell) are administered substantially simultaneously or sequentially.

In other embodiments, the immune cell comprising the CAR molecule is administered in combination with a molecule that targets GITR and/or modulates GITR function. In certain embodiments, the molecule targeting GITR and/or modulating GITR function is administered prior to the CAR-expressing cell or population of cells, or prior to apheresis.

In one embodiment, lymphocyte infusion, for example allogeneic lymphocyte infusion, is used in the treatment of the cancer, wherein the lymphocyte infusion comprises at least one CAR-expressing cell of the present invention. In one embodiment, autologous lymphocyte infusion is used in the treatment of the cancer, wherein the autologous lymphocyte infusion comprises at least one CAR-expressing cell described herein.

In one embodiment, the cell is a T cell and the T cell is diacylglycerol kinase (DGK) deficient. In one embodiment, the cell is a T cell and the T cell is Ikaros deficient. In one embodiment, the cell is a T cell and the T cell is both DGK and Ikaros deficient.

In one embodiment, the method includes administering a cell expressing the CAR molecule and/or RIAD or Ezrin polypeptide, e.g., as described herein, in combination with an agent which enhances the activity of a CAR-expressing cell, wherein the agent is a cytokine, e.g., IL-7, IL-15, IL-21, or a combination thereof. The cytokine can be delivered in combination with, e.g., simultaneously or shortly after, administration of the CAR-expressing cell. Alternatively, the cytokine can be delivered after a prolonged period of time after administration of the CAR-expressing cell, e.g., after assessment of the subject's response to the CAR-expressing cell. In one embodiment the cytokine is administered to the subject simultaneously (e.g., administered on the same day) with or shortly after administration (e.g., administered 1 day, 2 days, 3 days, 4 days, 5 days, 6 days, or 7 days after administration) of the cell or population of cells of any of claims 61-80. In other embodiments, the cytokine is administered to the subject after a prolonged period of time (e.g., e.g., at least 2 weeks, 3 weeks, 4 weeks, 6 weeks, 8 weeks, 10 weeks, or more) after administration of the cell or population of cells of any of claims 61-80, or after assessment of the subject's response to the cell.

In other embodiments, the cells expressing a CAR molecule are administered in combination with an agent that ameliorates one or more side effects associated with administration of a cell expressing a CAR molecule. Side effects associated with the CAR-expressing cell can be chosen from cytokine release syndrome (CRS) or hemophagocytic lymphohistiocytosis (HLH).

In embodiments of any of the aforesaid methods or uses, the cells expressing the CAR molecule are administered in combination with an agent that treats the disease associated with expression of the tumor antigen, e.g., any of the second or third therapies disclosed herein. Additional exemplary combinations include one or more of the following.

In another embodiment, the cell expressing the CAR molecule, e.g., as described herein, can be administered in combination with another agent, e.g., a kinase inhibitor and/or checkpoint inhibitor described herein. In an embodiment, a cell expressing the CAR molecule can further express another agent, e.g., an agent which enhances the activity of a CAR-expressing cell.

For example, in one embodiment, the agent that enhances the activity of a CAR-expressing cell can be an agent which inhibits an inhibitory molecule (e.g., an immune inhibitor molecule). Examples of inhibitory molecules include PD1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGFR beta.

In one embodiment, the agent that inhibits the inhibitory molecule is an inhibitory nucleic acid is a dsRNA, a siRNA, or a shRNA. In embodiments, the inhibitory nucleic acid is linked to the nucleic acid that encodes a component of the CAR molecule. For example, the inhibitory molecule can be expressed on the CAR-expressing cell.

In another embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 or TGFR beta, or a fragment of any of these (e.g., at least a portion of the extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one embodiment, the CAR-expressing immune effector cell of the present invention, e.g., T cell or NK cell, is administered to a subject that has received a previous stem cell transplantation, e.g., autologous stem cell transplantation.

In one embodiment, the CAR-expressing immune effector cell of the present invention, e.g., T cell or NK cells, is administered to a subject that has received a previous dose of melphalan.

In one embodiment, the cell expressing a CAR molecule, e.g., a CAR molecule described herein, is administered in combination with an agent that increases the efficacy of a cell expressing a CAR molecule, e.g., an agent described herein.

In one embodiment, the cells expressing a CAR molecule and/or RIAD or Ezrin polypeptide, e.g., as described herein, are administered in combination with a low, immune enhancing dose of an mTOR inhibitor. While not wishing to be bound by theory, it is believed that treatment with a low, immune enhancing, dose (e.g., a dose that is insufficient to completely suppress the immune system but sufficient to improve immune function) is accompanied by a decrease in PD-1 positive T cells or an increase in PD-1 negative cells. PD-1 positive T cells, but not PD-1 negative T cells, can be exhausted by engagement with cells which express a PD-1 ligand, e.g., PD-L1 or PD-L2.

In an embodiment this approach can be used to optimize the performance of CAR cells described herein in the subject. While not wishing to be bound by theory, it is believed that, in an embodiment, the performance of endogenous, non-modified immune effector cells, e.g., T cells or NK cells, is improved. While not wishing to be bound by theory, it is believed that, in an embodiment, the performance of a target antigen CAR-expressing cell is improved. In other embodiments, cells, e.g., T cells or NK cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In an embodiment, administration of a low, immune enhancing, dose of an mTOR inhibitor, e.g., an allosteric inhibitor, e.g., RAD001, or a catalytic inhibitor, is initiated prior to administration of an CAR expressing cell described herein, e.g., T cells or NK cells. In an embodiment, the CAR cells are administered after a sufficient time, or sufficient dosing, of an mTOR inhibitor, such that the level of PD1 negative immune effector cells, e.g., T cells or NK cells, or the ratio of PD1 negative immune effector cells, e.g., T cells/PD1 positive immune effector cells, e.g., T cells, has been, at least transiently, increased.

In an embodiment, the cell, e.g., T cell or NK cell, to be engineered to express a CAR, is harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In one embodiment, the cell expressing a CAR molecule and/or RIAD or Ezrin polypeptide, e.g., as described herein, is administered in combination with an agent that ameliorates one or more side effect associated with administration of a cell expressing a CAR molecule, e.g., an agent described herein.

In one embodiment, the cell expressing a CAR molecule and/or RIAD or Ezrin polypeptide, e.g., as described herein, is administered in combination with an agent that treats the disease associated with a cancer associated antigen as described herein, e.g., an agent described herein.

In one embodiment, a cell expressing two or more CAR molecules, e.g., as described herein, is administered to a subject in need thereof to treat cancer. In one embodiment, a population of cells including a CAR expressing cell, e.g., as described herein, is administered to a subject in need thereof to treat cancer.

In one embodiment, the cell expressing a CAR molecule and/or RIAD or Ezrin polypeptide, e.g., as described herein, is administered at a dose and/or dosing schedule described herein.

In one embodiment, the CAR molecule and/or RIAD or Ezrin polypeptide, e.g., as described herein is introduced into immune effector cells (e.g., T cells, NK cells), e.g., using in vitro transcription, and the subject (e.g., human) receives an initial administration of cells comprising a CAR molecule and/or RIAD or Ezrin polypeptide, e.g., as described herein, and one or more subsequent administrations of cells comprising a CAR molecule and/or RIAD or Ezrin polypeptide, e.g., as described herein, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of cells comprising a CAR molecule and/or RIAD or Ezrin polypeptide, e.g., as described herein are administered to the subject (e.g., human) per week, e.g., 2, 3, or 4 administrations of cells comprising a CAR molecule and/or RIAD or Ezrin polypeptide, e.g., as described herein are administered per week. In one embodiment, the subject (e.g., human subject) receives more than one administration of cells comprising a CAR molecule and/or RIAD or Ezrin polypeptide, e.g., as described herein per week (e.g., 2, 3 or 4 administrations per week) (also referred to herein as a cycle), followed by a week of no administration of cells comprising a CAR molecule and/or RIAD or Ezrin polypeptide, e.g., as described herein, and then one or more additional administration of cells comprising a CAR molecule and/or RIAD or Ezrin polypeptide, e.g., as described herein (e.g., more than one administration of the cells comprising a CAR molecule per week) is administered to the subject. In another embodiment, the subject (e.g., human subject) receives more than one cycle of cells comprising a CAR molecule, and the time between each cycle is less than 10, 9, 8, 7, 6, 5, 4, or 3 days. In one embodiment, the cells comprising a CAR molecule and/or RIAD or Ezrin polypeptide, e.g., as described herein are administered every other day for 3 administrations per week. In one embodiment, the cells comprising a CAR molecule are administered for at least two, three, four, five, six, seven, eight or more weeks.

In one embodiment, the cells expressing a CAR molecule and/or RIAD or Ezrin polypeptide, e.g., as described herein, are administered as a first line treatment for the disease, e.g., the cancer, e.g., the cancer described herein. In another embodiment, the cells expressing a and/or RIAD or Ezrin polypeptide, e.g., as described herein, are administered as a second, third, fourth line treatment for the disease, e.g., the cancer, e.g., the cancer described herein.

In one embodiment, a population of cells described herein is administered.

In another aspect, the invention pertains to the isolated nucleic acid molecule encoding a CAR of the invention, the isolated polypeptide molecule of a CAR of the invention, the vector comprising a CAR of the invention, and the cell comprising a CAR of the invention for use as a medicament.

In another aspect, the invention pertains to a the isolated nucleic acid molecule encoding a CAR of the invention, the isolated polypeptide molecule of a CAR of the invention, the vector comprising a CAR of the invention, and the cell comprising a CAR of the invention for use in the treatment of a disease expressing a cancer associated antigen as described herein.

In another aspect, the invention pertains to a cell expressing a CAR molecule and/or RIAD or Ezrin polypeptide, e.g., as described herein, for use as a medicament in combination with a cytokine, e.g., IL-7, IL-15 and/or IL-21 as described herein. In another aspect, the invention pertains to a cytokine described herein for use as a medicament in combination with a cell expressing a CAR molecule described herein.

In another aspect, the invention pertains to a cell expressing a CAR molecule and/or RIAD or Ezrin polypeptide, e.g., as described herein described herein for use as a medicament in combination with a kinase inhibitor and/or a checkpoint inhibitor as described herein. In another aspect, the invention pertains to a kinase inhibitor and/or a checkpoint inhibitor described herein for use as a medicament in combination with a cell expressing a CAR molecule described herein.

In another aspect, the invention pertains to a cell expressing a CAR molecule and/or RIAD or Ezrin polypeptide, e.g., as described herein, for use in combination with a cytokine, e.g., IL-7, IL-15 and/or IL-21 as described herein, in the treatment of a disease expressing a tumor antigen targeted by the CAR. In another aspect, the invention pertains to a cytokine described herein for use in combination with a cell expressing a CAR molecule described herein, in the treatment of a disease expressing a tumor antigen targeted by the CAR.

In another aspect, the invention pertains to a cell expressing a CAR molecule and/or RIAD or Ezrin polypeptide, e.g., as described herein, for use in combination with a kinase inhibitor and/or a checkpoint inhibitor as described herein, in the treatment of a disease expressing a tumor antigen targeted by the CAR. In another aspect, the invention pertains to a kinase inhibitor and/or a checkpoint inhibitor described herein for use in combination with a cell expressing a CAR molecule described herein, in the treatment of a disease expressing a tumor antigen targeted by the CAR.

In another aspect, the present invention provides a method comprising administering a CAR molecule and/or RIAD or Ezrin polypeptide, e.g., as described herein, or a cell comprising a nucleic acid encoding a CAR molecule and/or RIAD or Ezrin polypeptide, e.g., as described herein. In one embodiment, the subject has a disorder described herein, e.g., the subject has cancer, e.g., the subject has a cancer and has tumor-supporting cells which express a tumor-supporting antigen described herein. In one embodiment, the subject is a human.

In another aspect, the invention pertains to a method of treating a subject having a disease associated with expression of a tumor-supporting antigen as described herein comprising administering to the subject an effective amount of a cell comprising a CAR molecule and/or RIAD or Ezrin polypeptide, e.g., as described herein.

In yet another aspect, the invention features a method of treating a subject having a disease associated with expression of a tumor-supporting antigen, comprising administering to the subject an effective amount of a cell, e.g., an immune effector cell (e.g., a population of immune effector cells) comprising a CAR molecule and/or RIAD or Ezrin polypeptide, e.g., as described herein, wherein the CAR molecule comprises an antigen binding domain, a transmembrane domain, and an intracellular domain, said intracellular domain comprises a costimulatory domain and/or a primary signaling domain, wherein said antigen binding domain binds to the tumor-supporting antigen associated with the disease, e.g. a tumor-supporting antigen as described herein.

In a related aspect, the invention features a method of treating a subject having a disease associated with expression of a tumor-supporting antigen. The method comprises administering to the subject an effective amount of a cell, e.g., an immune effector cell (e.g., a population of immune effector cells) comprising a CAR molecule and/or RIAD or Ezrin polypeptide, e.g., as described herein, in combination with an agent that increases the efficacy of the immune cell, wherein:

the CAR molecule comprises an antigen binding domain, a transmembrane domain, and an intracellular domain comprising a costimulatory domain and/or a primary signaling domain, wherein said antigen binding domain binds to the tumor-supporting antigen associated with the disease, e.g. a tumor-supporting antigen as disclosed herein; and the agent that increases the efficacy of the immune cell is chosen from one or more of:

a protein phosphatase inhibitor;

a kinase inhibitor;

a cytokine;

an inhibitor of an immune inhibitory molecule; or an agent that decreases the level or activity of a $T_{REG}$ cell.

In a related aspect, the invention features a method of treating a subject having a disease associated with expression of a tumor-supporting antigen, comprising administering to the subject an effective amount of a cell, e.g., an immune effector cell (e.g., a population of immune effector cells) comprising a CAR molecule and/or RIAD or Ezrin polypeptide, e.g., as described herein, wherein:

the CAR molecule comprises an antigen binding domain, a transmembrane domain, and an intracellular domain comprising a costimulatory domain and/or a primary signaling domain, wherein said antigen binding domain binds to the tumor-supporting antigen associated with the disease, e.g., a tumor-supporting antigen as disclosed herein; and the antigen binding domain of the CAR molecule has a binding affinity at least 5-fold less than an antibody from which the antigen binding domain is derived.

In another aspect, the invention features a composition comprising an immune effector cell (e.g., a population of immune effector cells) comprising a CAR molecule and/or RIAD or Ezrin polypeptide, e.g., as described herein, for use in the treatment of a subject having a disease associated with expression of a tumor-supporting antigen, e.g., a disorder as described herein.

In any of the aforesaid methods or uses, the disease associated with expression of the tumor-supporting antigen is selected from the group consisting of a proliferative disease, a precancerous condition, a cancer, and a non-cancer related indication associated with expression of the tumor-supporting antigen. In an embodiment, the disease associated with a tumor-supporting antigen described herein is a solid tumor.

In one embodiment of the methods or uses described herein, the CAR molecule and/or RIAD or Ezrin polypeptide, e.g., as described herein, is administered in combination with another agent. In one embodiment, the agent can be a kinase inhibitor, e.g., a CDK4/6 inhibitor, a BTK inhibitor, an mTOR inhibitor, a MNK inhibitor, or a dual PI3K/mTOR inhibitor, and combinations thereof. In one embodiment, the kinase inhibitor is a CDK4 inhibitor, e.g., a CDK4 inhibitor described herein, e.g., a CD4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo[3,4-d]pyrimidine. The MNK inhibitor can be, e.g., a MNK1a, MNK1b, MNK2a and/or MNK2b inhibitor. The dual PI3K/mTOR inhibitor can be, e.g., PF-04695102.

In one embodiment of the methods or uses described herein, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment of the methods or uses described herein, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In one embodiment of the methods or uses described herein, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In one embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment of the methods or uses described herein, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In one embodiment, 1, 2, 3, 4, 5, 6, 7, 8, 9, 10, 11, 12 or more cycles of ibrutinib are administered.

In one embodiment of the methods or uses described herein, the kinase inhibitor is a BTK inhibitor that does not inhibit the kinase activity of ITK, e.g., RN-486, and RN-486 is administered at a dose of about 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg (e.g., 150 mg, 200 mg or 250 mg) daily for a period of time, e.g., daily a 28 day cycle. In one embodiment, 1, 2, 3, 4, 5, 6, 7, or more cycles of RN-486 are administered.

In one embodiment of the methods or uses described herein, the kinase inhibitor is an mTOR inhibitor selected from temsirolimus; ridaforolimus (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.$0^{4,9}$]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 112), inner salt (SF1126); and XL765.

In one embodiment of the methods or uses described herein, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment of the methods or uses described herein, the kinase inhibitor is an MNK inhibitor selected from CGP052088; 4-amino-3-(p-fluorophenylamino)-pyrazolo[3,4-d]pyrimidine (CGP57380); cercosporamide; ETC-1780445-2; and 4-amino-5-(4-fluoroanilino)-pyrazolo[3,4-d]pyrimidine.

In one embodiment of the methods or uses described herein, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propa- nenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In one embodiment of the methods or uses described herein, a CAR expressing immune effector cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor.

In one embodiment of the methods or uses described herein, the CAR molecule is administered in combination with another agent, and the agent is a cytokine. The cytokine can be, e.g., IL-7, IL-15, IL-21, or a combination thereof. In another embodiment, the CAR molecule is administered in combination with a checkpoint inhibitor, e.g., a checkpoint inhibitor described herein. For example, in one embodiment, the check point inhibitor inhibits an inhibitory molecule selected from PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGFR beta.

Methods of Making CAR-Expressing Cells

In another aspect, the invention pertains to a method of making a cell (e.g., an immune effector cell or population thereof) comprising introducing into (e.g., transducing) a cell, e.g., a T cell or a NK cell described herein, with a vector of comprising a nucleic acid encoding a CAR, e.g., a CAR and/or RIAD or Ezrin polypeptide, e.g., as described herein; or a nucleic acid encoding a CAR molecule and/or RIAD or Ezrin polypeptide, e.g., as described herein.

The cell in the methods is an immune effector cell (e.g., a T cell or a NK cell, or a combination thereof). In some embodiments, the cell in the methods is diacylglycerol kinase (DGK) and/or Ikaros deficient.

In some embodiment, the introducing the nucleic acid molecule encoding a CAR and/or RIAD or Ezrin polypeptide, e.g., as described herein, comprises transducing a vector comprising the nucleic acid molecule encoding a CAR and/or RIAD polypeptide, e.g., as described herein, or transfecting the nucleic acid molecule encoding a CAR and/or RIAD or Ezrin polypeptide, e.g., as described herein, wherein the nucleic acid molecule is an in vitro transcribed RNA.

In some embodiments, the method further comprises:

providing a population of immune effector cells (e.g., T cells or NK cells); and removing T regulatory cells from the population, thereby providing a population of T regulatory-depleted cells;

wherein steps a) and b) are performed prior to introducing the nucleic acid encoding the CAR to the population. The nucleic acid encoding the CARs can further comprises a RIAD polypeptide or Ezrin polypeptide, e.g., a RIAD polypeptide or Ezrin polypeptide as described herein.

In embodiments of the methods, the T regulatory cells comprise CD25+ T cells, and are removed from the cell population using an anti-CD25 antibody, or fragment thereof. The anti-CD25 antibody, or fragment thereof, can be conjugated to a substrate, e.g., a bead. In other embodiments, the population of T regulatory-depleted cells provided from step (b) contains less than 30%, 25%, 20%, 15%, 10%, 5%, 4%, 3%, 2%, 1% of CD25+ cells.

In yet other embodiments, the method further comprises:

removing cells from the population which express a tumor antigen that does not comprise CD25 to provide a population of T regulatory-depleted and tumor antigen depleted cells prior to introducing the nucleic acid encoding a CAR to the population. The tumor antigen can be selected from CD19, CD30, CD38, CD123, CD20, CD14 or CD11b, or a combination thereof.

In other embodiments, the method further comprises removing cells from the population which express a checkpoint inhibitor, to provide a population of T regulatory-depleted and inhibitory molecule depleted cells prior to introducing the nucleic acid encoding a CAR to the population. The checkpoint inhibitor can be chosen from PD-1, LAG-3, TIM3, B7-H1, CD160, P1H, 2B4, CEACAM (e.g., CEACAM-1, CEACAM-3, and/or CEACAM-5), TIGIT, CTLA-4, BTLA, and LAIR1. Further embodiments disclosed herein encompass providing a population of immune effector cells. The population of immune effector cells provided can be selected based upon the expression of one or more of CD3, CD28, CD4, CD8, CD45RA, and/or CD45RO. In certain embodiments, the population of immune effector cells provided are CD3+ and/or CD28+.

In certain embodiments of the method, the method further comprises expanding the population of cells after the nucleic acid molecule encoding a CAR has been introduced.

In embodiments, the population of cells is expanded for a period of 8 days or less.

In certain embodiments, the population of cells is expanded in culture for 5 days, and the resulting cells are more potent than the same cells expanded in culture for 9 days under the same culture conditions.

In other embodiments, the population of cells is expanded in culture for 5 days show at least a one, two, three or four fold increase in cell doublings upon antigen stimulation as compared to the same cells expanded in culture for 9 days under the same culture conditions.

In yet other embodiments, the population of cells is expanded in culture for 5 days, and the resulting cells exhibit higher proinflammatory IFN-γ and/or GM-CSF levels, as compared to the same cells expanded in culture for 9 days under the same culture conditions.

In other embodiments, the population of cells is expanded by culturing the cells in the presence of an agent that stimulates a CD3/TCR complex associated signal and/or a ligand that stimulates a costimulatory molecule on the surface of the cells. The agent can be a bead conjugated with anti-CD3 antibody, or a fragment thereof, and/or anti-CD28 antibody, or a fragment thereof.

In other embodiments, the population of cells is expanded in an appropriate media that includes one or more interleukin that result in at least a 200-fold, 250-fold, 300-fold, or 350-fold increase in cells over a 14 day expansion period, as measured by flow cytometry.

In other embodiments, the population of cells is expanded in the presence IL-15 and/or IL-7.

In certain embodiments, the method further includes cryopreserving the population of the cells after the appropriate expansion period.

In yet other embodiments, the method of making disclosed herein further comprises contacting the population of immune effector cells with a nucleic acid encoding a telomerase subunit, e.g., hTERT. The nucleic acid encoding the telomerase subunit can be DNA.

The present invention also provides a method of generating a population of RNA-engineered cells, e.g., cells described herein, e.g., immune effector cells (e.g., T cells, NK cells), transiently expressing exogenous RNA. The method comprises introducing an in vitro transcribed RNA or synthetic RNA into a cell, where the RNA comprises a nucleic acid encoding a CAR molecule and/or RIAD or Ezrin polypeptide, e.g., as described herein.

In another aspect, the invention pertains to a method of providing an anti-tumor immunity in a subject comprising administering to the subject an effective amount of a cell comprising a CAR molecule and/or RIAD or Ezrin polypeptide, e.g., as described herein. In one embodiment, the cell is an autologous T cell or NK cell. In one embodiment, the cell is an allogeneic T cell or NK cell. In one embodiment, the subject is a human.

In one aspect, the invention includes a population of autologous cells that are transfected or transduced with a vector comprising a nucleic acid molecule encoding a CAR molecule, e.g., as described herein. In one embodiment, the vector is a retroviral vector. In one embodiment, the vector is a self-inactivating lentiviral vector as described elsewhere herein.

In one embodiment, the vector is delivered (e.g., by transfecting or electroporating) to a cell, e.g., a T cell or a NK cell, wherein the vector comprises a nucleic acid molecule encoding a CAR and/or RIAD or Ezrin polypeptide, e.g., as described herein, which is transcribed as an mRNA molecule, and the CARs of the present invention is translated from the RNA molecule and expressed on the surface of the cell.

In another aspect, the present invention provides a population of CAR-expressing cells and/or RIAD or Ezrin polypeptide expressing cells, e.g., as described herein, e.g., CAR-expressing immune effector cells (e.g., T cells or NK cells). In some embodiments, the population of CAR-expressing cells comprises a mixture of cells expressing different CARs. For example, in one embodiment, the population of CAR-expressing immune effector cells (e.g., T cells or NK cells) can include a first cell expressing a CAR having an antigen binding domain that binds to a first tumor antigen as described herein, and a second cell expressing a CAR having a different antigen binding domain that binds to a second tumor antigen as described herein. As another example, the population of CAR-expressing cells can include a first cell expressing a CAR that includes an antigen binding domain that binds to a tumor antigen as described herein, and a second cell expressing a CAR that includes an antigen binding domain to a target other than a tumor antigen as described herein. In one embodiment, the population of CAR-expressing cells includes, e.g., a first cell expressing a CAR that includes a primary intracellular signaling domain, and a second cell expressing a CAR that includes a secondary signaling domain, e.g., a costimulatory signaling domain.

In another aspect, the present invention provides a population of cells wherein at least one cell in the population expresses a CAR having an antigen binding domain that binds to a tumor antigen as described herein, and a second cell expressing another agent, e.g., an agent which enhances the activity of a CAR-expressing cell. For example, in one embodiment, the agent can be an agent which inhibits an inhibitory molecule. Examples of inhibitory molecules include PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGFR beta. In one embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, LAG-3, CTLA-4, CD160, BTLA, LAIR1, TIM-3, CEACAM (e.g., CEACAM-1, CEACAM-3 and/or CEACAM-5), 2B4 and TIGIT, or a fragment of any of these, and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD-1 or a fragment thereof, and a second polypeptide of an intracellular signaling domain described herein (e.g., a CD28, CD27, OX40 or 4-IBB signaling domain described herein and/or a CD3 zeta signaling domain described herein).

In one embodiment, the nucleic acid molecule encoding a CAR of the present invention molecule, e.g., as described herein, is expressed as an mRNA molecule. In one embodiment, the genetically modified CAR of the present invention-expressing cells, e.g., immune effector cells (e.g., T cells, NK cells), can be generated by transfecting or electroporating an RNA molecule encoding the desired CARs (e.g., without a vector sequence) into the cell. In one embodiment, a CAR of the present invention molecule is translated from the RNA molecule once it is incorporated and expressed on the surface of the recombinant cell.

In another aspect, the invention features a composition including a nucleic acid molecule encoding any of the foregoing CARs and a nucleic acid molecule encoding an RIAD or Ezrin polypeptide.

In certain aspects, the RIAD polypeptide includes, e.g., a polypeptide having an amino acid sequence having at least 80%, 85%, 90%, 95%, 96%, 97%, 98%, or 99% identity to SEQ ID NO: 63. In related aspects, the RIAD polypeptide can be any of the "anchoring disruption molecule or AKAP mimic" disclosed in U.S. Patent Application Publication No. 20080248008, each of which is hereby specifically incorporated by reference. For example (as described the '008 publication), the RIAD polypeptide can have the following sequence: L E Q Y A N Q L A D Q I I K E A T E, (SEQ ID NO: 63), i.e., X1=L, X2=E, X3=Q, X4=N, X5=Q, X6=D, X7=Q, X8=I, X9=K, X10=E, X11=A, X12=T and X13=E, or a variant of this sequence wherein the variant has a substitution at any one, two, three, four or five of positions X1 to X13 of the sequence. Preferably the one or more substitutions are selected from X1=F, Y, I, V, W or C; X2=C, D, R or K; X3=F, K, R, A, I, L, M, S, T, V, G, N, W, D or E; X4=K, R, G, T, S, W, D or E; X5=S, F, K, R, M, W, Y, D or E; X6=E, I, A, R, S, F, H, W, K, L, Y, M, N, Q or G; X7=K, R, F, N, S, T, V, L, M, W, I, D or E; X8=V; X9=D, E, L, S, R, A, M, T, W, Y; X10=D, R, K or Q; X11=I or V; X12=F, C, M, K, R, I or L; and X13=D, N, V, Y, G, H, I, Q, A, F, K, L, M, R, S, T or W.

X5 can also be L or T and X11 can also be C.

Alternatively, the one or more substitutions are selected from X1=C, I or F; X2=D, K, R, V, A, I, L, Q, S or T; X3=D, E, A, I, S or V; X4=D, E, S, A, M or Q; X5=D, E, C, I, M or F; X6=G, S, E or M; X7=D, E, I or M; X8=V, D or E; X9=A, D, E, M, R, T, W or Y; X10=D; X12=L, V or W; and X13=D, R, K or W.

Especially preferably, (i) single amino acid substitutions are selected from the group consisting of X1=C; X2=D; X3=D or E; X4=D or E; X5=D or E; X6=E, G or S; X7=D, E or I; X9=D, E, A, M, R, T, W or Y; X10=D; and X13=D (referred to as L1C, E2D, Q3D, Q3E, N6D, N6E, Q7D, Q7E, D10E, D10G, MOS, Q11D, Q11E, Q11I, K14D, K14E, K14A, K14 M, K14R, K14T, K14W, K14Y, E15D and E18D respectively); further single amino acid substitutions are selected from X1=F, I or Y; X3=A, K, M, R, S or T; X4=G or T; X5=K, L M, R, S or T; X6=N; X7=K, L or R; X12=C or M; X13=M, N, Q or T (L1F, L1I, L1Y, Q3A, Q3K, Q3 M, Q3R, Q11K, Q11L, Q11R, T17C, T17 M, Q3S, Q3T, N6G, N6T, Q7K, Q7L, Q7 M, Q7R, Q7S, Q7T, D10N, E18 M, E18N, E18Q, E18T); and (ii) double amino acid substitutions of said sequence are selected from the group consisting of:

a) when X6 is S, either X2 is K or D, X5 is D or E or X8 is V (alternatively referred to as D10S E2K, D10S E2D, D10S Q7D, D10S Q7E or D10S I12V);

b) when X6 is E, either X2 is K or D, X5 is D or E or X8 is V (alternatively referred to as D10E E2K, D10E E2D, D10E Q7D, D10E Q7E, D10E I12V); and c) when X8 is V, either X2 is K or D, X6 is M or X12 is L (referred to as I12V E2K, I12V E2D, I12V D10 M or I12V T17L);

alternatively, double amino acid substitutions of said sequence may be selected from the group consisting of:

a) when X3 is A, either X4 is G; X5 is K, M or R; X7 is K, L or R; or X13 is M, N or Q;

b) when X13 is T, either X1 is F; X3 is A, K, E, M, R or S; X4 is T or G; X5 is M or R; X7 is R or K; or X9 is R;

c) when X13 is Q, either X3 is A, S, E, K, M, R or S; X4 is G; X5 is M, K or R; or X7 is K; or d) when X13 is M, either X3 is E, M, R, S or K; X4 is G; X5 is M, R or K; X7 is R; or X12 is C or M;

e) when X7 is K, either X3 is A, R, E, K or M; X4 is G; X5 is M; X9 is R; X12 is C or M; or X13 is Q, T, M or N; and f) when X5 is M, either X7 is K; or X13 is N, Q or T;

(iii) triple amino acid substitutions of said sequence are selected from the group consisting of:

a) when X2 is K, X4 is E and X6 is S (E2K N6E D10S);

b) when X2 is D, X4 is D or E and X6 is E or S (E2D N6D/N6E D10E/D10S);

c) when X2 is K, X6 is M and X8 is V (E2K D10 M I12V);

d) when X2 is D, X6 is E or M and X8 is D, E or V (E2D D10E/D10 M I12D/I12E/I12V);

e) when X7 is D, X8 is V and X12 is L (Q11D I12V T17L);

f) when X7 is E, X8 is V and X12 is L (Q11E I12V T17L);

g) when X6 is S, X8 is V and either

X1 is I or F;

X2 is A, I, L, Q, S, T, D or V;

X3 is E, D, S, A, I or V;

X4 is S, E, D, A, M or Q;

X5 is M, D, E, I or F;

X7 is D, E, M;

X9 is R;

X10 is D;

X12 is W or L; or

X13 is K or W; and h) when X6 is E, X8 is V and either

X1 is I or F;

X2 is A, I, L, Q, S, T, D or V;

X3 is E, D, S, A, I or V;

X4 is S, E, D, A, M or Q;

X5 is M, D, E, I or F;

X7 is D, E, M;

X9 is R;

X10 is D;

X12 is W or L; or

X13 is K or W; and iv) quadruple amino acid substitutions of said sequence are selected from the group consisting of:

a) when X5 is E, X6 is S, X8 is V and either

X3 is A, D, E or S;

X4 is E, D or S;

X12 is L or W;

b) when X5 is D, X6 is S, X8 is V and either

X3 is A, D, E or S;

X4 is E, D or S;

X12 is L or W;

c) when X4 is E, X6 is S or E, X8 is V and X2 is either K, D, V, A, I, L, Q, S or T;

d) when X4 is D, X6 is S or E, X8 is V and X2 is either K, D, V, A, I, L, Q, S or T;

e) when X2 is K, X6 is S, X8 is V and either

X1 is F;

X3 is E, D, A or S;

X4 is S, A, M, D or E;

X5 is F, I, M, D or E;

X7 is M, D or E;

X12 is L or W; or

X13 is D or K;

f) when X2 is D, X6 is S, X8 is V and either
X1 is F;
X3 is E, D, A or S;
X4 is S, A, M, D or E;
X5 is F, I, M, D or E;
X7 is M, D or E;
X12 is L or W; or
X13 is D or K;
g) when X2 is V; X3 is E or D, X6 is S or E and X8 is V;
h) when X2 is D; X3 is E or D, X6 is S or E and X8 is V;
i) when X2 is K; X4 is E or D, X6 is M or E and X8 is V; and
j) when X2 is D; X4 is E or D, X6 is M or E and X8 is V; and
v) quintuple amino acid substitutions of said sequence are selected from the groups consisting of:
a) when X2 is K, X4 is E or D, X6 is S or E, X8 is V and either
X1 is I or F;
X3 is D, E, A, I, S or V;
X5 is M, F, D, E or I;
X7 is D, E or M;
X9 is R;
X11 is D;
X12 is L or W; or
X13 is K, D or W;
b) when X2 is D, X4 is E or D, X6 is S or E, X8 is V and either
X1 is I or F;
X3 is D, E, A, I, S or V;
X5 is M, F, D, E or I;
X7 is D, E or M;
X9 is R;
X10 is D;
X12 is L or W; or
X13 is K, D or W;
c) when X2 is A, X4 is E or D, X5 is C, D or E, X6 is S or E and X8 is V;
d) when X2 is D, X4 is E or D, X5 is C, D or E, X6 is S or E and X8 is V;
e) when X2 is T, X4 is E or D, X5 is E or D, X6 is S or E and X8 is V;
f) when X2 is Q, X4 is E or D, X5 is E or D, X6 is S or E and X8 is V; and
or a peptidomimetic or analogue thereof.

Particularly preferred RIAD polypeptides are polypeptides comprising the above sequence or the sequence with a single amino acid substitution particularly as described above.

Highly preferred are polypeptides comprising the above sequence with a single amino acid substitution selected from the group consisting of X7=D or E or X9=A, M, T, W or Y.

In a further preferred feature, the RIAD polypeptide of the invention is a polypeptide of SEQ ID NO: 72 in which
X1=L, X2=K, X3=Q, X4=N, X5=Q, X6=S, X7=Q, X8=V, X9=K, X10=E, X11=A, X12=T and X13=E,
i.e. comprising the following sequence:

(SEQ ID NO: 72)
L K Q Y A N Q L A S Q V I K E A T E or a variant thereof, wherein said variant has a substitution at any one, two, three or four of positions X1 to X13 of said sequence.

Preferably said one or more substitutions are selected from X1=F or I; X2=A, E, D, R, V, Q, S, I, L or T; X3=A, S, E, D, V or I; X4=A, M, S, E, D or Q, X5=F, I, M, D or E; X6=M, E or D; X7=M, E or D; X8=I; X9=R or C; X10=D; X11=C; X12=L, C or W; and X13=D or the substitutions defined for the previous preferred sequence.

Alternatively, said one or more substitutions are selected from X1=C, I or F; X2=D, R, V, A, I, L, Q, S, E or T; X3=D, E, A, I, S or V; X4=D, E, S, A, M or Q; X5=D, E, I, M or F; X6=D, E, G or M; X7=D, E, I or M; X8=I; X9=A, D, E, M, R, T, W or Y; X10=D; X12=L or W; and X13=K, R, D or W.

Especially preferably
(i) single amino acid substitutions of the sequence are selected from the group consisting of X2=A, D, E, V, Q, S, I, L or T; X3=D, E, S or A; X4=D, E, A, S or M; X5=D, E or M; X6=D or E; X7=D or E; X8=I; X9=C; X10=D; X12=W or L; and X13=D; and
(ii) double amino acid substitutions of said sequence are selected from the group consisting of:
(a) when X2 is E or D, either
X1 is I or F;
X3 is A, E, D, S, I or V;
X4 is A, E, D, S, M or Q;
X5 is F, I, D, E or M;
X6 is M, D or E;
X7 is D, E or M;
X8 is I;
X9 is R;
X10 is D;
X12 is L or W; or
X13 is D, K or W;
(b) when X6 is E or D, either
X1 is I or F;
X2 is A, D, E, S, I, V, L, Q or T;
X3 is A, D, E, S, I or V;
X4 is D or E;
X5 is F, I, D, E or M;
X6 is M, D or E;
X7 is M, D or E;
X8 is I;
X9 is R;
X10 is D;
X12 is L or W; or
X13 is W, K or D; and
(c) when X2 is V, X3 is E or D; and
(iii) triple amino acid substitutions of said sequence are selected from the group consisting of:
(a) when X2 is E or D and X5 is E or D, either
X3 is S, D, E or A;
X4 is E, D or S;
X8 is I; or
X12 is W or L;
(b) X2 is T and X4 and X5 are both E or D;
(c) X2 is A, X4 is E or D and X5 is E or D;
(d) X2 is E or D, X6 is D or E and either X8 is I or X12 is L;
(e) X2 is E or D, X6 is G and X8 is I; (f) X2 is V, X4 is E or D and X5 is E or D; (g) X2 is D or E, X6 is D or E and X8 is I; (h) X2 is Q, X4 is E or D and X5 is E or D; and (i) X2 is E, X6 is N and X8 is I; and
(iv) quadruple amino acid substitutions of said sequence are selected from the group consisting of:
(a) when X2 is E or D, X6 is D or E and X, is I, either
X1 is C;
X3 is D or E;
X4 is D or E;

X5 is D or E;
X7 is D, E or I; or
X9 is A, D, E, M, R, T, W or Y;
X12 can be C or M;
X13 can be M, N, Q or T; and
X1 can also be F, I or Y;
X3 can also be A, K, M, R, S or T;
X4 can also be G or T;
X5 can also be K, L, M, R, S or T;
X7 can also be K, L or R;
(b) X2 is E or D, X6 and X7 are both D or E and X12 is L, or a peptidomimetic or analogue thereof.

Alternatively, the polypeptide may consist of any of the above sequences, or a 1-6, e.g. 1, 2, 3 or 4 (preferably 1 or 2) amino acid N- or C-terminal (preferably C-terminal) truncation of said polypeptide, provided that said truncated polypeptide retains the ability to bind to PKA I. Such polypeptides fall within the scope of derivatives as described herein. Examples of truncated polypeptides which are particularly useful are:

```
                    (SEQ ID NO: 80)
LVQYAEQLASQVIKEAT

                    (SEQ ID NO: 81)
LESYANQLASQVIKEAT

                    (SEQ ID NO: 82)
LESYASQLASQVIKEAT

                    (SEQ ID NO: 83)
LEQYAEQLASQVIKEAT

                    (SEQ ID NO: 84)
LEQYAEQLASQVIKEA

                    (SEQ ID NO: 85)
LVQYAEELASQVIKEAT

                    (SEQ ID NO: 86)
LVQYAEELASQVIKEA

                    (SEQ ID NO: 87)
LESYANELASQVIKEAT

                    (SEQ ID NO: 88)
LESYANELASQVIKEA

                    (SEQ ID NO: 89)
LEQYASELASQVIKEAT

                    (SEQ ID NO: 90)
LEQYAEELASQVIKEAT

                    (SEQ ID NO: 91)
LEQYAEELASQVIKEA

                    (SEQ ID NO: 92)
LEQYANELASQIIKEAT

                    (SEQ ID NO: 93)
LEQYANELASQIIKEA

                    (SEQ ID NO: 94)
LEQYANELASQVIKEAL

                    (SEQ ID NO: 95)
LEQYANELASQVIKEA

                    (SEQ ID NO: 96)
LEQYANQLASQIIKEAT

                    (SEQ ID NO: 97)
LEQYANQLASQIIKEA
```

-continued

```
                    (SEQ ID NO: 98)
LEQYANQLASQVIKEAL

                    (SEQ ID NO: 99)
LEQYANQLASQVIKEA

                    (SEQ ID NO: 100)
LEQYANQLADQIIKEAT

                    (SEQ ID NO: 101)
LEQYANQLADQIIKEA

                    (SEQ ID NO: 102)
LEQYANQLADDVIKEAL

                    (SEQ ID NO: 103)
LEQYANQLADDVIKEA

                    (SEQ ID NO: 104)
LEQYANQLADDIIKEAT

                    (SEQ ID NO: 105)
LEQYANQLADDIIKEA

                    (SEQ ID NO: 106)
LEQYANQLADDVIKEAL

                    (SEQ ID NO: 107)
LEQYANQLADDVIKEA
```

In certain embodiments, the RIAD polypeptide also includes a RISR subunit, e.g., a polypeptide having an amino acid sequence having at least 80%, 85%, 90%, 95%, 96%, 97%, 98%, or 99% identity to SEQ ID NO: 64 (e.g., a polypeptide having 100% identity to SEQ ID NO: 64). In preferred embodiments, the inclusion of a RISR subunit increases the affinity and/or selectivity of the RIAD polypeptide for PKA type I (including, e.g., the molecules described in Jarnaess et al., J. Biol. Chem. 283:33708 (2008) which are each incorporated by reference).

In certain aspects, the foregoing chimeric antigen receptor and RIAD polypeptides are encoded by a single nucleic molecule in the same frame and as a single polypeptide chain (e.g., the RIAD polypeptide is attached to the N-terminus or C-terminus of the chimeric antigen receptor). In this aspect, the RIAD polypeptide and chimeric antigen receptor can, e.g., be separated by one or more peptide cleavage sites. (e.g., an auto-cleavage site or a substrate for an intracellular protease). Examples of peptide cleavage sites include the following, wherein the GSG residues are optional:

```
T2A:
                                          (SEQ ID NO: 73)
(GSG) E G R G S L L T C G D V E E N P G P

P2A:
                                          (SEQ ID NO: 74)
(GSG) A T N F S L L K Q A G D V E E N P G P

E2A:
                                          (SEQ ID NO: 75)
(GSG) Q C T N Y A L L K L A G D V E S N P G P

F2A:
                                          (SEQ ID NO: 76)
(GSG) V K Q T L N F D L L K L A G D V E S N P G P
```

In a related aspect, the invention features a single protein, as described above, encoding a CAR and RIAD or Ezrin polypeptide.

In other aspects, the foregoing chimeric antigen receptor and RIAD or Ezrin polypeptides are encoded by a single, or multiple, nucleic molecules and are not expressed as a single polypeptide. Here, e.g., the chimeric antigen receptor and the RIAD or Ezrin polypeptide can be controlled by a common promoter or be separated by an internal ribosomal entry site. Alternatively, the expression of the chimeric antigen receptor and the RIAD polypeptide can be, e.g., controlled by separate promoters.

In yet another aspect, the invention features one or more vectors (e.g., any of the vectors described above) including the foregoing nucleic acid molecules encoding a CAR and RIAD or Ezrin polypeptide. As noted above, the vector can also include a promoter chosen from an EF-1 promoter (e.g., including a sequence of SEQ ID NO: 1), a CMV IE gene promoter, an EF-1α promoter, an ubiquitin C promoter, or a phosphoglycerate kinase (PGK) promoter.

In yet another aspect, the invention feature an immune effector cell (a human T cell (e.g., CD8+ T cell) or a human NK cell, optionally, wherein the T cell is diacylglycerol kinase (DGK) and/or Ikaros deficient)), including (i) the nucleic acid molecule encoding a chimeric antigen receptor and nucleic acid molecule encoding an RIAD or Ezrin polypeptide, as described above;

(ii) a foregoing polypeptide including a CAR and a RIAD or Ezrin polypeptide; and/or (iii) a vector encoding the above constructs.

The invention also features a method of making a chimeric antigen receptor and RIAD or Ezrin polypeptide-expressing immune effector cell (e.g., a population of chimeric antigen receptor-expressing immune effector cells), including introducing any of the foregoing nucleic acids and/or vectors, into an immune effector cell, under conditions such that the chimeric antigen receptor molecule is expressed.

As noted above, this method can, optionally, further include a) providing a population of immune effector cells (e.g., T cells or NK cells); and b) removing T regulatory cells from the population, thereby providing a population of T regulatory-depleted cells;

wherein steps a) and b) are performed prior to introducing the nucleic acid (or nucleic acids) encoding the chimeric antigen receptor and RIAD or Ezrin polypeptide to the population.

In yet another embodiment, the invention features any and all of the foregoing methods of providing anti-tumor immunity in a subject, wherein those methods also feature administering to the subject an effective amount of the foregoing immune effector cells.

The invention also features, in the place of, or in addition to, any of the foregoing RIAD polypeptides, a peptide comprising an amphipathic helix domain and at least one cluster of basic amino acids, wherein the peptide disrupts protein kinase A (PKA) and A-kinase anchoring protein (AKAP) association, e.g., wherein the amphipathic helix domain and the cluster of basic amino acids bind the PKA. Such a peptide can be, e.g., a fragment of an AKAP, wherein the fragment comprises an amphipathic helix domain of the AKAP. The term "A-kinase anchoring protein" or "AKAP" should be construed to include any one of AKAP1, AKAP2, AKAP3, AKAP4, AKAP5, AKAP6, AKAP7, AKAP8, AKAP9, AKAP10, AKAP11, AKAP12, AKAP13, AKAP15, AKAP18, AKAP28, AKAP75, AKAP78, AKAP79, AKAP80, AKAP82, AKAP84, AKAP95, AKAP110, AKAP121, AKAP140, AKAP149, AKAP150, AKAP220, AKAP350, AKAP450, AKAP-KL, AKAP-Lbc, DAKAP-1, mAKAP, T-AKAP80, BIG2, Ezrin, CG-NAP, Gravin, Ht31, Hyperion, MAP2B, MAP2D, Merlin, myeloid translocation gene 8, myeloid translocation gene 16b, Myospryn, Myosin VIIA, MyRIP, Neurobeachin, PAP7, Pericentrin, Rab32, Rt31, SFRS17A, SKIP, SSeCKS, Synemin, WAVE-1, and Yotiao. In such aspects, the peptide can have a length of, e.g., about 10 amino acids to about 60 amino acids in length.

By "amphipathic helix domain" refers to an A-kinase binding (AKB) domain of an AKAP that binds the dimerization and docking (D/D) domain of PKA that localizes to a particular location within the cell, such as the cell membrane.

DETAILED DESCRIPTION

Figure 1:
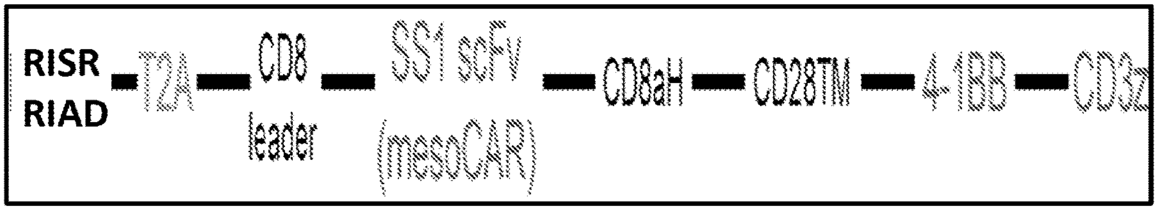
FIG. 1 is an illustration of the "regulatory subunit I specifier region/regulatory subunit I anchoring disruptor" (RISR-RIAD) sequence construct that was cloned into the mesoCAR plasmid, separated by a T2A sequence to yield stoichiometric expression of both CAR and RISR-RIAD.

In general, the invention features the expression of a RIAD polypeptide (e.g., RIAD, RISR, and/or RISR-RIAD) in a T-cell containing a chimeric antigen T cell receptor. This invention is based, at least in part, on the discovery that the co-expression of a chimeric antigen receptor and a RIAD polypeptide (e.g., RIAD, RISR, and/or RISR-RIAD) in T cells result in increased killing of tumor cells both in vitro and in vivo. The invention also features the use of Ezrin-derived polypeptides for a similar purpose.

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "RIAD polypeptide" is defined as a polypeptide comprising a PKA I anchoring disrupting molecule or AKAP mimic which comprises the following amino acid sequence (as set forth in U.S.: (SEQ ID NO: 77):

X1 X2 X3 Y A X4 X5 L A X6 X7 X8 I X9 X10 X11 X12 X13 wherein

X1 is L, C, I, Y, V, W or F (preferably L, C, I or F, especially preferably L);

X2 is K, R, H, E, D, C, V, A, I, Q, S, T or L (preferably K, R, D or E);

X3 is Q, D, E, A, S, I, F, K, R, L, M, T, G, N, W or V (preferably Q, D, E, A, S, I, V, especially preferably Q);

X4 is N, D, E, S, A, M, K, R, G, T, W or Q (preferably N, D, E or S);

X5 is Q, D, E, M, F, I, S, K, R, C, W or Y (preferably Q, D, E, F, I or M);

X6 is S, D, M, N, E, I, A, R, F, H, W, K, L, Y, Q or G (preferably S, M, E or D);

X7 is Q, D, E, I, K, R, T, V, F, N, S, L, W or M (preferably Q, M, E or D);

X8 is I, A, S, L, D, E, B or V;

X9 is K, C, D, E, R, A, M, T, W, H, Q or Y (preferably K or R);

X10 is E, D, R, Q or K (preferably E or D);

X11 is A, C, I, F, L, G, H or V (preferably A);

X12 is T, C, L, F, I, V, M, K, R or W (preferably T, L or W); and

X13 is E, D, N, V, Y, K, A, F, G, H, I, Q, L, M, R, S, T or W (preferably E, D, R, K or W), or a peptidomimetic or analogue thereof. Additionally X5 may be L or T, X9 may be L or S.

The term "RIAD polypeptide" is also meant to include a polypeptide comprising a PKA I anchoring disrupting molecule or AKAP mimic as defined in U.S. Patent Application Publication No. 20080248008, which is hereby incorporated by reference in its entirety. In general, the molecule or mimic is a polypeptide. A "RIAD polypeptide" binds PKA RI as assessed according to the KD between the RIAD polypeptide and the binding site of the PKA RI molecule as described in U.S. Patent Application No. 20080248008. Preferably the KD should be 0.01-500 nM, preferably 0.01-10 nM when assessed in vitro. The dissociation constants (KD) may be measured directly by fluorescence polarization as described in U.S. Patent Application No. 20080248008. In certain embodiments, the term "RIAD polypeptide" also includes a polypeptide having a RISR subunit (e.g., the amino acid sequence of SEQ ID NO: 64, or derivative thereof).

The term "RISR subunit" is meant to include a polypeptide having an amino acid sequence of SEQ ID NO: 64, or a derivative thereof. For example, the term "RISR subunit" includes polypeptides having greater than 80% (e.g., 85%, 90%, 95%, 97%, 98%, 99%) sequence identity to SEQ ID NO: 64. Additionally, or alternatively, the term "RISR subunit" includes polypeptides having the sequence of SEQ ID NO: 64 having one or more (e.g., 1, 2, 3, 4, 5, 6, 7, 8, 9, 10, or more) conservative amino acid substitutions (as defined herein).

The term "Ezrin polypeptide" is defined as a polypeptide comprising a PKA I anchoring disrupting molecule having an amino acid sequence of SEQ ID NO: 108 (KSQEQ-LAAELAEYTAKIALL), or a derivative thereof. As used herein, neither the term "Ezrin polypeptide" nor a polypeptide or protein comprising an Ezrin polypeptide, includes full length, naturally occurring human Ezrin (i.e., as set forth in GenBank accession number AAH68458.1), nor do they include a polypeptide having more than 120 consecutive amino acids with greater than 95% identity to naturally occurring human Ezrin. For example, the term "Ezrin polypeptide" is a polypeptide having at least 80% (e.g., 85%, 90%, 95%, 97%, 98%, 99%) sequence identity to SEQ ID NO: 108. Additionally, or alternatively, the term "Ezrin polypeptide" includes polypeptides having the sequence of SEQ ID NO: 108 having one or more (e.g., 1, 2, 3, 4, 5, 6, 7, 8, 9, 10, or more) conservative amino acid substitutions (as defined herein).

The term "Ezrin-derived RISR subunit" meant to include a polypeptide having an amino acid sequence of SEQ ID NO: 109 (MQMMREKEELMLRLQDYEEKTKKAERELSEQIQRALQLEEERKRAQEEAERLEA DRMAALRAKEELERQAVDQI), or a derivative thereof. For example, the term "Ezrin-derived RISR subunit" includes polypeptides having greater than 80% (e.g., 85%, 90%, 95%, 97%, 98%, 99%) sequence identity to SEQ ID NO: 109. Additionally, or alternatively, the term "Ezrin-derived RISR subunit" includes polypeptides having the sequence of SEQ ID NO: 109 having one or more (e.g., 1, 2, 3, 4, 5, 6, 7, 8, 9, 10, or more) conservative amino acid substitutions (as defined herein).

The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from the costimulatory molecules described herein, e.g., 4-1BB (i.e., CD137), CD27 and/or CD28. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

A CAR that comprises an antigen binding domain (e.g., a scFv, or TCR) that targets a specific tumor maker X, such as those described herein, is also referred to as XCAR. For example, a CAR that comprises an antigen binding domain that targets CD19 is referred to as CD19CAR.

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')$_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), or a combination thereof.

As used herein, the term "binding domain" or "antibody molecule" refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition.

An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically The term "xenogeneic" refers to a graft derived from an animal of a different species.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The phrase "disease associated with expression of a tumor antigen as described herein" includes, but is not limited to, a disease associated with expression of a tumor antigen as described herein or condition associated with cells which express a tumor antigen as described herein including, e.g., proliferative diseases such as a cancer or malignancy or a precancerous condition such as a myelodysplasia, a myelodysplastic syndrome or a preleukemia; or a noncancer related indication associated with cells which express a tumor antigen as described herein. In one aspect, a cancer associated with expression of a tumor antigen as described herein is a hematological cancer. In one aspect, a cancer associated with expression of a tumor antigen as described herein is a solid cancer. Further diseases associated with expression of a tumor antigen described herein include, but not limited to, e.g., atypical and/or non-classical cancers, malignancies, precancerous conditions or proliferative diseases associated with expression of a tumor antigen as described herein. Non-cancer related indications associated with expression of a tumor antigen as described herein include, but are not limited to, e.g., autoimmune disease, (e.g., lupus), inflammatory disorders (allergy and asthma) and transplantation. In some embodiments, the tumor antigen-expressing cells express, or at any time expressed, mRNA encoding the tumor antigen. In an embodiment, the tumor antigen-expressing cells produce the tumor antigen protein (e.g., wild-type or mutant), and the tumor antigen protein may be present at normal levels or reduced levels. In an embodiment, the tumor antigen-expressing cells produced detectable levels of a tumor antigen protein at one point, and subsequently produced substantially no detectable tumor antigen protein.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO:18, or the equivalent residues from a non-human species, e.g., mouse, rodent, monkey, ape and the like. In a specific CAR of the invention, the primary signaling sequence of CD3-zeta is the sequence as provided in SEQ ID NO:20, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12.

The term "zeta" or alternatively "zeta chain", "CD3-zeta" or "TCR-zeta" is defined as the protein provided as GenBank Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:18. In one aspect, the "zeta stimulatory domain" or a "CD3-zeta stimulatory domain" is the sequence provided as SEQ ID NO:20.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MHC class I molecule, BTLA and a Toll ligand receptor, as well as OX40, CD27, CD28, CD5, ICAM-1, LFA-1 (CD11a/CD18), ICOS (CD278), and 4-1BB (CD137). Further examples of such costimulatory molecules include CD5, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CD5, CD7, CD287, LIGHT, NKG2C, NKG2D, SLAMF7, NKp80, NKp30, NKp44, NKp46, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment or derivative thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as SEQ ID NO:14 or the equivalent residues from a non-human species, e.g., mouse, rodent, monkey, ape and the like.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "tumor-supporting antigen" or "cancer-supporting antigen" interchangeably refer to a molecule (typically a protein, carbohydrate or lipid) that is expressed on the surface of a cell that is, itself, not cancerous, but supports the cancer cells, e.g., by promoting their growth or survival e.g., resistance to immune cells. Exemplary cells of this type include stromal cells and myeloid-derived suppressor cells (MDSCs). The tumor-supporting antigen itself need not play a role in supporting the tumor cells so long as the antigen is present on a cell that supports cancer cells.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence $(Gly-Gly-Gly-Ser)_n$, where n is a positive integer equal to or greater than 1. For example, n=1, n=2, n=3. n=4, n=5 and n=6, n=7, n=8, n=9 and n=10 (SEQ ID NO:28). In one embodiment, the flexible polypeptide linkers include, but are not limited to, $(Gly_4\ Ser)_4$ (SEQ ID NO:29) or $(Gly_4\ Ser)_3$ (SEQ ID NO:30). In another embodiment, the linkers include multiple repeats of $(Gly_2Ser)$, (GlySer) or $(Gly_3Ser)$ (SEQ ID NO:31). Also included within the scope of the invention are linkers described in WO2012/138475, incorporated herein by reference).

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 34), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term “specifically binds,” refers to an antibody, or a ligand, which recognizes and binds with a binding partner (e.g., a tumor antigen) protein present in a sample, but which antibody or ligand does not substantially recognize or bind other molecules in the sample.

“Regulatable chimeric antigen receptor (RCAR),” as that term is used herein, refers to a set of polypeptides, typically two in the simplest embodiments, which when in a RCARX cell, provides the RCARX cell with specificity for a target cell, typically a cancer cell, and with regulatable intracellular signal generation or proliferation, which can optimize an immune effector property of the RCARX cell. An RCARX cell relies at least in part, on an antigen binding domain to provide specificity to a target cell that comprises the antigen bound by the antigen binding domain. In an embodiment, an RCAR includes a dimerization switch that, upon the presence of a dimerization molecule, can couple an intracellular signaling domain to the antigen binding domain.

“Membrane anchor” or “membrane tethering domain”, as that term is used herein, refers to a polypeptide or moiety, e.g., a myristoyl group, sufficient to anchor an extracellular or intracellular domain to the plasma membrane.

“Switch domain,” as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

“Dimerization molecule,” as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g., RAD001.

The term “bioequivalent” refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term “low, immune enhancing, dose” when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

- an increase in the expression of one or more of the following markers: $CD62L^{high}$, $CD127^{high}$, $CD27^{+}$, and BCL2, e.g., on memory T cells, e.g., memory T cell precursors; a decrease in the expression of KLRG1, e.g., on memory T cells, e.g., memory T cell precursors; and
- an increase in the number of memory T cell precursors, e.g., cells with any one or combination of the following characteristics: increased $CD62L^{high}$ increased $CD127^{high}$, increased $CD27^{+}$, decreased KLRG1, and increased BCL2;
- wherein any of the changes described above occurs, e.g., at least transiently, e.g., as compared to a non-treated subject.

“Refractory” as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

“Relapsed” as used herein refers to the return of a disease (e.g., cancer) or the signs and symptoms of a disease such as cancer after a period of improvement, e.g., after prior treatment of a therapy, e.g., cancer therapy Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

DESCRIPTION

Provided herein are compositions of matter and methods of use for the treatment of a disease such as cancer using immune effector cells (e.g., T cells, NK cells) engineered with CARs of the invention.

In one aspect, the invention provides a number of chimeric antigen receptors (CAR) comprising an antigen binding domain (e.g., antibody or antibody fragment, TCR or TCR fragment) engineered for specific binding to a tumor antigen, e.g., a tumor antigen described herein. In one aspect, the invention provides an immune effector cell (e.g., T cell, NK cell) engineered to express a CAR, wherein the engineered immune effector cell exhibits an anticancer property. In one aspect, a cell is transformed with the CAR and the CAR is expressed on the cell surface. In some embodiments, the cell (e.g., T cell, NK cell) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., T cell, NK cell) is transfected with a nucleic acid, e.g., mRNA, cDNA, DNA, encoding a CAR. In some such embodiments, the cell may transiently express the CAR.

In one aspect, the antigen binding domain of a CAR described herein is a scFv antibody fragment. In one aspect, such antibody fragments are functional in that they retain the equivalent binding affinity, e.g., they bind the same antigen with comparable affinity, as the IgG antibody from which it is derived. In other embodiments, the antibody fragment has a lower binding affinity, e.g., it binds the same antigen with a lower binding affinity than the antibody from which it is derived, but is functional in that it provides a biological response described herein. In one embodiment, the CAR molecule comprises an antibody fragment that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In one embodiment, the antibody fragment has a binding affinity that is at least five-fold, 10-fold, 20-fold, 30-fold, 50-fold, 100-fold or 1,000-fold less than a reference antibody, e.g., an antibody described herein.

In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan.

In one aspect, the antigen binding domain of the CAR is a scFv antibody fragment that is humanized compared to the murine sequence of the scFv from which it is derived.

In one aspect, the antigen binding domain of a CAR of the invention (e.g., a scFv) is encoded by a nucleic acid molecule whose sequence has been codon optimized for expression in a mammalian cell. In one aspect, entire CAR construct of the invention is encoded by a nucleic acid molecule whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

In one aspect, the CARs of the invention combine an antigen binding domain of a specific antibody with an intracellular signaling molecule. For example, in some aspects, the intracellular signaling molecule includes, but is not limited to, CD3-zeta chain, 4-1BB and CD28 signaling modules and combinations thereof. In one aspect, the antigen binding domain binds to a tumor antigen as described herein.

Furthermore, the present invention provides CARs and CAR-expressing cells and their use in medicaments or methods for treating, among other diseases, cancer or any malignancy or autoimmune diseases involving cells or tissues which express a tumor antigen as described herein.

In one aspect, the CAR of the invention can be used to eradicate a normal cell that express a tumor antigen as described herein, thereby applicable for use as a cellular conditioning therapy prior to cell transplantation. In one aspect, the normal cell that expresses a tumor antigen as described herein is a normal stem cell and the cell transplantation is a stem cell transplantation.

In one aspect, the invention provides an immune effector cell (e.g., T cell, NK cell) engineered to express a chimeric antigen receptor (CAR), wherein the engineered immune effector cell exhibits an antitumor property. A preferred antigen is a cancer associated antigen (i.e., tumor antigen) described herein. In one aspect, the antigen binding domain of the CAR comprises a partially humanized antibody fragment. In one aspect, the antigen binding domain of the CAR comprises a partially humanized scFv. Accordingly, the invention provides CARs that comprises a humanized antigen binding domain and is engineered into a cell, e.g., a T cell or a NK cell, and methods of their use for adoptive therapy.

In one aspect, the CARs of the invention comprise at least one intracellular domain selected from the group of a CD137 (4-1BB) signaling domain, a CD28 signaling domain, a CD27 signal domain, a CD3zeta signal domain, and any combination thereof. In one aspect, the CARs of the invention comprise at least one intracellular signaling domain is from one or more costimulatory molecule(s) other than a CD137 (4-1BB) or CD28.

Sequences of some examples of various components of CARs of the instant invention is listed in Table 1A, where aa stands for amino acids, and na stands for nucleic acids that encode the corresponding peptide.

TABLE 1A

Sequences of various components of CAR (aa—amino acids, na—nucleic acids that encodes the corresponding protein)

| SEQ ID NO | description | Sequence | Corresp. To huCD19 |
|---|---|---|---|
| 1 | EF-1 promoter | CGTGAGGCTCCGGTGCCCGTCAGTGGGCAGAGCGCACA<br>TCGCCCACAGTCCCCGAGAAGTTGGGGGGAGGGGTCGG<br>CAATTGAACCGGTGCCTAGAGAAGGTGGCGCGGGGTAA<br>ACTGGGAAAGTGATGTCGTGTACTGGCTCCGCCTTTTTC<br>CCGAGGGTGGGGGAGAACCGTATATAAGTGCAGTAGTC<br>GCCGTGAACGTTCTTTTTCGCAACGGGTTTGCCGCCAGA<br>ACACAGGTAAGTGCCGTGTGTGGTTCCCGCGGGCCTGG<br>CCTCTTTACGGGTTATGGCCCTTGCGTGCCTTGAATTAC<br>TTCCACCTGGCTGCAGTACGTGATTCTTGATCCCGAGCT<br>TCGGGTTGGAAGTGGGTGGGAGAGTTCGAGGCCTTGCG<br>CTTAAGGAGCCCCTTCGCCTCGTGCTTGAGTTGAGGCCT<br>GGCCTGGGCGCTGGGGCCGCCGCGTGCGAATCTGGTGG<br>CACCTTCGCGCCTGTCTCGCTGCTTTCGATAAGTCTCTA<br>GCCATTTAAAATTTTTGATGACCTGCTGCGACGCTTTTT<br>TTCTGGCAAGATAGTCTTGTAAATGCGGGCCAAGATCT<br>GCACACTGGTATTTCGGTTTTTGGGGCCGCGGGCGGCG<br>ACGGGGCCCGTGCGTCCCAGCGCACATGTTCGGCGAGG<br>CGGGGCCTGCGAGCGCGGCCACCGAGAATCGGACGGG<br>GGTAGTCTCAAGCTGGCCGGCCTGCTCTGGTGCCTGGC<br>CTCGCGCCGCCGTGTATCGCCCCGCCCTGGGCGGCAAG<br>GCTGGCCCGGTCGGCACCAGTTGCGTGAGCGGAAAGAT<br>GGCCGCTTCCCGGCCCTGCTGCAGGGAGCTCAAAATGG<br>AGGACGCGGCGCTCGGGAGAGCGGGCGGGTGAGTCAC<br>CCACACAAAGGAAAAGGGCCTTTCCGTCCTCAGCCGTC<br>GCTTCATGTGACTCCACGGAGTACCGGGCGCCGTCCAG<br>GCACCTCGATTAGTTCTCGAGCTTTTGGAGTACGTCGTC<br>TTTAGGTTGGGGGGAGGGGTTTTATGCGATGGAGTTTC<br>CCCACACTGAGTGGGTGGAGACTGAAGTTAGGCCAGCT<br>TGGCACTTGATGTAATTCTCCTTGGAATTTGCCCTTTTT<br>GAGTTTGGATCTTGGTTCATTCTCAAGCCTCAGACAGTG<br>GTTCAAAGTTTTTTTCTTCCATTTCAGGTGTCGTGA | 100 |
| 2 | Leader (aa) | MALPVTALLLPLALLLHAARP | 13 |
| 3 | Leader (na) | ATGGCCCTGCCTGTGACAGCCCTGCTGCTGCCTCTGGCT<br>CTGCTGCTGCATGCCGCTAGACCC | 54 |
| 4 | CD 8 hinge (aa) | TTTPAPRPPTPAPTIASQPLSLRPEACRPAAGGAVHTRGLD<br>FACD | 14 |
| 5 | CD8 hinge (na) | ACCACGACGCCAGCGCCGCGACCACCAACACCGGCGCC<br>CACCATCGCGTCGCAGCCCCTGTCCCTGCGCCCAGAGG<br>CGTGCCGGCCAGCGGCGGGGGGCGCAGTGCACACGAG<br>GGGGCTGGACTTCGCCTGTGAT | 55 |
| 6 | Ig4 hinge (aa) | ESKYGPPCPPCPAPEFLGGPSVFLFPPKPKDTLMISRTPEVT<br>CVVVDVSQEDPEVQFNWYVDGVEVHNAKTKPREEQFNS<br>TYRVVSVLTVLHQDWLNGKEYKCKVSNKGLPSSIEKTISK<br>AKGQPREPQVYTLPPSQEEMTKNQVSLTCLVKGFYPSDIA<br>VEWESNGQPENNYKTTPPVLDSDGSFFLYSRLTVDKSRW<br>QEGNVFSCSVMHEALHNHYTQKSLSLSLGKM | 102 |
| 7 | Ig4 hinge (na) | GAGAGCAAGTACGGCCCTCCCTGCCCCCCTTGCCCTGC<br>CCCCGAGTTCCTGGGCGGACCCAGCGTGTTCCTGTTCCC<br>CCCCAAGCCCAAGGACACCCTGATGATCAGCCGGACCC<br>CCGAGGTGACCTGTGTGGTGGTGGACGTGTCCCAGGAG<br>GACCCCGAGGTCCAGTTCAACTGGTACGTGGACGGCGT<br>GGAGGTGCACAACGCCAAGACCAAGCCCCGGGAGGAG<br>CAGTTCAATAGCACCTACCGGGTGGTGTCCGTGCTGAC<br>CGTGCTGCACCAGGACTGGCTGAACGGCAAGGAATACA<br>AGTGTAAGGTGTCCAACAAGGGCCTGCCCAGCAGCATC<br>GAGAAAACCATCAGCAAGGCCAAGGGCCAGCCTCGGG<br>AGCCCCAGGTGTACACCCTGCCCCCTAGCCAAGAGGAG<br>ATGACCAAGAACCAGGTGTCCCTGACCTGCCTGGTGAA<br>GGGCTTCTACCCCAGCGACATCGCCGTGGAGTGGGAGA<br>GCAACGGCCAGCCCGAGAACAACTACAAGACCACCCCC<br>CCTGTGCTGGACAGCGACGGCAGCTTCTTCCTGTACAG<br>CCGGCTGACCGTGGACAAGAGCCGGTGGCAGGAGGGC<br>AACGTCTTTAGCTGCTCCGTGATGCACGAGGCCCTGCA<br>CAACCACTACACCCAGAAGAGCCTGAGCCTGTCCCTGG<br>GCAAGATG | 103 |

TABLE 1A-continued

Sequences of various components of CAR (aa—amino acids, na—nucleic acids that encodes the corresponding protein)

| SEQ ID NO | description | Sequence | Corresp. To huCD19 |
|---|---|---|---|
| 8 | IgD hinge (aa) | RWPESPKAQASSVPTAQPQAEGSLAKATTAPATTRNTGR GGEEKKKEKEKEEQEERETKTPECPSHTQPLGVYLLTPAV QDLWLRDKATFTCFVVGSDLKDAHLTWEVAGKVPTGGV EEGLLERHSNGSQSQHSRLTLPRSLWNAGTSVTCTLNHPS LPPQRLMALREPAAQAPVKLSLNLLASSDPPEAASWLLCE VSGFSPPNILLMWLEDQREVNTSGFAPARPPPQPGSTTFW AWSVLRVPAPPSPQPATYTCVVSHEDSRTLLNASRSLEVS YVTDH | 47 |
| 9 | IgD hinge (na) | AGGTGGCCCGAAAGTCCCAAGGCCCAGGCATCTAGTGT TCCTACTGCACAGCCCCAGGCAGAAGGCAGCCTAGCCA AAGCTACTACTGCACCTGCCACTACGCGCAATACTGGC CGTGGCGGGGAGGAGAAGAAAAAGGAGAAAGAGAAA GAAGAACAGGAAGAGAGGGAGACCAAGACCCCTGAAT GTCCATCCCATACCCAGCCGCTGGGCGTCTATCTCTTGA CTCCCGCAGTACAGGACTTGTGGCTTAGAGATAAGGCC ACCTTTACATGTTTCGTCGTGGGCTCTGACCTGAAGGAT GCCCATTTGACTTGGGAGGTTGCCGGAAAGGTACCCAC AGGGGGGGTTGAGGAAGGGTTGCTGGAGCGCCATTCCA ATGGCTCTCAGAGCCAGCACTCAAGACTCACCCTTCCG AGATCCCTGTGGAACGCCGGGACCTCTGTCACATGTAC TCTAAATCATCCTAGCCTGCCCCCACAGCGTCTGATGGC CCTTAGAGAGCCAGCCGCCCAGGCACCAGTTAAGCTTA GCCTGAATCTGCTCGCCAGTAGTGATCCCCCAGAGGCC GCCAGCTGGCTCTTATGCGAAGTGTCCGGCTTTAGCCCG CCCAACATCTTGCTCATGTGGCTGGAGGACCAGCGAGA AGTGAACACCAGCGGCTTCGCTCCAGCCCGGCCCCCAC CCCAGCCGGGTTCTACCACATTCTGGGCCTGGAGTGTCT TAAGGGTCCCAGCACCACCTAGCCCCCAGCCAGCCACA TACACCTGTGTTGTGTCCCATGAAGATAGCAGGACCCT GCTAAATGCTTCTAGGAGTCTGGAGGTTTCCTACGTGAC TGACCATT | 48 |
| 10 | GS hinge/linker (aa) | GGGGSGGGGS | 49 |
| 11 | GS hinge/linker (na) | GGTGGCGGAGGTTCTGGAGGTGGAGGTTCC | 50 |
| 12 | CD8TM (aa) | IYIWAPLAGTCGVLLLSLVITLYC | 15 |
| 13 | CD8 TM (na) | ATCTACATCTGGGCGCCCTTGGCCGGGACTTGTGGGGT CCTTCTCCTGTCACTGGTTATCACCCTTTACTGC | 56 |
| 14 | 4-1BB intracellular domain (aa) | KRGRKKLLYIFKQPFMRPVQTTQEEDGCSCRFPEEEEGGC EL | 16 |
| 15 | 4-1BB intracellular domain (na) | AAACGGGGCAGAAAGAAACTCCTGTATATATTCAAACA ACCATTTATGAGACCAGTACAAACTACTCAAGAGGAAG ATGGCTGTAGCTGCCGATTTCCAGAAGAAGAAGAAGGA GGATGTGAACTG | 60 |
| 16 | CD27 (aa) | QRRKYRSNKGESPVEPAEPCRYSCPREEEGSTIPIQEDYRK PEPACSP | 51 |
| 17 | CD27 (na) | AGGAGTAAGAGGAGCAGGCTCCTGCACAGTGACTACAT GAACATGACTCCCCGCCGCCCCGGGCCCACCCGCAAGC ATTACCAGCCCTATGCCCCACCACGCGACTTCGCAGCCT ATCGCTCC | 52 |
| 18 | CD3-zeta (aa) | RVKFSRSADAPAYKQGQNQLYNELNLGRREEYDVLDKRR GRDPEMGGKPRRKNPQEGLYNELQKDKMAEAYSEIGMK GERRRGKGHDGLYQGLSTATKDTYDALHMQALPPR | 17 |
| 19 | CD3-zeta (na) | AGAGTGAAGTTCAGCAGGAGCGCAGACGCCCCCGCGTA CAAGCAGGGCCAGAACCAGCTCTATAACGAGCTCAATC TAGGACGAAGAGAGGAGTACGATGTTTTGGACAAGAG ACGTGGCCGGGACCCTGAGATGGGGGGAAAGCCGAGA AGGAAGAACCCTCAGGAAGGCCTGTACAATGAACTGCA | 101 |

TABLE 1A-continued

Sequences of various components of CAR (aa—amino acids, na—nucleic acids that encodes the corresponding protein)

| SEQ ID NO | description | Sequence | Corresp. To huCD19 |
|---|---|---|---|
| | | GAAAGATAAGATGGCGGAGGCCTACAGTGAGATTGGG<br>ATGAAAGGCGAGCGCCGGAGGGGCAAGGGGCACGATG<br>GCCTTTACCAGGGTCTCAGTACAGCCACCAAGGACACC<br>TACGACGCCCTTCACATGCAGGCCCTGCCCCCTCGC | |
| 20 | CD3-zeta (aa) | RVKFSRSADAPAYQQGQNQLYNELNLGRREEYDVLDKRR<br>GRDPEMGGKPRRKNPQEGLYNELQKDKMAEAYSEIGMK<br>GERRRGKGHDGLYQGLSTATKDTYDALHMQALPPR | 43 |
| 21 | CD3-zeta (na) | AGAGTGAAGTTCAGCAGGAGCGCAGACGCCCCCGCGTA<br>CCAGCAGGGCCAG<br>AACCAGCTCTATAACGAGCTCAATCTAGGACGAAGAGA<br>GGAGTACGATGTTT<br>TGGACAAGAGACGTGGCCGGGACCCTGAGATGGGGGG<br>AAAGCCGAGAAGGA<br>AGAACCCTCAGGAAGGCCTGTACAATGAACTGCAGAAA<br>GATAAGATGGCGG<br>AGGCCTACAGTGAGATTGGGATGAAAGGCGAGCGCCG<br>GAGGGGCAAGGGGC<br>ACGATGGCCTTTACCAGGGTCTCAGTACAGCCACCAAG<br>GACACCTACGACGC<br>CCTTCACATGCAGGCCCTGCCCCCTCGC | 44 |
| 22 | linker | GGGGS | 18 |
| 23 | linker | GGTGGCGGAGGTTCTGGAGGTGGAGGTTCC | 50 |
| 24 | PD-1 extracellular domain (aa) | Pgwfldspdrpwnpptfspallvvtegdnatftcsfsntsesfvlnwyrmspsnqtdkla<br>afpedrsqpgqdcrfrvtqlpngrdfhmsvvrarrndsgtylcgaislapkaqikeslrael<br>rvterraeyptahpspsprpagqfqtlv | |
| 25 | PD-1 extracellular domain (na) | Cccggatggtttctggactctccggatcgcccgtggaatcccccaaccttctcaccggcact<br>cttggttgtgactgagggcgataatgcgaccttcacgtgctcgttctccaacacctccgaatca<br>ttcgtgctgaactggtaccgcatgagcccgtcaaaccagaccgacaagctcgccgcgtttcc<br>ggaagatcggtcgcaaccgggacaggattgtcggttccgcgtgactcaactgccgaatgg<br>cagagacttccacatgagcgtggtccgcgctaggcgaaacgactccgggacctacctgtgc<br>ggagccatctcgctggcgcctaaggcccaaatcaaagagagcttgagggccgaactgaga<br>gtgaccgagcgcagagctgaggtgccaactgcacatccatccccatcgcctcggcctgcg<br>gggcagtttcagaccctggtc | |
| 26 | PD-1 CAR (aa) with signal | Malpvtalllplalllhaarppgwfldspdrpwnpptfspallvvtegdnatftcsfsntses<br>fvlnwyrmspsnqtdklaafpedrsqpgqdcrfrvtqlpngrdfhmsvvrarrndsgtyl<br>cgaislapkaqikeslraelrvterraevptahpspsprpagqfqtlvtttpaprpptpaptia<br>sqplslrpeacrpaaggavhtrgldfacdiyiwaplagtcgvlllslvitlyckrgrkkllyif<br>kqpfmrpvqttqeedgcscrfpeeeeggcelrvkfsrsadapaykqgqnqlynelnlgrr<br>eeydvldkrrgrdpemggkprrknpqeglynelqkdkmaeayseigmkgerrrgkg<br>hdglyqglstatkdtydalhmqalppr | |
| 27 | PD-1 CAR (na) | Atggccctccctgtcactgccctgcttctccccctcgcactcctgctccacgccgctagacc<br>acccggatggtttctggactctccggatcgcccgtggaatcccccaaccttctcaccggcact<br>cttggttgtgactgagggcgataatgcgaccttcacgtgctcgttctccaacacctccgaatca<br>ttcgtgctgaactggtaccgcatgagcccgtcaaaccagaccgacaagctcgccgcgtttcc<br>ggaagatcggtcgcaaccgggacaggattgtcggttccgcgtgactcaactgccgaatgg<br>cagagacttccacatgagcgtggtccgcgctaggcgaaacgactccgggacctacctgtgc<br>ggagccatctcgctggcgcctaaggcccaaatcaaagagagcttgagggccgaactgaga<br>gtgaccgagcgcagagctgaggtgccaactgcacatccatccccatcgcctcggcctgcg<br>gggcagtttcagaccctggtcacgaccactccggcgccgcgcccaccgactccggcccca<br>actatcgcgagccagcccctgtcgctgaggccggaagcatgccgccctgccgccggaggt<br>gctgtgcatacccggggattggacttcgcatgcgacatctacatttgggctcctctcgccgga<br>acttgtggcgtgctccttctgtccctggtcatcaccctgtactgcaagcggggtcggaaaaag<br>cttctgtacattttcaagcagcccttcatgaggcccgtgcaaaccacccaggaggaggacgg<br>ttgctcctgccggttccccgaagaggaagaaggaggttgcgagctgcgcgtgaagttctcc<br>cggagcgccgacgcccccgcctataagcagggccagaaccagctgtacaacgaactgaa<br>cctgggacggcgggaagagtacgatgtgctggacaagcggcgcggccgggaccccgaa<br>atgggcgggaagcctagaagaaagaaccctcaggaaggcctgtataacgagctgcagaa<br>ggacaagatggccgaggcctactccgaaattgggatgaagggagagcggcggaggggga<br>aaggggcacgacggcctgtaccaaggactgtccaccgccaccaaggacacatacgatgc<br>cctgcacatgcaggcccttccccctcgc | |
| 28 | linker | (Gly-Gly-Gly-Ser)$_n$, where n = 1-10 | 105 |
| 29 | linker | (Gly4 Ser)4 | 106 |

TABLE 1A-continued

Sequences of various components of CAR (aa—amino acids, na—nucleic acids that encodes the corresponding protein)

| SEQ ID NO | description | Sequence | Corresp. To huCD19 |
|---|---|---|---|
| 30 | linker | (Gly4 Ser)3 | 107 |
| 31 | linker | (Gly3Ser) | 108 |
| 32 | polyA | aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa | 118 |
| 33 | polyA | aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa | 104 |
| 34 | polyA | aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa | 109 |

TABLE 1A-continued

Sequences of various components of CAR (aa—amino acids, na—nucleic acids that encodes the corresponding protein)

| SEQ ID NO | description | Sequence | Corresp. To huCD19 |
|---|---|---|---|
| | | aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa | |

TABLE 1A-continued

Sequences of various components of CAR (aa—amino acids, na—nucleic acids that encodes the corresponding protein)

| SEQ ID NO | description | Sequence | Corresp. To huCD19 |
|---|---|---|---|
| | | aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa | |
| 35 | polyA | tttttttttt tttttttttt tttttttttt tttttttttt tttttttttt tttttttttt<br>tttttttttt tttttttttt tttttttttt tttttttttt | 110 |
| 36 | polyA | tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt | 111 |

TABLE 1A-continued

| Sequences of various components of CAR (aa—amino acids, na—nucleic acids that encodes the corresponding protein) | | | |
|---|---|---|---|
| SEQ ID NO | description | Sequence | Corresp. To huCD19 |
| | | tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt | |
| 37 | polyA | aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa | 112 |

TABLE 1A-continued

Sequences of various components of CAR (aa—amino acids, na—nucleic acids that encodes the corresponding protein)

| SEQ ID NO | description | Sequence | Corresp. To huCD19 |
|---|---|---|---|
| | | aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa | |
| 38 | polyA | aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa | 113 |
| 39 | PD1 CAR (aa) | Pgwfldspdrpwnpptfspallvvtegdnatftcsfsntsesfvlnwyrmspsnqtdkla<br>afpedrsqpgqdcrfrvtqlpngrdfhmsvvrarrndsgtylcgaislapkaqikeslrael<br>rvterraevptahpspsprpagqfqtlvtttpaprpptpaptiasqplslrpeacrpaaggav<br>htrgldfacdiyiwaplagtcgvlllslvitlyckrgrkkllyifkqpfmrpvqttqeedgcs<br>crfpeeeeggcelrvkfsrsadapaykqgqnqlynelnlgrreeydvldkrrgrdpemg<br>gkprrknpqeglynelqkdkmaeayseigmkgerrrgkghdglyqglstatkdtydal<br>hmqalppr | |

RIAD Peptides

Adenosine and prostaglandin E2 are among the most important of immunosuppressive factors that may interfere with CAR mediated killing of tumors (e.g., solid tumors). Both these ligands, through their own G-coupled receptors, trigger the production of cyclic AMP (cAMP) which in turn can activate the enzyme protein kinase A, or PKA. It is well established that prolonged cAMP signaling induces PKA activity, which then affects multiple proteins in the T cell signaling cascade. One of the most important and proximal effects is activation of the kinase Csk which then inhibits Lck. This results in inhibition of T cell signaling which blocks T cell receptor (TCR)-induced T cell proliferation and cytotoxic activity.

In order for PKA to elicit its functions, it must be tethered to lipid rafts in close proximity to adenylyl cyclase, the enzyme that metabolizes ATP to generate cAMP. The tethering and subsequent compartmentalization of PKA and its effects are mediated by A-kinase anchoring proteins (AKAP). AKAP therefore serve as a platform on which cAMP and PKA signaling converge, and provide temporal and spatial regulation of these entities. With regard to T cell signaling PKA must be directed to the TCR by binding to a protein called ezrin which inserts into the membrane and serves as the AKAP.

The PKA holoenzyme is a heterotetramer consisting of 2 regulatory subunits (RI and RII) and 2 catalytic subunits (CI and CII). Upon activation by cAMP, the R subunits dissociate, and the C subunits proceed to phosphorylate a large myriad of target substrates; the cAMP-PKA signaling cascade is one of the most ubiquitous and well-established second messenger systems to date. Within the tumor microenvironment, suppressive factors such as prostaglandin E2 (PGE2), adenosine, and other cAMP-activating ligands may neutralize T cell ability to kill tumors. The invention features the attenuation of cAMP signaling in T cells, and more specifically CAR T cells, to prolong TCR-mediated signaling and better killing capacity.

Figure 22:
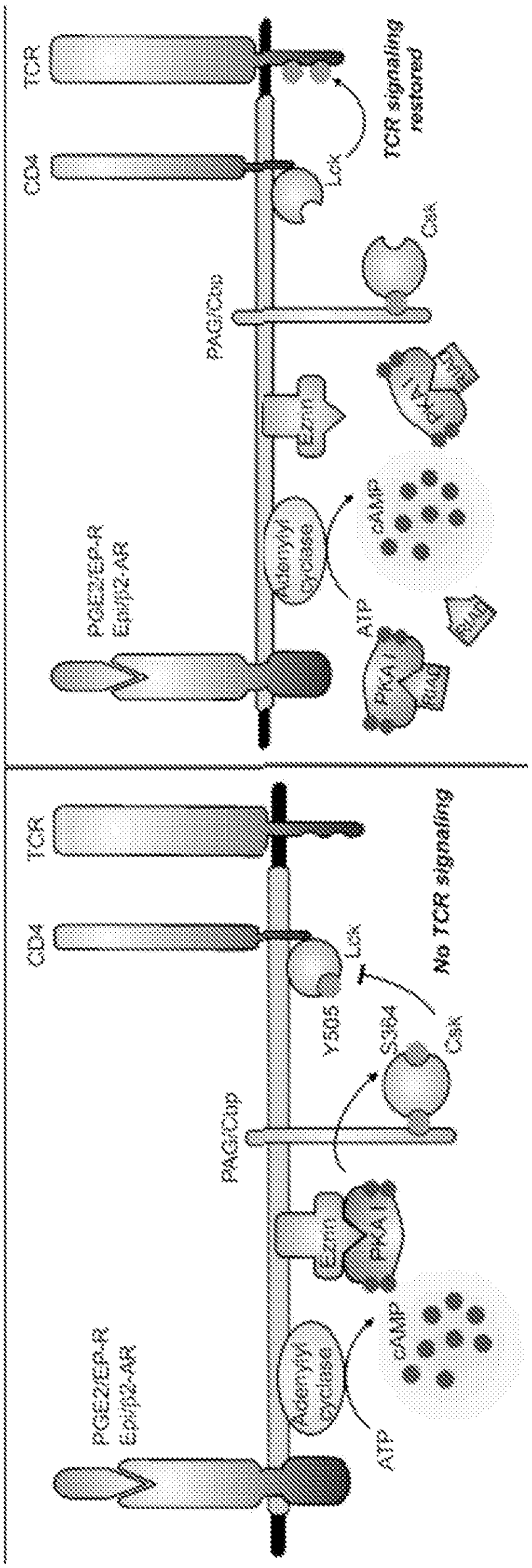
FIG. 22 is a schematic showing that the RIAD peptide specifically binds to PKA and displaces them from the lipid membrane, therefore abrogating PKA-mediated signaling.

RIAD binds to the RI subunit of PKA with high affinity and disrupts PKA anchoring to ezrin, thereby neutralizing PKA signaling (Carlson C, et al. J Biol Chem 281: 30, 2006). FIG. 22 shows how this works. Normally (left panel of FIG. 22), cAMP binds to PKA which activates it. The PKA binds to ezrin and is brought in contact with Csk. Csk is activated which then phosphorylates and inactivates Lck which stops TCR signaling. With RIAD present (right panel of FIG. 22), the PKA-cAMP complex cannot localize to ezrin and, thus, does not have access to Csk. Carlson et al. reported that the RIAD-mediated displacement of PKA ultimately diminished phosphorylation of Tyr-505 on Lck, and hence upregulated TCR signaling.

RISR (RI specifier region) is a polypeptide that enhances RIAD binding to PKA, thereby augmenting the release of T cell inhibition by cAMP.

The sequences of RIAD, RISR, RISR-RIAD, RIAD-T2A, and RISR-RIAD-T2A are set forth below.

In some embodiments, the RIAD sequence comprises LEQYANQLADQIIKEATE (SEQ ID NO: 63), conservative changes to the sequence, homologous sequences from related proteins, and fragments thereof. In another embodiment, a nucleic acid sequence encoding the RIAD sequence comprises 5'-GTCGACCTGGAGCAGTACGC-CAACCAGCTGGCCGACCAGATCATCAAGGAGGC CACCGAGGGATCC-3' (SEQ ID NO: 113), conservative changes to the sequence, homologous sequences from related genes, and fragments thereof.

Ezrin polypeptides include, e.g., SEQ ID NO: 108 and, optionally, SEQ ID NO: 109. In one embodiment, the Ezrin polypeptide comprises the amino acid sequence of MQMM-REKEELMLRLQDYEEKTKKAERELSE-QIQRALQLEEERKRAQEEAERLEAD RMAALRA-KEELERQAVDQIKSQEQLAAELAEYTAKIALL (SEQ ID NO: 110). The Ezrin polypeptide can be encoded by, e.g., a nucleic acid having the sequence set forth in SEQ ID NO: 111 (ATGCAGATGATGCGCGAAAAAGAAGAACT-GATGCTGCGCCTGCAGGATTATGA AGAAAAAAC-CAAAAAAGCGGAACGCGAACTGAGCGAACAGAT-TCAGCGCGCG CTGCAGCTGGAAGAAGAACGC AAACGCGCGCAGGAAGAAGCGGAACGCCTGG AAGCGGATCGCATGGCGGCGCTGCGCGCGAA AGAAGAACTGGAACGCCAGGC GGTGGATCAGAT-TAAAAGCCAGGAACAGCTGGCGGCGGAACTGGC GGAATATA CCGCGAAAATTGCGCTGCTG).

In some embodiments, a peptide (RIAD) further comprises a region to enhance specificity to PKA; e.g., the regulatory subunit I (RI) specifier region, or RISR. In one embodiment, the peptide comprises at least one domain selected from the group consisting of a regulatory subunit I anchoring disruptor (RIAD), a regulatory subunit I specifier region (RISR), and a combination thereof.

In some embodiments, the peptide binds a PKA, an A-kinase anchoring protein (AKAP) (such as Ezrin), or another molecule that disrupts PKA and AKAP binding. In one embodiment, the peptide binds a regulatory subunit of PKA. In an embodiment, the peptide comprises an amphipathic helix domain. In another embodiment, the peptide

TABLE 1B

| RIAD and RISR sequences | | |
|---|---|---|
| Gene | Nucleic acid sequence | Amino acid sequence |
| RIAD | ctggaacagtatgcgaaccagctggcggatcagattatta aagaagcgaccgaa (SEQ ID NO: 68) | LEQYANQLADQIIKEATE (SEQ ID NO: 63) |
| RISR | gaaagcaaacgccaggaagaagcggaacagcgcaaa (SEQ ID NO: 69) | ESKRRQEEAEQRK (SEQ ID NO: 64) |
| RISR-RIAD | gaaagcaaacgccaggaagaagcggaacagcgcaaa ctggaacagtatgcgaaccagctggcggatcagattatta aagaagcgaccgaa (SEQ ID NO: 70) | ESKRRQEEAEQRK-LEQYANQLADQIIKEATE (SEQ ID NO: 65) |
| RIAD-T2A | ctggaacagtatgcgaaccagctggcggatcagattatta aagaagcgaccgaaacgcgtacgcggccgctcgagca gaaactcatctcagaagaggatctggcagcaaatgatatc ctggattacaaggatgacgacgataagggcagcggaga gggcagaggaagtcttctaacatgcggtgacgtggagg agaatcccggc (SEQ ID NO: 71) | Leqyanqladqiikeatetrtrpleqkli seedlaandildykddddkgsgegrg slltcgdveenpg (SEQ ID NO: 66) |
| RISR-RIAD-T2A | ccaccatggaaagcaaacgccgccaggaagaagcgga acagcgcaaactggaacagtatgcgaaccagctggcgg atcagattattaaagaagcgaccgaaacgcgtacgcggc cgctcgagcagaaactcatctcagaagaggatctggcag caaatgatatcctggattacaaggatgacgacgataagg gcagcggagagggcagaggaagtcttctaacatgcggt gacgtggaggagaatcccggc (SEQ ID NO: 79) | Eskrrqeeaeqrkleqyanqladqiik eatetrtrpleqkliseedlaandildyk ddddkgsgegrgslltcgdveenpg (SEQ ID NO: 67) |

comprises a fragment of an AKAP, wherein the fragment comprises an amphipathic helix domain of the AKAP.

In an embodiment, the peptide comprises a cluster of amino acids with basic side chains. The peptide including a cluster of basic amino acids is capable of binding to a regulatory subunit of PKA. In one embodiment, the cluster of basic amino acids binds PKA. In another embodiment, the peptide comprises a fragment of an AKAP, wherein the fragment comprises at least one cluster of basic amino acids of the AKAP.

In another embodiment, the peptide comprises an amphipathic helix domain and at least one cluster of basic amino acids. In one embodiment, the peptide comprises at least one fragment of an AKAP, wherein the fragment comprises an amphipathic helix domain and at least one cluster of basic amino acids from the AKAP. The peptide including the amphipathic helix domain and cluster of basic amino acids is capable of binding to a regulatory subunit of PKA. In one embodiment, the amphipathic helix domain and the cluster of basic amino acids bind PKA. In embodiments, the inclusion of both an amphipathic helix domain and at least one cluster of basic amino acids enhances binding to the regulatory subunit of PKA. The enhanced binding can include higher binding efficiency, higher affinity for PKA, greater specificity for PKA, etc.

In another embodiment, the peptide is capable of binding an amphipathic helix domain. In one embodiment, the peptide comprises a fragment of PKA, wherein the fragment comprises a PKA domain that binds to an amphipathic helix domain. In such an embodiment, the peptide is capable of binding the amphipathic helix domain of the AKAP, thereby disrupting PKA binding to the AKAP.

In still another embodiment, the peptide binds one or more other molecules to disrupt PKA and AKAP binding.

In embodiments, the peptide has a length of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 58, 59, or 60, or more amino acids. In one embodiment, the peptide has a length in the range of about 10 to about 60 amino acids. In an exemplary embodiment, the peptide comprises a RIAD. In another embodiment, the peptide comprises an amphipathic helix domain. The amphipathic helix domain has a length in the range of about 10-30 amino acids. In another embodiment, the peptide comprises a RISR. In some embodiments, the peptide comprises at least one cluster of basic amino acids. In other embodiments, the peptide comprising the cluster of basic amino acids has a length in the range of about 10 to about 40 amino acids. The molar mass of the peptide may be about 5 kD, 6 kD, 7 kD, 8 kD, 9 kD, 10 kD, 11 kD, 12 kD, 13 kD, 14 kD, 15 kD, 16 kD, 17 kD, 18 kD, 19 kD, 20 kD, 21 kD, 22 kD, 23 kD, 24 kD, 25 kD, 26 kD, 27 kD, 28 kD, 29 kD, 30 kD, or more or any molar mass therebetween or less.

In certain embodiments, the peptide includes a RIAD polypeptide or includes a polypeptide having an amino acid sequence having at least 80%, 85%, 90%, 91%, 92%, 93%, 94%, 95%, 96%, 97%, 98%, or 99% identity or homology to SEQ ID NO: 63. In certain aspects, the invention includes a nucleic acid sequence encoding the RIAD peptide or includes a nucleic acid encoding a polypeptide having a nucleic acid sequence at least 80%, 85%, 90%, 91%, 92%, 93%, 94%, 95%, 96%, 97%, 98%, or 99% identical or homologous to SEQ ID NO: 68. In certain aspects, the peptide includes a RISR polypeptide or includes a polypeptide having an amino acid sequence having at least 80%, 85%, 90%, 91%, 92%, 93%, 94%, 95%, 96%, 97%, 98%, or 99% identity or homology to SEQ ID NO: 64. In certain aspects, the invention includes a nucleic acid sequence encoding the RISR peptide or includes a nucleic acid sequence encoding a polypeptide having a nucleic acid sequence at least 80%, 85%, 90%, 91%, 92%, 93%, 94%, 95%, 96%, 97%, 98%, or 99% identical or homologous to a nucleic acid sequence encoding SEQ ID NO: 64 or homologous to SEQ ID NO: 69. In related aspects, the peptide can be any of the "anchoring disruption molecule or AKAP mimic" disclosed in U.S. Patent Application Publication No. 20080248008, each of which is hereby specifically incorporated by reference.

In certain embodiments, the present invention features the use of a RIAD polypeptide (e.g., RIAD, RISR, or RISR-RIAD) or Ezrin polypeptide in CAR and transgenic TCR-transduced T cells. In certain embodiments, the RIAD polypeptide can be expressed in frame, as a single peptide with the CAR (e.g., at the N terminus of the CAR or at the C terminus of the CAR). The RIAD polypeptide portion or Ezrin polypeptide portion of this construct can be separated from the CAR by a self cleaving sequences (e.g., T2A) or the substrate for an intracellular protease.

Self-cleaving sequences useful in certain embodiments of the invention include those set forth in the following table (in certain embodiments, the residues in parenthesis are optional) (SEQ ID NOS 73-76, respectively, in order of appearance):

TABLE 1C

| Self-cleaving sequences |
|---|
| T2A: (GSG) E G R G S L L T C G D V E E N P G P |
| P2A: (GSG) A T N F S L L K Q A G D V E E N P G P |
| E2A: (GSG) Q C T N Y A L L K L A G D V E S N P G P |
| F2A: (GSG) V K Q T L N F D L L K L A G D V E S N P G P |

In other embodiments, the RIAD polypeptide or Ezrin polypeptide can be expressed as a protein separate from the CAR. In such circumstances, the RIAD polypeptide or Ezrin polypeptide and CAR can be under the control of separate promoters or under the control of a single promoter, and separated by an internal ribosomal entry site.

Peptide and Nucleic Acid Compositions

Peptide and nucleic acid compositions are described herein that can attenuate the effect immunosuppressive factors have on T cell activation and signaling. In embodiments, the compositions disrupt PKA localization, namely preventing PKA from anchoring to the cell membrane, and enhance the effectiveness of a T cell.

In one aspect, the invention includes a composition comprising a nucleic acid sequence encoding a CAR and a nucleic acid sequence encoding a peptide comprising an amphipathic helix domain and a cluster of basic amino acids, wherein the peptide disrupts PKA and AKAP association. The nucleic acid encoding the peptide may be a separate molecule from the nucleic acid that encodes the CAR. In this embodiment, the composition comprises at least two nucleic acid sequences. The nucleic acid sequences include DNA, RNA, synthetic constructs, and any combination thereof. The nucleic acid sequences can be included as part of a vector, such as an expression vector or viral vector.

In one embodiment, a single nucleic acid molecule may encode both the peptide and the CAR, e.g. a bicistronic transcript. In an embodiment, the nucleic acids encoding the peptide are separated from the nucleic acids encoding the CAR by an internal ribosome entry site. In another embodiment, the nucleic acid molecule includes a common promoter for the peptide and the CAR, or separate promoters.

In another embodiment of a single nucleic acid molecule, the nucleic acid sequence may be cleaved, such that the nucleic acids encoding the peptide are cleaved from the nucleic acids encoding the CAR. In such an embodiment, the nucleic acid sequence further comprises a cleavage site, such as a restriction site, between the nucleic acids encoding the peptide and the nucleic acids encoding the CAR. The cleavage occurs before, during, and/or after transcription of the mRNA and before translation into a polypeptide.

In another aspect, a composition comprises a CAR and a peptide that disrupts PKA and AKAP binding. The CAR and the peptide may be expressed as a single polypeptide with a cleavage site, such as an enzymatic site, between the two molecules, such that the peptide is cleaved from the CAR intracellularly. In this embodiment, during and/or after translation of the mRNA encoding the peptide and the CAR, the polypeptide molecule is cleaved, thus the peptide is cleaved from the CAR. The cleavage site may be an enzymatic site that a proteinase, peptidase, or other enzyme can cleave or an auto-cleavage site between the peptide and the CAR.

In another aspect, the invention includes a composition comprising the CAR and the peptide as separate molecules.

In yet another aspect, the invention includes a composition comprising one or more vectors (e.g., an expression vector) comprising a nucleic acid sequence encoding the CAR and a nucleic acid sequence encoding the peptide.

Cancer Associated Antigens

In certain aspects, the present invention provides immune effector cells (e.g., T cells, NK cells) that are engineered to contain one or more CARs that direct the immune effector cells to cancer. This is achieved through an antigen binding domain on the CAR that is specific for a cancer associated antigen. There are two classes of cancer associated antigens (tumor antigens) that can be targeted by the CARs of the instant invention: (1) cancer associated antigens that are expressed on the surface of cancer cells; and (2) cancer associated antigens that itself is intracellular, however, a fragment of such antigen (peptide) is presented on the surface of the cancer cells by MHC (major histocompatibility complex).

Accordingly, the present invention provides CARs that target the following cancer associated antigens (tumor antigens): CD19, CD123, CD22, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2 M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6, E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

Tumor-Supporting Antigens

A CAR described herein can comprise an antigen binding domain (e.g., antibody or antibody fragment, TCR or TCR fragment) that binds to a tumor-supporting antigen (e.g., a tumor-supporting antigen as described herein). In some embodiments, the tumor-supporting antigen is an antigen present on a stromal cell or a myeloid-derived suppressor cell (MDSC). Stromal cells can secrete growth factors to promote cell division in the microenvironment. MDSC cells can inhibit T cell proliferation and activation. Without wishing to be bound by theory, in some embodiments, the CAR-expressing cells destroy the tumor-supporting cells, thereby indirectly inhibiting tumor growth or survival.

In embodiments, the stromal cell antigen is chosen from one or more of: bone marrow stromal cell antigen 2 (BST2), fibroblast activation protein (FAP) and tenascin. In an embodiment, the FAP-specific antibody is, competes for binding with, or has the same CDRs as, sibrotuzumab. In embodiments, the MDSC antigen is chosen from one or more of: CD33, CD11b, C14, CD15, and CD66b. Accordingly, in some embodiments, the tumor-supporting antigen is chosen from one or more of: bone marrow stromal cell antigen 2 (BST2), fibroblast activation protein (FAP) or tenascin, CD33, CD11b, C14, CD15, and CD66b.

Chimeric Antigen Receptor (CAR)

The present invention encompasses a recombinant DNA construct comprising sequences encoding a CAR, wherein the CAR comprises an antigen binding domain (e.g., antibody or antibody fragment, TCR or TCR fragment) that binds specifically to a cancer associated antigen described herein, wherein the sequence of the antigen binding domain is contiguous with and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule.

In specific aspects, a CAR construct of the invention comprises a scFv domain, wherein the scFv may be preceded by an optional leader sequence such as provided in SEQ ID NO: 2, and followed by an optional hinge sequence such as provided in SEQ ID NO:4 or SEQ ID NO:6 or SEQ ID NO:8 or SEQ ID NO:10, a transmembrane region such as provided in SEQ ID NO:12, an intracellular signalling domain that includes SEQ ID NO:14 or SEQ ID NO:16 and a CD3 zeta sequence that includes SEQ ID NO:18 or SEQ ID NO:20, e.g., wherein the domains are contiguous with and in the same reading frame to form a single fusion protein.

In one aspect, an exemplary CAR constructs comprise an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), and an intracellular stimulatory domain (e.g., an intracellular stimulatory domain described herein). In one aspect, an exemplary CAR construct comprises an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), an intracellular costimulatory signaling domain (e.g., a costimulatory signaling domain described herein) and/or an intracellular primary signaling domain (e.g., a primary signaling domain described herein).

An exemplary leader sequence is provided as SEQ ID NO: 2. An exemplary hinge/spacer sequence is provided as SEQ ID NO: 4 or SEQ ID NO:6 or SEQ ID NO:8 or SEQ ID NO:10. An exemplary transmembrane domain sequence is provided as SEQ ID NO:12. An exemplary sequence of the intracellular signaling domain of the 4-1BB protein is provided as SEQ ID NO: 14. An exemplary sequence of the intracellular signaling domain of CD27 is provided as SEQ ID NO:16. An exemplary CD3zeta domain sequence is provided as SEQ ID NO: 18 or SEQ ID NO:20.

In one aspect, the present invention encompasses a recombinant nucleic acid construct comprising a nucleic acid molecule encoding a CAR, wherein the nucleic acid molecule comprises the nucleic acid sequence encoding an antigen binding domain, e.g., described herein, that is contiguous with and in the same reading frame as a nucleic acid sequence encoding an intracellular signaling domain.

In one aspect, the present invention encompasses a recombinant nucleic acid construct comprising a nucleic acid molecule encoding a CAR, wherein the nucleic acid molecule comprises a nucleic acid sequence encoding an antigen binding domain, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, CD27, 4-1BB, and the like. In some instances, the CAR can comprise any combination of CD3-zeta, CD28, 4-1BB, and the like.

The nucleic acid sequences coding for the desired molecules can be obtained using recombinant methods known in the art, such as, for example by screening libraries from cells expressing the nucleic acid molecule, by deriving the nucleic acid molecule from a vector known to include the same, or by isolating directly from cells and tissues containing the same, using standard techniques. Alternatively, the nucleic acid of interest can be produced synthetically, rather than cloned.

The present invention includes retroviral and lentiviral vector constructs expressing a CAR that can be directly transduced into a cell.

The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR") (e.g., a 3' and/or 5' UTR described herein), a 5' cap (e.g., a 5' cap described herein) and/or Internal Ribosome Entry Site (IRES) (e.g., an IRES described herein), the nucleic acid to be expressed, and a polyA tail, typically 50-2000 bases in length (SEQ ID NO:32). RNA so produced can efficiently transfect different kinds of cells. In one embodiment, the template includes sequences for the CAR. In an embodiment, an RNA CAR vector is transduced into a cell, e.g., a T cell or a NK cell, by electroporation.

Antigen Binding Domain

In one aspect, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a CAR of the invention include those associated with viral, bacterial and parasitic infections, autoimmune disease and cancer cells.

In one aspect, the CAR-mediated T-cell response can be directed to an antigen of interest by way of engineering an antigen binding domain that specifically binds a desired antigen into the CAR.

In one aspect, the portion of the CAR comprising the antigen binding domain comprises an antigen binding domain that targets a tumor antigen, e.g., a tumor antigen described herein.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

In one embodiment, an antigen binding domain against CD22 is an antigen binding portion, e.g., CDRs, of an antibody described in, e.g., Haso et al., Blood, 121(7): 1165-1174 (2013); Wayne et al., Clin Cancer Res 16(6): 1894-1903 (2010); Kato et al., Leuk Res 37(1):83-88 (2013); Creative BioMart (creativebiomart.net): MOM-18047-S(P).

In one embodiment, an antigen binding domain against CS-1 is an antigen binding portion, e.g., CDRs, of Elotuzumab (BMS), see e.g., Tai et al., 2008, Blood 112(4): 1329-37; Tai et al., 2007, Blood. 110(5):1656-63.

In one embodiment, an antigen binding domain against CLL-1 is an antigen binding portion, e.g., CDRs, of an antibody available from R&D, ebiosciences, Abcam, for example, PE-CLL1-hu Cat #353604 (BioLegend); and PE-CLL1 (CLEC12A) Cat #562566 (BD).

In one embodiment, an antigen binding domain against CD33 is an antigen binding portion, e.g., CDRs, of an antibody described in, e.g., Bross et al., Clin Cancer Res 7(6):1490-1496 (2001) (Gemtuzumab Ozogamicin, hP67.6), Caron et al., Cancer Res 52(24):6761-6767 (1992) (Lintuzumab, HuM195), Lapusan et al., Invest New Drugs 30(3):1121-1131 (2012) (AVE9633), Aigner et al., Leukemia 27(5): 1107-1115 (2013) (AMG330, CD33 BiTE), Dutour et al., Adv hematol 2012:683065 (2012), and Pizzitola et al., Leukemia doi:10.1038/Lue.2014.62 (2014).

In one embodiment, an antigen binding domain against GD2 is an antigen binding portion, e.g., CDRs, of an antibody described in, e.g., Mujoo et al., Cancer Res. 47(4):1098-1104 (1987); Cheung et al., Cancer Res 45(6): 2642-2649 (1985), Cheung et al., J Clin Oncol 5(9):1430-1440 (1987), Cheung et al., J Clin Oncol 16(9):3053-3060

(1998), Handgretinger et al., Cancer Immunol Immunother 35(3):199-204 (1992). In some embodiments, an antigen binding domain against GD2 is an antigen binding portion of an antibody selected from mAb 14.18, 14G2a, ch14.18, hu14.18, 3F8, hu3F8, 3G6, 8B6, 60C3, 10B8, ME36.1, and 8H9, see e.g., WO2012033885, WO2013040371, WO2013192294, WO2013061273, WO2013123061, WO2013074916, and WO201385552. In some embodiments, an antigen binding domain against GD2 is an antigen binding portion of an antibody described in US Publication No.: 20100150910 or PCT Publication No.: WO 2011160119.

In one embodiment, an antigen binding domain against BCMA is an antigen binding portion, e.g., CDRs, of an antibody described in, e.g., WO2012163805, WO200112812, and WO2003062401.

In one embodiment, an antigen binding domain against Tn antigen is an antigen binding portion, e.g., CDRs, of an antibody described in, e.g., U.S. Pat. No. 8,440,798, Brooks et al., PNAS 107(22):10056-10061 (2010), and Stone et al., OncoImmunology 1(6):863-873(2012).

In one embodiment, an antigen binding domain against PSMA is an antigen binding portion, e.g., CDRs, of an antibody described in, e.g., Parker et al., Protein Expr Purif 89(2):136-145 (2013), US 20110268656 (J591 ScFv); Frigerio et al, European J Cancer 49(9):2223-2232 (2013) (scFvD2B); WO 2006125481 (mAbs 3/A12, 3/E7 and 3/F11) and single chain antibody fragments (scFv A5 and D7).

In one embodiment, an antigen binding domain against ROR1 is an antigen binding portion, e.g., CDRs, of an antibody described in, e.g., Hudecek et al., Clin Cancer Res 19(12):3153-3164 (2013); WO 2011159847; and US20130101607.

In one embodiment, an antigen binding domain against FLT3 is an antigen binding portion, e.g., CDRs, of an antibody described in, e.g., WO2011076922, U.S. Pat. No. 5,777,084, EP0754230, US20090297529, and several commercial catalog antibodies (R&D, ebiosciences, Abcam).

In one embodiment, an antigen binding domain against TAG72 is an antigen binding portion, e.g., CDRs, of an antibody described in, e.g., Hombach et al., Gastroenterology 113(4):1163-1170 (1997); and Abcam ab691.

In one embodiment, an antigen binding domain against FAP is an antigen binding portion, e.g., CDRs, of an antibody described in, e.g., Ostermann et al., Clinical Cancer Research 14:4584-4592 (2008) (FAP5), US Pat. Publication No. 2009/0304718; sibrotuzumab (see e.g., Hofheinz et al., Oncology Research and Treatment 26(1), 2003); and Tran et al., J Exp Med 210(6):1125-1135 (2013).

In one embodiment, an antigen binding domain against CD38 is an antigen binding portion, e.g., CDRs, of daratumumab (see, e.g., Groen et al., Blood 116(21):1261-1262 (2010); MOR202 (see, e.g., U.S. Pat. No. 8,263,746); or antibodies described in U.S. Pat. No. 8,362,211.

In one embodiment, an antigen binding domain against CD44v6 is an antigen binding portion, e.g., CDRs, of an antibody described in, e.g., Casucci et al., Blood 122(20): 3461-3472 (2013).

In one embodiment, an antigen binding domain against CEA is an antigen binding portion, e.g., CDRs, of an antibody described in, e.g., Chmielewski et al., Gastroenterology 143(4):1095-1107 (2012).

In one embodiment, an antigen binding domain against EPCAM is an antigen binding portion, e.g., CDRS, of an antibody selected from MT110, EpCAM-CD3 bispecific Ab (see, e.g., clinicaltrials.gov/ct2/show/NCT00635596); Edrecolomab; 3622W94; ING-1; and adecatumumab (MT201).

In one embodiment, an antigen binding domain against PRSS21 is an antigen binding portion, e.g., CDRs, of an antibody described in U.S. Pat. No. 8,080,650.

In one embodiment, an antigen binding domain against B7H3 is an antigen binding portion, e.g., CDRs, of an antibody MGA271 (Macrogenics).

In one embodiment, an antigen binding domain against KIT is an antigen binding portion, e.g., CDRs, of an antibody described in, e.g., U.S. Pat. No. 7,915,391, US20120288506, and several commercial catalog antibodies.

In one embodiment, an antigen binding domain against IL-13Ra2 is an antigen binding portion, e.g., CDRs, of an antibody described in, e.g., WO2008/146911, WO2004087758, several commercial catalog antibodies, and WO2004087758.

In one embodiment, an antigen binding domain against CD30 is an antigen binding portion, e.g., CDRs, of an antibody described in, e.g., U.S. Pat. No. 7,090,843 B1, and EP0805871.

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761; WO2005035577; and U.S. Pat. No. 6,437,098.

In one embodiment, an antigen binding domain against CD171 is an antigen binding portion, e.g., CDRs, of an antibody described in, e.g., Hong et al., J Immunother 37(2):93-104 (2014).

In one embodiment, an antigen binding domain against IL-11Ra is an antigen binding portion, e.g., CDRs, of an antibody available from Abcam (cat # ab55262) or Novus Biologicals (cat # EPR5446). In another embodiment, an antigen binding domain again IL-11Ra is a peptide, see, e.g., Huang et al., Cancer Res 72(1):271-281 (2012).

In one embodiment, an antigen binding domain against PSCA is an antigen binding portion, e.g., CDRs, of an antibody described in, e.g., Morgenroth et al., Prostate 67(10):1121-1131 (2007) (scFv 7F5); Nejatollahi et al., J of Oncology 2013(2013), article ID 839831 (scFv C5-II); and US Pat Publication No. 20090311181.

In one embodiment, an antigen binding domain against VEGFR2 is an antigen binding portion, e.g., CDRs, of an antibody described in, e.g., Chinnasamy et al., J Clin Invest 120(11):3953-3968 (2010).

In one embodiment, an antigen binding domain against LewisY is an antigen binding portion, e.g., CDRs, of an antibody described in, e.g., Kelly et al., Cancer Biother Radiopharm 23(4):411-423 (2008) (hu3S193 Ab (scFvs)); Dolezal et al., Protein Engineering 16(1):47-56 (2003) (NC10 scFv).

In one embodiment, an antigen binding domain against CD24 is an antigen binding portion, e.g., CDRs, of an antibody described in, e.g., Maliar et al., Gastroenterology 143(5):1375-1384 (2012).

In one embodiment, an antigen binding domain against PDGFR-beta is an antigen binding portion, e.g., CDRs, of an antibody Abcam ab32570.

In one embodiment, an antigen binding domain against SSEA-4 is an antigen binding portion, e.g., CDRs, of antibody MC813 (Cell Signaling), or other commercially available antibodies.

In one embodiment, an antigen binding domain against CD20 is an antigen binding portion, e.g., CDRs, of the antibody Rituximab, Ofatumumab, Ocrelizumab, Veltuzumab, or GA101.

In one embodiment, an antigen binding domain against Folate receptor alpha is an antigen binding portion, e.g., CDRs, of the antibody IMGN853, or an antibody described in US20120009181; U.S. Pat. No. 4,851,332, LK26: U.S. Pat. No. 5,952,484.

In one embodiment, an antigen binding domain against ERBB2 (Her2/neu) is an antigen binding portion, e.g., CDRs, of the antibody trastuzumab, or pertuzumab.

In one embodiment, an antigen binding domain against MUC1 is an antigen binding portion, e.g., CDRs, of the antibody SAR566658.

In one embodiment, the antigen binding domain against EGFR is antigen binding portion, e.g., CDRs, of the antibody cetuximab, panitumumab, zalutumumab, nimotuzumab, or matuzumab.

In one embodiment, an antigen binding domain against NCAM is an antigen binding portion, e.g., CDRs, of the antibody clone 2-2B: MAB5324 (EMD Millipore)

In one embodiment, an antigen binding domain against Ephrin B2 is an antigen binding portion, e.g., CDRs, of an antibody described in, e.g., Abengozar et al., Blood 119(19): 4565-4576 (2012).

In one embodiment, an antigen binding domain against IGF-I receptor is an antigen binding portion, e.g., CDRs, of an antibody described in, e.g., U.S. Pat. No. 8,344,112 B2; EP2322550 A1; WO 2006/138315, or PCT/US2006/022995.

In one embodiment, an antigen binding domain against CAIX is an antigen binding portion, e.g., CDRs, of the antibody clone 303123 (R&D Systems).

In one embodiment, an antigen binding domain against LMP2 is an antigen binding portion, e.g., CDRs, of an antibody described in, e.g., U.S. Pat. No. 7,410,640, or US20050129701.

In one embodiment, an antigen binding domain against gp100 is an antigen binding portion, e.g., CDRs, of the antibody HMB45, NKIbetaB, or an antibody described in WO2013165940, or US20130295007

In one embodiment, an antigen binding domain against tyrosinase is an antigen binding portion, e.g., CDRs, of an antibody described in, e.g., U.S. Pat. No. 5,843,674; or US19950504048.

In one embodiment, an antigen binding domain against EphA2 is an antigen binding portion, e.g., CDRs, of an antibody described in, e.g., Yu et al., Mol Ther 22(1):102-111 (2014).

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761 A3; 20120276046; WO2005035577; or U.S. Pat. No. 6,437,098.

In one embodiment, an antigen binding domain against fucosyl GM1 is an antigen binding portion, e.g., CDRs, of an antibody described in, e.g., US20100297138; or WO2007/067992.

In one embodiment, an antigen binding domain against sLe is an antigen binding portion, e.g., CDRs, of the antibody G193 (for lewis Y), see Scott A M et al, Cancer Res 60: 3254-61 (2000), also as described in Neeson et al, J Immunol May 2013 190 (Meeting Abstract Supplement) 177.10.

In one embodiment, an antigen binding domain against GM3 is an antigen binding portion, e.g., CDRs, of the antibody CA 2523449 (mAb 14F7).

In one embodiment, an antigen binding domain against HMWMAA is an antigen binding portion, e.g., CDRs, of an antibody described in, e.g., Kmiecik et al., Oncoimmunology 3(1):e27185 (2014) (PMID: 24575382) (mAb9.2.27); U.S. Pat. No. 6,528,481; WO2010033866; or US 20140004124.

In one embodiment, an antigen binding domain against o-acetyl-GD2 is an antigen binding portion, e.g., CDRs, of the antibody 8B6.

In one embodiment, an antigen binding domain against TEM1/CD248 is an antigen binding portion, e.g., CDRs, of an antibody described in, e.g., Marty et al., Cancer Lett 235(2):298-308 (2006); Zhao et al., J Immunol Methods 363(2):221-232 (2011).

In one embodiment, an antigen binding domain against CLDN6 is an antigen binding portion, e.g., CDRs, of the antibody IMAB027 (Ganymed Pharmaceuticals), see e.g., clinicaltrial.gov/show/NCT02054351.

In one embodiment, an antigen binding domain against TSHR is an antigen binding portion, e.g., CDRs, of an antibody described in, e.g., U.S. Pat. Nos. 8,603,466; 8,501,415; or U.S. Pat. No. 8,309,693.

In one embodiment, an antigen binding domain against GPRC5D is an antigen binding portion, e.g., CDRs, of the antibody FAB6300A (R&D Systems); or LS-A4180 (Lifespan Biosciences).

In one embodiment, an antigen binding domain against CD97 is an antigen binding portion, e.g., CDRs, of an antibody described in, e.g., U.S. Pat. No. 6,846,911; de Groot et al., J Immunol 183(6):4127-4134 (2009); or an antibody from R&D: MAB3734.

In one embodiment, an antigen binding domain against ALK is an antigen binding portion, e.g., CDRs, of an antibody described in, e.g., Mino-Kenudson et al., Clin Cancer Res 16(5):1561-1571 (2010).

In one embodiment, an antigen binding domain against polysialic acid is an antigen binding portion, e.g., CDRs, of an antibody described in, e.g., Nagae et al., J Biol Chem 288(47):33784-33796 (2013).

In one embodiment, an antigen binding domain against PLAC1 is an antigen binding portion, e.g., CDRs, of an antibody described in, e.g., Ghods et al., Biotechnol Appl Biochem 2013 doi:10.1002/bab.1177.

In one embodiment, an antigen binding domain against GloboH is an antigen binding portion of the antibody VK9; or an antibody described in, e.g., Kudryashov V et al, Glycoconj J. 15(3):243-9 (1998), Lou et al., Proc Natl Acad Sci USA 111(7):2482-2487 (2014); MBr1: Bremer E-G et al. J Biol Chem 259:14773-14777 (1984).

In one embodiment, an antigen binding domain against NY-BR-1 is an antigen binding portion, e.g., CDRs of an antibody described in, e.g., Jager et al., Appl Immunohistochem Mol Morphol 15(1):77-83 (2007).

In one embodiment, an antigen binding domain against WT-1 is an antigen binding portion, e.g., CDRs, of an antibody described in, e.g., Dao et al., Sci Transl Med 5(176):176ra33 (2013); or WO2012/135854.

In one embodiment, an antigen binding domain against MAGE-A1 is an antigen binding portion, e.g., CDRs, of an antibody described in, e.g., Willemsen et al., J Immunol 174(12):7853-7858 (2005) (TCR-like scFv).

In one embodiment, an antigen binding domain against sperm protein 17 is an antigen binding portion, e.g., CDRs, of an antibody described in, e.g., Song et al., Target Oncol 2013 Aug. 14 (PMID: 23943313); Song et al., Med Oncol 29(4):2923-2931 (2012).

In one embodiment, an antigen binding domain against Tie 2 is an antigen binding portion, e.g., CDRs, of the antibody AB33 (Cell Signaling Technology).

In one embodiment, an antigen binding domain against MAD-CT-2 is an antigen binding portion, e.g., CDRs, of an antibody described in, e.g., PMID: 2450952; U.S. Pat. No. 7,635,753.

In one embodiment, an antigen binding domain against Fos-related antigen 1 is an antigen binding portion, e.g., CDRs, of the antibody 12F9 (Novus Biologicals).

In one embodiment, an antigen binding domain against MelanA/MART1 is an antigen binding portion, e.g., CDRs, of an antibody described in, EP2514766 A2; or U.S. Pat. No. 7,749,719.

In one embodiment, an antigen binding domain against sarcoma translocation breakpoints is an antigen binding portion, e.g., CDRs, of an antibody described in, e.g., Luo et al, EMBO Mol. Med. 4(6):453-461 (2012).

In one embodiment, an antigen binding domain against TRP-2 is an antigen binding portion, e.g., CDRs, of an antibody described in, e.g., Wang et al, J Exp Med. 184(6): 2207-16 (1996).

In one embodiment, an antigen binding domain against CYP1B1 is an antigen binding portion, e.g., CDRs, of an antibody described in, e.g., Maecker et al, Blood 102 (9): 3287-3294 (2003).

In one embodiment, an antigen binding domain against RAGE-1 is an antigen binding portion, e.g., CDRs, of the antibody MAB5328 (EMD Millipore).

In one embodiment, an antigen binding domain against human telomerase reverse transcriptase is an antigen binding portion, e.g., CDRs, of the antibody cat no: LS-B95-100 (Lifespan Biosciences)

In one embodiment, an antigen binding domain against intestinal carboxyl esterase is an antigen binding portion, e.g., CDRs, of the antibody 4F12: cat no: LS-B6190-50 (Lifespan Biosciences).

In one embodiment, an antigen binding domain against mut hsp70-2 is an antigen binding portion, e.g., CDRs, of the antibody Lifespan Biosciences: monoclonal: cat no: LS-C133261-100 (Lifespan Biosciences).

In one embodiment, an antigen binding domain against CD79a is an antigen binding portion, e.g., CDRs, of the antibody Anti-CD79a antibody [HM47/A9] (ab3121), available from Abcam; antibody CD79A Antibody #3351 available from Cell Signalling Technology; or antibody HPA017748—Anti-CD79A antibody produced in rabbit, available from Sigma Aldrich.

In one embodiment, an antigen binding domain against CD79b is an antigen binding portion, e.g., CDRs, of the antibody polatuzumab vedotin, anti-CD79b described in Dornan et al., "Therapeutic potential of an anti-CD79b antibody-drug conjugate, anti-CD79b-vc-MMAE, for the treatment of non-Hodgkin lymphoma" Blood. 2009 Sep. 24; 114(13):2721-9. doi: 10.1182/blood-2009-02-205500. Epub 2009 Jul. 24, or the bispecific antibody Anti-CD79b/CD3 described in "4507 Pre-Clinical Characterization of T Cell-Dependent Bispecific Antibody Anti-CD79b/CD3 As a Potential Therapy for B Cell Malignancies" Abstracts of 56$^{th}$ ASH Annual Meeting and Exposition, San Francisco, CA Dec. 6-9 2014.

In one embodiment, an antigen binding domain against CD72 is an antigen binding portion, e.g., CDRs, of the antibody J3-109 described in Myers, and Uckun, "An anti-CD72 immunotoxin against therapy-refractory B-lineage acute lymphoblastic leukemia." Leuk Lymphoma. 1995 June; 18(1-2):119-22, or anti-CD72 (10D6.8.1, mIgG1) described in Polson et al., "Antibody-Drug Conjugates for the Treatment of Non-Hodgkin's Lymphoma: Target and Linker-Drug Selection" Cancer Res Mar. 15, 2009 69; 2358.

In one embodiment, an antigen binding domain against LAIR1 is an antigen binding portion, e.g., CDRs, of the antibody ANT-301 LAIR1 antibody, available from ProSpec; or anti-human CD305 (LAIR1) Antibody, available from BioLegend.

In one embodiment, an antigen binding domain against FCAR is an antigen binding portion, e.g., CDRs, of the antibody CD89/FCARAntibody (Catalog #10414-H08H), available from Sino Biological Inc.

In one embodiment, an antigen binding domain against LILRA2 is an antigen binding portion, e.g., CDRs, of the antibody LILRA2 monoclonal antibody (M17), clone 3C7, available from Abnova, or Mouse Anti-LILRA2 antibody, Monoclonal (2D7), available from Lifespan Biosciences.

In one embodiment, an antigen binding domain against CD300LF is an antigen binding portion, e.g., CDRs, of the antibody Mouse Anti-CMRF35-like molecule 1 antibody, Monoclonal[UP-D2], available from BioLegend, or Rat Anti-CMRF35-like molecule 1 antibody, Monoclonal [234903], available from R&D Systems.

In one embodiment, an antigen binding domain against CLEC12A is an antigen binding portion, e.g., CDRs, of the antibody Bispecific T cell Engager (BiTE) scFv-antibody and ADC described in Noordhuis et al., "Targeting of CLEC12A In Acute Myeloid Leukemia by Antibody-Drug-Conjugates and Bispecific CLL-1×CD3 BiTE Antibody" 53$^{rd}$ ASH Annual Meeting and Exposition, Dec. 10-13, 2011, and MCLA-117 (Merus).

In one embodiment, an antigen binding domain against BST2 (also called CD317) is an antigen binding portion, e.g., CDRs, of the antibody Mouse Anti-CD317 antibody, Monoclonal[3H4], available from Antibodies-Online or Mouse Anti-CD317 antibody, Monoclonal[696739], available from R&D Systems.

In one embodiment, an antigen binding domain against EMR2 (also called CD312) is an antigen binding portion, e.g., CDRs, of the antibody Mouse Anti-CD312 antibody, Monoclonal[LS-B8033] available from Lifespan Biosciences, or Mouse Anti-CD312 antibody, Monoclonal [494025] available from R&D Systems.

In one embodiment, an antigen binding domain against LY75 is an antigen binding portion, e.g., CDRs, of the antibody Mouse Anti-Lymphocyte antigen 75 antibody, Monoclonal[HD30] available from EMD Millipore or Mouse Anti-Lymphocyte antigen 75 antibody, Monoclonal [A15797] available from Life Technologies.

In one embodiment, an antigen binding domain against GPC3 is an antigen binding portion, e.g., CDRs, of the antibody hGC33 described in Nakano K, Ishiguro T, Konishi H, et al. Generation of a humanized anti-glypican 3 antibody by CDR grafting and stability optimization. Anticancer Drugs. 2010 November; 21(10):907-916, or MDX-1414, HN3, or YP7, all three of which are described in Feng et al., "Glypican-3 antibodies: a new therapeutic target for liver cancer." FEBS Lett. 2014 Jan. 21; 588(2):377-82.

In one embodiment, an antigen binding domain against FCRL5 is an antigen binding portion, e.g., CDRs, of the anti-FcRL5 antibody described in Elkins et al., "FcRL5 as a target of antibody-drug conjugates for the treatment of multiple myeloma" Mol Cancer Ther. 2012 October; 11(10): 2222-32.

In one embodiment, an antigen binding domain against IGLL1 is an antigen binding portion, e.g., CDRs, of the antibody Mouse Anti-Immunoglobulin lambda-like polypeptide 1 antibody, Monoclonal[AT1G4] available from Lifespan Biosciences, Mouse Anti-Immunoglobulin lambda-like polypeptide 1 antibody, Monoclonal[HSL11] available from BioLegend.

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed above.

In another aspect, the antigen binding domain comprises a humanized antibody or an antibody fragment. In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Nicholson et al. Mol. Immun 34 (16-17): 1157-1165 (1997); Carter et al., Proc. Natl. Acad. Sci. USA, 89:4285 (1992); Presta et al., J. Immunol., 151:2623 (1993), the contents of which are incorporated herein by reference herein in their entirety). In some embodiments, the framework region, e.g., all four framework regions, of the heavy chain variable region are derived from a VH4_4-59 germline sequence. In one embodiment, the framework region can comprise, one, two, three, four or five modifications, e.g., substitutions, e.g., from the amino acid at the corresponding murine sequence. In one embodiment, the framework region, e.g., all four framework regions of the light chain variable region are derived from a VK3_1.25 germline sequence. In one embodiment, the framework region can comprise, one, two, three, four or five modifications, e.g., substitutions, e.g., from the amino acid at the corresponding murine sequence.

In some aspects, the portion of a CAR composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

A humanized antibody or antibody fragment may retain a similar antigenic specificity as the original antibody, e.g., in the present invention, the ability to bind human a cancer associated antigen as described herein. In some embodiments, a humanized antibody or antibody fragment may have improved affinity and/or specificity of binding to human a cancer associated antigen as described herein.

In one aspect, the antigen binding domain of the invention is characterized by particular functional features or properties of an antibody or antibody fragment. For example, in one aspect, the portion of a CAR composition of the invention that comprises an antigen binding domain specifically binds a tumor antigen as described herein.

In one aspect, the anti-cancer associated antigen as described herein binding domain is a fragment, e.g., a single chain variable fragment (scFv). In one aspect, the anti-cancer associated antigen as described herein binding domain is a Fv, a Fab, a (Fab')2, or a bifunctional (e.g. bi-specific) hybrid antibody (e.g., Lanzavecchia et al., Eur. J. Immunol. 17, 105 (1987)). In one aspect, the antibodies and fragments thereof of the invention binds a cancer associated antigen as described herein protein with wild-type or enhanced affinity.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)n$, where n is a positive integer equal to or greater than 1 (SEQ ID NO:22). In one embodiment, the linker can be $(Gly_4Ser)_4$ (SEQ ID NO:29) or $(Gly_4Ser)_3$(SEQ ID NO:30). Variation in the linker length may retain or enhance activity, giving rise to superior efficacy in activity studies.

In another aspect, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellular, however, a fragment of such antigen (peptide) is presented on the surface of the cancer cells by MHC.

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multi-specific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with cross-linkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$. In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$-$VH_1$-$VH_2$-$VL_2$. Optionally, a linker is disposed between the two antibodies or antibody fragments (e.g., scFvs), e.g., between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$-$VH_2$-$VL_2$. The linker may be a linker as described herein, e.g., a ($Gly_4$-Ser)n linker, wherein n is 1, 2, 3, 4, 5, or 6, preferably 4 (SEQ ID NO: 78). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

Stability and Mutations

The stability of an antigen binding domain to a cancer associated antigen as described herein, e.g., scFv molecules (e.g., soluble scFv), can be evaluated in reference to the biophysical properties (e.g., thermal stability) of a conventional control scFv molecule or a full length antibody. In one embodiment, the humanized scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a control binding molecule (e.g. a conventional scFv molecule) in the described assays.

The improved thermal stability of the antigen binding domain to a cancer associated antigen described herein, e.g., scFv is subsequently conferred to the entire CAR construct, leading to improved therapeutic properties of the CAR construct. The thermal stability of the antigen binding domain of –a cancer associated antigen described herein, e.g., scFv, can be improved by at least about 2° C. or 3° C. as compared to a conventional antibody. In one embodiment, the antigen binding domain of –a cancer associated antigen described herein, e.g., scFv, has a 1° C. improved thermal stability as compared to a conventional antibody. In another embodiment, the antigen binding domain of a cancer associated antigen described herein, e.g., scFv, has a 2° C. improved thermal stability as compared to a conventional antibody. In another embodiment, the scFv has a 4, 5, 6, 7, 8, 9, 10, 11, 12, 13, 14, 15° C. improved thermal stability as compared to a conventional antibody. Comparisons can be made, for example, between the scFv molecules disclosed herein and scFv molecules or Fab fragments of an antibody from which the scFv VH and VL were derived. Thermal stability can be measured using methods known in the art. For example, in one embodiment, Tm can be measured. Methods for measuring Tm and other methods of determining protein stability are described in more detail below.

Mutations in scFv (arising through humanization or direct mutagenesis of the soluble scFv) can alter the stability of the scFv and improve the overall stability of the scFv and the CAR construct. Stability of the humanized scFv is compared against the murine scFv using measurements such as Tm, temperature denaturation and temperature aggregation.

The binding capacity of the mutant scFvs can be determined using assays know in the art and described herein.

In one embodiment, the antigen binding domain of –a cancer associated antigen described herein, e.g., scFv, comprises at least one mutation arising from the humanization process such that the mutated scFv confers improved stability to the CAR construct. In another embodiment, the antigen binding domain of –a cancer associated antigen described herein, e.g., scFv, comprises at least 1, 2, 3, 4, 5, 6, 7, 8, 9, 10 mutations arising from the humanization process such that the mutated scFv confers improved stability to the CAR construct.

Methods of Evaluating Protein Stability

The stability of an antigen binding domain may be assessed using, e.g., the methods described below. Such methods allow for the determination of multiple thermal unfolding transitions where the least stable domain either unfolds first or limits the overall stability threshold of a multidomain unit that unfolds cooperatively (e.g., a multidomain protein which exhibits a single unfolding transition). The least stable domain can be identified in a number of additional ways. Mutagenesis can be performed to probe which domain limits the overall stability. Additionally, protease resistance of a multidomain protein can be performed under conditions where the least stable domain is known to be intrinsically unfolded via DSC or other spectroscopic methods (Fontana, et al., (1997) Fold. Des., 2: R17-26; Dimasi et al. (2009) J. Mol. Biol. 393: 672-692). Once the least stable domain is identified, the sequence encoding this domain (or a portion thereof) may be employed as a test sequence in the methods.

Thermal Stability

The thermal stability of the compositions may be analyzed using a number of non-limiting biophysical or biochemical techniques known in the art. In certain embodiments, thermal stability is evaluated by analytical spectroscopy.

An exemplary analytical spectroscopy method is Differential Scanning calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fab or scFv unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol., 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

The thermal stability of a composition can be measured biochemically. An exemplary biochemical method for assessing thermal stability is a thermal challenge assay. In a "thermal challenge assay", a composition is subjected to a range of elevated temperatures for a set period of time. For example, in one embodiment, test scFv molecules or molecules comprising scFv molecules are subject to a range of increasing temperatures, e.g., for 1-1.5 hours. The activity of the protein is then assayed by a relevant biochemical assay. For example, if the protein is a binding protein (e.g. an scFv or scFv-containing polypeptide) the binding activity of the binding protein may be determined by a functional or quantitative ELISA.

Such an assay may be done in a high-throughput format and those disclosed in the Examples using *E. coli* and high throughput screening. A library of antigen binding domains, e.g., that includes an antigen binding domain to –a cancer associated antigen described herein, e.g., scFv variants, may be created using methods known in the art. Antigen binding domain, e.g., to –a cancer associated antigen described herein, e.g., scFv, expression may be induced and the antigen binding domain, e.g., to –a cancer associated antigen described herein, e.g., scFv, may be subjected to thermal challenge. The challenged test samples may be assayed for binding and those antigen binding domains to –a cancer associated antigen described herein, e.g., scFvs, which are stable may be scaled up and further characterized.

Thermal stability is evaluated by measuring the melting temperature (Tm) of a composition using any of the above techniques (e.g. analytical spectroscopy techniques). The melting temperature is the temperature at the midpoint of a thermal transition curve wherein 50% of molecules of a composition are in a folded state (See e.g., Dimasi et al. (2009) J. Mol Biol. 393: 672-692). In one embodiment, Tm values for an antigen binding domain to –a cancer associated antigen described herein, e.g., scFv, are about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an IgG is about 40° C., 41° C., 42° C., 43° C., 44° C., 45° C., 46° C., 47° C., 48° C., 49° C., 50° C., 51° C., 52°

C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an multivalent antibody is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C.

Thermal stability is also evaluated by measuring the specific heat or heat capacity (Cp) of a composition using an analytical calorimetric technique (e.g. DSC). The specific heat of a composition is the energy (e.g. in kcal/mol) is required to rise by 1° C., the temperature of 1 mol of water. As large Cp is a hallmark of a denatured or inactive protein composition. The change in heat capacity (ΔCp) of a composition is measured by determining the specific heat of a composition before and after its thermal transition. Thermal stability may also be evaluated by measuring or determining other parameters of thermodynamic stability including Gibbs free energy of unfolding (ΔG), enthalpy of unfolding (ΔH), or entropy of unfolding (ΔS). One or more of the above biochemical assays (e.g. a thermal challenge assay) are used to determine the temperature (i.e. the $T_C$ value) at which 50% of the composition retains its activity (e.g. binding activity).

In addition, mutations to the antigen binding domain of a cancer associated antigen described herein, e.g., scFv, can be made to alter the thermal stability of the antigen binding domain of a cancer associated antigen described herein, e.g., scFv, as compared with the unmutated antigen binding domain of a cancer associated antigen described herein, e.g., scFv. When the humanized antigen binding domain of a cancer associated antigen described herein, e.g., scFv, is incorporated into a CAR construct, the antigen binding domain of the cancer associated antigen described herein, e.g., humanized scFv, confers thermal stability to the overall CARs of the present invention. In one embodiment, the antigen binding domain to a cancer associated antigen described herein, e.g., scFv, comprises a single mutation that confers thermal stability to the antigen binding domain of the cancer associated antigen described herein, e.g., scFv. In another embodiment, the antigen binding domain to a cancer associated antigen described herein, e.g., scFv, comprises multiple mutations that confer thermal stability to the antigen binding domain to the cancer associated antigen described herein, e.g., scFv. In one embodiment, the multiple mutations in the antigen binding domain to a cancer associated antigen described herein, e.g., scFv, have an additive effect on thermal stability of the antigen binding domain to the cancer associated antigen described herein binding domain, e.g., scFv.

b) % Aggregation

The stability of a composition can be determined by measuring its propensity to aggregate. Aggregation can be measured by a number of non-limiting biochemical or biophysical techniques. For example, the aggregation of a composition may be evaluated using chromatography, e.g. Size-Exclusion Chromatography (SEC). SEC separates molecules on the basis of size. A column is filled with semi-solid beads of a polymeric gel that will admit ions and small molecules into their interior but not large ones. When a protein composition is applied to the top of the column, the compact folded proteins (i.e. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition can be determined by comparing the concentration of a fraction with the total concentration of protein applied to the gel. Stable compositions elute from the column as essentially a single fraction and appear as essentially a single peak in the elution profile or chromatogram.

c) Binding Affinity

The stability of a composition can be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., i (1991) Biotechniques 11:620-627; Johnsson, B., et al. (1995) J. Mol. Recognit. 8:125-131; and Johnnson, B., et al. (1991) Anal. Biochem. 198:268-277.

In one aspect, the antigen binding domain of the CAR comprises an amino acid sequence that is homologous to an antigen binding domain amino acid sequence described herein, and the antigen binding domain retains the desired functional properties of the antigen binding domain described herein.

In one specific aspect, the CAR composition of the invention comprises an antibody fragment. In a further aspect, the antibody fragment comprises an scFv.

In various aspects, the antigen binding domain of the CAR is engineered by modifying one or more amino acids within one or both variable regions (e.g., VH and/or VL), for example within one or more CDR regions and/or within one or more framework regions. In one specific aspect, the CAR composition of the invention comprises an antibody fragment. In a further aspect, the antibody fragment comprises an scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the VH or VL of an antigen binding domain to –a cancer associated antigen described herein, e.g., scFv, comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the antigen binding domain to the cancer associated antigen described herein, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD27, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO:4. In one aspect, the transmembrane domain comprises (e.g., consists of) a transmembrane domain of SEQ ID NO: 12.

In one aspect, the hinge or spacer comprises an IgG4 hinge. For example, in one embodiment, the hinge or spacer comprises a hinge of the amino acid sequence ESKYGPPCPPCPAPEFLGGPSVFLFPPKPKDTLMISRTPEVTCVVVDVSQEDPEVQFN WYVDGVEVHNA KTKPREEQFNSTYRVVSVLTVLHQDWLNGKEYK CKVSNKGLPS SIEKTISKAKGQPREPQVYTLPPSQEEMTKNQVSLTCLVKGFYPSDIAVEWESNGQP ENNYKTTPPVLDSDGSFFLYSRLTVDKSRWQEG NVFSCSVMHEALHNHYTQKSLS LSLGKM (SEQ ID NO:6). In some embodiments, the hinge or spacer comprises a hinge encoded by a nucleotide sequence of GAGAGCAAGTACGGCCCTCCCTGCCCCCCTTGC CCTGCCCCCGAGTTCCTGGGC GGACCCAGCG TGTTCCTGTTCCCCCCCAAGCCCAAGGACACCCTGATGATCAGC CGGACCCCCGAGGTGACCTGTG TGGTGGTGGACGTGTCCCAGGAGGACCCCGA GGTCCAGTTCAACTGGTACGTGGACGGCGTGGAGGTGCACAACGCCAAGACCA AGCCCCGGGAGGAGCAGTTCAATAGCACCTACCGGGTGGT GTCCGTGCTGACC GTGCTGCACCAGGACTGGCTGAACGGCAAGGAATACAAGTGTAAGGTGTCCAA CAAGGGCCTGCCCAGCAGCATCGAGAAAACCATCAGCAAGGCCAAGGGCCAGC CTCGGGAGCCCCAGGTGTACACCCTGCCCCCTAGCCAAGAGGAGATGACCAAG AACCAGGTGTCC CTGACCTGCCTGGTGAAGGGCTTCTACCCCAGCG ACATCGCC GTGGAGTGGGAGAGCAACGGCCA GCCCGAGAACAACTACAAGACCACCCCCCC TGTGCTGGACAGCGACGGCAGCTTCTTCCTGTACAGCCGGCTGACCGTGGACAA GAGCCGGTGG CAGGAGGGCAACGTCTTTAGCTGCTCCGTGATGCACGAGGCCC TGCACAACCACTACACCCAGAAGAGCCTGAGCCTGTCCCTGGGCAAGATG (SEQ ID NO:7).

In one aspect, the hinge or spacer comprises an IgD hinge. For example, in one embodiment, the hinge or spacer comprises a hinge of the amino acid sequence RWPESPKAQASSVPTAQPQAEGSLAKATTAPATTRNTGRGGEEKKKEKEKEEQEE RETKTPECPSHTQPLGVYLLTPAVQDLWLRDKATFTCFVVGSDLKDAHLTWEVAG KVPTGGVEEGLLERHSNG SQSQHSRLTLPRSLWNAGTSVTCTLNHPSLPPQRLMAL REPAAQAPVKLSLNLLASSDPPEAASWLLCEVSGFSPPNILLMWLEDQREVNTSGF APARPPPQPGSTTFWAWSVLRVPAPPSPQPATYTCVVSHEDSRTLLN ASRSLEVSYV TDH (SEQ ID NO:8). In some embodiments, the hinge or spacer comprises a hinge encoded by a nucleotide sequence of AGGTGGCCCGAAAGTCCCAAGGCCCAGGCATCTAGTGTTCCTACTGCACA GCCC CAGGCAGAAGGCAGCCTAGCCAAAGCTACTACTGCACCTGCCACTACGCGCAA TACTGGCCG TGGCGGGGAGGAGAAGAAAAAGGAGAAAG AGAAAGAAGAACAG GAAGAGAGGGAGACCAAGACCCCTGAATGTCCATCCCATACCCAGCCGC TGGG CGTCTATCTCTTGACTCCCGCAGTACAGGACTTGTGGCTTAGAGATAAGGCCAC CTTTACATGTTTCGTCGTGGGCTCTGACCTGAAGGATGCCCATTTGACTTGGGA GGTTGCCGGAAAGGTACC CACAGGGGGGGTTGAGGAAGGGTTGCTGGAGCGCC ATTCCAATGGCTCTCAGAGCCAGCACTCAAGACTCACCCTTCCGAGATCCCTGT GGAACGCC GGGACCTCTGTCACATGTACTCTAAATCATCCTAG CCTGCCCCCAC AGCGTCTGATGGCCCTTAGAG AGCCAGCCGCCCAGGCACCAGTTAAGCTTAGCC TGAATCTGCTCGCCAGTAGTGATCCCCCAGAGG CCGCCAGCTGGCTCTTATGCG AAGTGTCCGGCTTTAGCCCGCCCAACATCTTGCTCATGTGGCTGGAGGACCAGC GAGAAGTGAACACCAGCGGCT TCGCTCCAGCCCGGCCCCCACCCCAGCCGGGT TCTACCACATTCTGGGCCTGGAGTGTCTTAAGGG TCCCAGCACCACCTAGCCCC CAGCCAGCCACATACACCTGTGTTGTGTCCCATGAAGATAGCAGG ACCCTGCTA AATGCTTCTAGGAGTCTGGAGGTTT CCTACGTGACTGACCATT (SEQ ID NO:9).

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO:10).

In some embodiments, the linker is encoded by a nucleotide sequence of GGTGGCGGAGGTTCTGGAGGTGGAGGTTCC (SEQ ID NO:11).

In one aspect, the hinge or spacer comprises a KIR2DS2 hinge.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term “effector function” refers to a specialized function of a cell. Effector function of a T cell, for example, may be cytolytic activity or helper activity including the secretion of cytokines. Thus the term “intracellular signaling domain” refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In one embodiment, a CAR of the invention comprises an intracellular signaling domain, e.g., a primary signaling domain of CD3-zeta.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signalling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). Further examples of such costimulatory molecules include CD5, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 14. In one aspect, the signaling domain of CD3-zeta is a signaling domain of SEQ ID NO: 18.

In one aspect, the intracellular signaling domain is designed to comprise the signaling domain of CD3-zeta and the signaling domain of CD27. In one aspect, the signaling domain of CD27 comprises an amino acid sequence of QRRKYRSNKGESPVEPAEPCRYSCPREEEGSTIP-IQEDYRKPEPACSP (SEQ ID NO:16). In one aspect, the signalling domain of CD27 is encoded by a nucleic acid sequence of AGGAGTAAGAGGAGCAGGCTCC TGCACAGTGACTACATGAACATGACTCCCCG CCGCCCCGGGCCCACCCGCAAGCATTACCAGCCC-TATGCCCCACCACGCGACTT CGCAGCC-TATCGCTCC (SEQ ID NO:17).

In one aspect, the CAR-expressing cell described herein can further comprise a second CAR, e.g., a second CAR that includes a different antigen binding domain, e.g., to the same target or a different target (e.g., a target other than a cancer associated antigen described herein or a different cancer associated antigen described herein). In one embodiment, the second CAR includes an antigen binding domain to a target expressed the same cancer cell type as the cancer associated antigen. In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, CD27 or OX-40, onto the first CAR, and the primary signaling domain, e.g., CD3 zeta, on the second CAR can limit the CAR activity to cells where both targets are expressed. In one embodiment, the CAR expressing cell comprises a first cancer associated antigen CAR that includes an antigen binding domain that binds a target antigen described herein, a transmembrane domain and a costimulatory domain and a second CAR that targets a different target antigen (e.g., an antigen expressed on that same cancer cell type as the first target antigen) and includes an antigen binding domain, a transmembrane domain and a primary signaling domain. In another embodiment, the CAR expressing cell comprises a first CAR that includes an antigen binding domain that binds a target antigen described herein, a transmembrane domain and a primary signaling domain and a second CAR that targets an antigen other than the first target antigen (e.g., an antigen expressed on the same cancer cell type as the first target antigen) and includes an antigen binding domain to the antigen, a transmembrane domain and a costimulatory signaling domain.

In one embodiment, the CAR-expressing cell comprises an XCAR described herein and an inhibitory CAR. In one embodiment, the inhibitory CAR comprises an antigen binding domain that binds an antigen found on normal cells but not cancer cells, e.g., normal cells that also express CLL. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 or TGFR beta.

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising antigen binding domains that minimize such interactions, as well as methods of making and using such cells and nucleic acids. In an embodiment the antigen binding domain of one of said first said second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, the claimed invention comprises a first and second CAR, wherein the antigen binding domain of one of said first CAR said second CAR does not comprise a variable light domain and a variable heavy domain. In some embodiments, the antigen binding domain of one of said first CAR said second CAR is an scFv, and the other is not an scFv. In some embodiments, the antigen binding domain of one of said first CAR said second CAR comprises a single VH domain, e.g., a camelid, shark, or lamprey single VH domain, or a single VH domain derived from a human or mouse sequence. In some embodiments, the antigen binding domain of one of said first CAR said second CAR comprises a nanobody. In some embodiments, the antigen binding domain of one of said first CAR said second CAR comprises a camelid VHH domain.

In some embodiments, the antigen binding domain of one of said first CAR said second CAR comprises an scFv, and the other comprises a single VH domain, e.g., a camelid, shark, or lamprey single VH domain, or a single VH domain derived from a human or mouse sequence. In some embodiments, the antigen binding domain of one of said first CAR said second CAR comprises an scFv, and the other comprises a nanobody. In some embodiments, the antigen binding domain of one of said first CAR said second CAR comprises an scFv, and the other comprises a camelid VHH domain.

In some embodiments, when present on the surface of a cell, binding of the antigen binding domain of said first CAR to its cognate antigen is not substantially reduced by the presence of said second CAR. In some embodiments, binding of the antigen binding domain of said first CAR to its cognate antigen in the presence of said second CAR is 85%, 90%, 95%, 96%, 97%, 98% or 99% of binding of the antigen binding domain of said first CAR to its cognate antigen in the absence of said second CAR.

In some embodiments, when present on the surface of a cell, the antigen binding domains of said first CAR said second CAR, associate with one another less than if both were scFv antigen binding domains. In some embodiments, the antigen binding domains of said first CAR said second CAR, associate with one another 85%, 90%, 95%, 96%, 97%, 98% or 99% less than if both were scFv antigen binding domains.

In another aspect, the CAR-expressing cell described herein can further express another agent, e.g., an agent which enhances the activity of a CAR-expressing cell. For example, in one embodiment, the agent can be an agent which inhibits an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. In one embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094) Immune suppression can be reversed by inhibiting the local interaction of PD1 with PD-L1.

In one embodiment, the agent comprises the extracellular domain (ECD) of an inhibitory molecule, e.g., Programmed Death 1 (PD1), fused to a transmembrane domain and intracellular signaling domains such as 41BB and CD3 zeta (also referred to herein as a PD1 CAR). In one embodiment, the PD1 CAR, when used in combinations with a XCAR described herein, improves the persistence of the T cell. In one embodiment, the CAR is a PD1 CAR comprising the extracellular domain of PD1 indicated as underlined in SEQ ID NO: 26. In one embodiment, the PD1 CAR comprises the amino acid sequence of SEQ ID NO:26.

(SEQ ID NO: 26)

```
Malpvtalllplalllhaarppgwfldspdrpwnpptfspallvvtegdn
atftcsfsntsesfvlnwyrmspsnqtdklaafpedrsqpgqdcrfrvtq
lpngrdfhmsvvrarrndsgtylcgaislapkaqikeshaelryterrae
vptahpspsprpagqfqtlvtttpaprpptpaptiasqplslrpeacrpa
aggavhtrgldfacdiyiwaplagtcgvlllslvitlyckrgrkkllyif
kqpfmrpvqttqeedgcscrfpeeeeggcelrvkfsrsadapaykqgqnq
lynelnlgrreeydvldkrrgrdpemggkprrknpqeglynelqkdkmae
ayseigmkgerrrgkghdglyqglstatkdtydalhmqalppr.
```

In one embodiment, the PD1 CAR comprises the amino acid sequence provided below (SEQ ID NO:39).

(SEQ ID NO: 39)

```
pgwfldspdrpwnpptfspallvvtegdnatftcsfsntsesfylnwyrm
spsnqtdklaafpedrsqpgqdcrfrvtqlpngrdfhmsvvrarrndsgt
ylcgaislapkaqikeshaelrvterraevptahpspsprpagqfqtlvt
ttpaprpptpaptiasqplslrpeacrpaaggavhtrgldfacdiyiwap
lagtcgvlllslvitlyckrgrkkllyifkqpfmrpvqttqeedgcscrf
peeeeggcelrvkfsrsadapaykqgqnqlynelnlgrreeydvldkrrg
rdpemggkprrknpqeglynelqkdkmaeayseigmkgerrrgkghdgly
qglstatkdtydalhmqalppr.
```

In one embodiment, the agent comprises a nucleic acid sequence encoding the PD1 CAR, e.g., the PD1 CAR described herein. In one embodiment, the nucleic acid sequence for the PD1 CAR is shown below, with the PD1 ECD underlined below in SEQ ID NO: 27

(SEQ ID NO: 27)

```
atggccctccctgtcactgccctgcttctccccctcgcactcctgctcca
cgccgctagaccacccggatggtttctggactctccggatcgcccgtgga
atcccccaaccttctcaccggcactcaggagtgactgagggcgataatgc
gaccacacgtgctcgttctccaacacctccgaatcattcgtgctgaactg
gtaccgcatgagcccgtcaaaccagaccgacaagctcgccgcgtaccgga
agatcggtcgcaaccgggacaggattgtcggttccgcgtgactcaactgc
cgaatggcagagacttccacatgagcgtggtccgcgctaggcgaaacgac
tccgggacctacctgtgcggagccatctcgctggcgcctaaggcccaaat
caaagagagcttgagggccgaactgagagtgaccgagcgcagagctgagg
tgccaactgcacatccatccccatcgcctcggcctgcggggcagtttcag
accctggtcacgaccactccggcgccgcgcccaccgactccggccccaac
tatcgcgagccagcccctgtcgctgaggccggaagcatgccgccctgccg
ccggaggtgctgtgcatacccggggattggacttcgcatgcgacatctac
```

-continued

```
atagggctcctctcgccggaacttgtggcgtgctccttctgtccctggtc

atcaccctgtactgcaagcggggtcggaaaaagatctgtacattacaagc

agccatcatgaggcccgtgcaaaccacccaggaggaggacggagctcctg

ccggaccccgaagaggaagaaggaggagcgagctgcgcgtgaagactccc

ggagcgccgacgcccccgcctataagcagggccagaaccagctgtacaac

gaactgaacctgggacggcgggaagagtacgatgtgctggacaagcggcg

cggccgggaccccgaaatgggcgggaagcctagaagaaagaaccctcagg

aaggcctgtataacgagctgcagaaggacaagatggccgaggcctactcc

gaaattgggatgaagggagagcggcggaggggaaaggggcacgacggcct

gtaccaaggactgtccaccgccaccaaggacacatacgatgccctgcaca

tgcaggcccttccccctcgc.
```

In another aspect, the present invention provides a population of CAR-expressing cells, e.g., CART cells. In some embodiments, the population of CAR-expressing cells comprises a mixture of cells expressing different CARs. For example, in one embodiment, the population of CART cells can include a first cell expressing a CAR having an antigen binding domain to a cancer associated antigen described herein, and a second cell expressing a CAR having a different antigen binding domain, e.g., an antigen binding domain to a different a cancer associated antigen described herein, e.g., an antigen binding domain to a cancer associated antigen described herein that differs from the cancer associated antigen bound by the antigen binding domain of the CAR expressed by the first cell. As another example, the population of CAR-expressing cells can include a first cell expressing a CAR that includes an antigen binding domain to a cancer associated antigen described herein, and a second cell expressing a CAR that includes an antigen binding domain to a target other than a cancer associated antigen as described herein. In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an antigen binding domain to a cancer associated antigen described herein, and a second cell expressing another agent, e.g., an agent which enhances the activity of a CAR-expressing cell. For example, in one embodiment, the agent can be an agent which inhibits an inhibitory molecule. Inhibitory molecules, e.g., PD-1, can, in some embodiments, decrease the ability of a CAR-expressing cell to mount an immune effector response. Examples of inhibitory molecules include PD-1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. In one embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 or TGFR beta, or a fragment of any of these, and a second polypeptide which is an intracellular signaling domain described herein (e.g., comprising a costimulatory domain (e.g., 41BB, CD27, OX40 or CD28, e.g., as described herein) and/or a primary signaling domain (e.g., a CD3 zeta signaling domain described herein). In one embodiment, the agent comprises a first polypeptide of PD-1 or a fragment thereof, and a second polypeptide of an intracellular signaling domain described herein (e.g., a CD28 signaling domain described herein and/or a CD3 zeta signaling domain described herein).

In one aspect, the present invention provides methods comprising administering a population of CAR-expressing cells, e.g., CART cells, e.g., a mixture of cells expressing different CARs, in combination with another agent, e.g., a kinase inhibitor, such as a kinase inhibitor described herein. In another aspect, the present invention provides methods comprising administering a population of cells wherein at least one cell in the population expresses a CAR having an antigen binding domain of a cancer associated antigen described herein, and a second cell expressing another agent, e.g., an agent which enhances the activity of a CAR-expressing cell, in combination with another agent, e.g., a kinase inhibitor, such as a kinase inhibitor described herein.

Regulatable Chimeric Antigen Receptors

In some embodiments, a regulatable CAR (RCAR) where the CAR activity can be controlled is desirable to optimize the safety and efficacy of a CAR therapy. There are many ways CAR activities can be regulated. For example, inducible apoptosis using, e.g., a caspase fused to a dimerization domain (see, e.g., Di et al., N Egnl. J. Med. 2011 Nov. 3; 365(18):1673-1683), can be used as a safety switch in the CAR therapy of the instant invention. In an aspect, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain.

In an aspect, an RCAR comprises two polypeptides or members: 1) an intracellular signaling member comprising an intracellular signaling domain, e.g., a primary intracellular signaling domain described herein, and a first switch domain; 2) an antigen binding member comprising an antigen binding domain, e.g., that targets a tumor antigen described herein, as described herein and a second switch domain Optionally, the RCAR comprises a transmembrane domain described herein. In an embodiment, a transmembrane domain can be disposed on the intracellular signaling member, on the antigen binding member, or on both. (Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to a intracellular signaling domain can be different, e.g., reversed).

In an embodiment, the first and second switch domains can form an intracellular or an extracellular dimerization switch. In an embodiment, the dimerization switch can be a homodimerization switch, e.g., where the first and second switch domain are the same, or a heterodimerization switch, e.g., where the first and second switch domain are different from one another.

In embodiments, an RCAR can comprise a “multi switch.” A multi switch can comprise heterodimerization switch domains or homodimerization switch domains. A multi switch comprises a plurality of, e.g., 2, 3, 4, 5, 6, 7, 8, 9, or 10, switch domains, independently, on a first member, e.g., an antigen binding member, and a second member, e.g., an intracellular signaling member. In an embodiment, the first member can comprise a plurality of first switch domains, e.g., FKBP-based switch domains, and the second member can comprise a plurality of second switch domains, e.g., FRB-based switch domains. In an embodiment, the first member can comprise a first and a second switch domain, e.g., a FKBP-based switch domain and a FRB-based switch domain, and the second member can comprise a first and a second switch domain, e.g., a FKBP-based switch domain and a FRB-based switch domain.

In an embodiment, the intracellular signaling member comprises one or more intracellular signaling domains, e.g., a primary intracellular signaling domain and one or more costimulatory signaling domains.

In an embodiment, the antigen binding member may comprise one or more intracellular signaling domains, e.g., one or more costimulatory signaling domains. In an embodiment, the antigen binding member comprises a plurality, e.g., 2 or 3 costimulatory signaling domains described herein, e.g., selected from 41BB, CD28, CD27, ICOS, and OX40, and in embodiments, no primary intracellular signaling domain. In an embodiment, the antigen binding member comprises the following costimulatory signaling domains, from the extracellular to intracellular direction: 41BB-CD27; 41BB-CD27; CD27-41BB; 41BB-CD28; CD28-41BB; OX40-CD28; CD28-OX40; CD28-41BB; or 41BB-CD28. In such embodiments, the intracellular binding member comprises a CD3zeta domain. In one such embodiment the RCAR comprises (1) an antigen binding member comprising, an antigen binding domain, a transmembrane domain, and two costimulatory domains and a first switch domain; and (2) an intracellular signaling domain comprising a transmembrane domain or membrane tethering domain and at least one primary intracellular signaling domain, and a second switch domain.

An embodiment provides RCARs wherein the antigen binding member is not tethered to the surface of the CAR cell. This allows a cell having an intracellular signaling member to be conveniently paired with one or more antigen binding domains, without transforming the cell with a sequence that encodes the antigen binding member. In such embodiments, the RCAR comprises: 1) an intracellular signaling member comprising: a first switch domain, a transmembrane domain, an intracellular signaling domain, e.g., a primary intracellular signaling domain, and a first switch domain; and 2) an antigen binding member comprising: an antigen binding domain, and a second switch domain, wherein the antigen binding member does not comprise a transmembrane domain or membrane tethering domain, and, optionally, does not comprise an intracellular signaling domain. In some embodiments, the RCAR may further comprise 3) a second antigen binding member comprising: a second antigen binding domain, e.g., a second antigen binding domain that binds a different antigen than is bound by the antigen binding domain; and a second switch domain.

Also provided herein are RCARs wherein the antigen binding member comprises bispecific activation and targeting capacity. In this embodiment, the antigen binding member can comprise a plurality, e.g., 2, 3, 4, or 5 antigen binding domains, e.g., scFvs, wherein each antigen binding domain binds to a target antigen, e.g. different antigens or the same antigen, e.g., the same or different epitopes on the same antigen. In an embodiment, the plurality of antigen binding domains are in tandem, and optionally, a linker or hinge region is disposed between each of the antigen binding domains. Suitable linkers and hinge regions are described herein.

An embodiment provides RCARs having a configuration that allows switching of proliferation. In this embodiment, the RCAR comprises: 1) an intracellular signaling member comprising: optionally, a transmembrane domain or membrane tethering domain; one or more co-stimulatory signaling domain, e.g., selected from 41BB, CD28, CD27, ICOS, and OX40, and a switch domain; and 2) an antigen binding member comprising: an antigen binding domain, a transmembrane domain, and a primary intracellular signaling domain, e.g., a CD3zeta domain, wherein the antigen binding member does not comprise a switch domain, or does not comprise a switch domain that dimerizes with a switch domain on the intracellular signaling member. In an embodiment, the antigen binding member does not comprise a co-stimulatory signaling domain. In an embodiment, the intracellular signaling member comprises a switch domain from a homodimerization switch. In an embodiment, the intracellular signaling member comprises a first switch domain of a heterodimerization switch and the RCAR comprises a second intracellular signaling member which comprises a second switch domain of the heterodimerization switch. In such embodiments, the second intracellular signaling member comprises the same intracellular signaling domains as the intracellular signaling member. In an embodiment, the dimerization switch is intracellular. In an embodiment, the dimerization switch is extracellular.

In any of the RCAR configurations described here, the first and second switch domains comprise a FKBP-FRB based switch as described herein.

Also provided herein are cells comprising an RCAR described herein. Any cell that is engineered to express a RCAR can be used as a RCARX cell. In an embodiment the RCARX cell is a T cell, and is referred to as a RCART cell. In an embodiment the RCARX cell is an NK cell, and is referred to as a RCARN cell.

Also provided herein are nucleic acids and vectors comprising RCAR encoding sequences. Sequence encoding various elements of an RCAR can be disposed on the same nucleic acid molecule, e.g., the same plasmid or vector, e.g., viral vector, e.g., lentiviral vector. In an embodiment, (i) sequence encoding an antigen binding member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products). In an embodiment, a sequence encoding a cleavable peptide, e.g., a P2A or F2A sequence, is disposed between (i) and (ii). In an embodiment, a sequence encoding an IRES, e.g., an EMCV or EV71 IRES, is disposed between (i) and (ii). In these embodiments, (i) and (ii) are transcribed as a single RNA. In an embodiment, a first promoter is operably linked to (i) and a second promoter is operably linked to (ii), such that (i) and (ii) are transcribed as separate mRNAs.

Alternatively, the sequence encoding various elements of an RCAR can be disposed on the different nucleic acid molecules, e.g., different plasmids or vectors, e.g., viral vector, e.g., lentiviral vector. E.g., the (i) sequence encoding an antigen binding member can be present on a first nucleic acid, e.g., a first vector, and the (ii) sequence encoding an intracellular signaling member can be present on the second nucleic acid, e.g., the second vector.

Dimerization Switches

Dimerization switches can be non-covalent or covalent. In a non-covalent dimerization switch, the dimerization molecule promotes a non-covalent interaction between the switch domains. In a covalent dimerization switch, the dimerization molecule promotes a covalent interaction between the switch domains.

In an embodiment, the RCAR comprises a FKBP/FRAP, or FKBP/FRB-based dimerization switch. FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR). FRB is a 93 amino acid portion of FRAP, that is sufficient for binding the FKBP-rapamycin complex (Chen, J., Zheng, X. F., Brown, E. J. & Schreiber, S. L. (1995) *Identification of an 11-kDa FKBP12-rapamycin-binding domain within the 289-kDa FKBP12-rapamycin-associated protein and characterization of a critical serine residue*. Proc Natl Acad Sci USA 92: 4947-51.)

In embodiments, an FKBP/FRAP, e.g., an FKBP/FRB, based switch can use a dimerization molecule, e.g., rapamycin or a rapamycin analog.

The amino acid sequence of FKBP is as follows:

(SEQ ID NO: 52)

```
D V P D Y A S L G G P S S P K K K R K V S R G V Q
V E T I S P G D G R T F P K R G Q T C V V H Y T G
M L E D G K K F D S S R D R N K P F K F M L G K Q
E V I R G W E E G V A Q M S V G Q R A K L T I S P
D Y A Y G A T G H P G I I P P H A T L V F D V E L
L K L E T S Y
```

In embodiments, an FKBP switch domain can comprise a fragment of FKBP having the ability to bind with FRB, or a fragment or analog thereof, in the presence of rapamycin or a rapalog, e.g., the underlined portion of SEQ ID NO: 52, which is:

(SEQ ID NO: 53)

```
V Q V E T I S P G D G R T F P K R G Q T C V V H Y
T G M L E D G K K F D S S R D R N K P F K F M L G
K Q E V I R G W E E G V A Q M S V G Q R A K L T I
S P D Y A Y G A T G H P G I I P P H A T L V F D V
E L L K L E T S
```

The amino acid sequence of FRB is as follows:

(SEQ ID NO: 54)

```
ILWHEMWHEG LEEASRLYFG ERNVKGMFEV LEPLHAMMER
GPQTLKETSF NQAYGRDLME AQEWCRKYMK SGNVKDLTQA
WDLYYHVFRR ISK
```

"FKBP/FRAP, e.g., an FKBP/FRB, based switch" as that term is used herein, refers to a dimerization switch comprising: a first switch domain, which comprises an FKBP fragment or analog thereof having the ability to bind with FRB, or a fragment or analog thereof, in the presence of rapamycin or a rapalog, e.g., RAD001, and has at least 70, 75, 80, 85, 90, 95, 96, 97, 98, or 99% identity with, or differs by no more than 30, 25, 20, 15, 10, 5, 4, 3, 2, or 1 amino acid residues from, the FKBP sequence of SEQ ID NO: 52 or 53; and a second switch domain, which comprises an FRB fragment or analog thereof having the ability to bind with FRB, or a fragment or analog thereof, in the presence of rapamycin or a rapalog, and has at least 70, 75, 80, 85, 90, 95, 96, 97, 98, or 99% identity with, or differs by no more than 30, 25, 20, 15, 10, 5, 4, 3, 2, or 1 amino acid residues from, the FRB sequence of SEQ ID NO: 54. In an embodiment, a RCAR described herein comprises one switch domain comprises amino acid residues disclosed in SEQ ID NO: 52 (or SEQ ID NO: 53), and one switch domain comprises amino acid residues disclosed in SEQ ID NO: 54.

In embodiments, the FKBP/FRB dimerization switch comprises a modified FRB switch domain that exhibits altered, e.g., enhanced, complex formation between an FRB-based switch domain, e.g., the modified FRB switch domain, a FKBP-based switch domain, and the dimerization molecule, e.g., rapamycin or a rapalogue, e.g., RAD001. In an embodiment, the modified FRB switch domain comprises one or more mutations, e.g., 2, 3, 4, 5, 6, 7, 8, 9, 10 or more, selected from mutations at amino acid position(s) L2031, E2032, S2035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032 M), arginine (E2032R), valine (E2032V), tyrosine (E2032Y), isoleucine (E2032I), e.g., SEQ ID NO: 55, or leucine (E2032L), e.g., SEQ ID NO: 56. In an embodiment, a mutant FRB comprises a mutation at T2098, where T2098 is mutated to phenylalanine (T2098F) or leucine (T2098L), e.g., SEQ ID NO: 57. In an embodiment, a mutant FRB comprises a mutation at E2032 and at T2098, where E2032 is mutated to any amino acid, and where T2098 is mutated to any amino acid, e.g., SEQ ID NO: 58. In an embodiment, a mutant FRB comprises an E2032I and a T2098L mutation, e.g., SEQ ID NO: 59. In an embodiment, a mutant FRB comprises an E2032L and a T2098L mutation, e.g., SEQ ID NO: 60.

TABLE 1D

Exemplary mutant FRB having increased affinity for a dimerization molecule.

| FRB mutant | Amino Acid Sequence | SEQ ID NO: |
|---|---|---|
| E2032I mutant | ILWHEMWHEGLIEASRLYFGERNVKGMFEVLEPLHAMMERGPQTLKETSFN QAYGRDLMEAQEWCRKYMKSGNVKDLTQAWDLYYHVFRRISKTS | 55 |
| E2032L mutant | ILWHEMWHEGLLEASRLYFGERNVKGMFEVLEPLHAMMERGPQTLKETSFN QAYGRDLMEAQEWCRKYMKSGNVKDLTQAWDLYYHVFRRISKTS | 56 |
| T2098L mutant | ILWHEMWHEGLEEASRLYFGERNVKGMFEVLEPLHAMMERGPQTLKETSFN QAYGRDLMEAQEWCRKYMKSGNVKDLLQAWDLYYHVFRRISKTS | 57 |
| E2032, T2098 mutant | ILWHEMWHEGL**X**EASRLYFGERNVKGMFEVLEPLHAMMERGPQTLKETSFN QAYGRDLMEAQEWCRKYMKSGNVKDL**X**QAWDLYYHVFRRISKTS | 58 |
| E2032I, T2098L mutant | ILWHEMWHEGLIEASRLYFGERNVKGMFEVLEPLHAMMERGPQTLKETSFN QAYGRDLMEAQEWCRKYMKSGNVKDLLQAWDLYYHVFRRISKTS | 59 |
| E2032L, T2098L mutant | ILWHEMWHEGLLEASRLYFGERNVKGMFEVLEPLHAMMERGPQTLKETSFN QAYGRDLMEAQEWCRKYMKSGNVKDLLQAWDLYYHVFRRISKTS | 60 |

Other suitable dimerization switches include a GyrB-GyrB based dimerization switch, a Gibberellin-based dimerization switch, a tag/binder dimerization switch, and a halo-tag/snap-tag dimerization switch. Following the guidance provided herein, such switches and relevant dimerization molecules will be apparent to one of ordinary skill.

Dimerization Molecule

Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

Rapamycin and rapamycin analogs (sometimes referred to as rapalogues), e.g., RAD001, can be used as dimerization molecules in a FKBP/FRB-based dimerization switch described herein. In an embodiment the dimerization molecule can be selected from rapamycin (sirolimus), RAD001 (everolimus), zotarolimus, temsirolimus, AP-23573 (ridaforolimus), biolimus and AP21967. Additional rapamycin analogs suitable for use with FKBP/FRB-based dimerization switches are further described in the section entitled "Combination Therapies", or in the subsection entitled "Exemplary mTOR inhibitors".

Split CAR

In some embodiments, the CAR-expressing cell uses a split CAR. The split CAR approach is described in more detail in publications WO2014/055442 and WO2014/055657. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:32). RNA so produced can efficiently transfect different kinds of cells. In one aspect, the template includes sequences for the CAR.

In one aspect, a CAR of the present invention is encoded by a messenger RNA (mRNA). In one aspect, the mRNA encoding a CAR described herein is introduced into an immune effector cell, e.g., a T cell or a NK cell, for production of a CAR-expressing cell, e.g., a CART cell or a CAR NK cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR described herein. For example, the template for the RNA CAR comprises an extracellular region comprising a single chain variable domain of an antibody to a tumor associated antigen described herein; a hinge region (e.g., a hinge region described herein), a transmembrane domain (e.g., a transmembrane domain described herein such as a transmembrane domain of CD8a); and a cytoplasmic region that includes an intracellular signaling domain, e.g., an intracellular signaling domain described herein, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. “Substantially complementary,” as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. “Forward primers” are primers that contain a region of nucleotides that are substantially complementary to nucleotides on the DNA template that are upstream of the DNA sequence that is to be amplified. “Upstream” is used herein to refer to a location 5, to the DNA sequence to be amplified relative to the coding strand. “Reverse primers” are primers that contain a region of nucleotides that are substantially complementary to a double-stranded DNA template that are downstream of the DNA sequence that is to be amplified. “Downstream” is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 35) (size can be 50-5000 T (SEQ ID NO: 36)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 37).

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides (SEQ ID NO: 38) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1 (2011):R14-20; Singh et al. Cancer Res. 15 (2008):2961-2971; Huang et al. Mol. Ther. 16 (2008):580-589; Grabundzija et al. Mol. Ther. 18 (2010):1200-1209; Kebriaei et al. Blood. 122.21 (2013): 166; Williams. Molecular Therapy 16.9 (2008):1515-16; Bell et al. Nat. Protoc. 2.12 (2007):3153-65; and Ding et al. Cell. 122.3 (2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3 (2013): 1829-47; and Singh et al. Cancer Res. 68.8 (2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Nucleic Acid Constructs Encoding a CAR

The present invention also provides nucleic acid molecules encoding one or more CAR constructs described herein. In one aspect, the nucleic acid molecule is provided as a messenger RNA transcript. In one aspect, the nucleic acid molecule is provided as a DNA construct.

Accordingly, in one aspect, the invention pertains to a nucleic acid molecule encoding a chimeric antigen receptor (CAR), wherein the CAR comprises an antigen binding domain that binds to a tumor antigen described herein, a transmembrane domain (e.g., a transmembrane domain described herein), and an intracellular signaling domain (e.g., an intracellular signaling domain described herein) comprising a stimulatory domain, e.g., a costimulatory signaling domain (e.g., a costimulatory signaling domain described herein) and/or a primary signaling domain (e.g., a primary signaling domain described herein, e.g., a zeta chain described herein). In one embodiment, the transmembrane domain is transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp.

In one embodiment, the transmembrane domain comprises a sequence of SEQ ID NO: 12, or a sequence with 95-99% identity thereof. In one embodiment, the antigen binding domain is connected to the transmembrane domain by a hinge region, e.g., a hinge described herein. In one embodiment, the hinge region comprises SEQ ID NO:4 or SEQ ID NO:6 or SEQ ID NO:8 or SEQ ID NO:10, or a sequence with 95-99% identity thereof. In one embodiment, the isolated nucleic acid molecule further comprises a sequence encoding a costimulatory domain. In one embodiment, the costimulatory domain is a functional signaling domain of a protein selected from the group consisting of OX40, CD27, CD28, CD5, ICAM-1, LFA-1 (CD11a/CD18), ICOS (CD278), and 4-1BB (CD137). Further examples of such costimulatory molecules include CD5, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, and PAG/Cbp. In one embodiment, the costimulatory domain comprises a sequence of SEQ ID NO:16, or a sequence with 95-99% identity thereof. In one embodiment, the intracellular signaling domain comprises a functional signaling domain of 4-1BB and a functional signaling domain of CD3 zeta. In one embodiment, the intracellular signaling domain comprises the sequence of SEQ ID NO: 14 or SEQ ID NO:16, or a sequence with 95-99% identity thereof, and the sequence of SEQ ID NO: 18 or SEQ ID NO:20, or a sequence with 95-99% identity thereof, wherein the sequences comprising the intracellular signaling domain are expressed in the same frame and as a single polypeptide chain.

In another aspect, the invention pertains to an isolated nucleic acid molecule encoding a CAR construct comprising a leader sequence of SEQ ID NO: 2, a scFv domain as described herein, a hinge region of SEQ ID NO:4 or SEQ ID NO:6 or SEQ ID NO:8 or SEQ ID NO:10 (or a sequence with 95-99% identity thereof), a transmembrane domain having a sequence of SEQ ID NO: 12 (or a sequence with 95-99% identity thereof), a 4-1BB costimulatory domain having a sequence of SEQ ID NO:14 or a CD27 costimulatory domain having a sequence of SEQ ID NO:16 (or a sequence with 95-99% identity thereof), and a CD3 zeta stimulatory domain having a sequence of SEQ ID NO:18 or SEQ ID NO:20 (or a sequence with 95-99% identity thereof).

In another aspect, the invention pertains to a nucleic acid molecule encoding a chimeric antigen receptor (CAR) molecule that comprises an antigen binding domain, a transmembrane domain, and an intracellular signaling domain comprising a stimulatory domain, and wherein said antigen binding domain binds to a tumor antigen selected from a group consisting of: CD19, CD123, CD22, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, SSEA-4, CD20, Folate receptor alpha, ERBB2 (Her2/neu), MUC1, EGFR, NCAM, Prostase, PRSS21, PAP, ELF2 M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In one embodiment, the encoded CAR molecule further comprises a sequence encoding a costimulatory domain. In one embodiment, the costimulatory domain is a functional signaling domain of a protein selected from the group consisting of OX40, CD27, CD28, CD5, ICAM-1, LFA-1 (CD11a/CD18) and 4-1BB (CD137). In one embodiment, the costimulatory domain comprises a sequence of SEQ ID NO:14. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO:12. In one embodiment, the intracellular signaling domain comprises a functional signaling domain of 4-1BB and a functional signaling domain of zeta. In one embodiment, the intracellular signaling domain comprises the sequence of SEQ ID NO: 14 and the sequence of SEQ ID NO: 18, wherein the sequences comprising the intracellular signaling domain are expressed in the same frame and as a single polypeptide chain. In one embodiment, the anti-a cancer associated antigen as described herein binding domain is connected to the transmembrane domain by a hinge region. In one embodiment, the hinge region comprises SEQ ID NO:4. In one embodiment, the hinge region comprises SEQ ID NO:6 or SEQ ID NO:8 or SEQ ID NO:10.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, crisper, CAS9, and zinc finger nucleases. See below June et al. 2009 *Nature Reviews Immunology* 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

An example of a promoter that is capable of expressing a CAR encoding nucleic acid molecule in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from nucleic acid molecules cloned into a lentiviral vector. See, e.g., Milone et al., Mol. Ther. 17(8): 1453-1464 (2009). In one aspect, the EF1a promoter comprises the sequence provided as SEQ ID NO:1.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell or a NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian immune effector cells (e.g., T cells, NK cells). In one aspect, the mammalian T cell is a human T cell. In one aspect, the mammalian NK cell is a human NK cell.

Sources of Cells

Prior to expansion and genetic modification or other modification, a source of cells, e.g., T cells or natural killer (NK) cells, can be obtained from a subject. The term "subject" is intended to include living organisms in which an immune response can be elicited (e.g., mammals). Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain aspects of the present disclosure, immune effector cells, e.g., T cells, can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In one aspect, T cells are isolated from peripheral blood lymphocytes by lysing the red blood cells and depleting the monocytes, for example, by centrifugation through a PERCOLL™ gradient or by counterflow centrifugal elutriation.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6\times10^9$ CD25+ T cells. In other aspects, the population of immune effector cells to be depleted include about $1\times10^9$ to $1\times10^{10}$ CD25+ T cell, and any integer value in between. In one embodiment, the resulting population T regulatory depleted cells has $2\times10^9$ T regulatory cells, e.g., CD25+ cells, or less (e.g., $1\times10^9$, $5\times10^8$, $1\times10^8$, $5\times10^7$, $1\times10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B7-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

Methods described herein can include a positive selection step. For example, T cells can isolated by incubation with anti-CD3/anti-CD28 (e.g., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours, e.g., 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 10 billion cells/ml, 9 billion/ml, 8 billion/ml, 7 billion/ml, 6 billion/ml, or 5 billion/ml is used. In one aspect, a concentration of 1 billion cells/ml is used. In yet one aspect, a concentration of cells from 75, 80, 85, 90, 95, or 100 million cells/ml is used. In further aspects, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5\times10^6$/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diacylglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression.

Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogeneic CAR

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class I and/or HLA class II, is downregulated.

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not express or expresses at low levels an inhibitory molecule, e.g. by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA in a T cell.

Expression of siRNA and shRNAs in T cells can be achieved using any conventional expression system, e.g., such as a lentiviral expression system.

Exemplary shRNAs that downregulate expression of components of the TCR are described, e.g., in US Publication No.: 2012/0321667. Exemplary siRNA and shRNA that downregulate expression of HLA class I and/or HLA class II genes are described, e.g., in U.S. publication No.: US 2007/0036773.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene.

Naturally-occurring CRISPR/Cas systems are found in approximately 40% of sequenced eubacteria genomes and 90% of sequenced archaea. Grissa et al. (2007) *BMC Bioinformatics* 8: 172. This system is a type of prokaryotic immune system that confers resistance to foreign genetic elements such as plasmids and phages and provides a form of acquired immunity. Barrangou et al. (2007) *Science* 315: 1709-1712; Marragini et al. (2008) *Science* 322: 1843-1845.

The CRISPR/Cas system has been modified for use in gene editing (silencing, enhancing or changing specific genes) in eukaryotes such as mice or primates. Wiedenheft et al. (2012) *Nature* 482: 331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) *Science* 327: 167-170; Makarova et al. (2006) *Biology Direct* 1: 7. The spacers thus serve as templates for RNA molecules, analogously to siRNAs. Pennisi (2013) *Science* 341: 833-836.

As these naturally occur in many different types of bacteria, the exact arrangements of the CRISPR and structure, function and number of Cas genes and their product differ somewhat from species to species. Haft et al. (2005)

*PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341: 833-836.

The CRISPR/Cas system can thus be used to edit a TCR and/or HLA gene (adding or deleting a basepair), or introducing a premature stop which thus decreases expression of a TCR and/or HLA. The CRISPR/Cas system can alternatively be used like RNA interference, turning off TCR and/or HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in U.S. Publication No. 20140068797, and Cong (2013) Science 339: 819-823. Other artificial CRISPR/Cas systems that are known in the art may also be generated which inhibit TCR and/or HLA, e.g., that described in Tsai (2014) Nature Biotechnol., 32:6 569-576, U.S. Pat. Nos. 8,871,445; 8,865,406; 8,795,965; 8,771,945; and 8,697,359.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene.

TALENs are produced artificially by fusing a TAL effector DNA binding domain to a DNA cleavage domain. Transcription activator-like effects (TALEs) can be engineered to bind any desired DNA sequence, including a portion of the HLA or TCR gene. By combining an engineered TALE with a DNA cleavage domain, a restriction enzyme can be produced which is specific to any desired DNA sequence, including a HLA or TCR sequence. These can then be introduced into a cell, wherein they can be used for genome editing. Boch (2011) *Nature Biotech.* 29: 135-6; and Boch et al. (2009) *Science* 326: 1509-12; Moscou et al. (2009) *Science* 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated Fold endonuclease. Several mutations to FokI have been made for its use in TALENs; these, for example, improve cleavage specificity or activity. Cermak et al. (2011) *Nucl. Acids Res.* 39: e82; Miller et al. (2011) *Nature Biotech.* 29: 143-8; Hockemeyer et al. (2011) *Nature Biotech.* 29: 731-734; Wood et al. (2011) *Science* 333: 307; Doyon et al. (2010) *Nature Methods* 8: 74-79; Szczepek et al. (2007) *Nature Biotech.* 25: 786-793; and Guo et al. (2010) *J. Mol. Biol.* 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29: 143-8.

A HLA or TCR TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the HLA or TCR gene or introduce such a defect into a wt HLA or TCR gene, thus decreasing expression of HLA or TCR.

TALENs specific to sequences in HLA or TCR can be constructed using any method known in the art, including various schemes using modular components. Zhang et al. (2011) *Nature Biotech.* 29: 149-53; Geibler et al. (2011) *PLoS ONE* 6: e19509.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene.

Like a TALEN, a ZFN comprises a Fold nuclease domain (or derivative thereof) fused to a DNA-binding domain. In the case of a ZFN, the DNA-binding domain comprises one or more zinc fingers. Carroll et al. (2011) *Genetics Society of America* 188: 773-782; and Kim et al. (1996) *Proc. Natl. Acad. Sci. USA* 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) *Proc. Natl. Acad. Sci. USA* 95: 10570-5.

Also like a TALEN, a ZFN can create a double-stranded break in the DNA, which can create a frame-shift mutation if improperly repaired, leading to a decrease in the expression and amount of HLA and/or TCR in a cell. ZFNs can also be used with homologous recombination to mutate in the HLA or TCR gene.

ZFNs specific to sequences in HLA AND/OR TCR can be constructed using any method known in the art. See, e.g., Provasi (2011) Nature Med. 18: 807-815; Torikai (2013)

Blood 122: 1341-1349; Cathomen et al. (2008) *Mol. Ther.* 16: 1200-7; Guo et al. (2010) *J. Mol. Biol.* 400: 96; U.S. Patent Publication 2011/0158957; and U.S. Patent Publication 2012/0060230.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In one aspect, the disclosure features a method of making a population of immune effector cells (e.g., T cells, NK cells). In an embodiment, the method comprises: providing a population of immune effector cells (e.g., T cells or NK cells), contacting the population of immune effector cells with a nucleic acid encoding a CAR; and contacting the population of immune effector cells with a nucleic acid encoding a telomerase subunit, e.g., hTERT, under conditions that allow for CAR and telomerase expression.

In an embodiment, the nucleic acid encoding the telomerase subunit is DNA. In an embodiment, the nucleic acid encoding the telomerase subunit comprises a promoter capable of driving expression of the telomerase subunit.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as follows:

```
                                       (SEQ ID NO: 61)
MPRAPRCRAVRSLLRSHYREVLPLATFVRRLGPQGWRLVQRGDPAAFRAL

VAQCLVCVPWDARPPPAAPSFRQVSCLKELVARVLQRLCERGAKNVLAFG

FALLDGARGGPPEAFTTSVRSYLPNTVTDALRGSGAWGLLLRRVGDDVLV
```

-continued

```
HLLARCALFVLVAPSCAYQVCGPPLYQLGAATQARPPPHASGPRRRLGCE

RAWNHSVREAGVPLGLPAPGARRRGGSASRSLPLPKRPRRGAAPEPERTP

VGQGSWAHPGRTRGPSDRGFCVVSPARPAEEATSLEGALSGTRHSHPSVG

RQHHAGPPSTSRPPRPWDTPCPPVYAETKHFLYSSGDKEQLRPSFLLSSL

RPSLTGARRLVETIFLGSRPWMPGTPRRLPRLPQRYWQMRPLFLELLGNH

AQCPYGVLLKTHCPLRAAVTPAAGVCAREKPQGSVAAPEEEDTDPRRLVQ

LLRQHSSPWQVYGFVRACLRRLVPPGLWGSRHNERRFLRNTKKFISLGKH

AKLSLQELTWKMSVRGCAWLRRSPGVGCVPAAEHRLREEILAKFLHWLMS

VYVVELLRSFFYVTETTFQKNRLFFYRKSVWSKLQSIGIRQHLKRVQLRE

LSEAEVRQHREARPALLTSRLRFIPKPDGLRPIVNMDYVVGARTFRREKR

AERLTSRVKALFSVLNYERARRPGLLGASVLGLDDIHRAWRTFVLRVRAQ

DPPPELYFVKVDVTGAYDTIPQDRLTEVIASIIKPQNTYCVRRYAVVQKA

AHGHVRKAFKSHVSTLTDLQPYMRQFVAHLQETSPLRDAVVIEQSSSLNE

ASSGLFDVFLRFMCHHAVRIRGKSYVQCQGIPQGSILSTLLCSLCYGDME

NKLFAGIRRDGLLLRLVDDFLLVTPHLTHAKTFLRTLVRGVPEYGCVVNL

RKTVVNFPVEDEALGGTAFVQMPAHGLFPWCGLLLDTRTLEVQSDYSSYA

RTSIRASLTFNRGFKAGRNMRRKLFGVLRLKCHSLFLDLQVNSLQTVCTN

IYKILLLQAYRFHACVLQLPFHQQVWKNPTFFLRVISDTASLCYSILKAK

NAGMSLGAKGAAGPLPSEAVQWLCHQAFLLKLTRHRVTYVPLLGSLRTAQ

TQLSRKLPGTTLTALEAAANPALPSDFKTILD
```

In an embodiment, the hTERT has a sequence at least 80%, 85%, 90%, 95%, 96ˆ, 97%, 98%, or 99% identical to the sequence of SEQ ID NO: 61. In an embodiment, the hTERT has a sequence of SEQ ID NO: 61. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both. In an embodiment, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795):

```
                                                         (SEQ ID NO: 62)
  1 caggcagcgt ggtcctgctg cgcacgtggg aagccctggc cccggccacc cccgcgatgc

 61 cgcgcgctcc ccgctgccga gccgtgcgct ccctgctgcg cagccactac cgcgaggtgc

121 tgccgctggc cacgttcgtg cggcgcctgg ggccccaggg ctggcggctg gtgcagcgcg

181 gggacccggc ggctttccgc gcgctggtgg cccagtgcct ggtgtgcgtg ccctgggacg

241 cacggccgcc ccccgccgcc ccctccttcc gccaggtgtc ctgcctgaag gagctggtgg

301 cccgagtgct gcagaggctg tgcgagcgcg gcgcgaagaa cgtgctggcc ttcggcttcg

361 cgctgctgga cggggcccgc gggggccccc ccgaggcctt caccaccagc gtgcgcagct

421 acctgcccaa cacggtgacc gacgcactgc gggggagcgg ggcgtggggg ctgctgttgc

481 gccgcgtggg cgacgacgtg ctggttcacc tgctggcacg ctgcgcgctc tttgtgctgg
```

-continued

```
541 tggctcccag ctgcgcctac caggtgtgcg ggccgccgct gtaccagctc ggcgctgcca

601 ctcaggcccg gcccccgcca cacgctagtg gaccccgaag gcgtctggga tgcgaacggg

661 cctggaacca tagcgtcagg gaggccgggg tccccctggg cctgccagcc ccgggtgcga

721 ggaggcgcgg gggcagtgcc agccgaagtc tgccgttgcc caagaggccc aggcgtggcg

781 ctgcccctga gccggagcgg acgcccgttg ggcaggggtc ctgggcccac ccgggcagga

841 cgcgtggacc gagtgaccgt ggtttctgtg tggtgtcacc tgccagaccc gccgaagaag

901 ccacctcttt ggagggtgcg ctctctggca cgcgccactc ccacccatcc gtgggccgcc

961 agcaccacgc gggcccccca tccacatcgc ggccaccacg tccctgggac acgccttgtc

1021 ccccggtgta cgccgagacc aagcacttcc tctactcctc aggcgacaag gagcagctgc

1081 ggccctcctt cctactcagc tctctgaggc ccagcctgac tggcgctcgg aggctcgtgg

1141 agaccatctt tctgggttcc aggccctgga tgccagggac tccccgcagg ttgccccgcc

1201 tgccccagcg ctactggcaa atgcggcccc tgtttctgga gctgcttggg aaccacgcgc

1261 agtgccccta cggggtgctc ctcaagacgc actgcccgct gcgagctgcg gtcaccccag

1321 cagccggtgt ctgtgcccgg gagaagcccc agggctctgt ggcggccccc gaggaggagg

1381 acacagaccc ccgtcgcctg gtgcagctgc tccgccagca cagcagcccc tggcaggtgt

1441 acggcttcgt gcgggcctgc ctgcgccggc tggtgccccc aggcctctgg ggctccaggc

1501 acaacgaacg ccgcttcctc aggaacacca agaagttcat ctccctgggg aagcatgcca

1561 agctctcgct gcaggagctg acgtggaaga tgagcgtgcg gggctgcgct tggctgcgca

1621 ggagcccagg ggttggctgt gttccggccg cagagcaccg tctgcgtgag gagatcctgg

1681 ccaagttcct gcactggctg atgagtgtgt acgtcgtcga gctgctcagg tctttctttt

1741 atgtcacgga gaccacgat caaaagaaca ggctcttttt ctaccggaag agtgtctgga

1801 gcaagttgca aagcattgga atcagacagc acttgaagag ggtgcagctg cgggagctgt

1861 cggaagcaga ggtcaggcag catcgggaag ccaggcccgc cctgctgacg tccagactcc

1921 gcttcatccc caagcctgac gggctgcggc cgattgtgaa catggactac gtcgtgggag

1981 ccagaacgtt ccgcagagaa aagagggccg agcgtctcac ctcgagggtg aaggcactgt

2041 tcagcgtgct caactacgag cgggcgcggc gccccggcct cctgggcgcc tctgtgctgg

2101 gcctggacga tatccacagg gcctggcgca ccttcgtgct gcgtgtgcgg gcccaggacc

2161 cgccgcctga gctgtacttt gtcaaggtgg atgtgacggg cgcgtacgac accatccccc

2221 aggacaggct cacggaggtc atcgccagca tcatcaaacc ccagaacacg tactgcgtgc

2281 gtcggtatgc cgtggtccag aaggccgccc atgggcacgt ccgcaaggcc ttcaagagcc

2341 acgtctctac cttgacagac ctccagccgt acatgcgaca gttcgtggct cacctgcagg

2401 agaccagccc gctgagggat gccgtcgtca tcgagcagag ctcctccctg aatgaggcca

2461 gcagtggcct cttcgacgtc ttcctacgct tcatgtgcca ccacgccgtg cgcatcaggg

2521 gcaagtccta cgtccagtgc caggggatcc cgcagggctc catcctctcc acgctgctct

2581 gcagcctgtg ctacggcgac atggagaaca agctgtttgc ggggattcgg cgggacgggc

2641 tgctcctgcg tttggtggat gatttcttgt tggtgacacc tcacctcacc cacgcgaaaa

2701 ccttcctcag gaccctggtc cgaggtgtcc ctgagtatgg ctgcgtggtg aacttgcgga

2761 agacagtggt gaacttccct gtagaagacg aggccctggg tggcacggct tttgttcaga

2821 tgccggccca cggcctattc ccctggtgcg gcctgctgct ggatacccgg accctggagg

2881 tgcagagcga ctactccagc tatgcccgga cctccatcag agccagtctc accttcaacc

2941 gcggcttcaa ggctgggagg aacatgcgtc gcaaactctt tggggtcttg cggctgaagt
```

-continued

```
3001 gtcacagcct gtttctggat ttgcaggtga acagcctcca gacggtgtgc accaacatct
3061 acaagatcct cctgctgcag gcgtacaggt ttcacgcatg tgtgctgcag ctcccatttc
3121 atcagcaagt ttggaagaac cccacatttt tcctgcgcgt catctctgac acggcctccc
3181 tctgctactc catcctgaaa gccaagaacg cagggatgtc gctgggggcc aagggcgccg
3241 ccggccctct gccctccgag gccgtgcagt ggctgtgcca ccaagcattc ctgctcaagc
3301 tgactcgaca ccgtgtcacc tacgtgccac tcctggggtc actcaggaca gcccagacgc
3361 agctgagtcg gaagctcccg gggacgacgc tgactgccct ggaggccgca gccaacccgg
3421 cactgccctc agacttcaag accatcctgg actgatggcc acccgcccac agccaggccg
3481 agagcagaca ccagcagccc tgtcacgccg ggctctacgt cccagggagg gaggggcggc
3541 ccacacccag gcccgcaccg ctgggagtct gaggcctgag tgagtgtttg gccgaggcct
3601 gcatgtccgg ctgaaggctg agtgtccggc tgaggcctga gcgagtgtcc agccaagggc
3661 tgagtgtcca gcacacctgc cgtcttcact tccccacagg ctggcgctcg gctccacccc
3721 agggccagct tacctcacc aggagcccgg cttccactcc ccacatagga atagtccatc
3781 cccagattcg ccattgttca cccctcgccc tgccctcctt tgccttccac ccccaccatc
3841 caggtggaga ccctgagaag gaccctggga gctctgggaa tttggagtga ccaaaggtgt
3901 gccctgtaca caggcgagga ccctgcacct ggatgggggt ccctgtgggt caaattgggg
3961 ggaggtgctg tgggagtaaa atactgaata tatgagtttt tcagttttga aaaaaaaaaa
4021 aaaaaaa
```

In an embodiment, the hTERT is encoded by a nucleic acid having a sequence at least 80%, 85%, 90%, 95%, 96, 97%, 98%, or 99% identical to the sequence of SEQ ID NO: 62. In an embodiment, the hTERT is encoded by a nucleic acid of SEQ ID NO: 62.

Activation and Expansion of Immune Effector Cells (e.g., T Cells)

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

As demonstrated by the data disclosed herein, expanding the T cells by the methods disclosed herein can multiply the cells by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Generally, a population of immune effector cells e.g., T regulatory cell depleted cells, may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect, more anti-CD28 antibody is bound to the particles than anti-CD3 antibody, i.e., the ratio of CD3:CD28 is less than one. In certain aspects, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, 5 billion/ml, or 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a CD19 CAR cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CD19 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CD19 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CD19 CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence of IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a CAR described herein is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a cars of the present invention are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of $CD4^+$ and $CD8^+$ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of $CAR^+$ T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the $CD4^+$ and/or $CD8^+$ T cell subsets by flow cytometry. See, e.g., Milone et al., Molecular Therapy 17(8): 1453-1464 (2009). Alternatively, a mixture of $CD4^+$ and $CD8^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either a cancer associated antigen as described herein$^+$ K562 cells (K562 expressing a cancer associated antigen as described herein), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/ml. $GFP^+$ T cells are enumerated by flow cytometry using bead-based counting. See, e.g., Milone et al., Molecular Therapy 17(8): 1453-1464 (2009).

Sustained $CAR^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter, a Nexcelom Cellometer Vision or Millipore Scepter, following stimulation with αCD3/αCD28 coated magnetic beads on day 0, and transduction with the indicated CAR on day 1.

Animal models can also be used to measure a CART activity. For example, xenograft model using human a cancer associated antigen described herein-specific $CAR^+$ T cells to treat a primary human pre-B ALL in immunodeficient mice can be used. See, e.g., Milone et al., Molecular Therapy 17(8): 1453-1464 (2009). Very briefly, after establishment of ALL, mice are randomized as to treatment groups. Different numbers of a cancer associated antigen-specific CAR engineered T cells are coinjected at a 1:1 ratio into NOD-SCID-$\gamma^{-/-}$ mice bearing B-ALL. The number of copies of a cancer associated antigen-specific CAR vector in spleen DNA from mice is evaluated at various times following T cell injection. Animals are assessed for leukemia at weekly intervals. Peripheral blood a cancer associate antigen as described herein$^+$ B-ALL blast cell counts are measured in mice that are injected with a cancer associated antigen described herein-ζ $CAR^+$ T cells or mock-transduced T cells. Survival curves for the groups are compared using the log-rank test. In addition, absolute peripheral blood $CD4^+$ and $CD8^+$ T cell counts 4 weeks following T cell injection in NOD-SCID-$\gamma^{-/-}$ mice can also be analyzed. Mice are injected with leukemic cells and 3 weeks later are injected with T cells engineered to express CAR by a bicistronic lentiviral vector that encodes the CAR linked to eGFP. T cells are normalized to 45-50% input $GFP^+$ T cells by mixing with mock-transduced cells prior to injection, and confirmed by flow cytometry. Animals are assessed for leukemia at 1-week intervals. Survival curves for the $CAR^+$ T cell groups are compared using the log-rank test.

Dose dependent CAR treatment response can be evaluated. See, e.g., Milone et al., Molecular Therapy 17(8): 1453-1464 (2009). For example, peripheral blood is obtained 35-70 days after establishing leukemia in mice injected on day 21 with CAR T cells, an equivalent number of mock-transduced T cells, or no T cells. Mice from each group are randomly bled for determination of peripheral blood a cancer associate antigen as described herein$^+$ ALL blast counts and then killed on days 35 and 49. The remaining animals are evaluated on days 57 and 70.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with K562 cells expressing a cancer associated antigen described herein (K19) or CD32 and CD137 (KT32-BBL) for a final T-cell:K562 ratio of 2:1. K562 cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term $CD8^+$ T cell expansion ex vivo. T cells are enumerated in cultures using CountBright™ fluorescent beads (Invitrogen, Carlsbad, CA) and flow cytometry as described by the manufacturer. $CAR^+$ T cells are identified by GFP expression using T cells that are engineered with eGFP-2A linked CAR-expressing lentiviral vectors. For CAR+ T cells not expressing GFP, the CAR+ T cells are detected with biotinylated recombinant a cancer associate antigen as described herein protein and a secondary avidin-PE conjugate. CD4+ and $CD8^+$ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, CA) according the manufacturer's instructions. Fluorescence is assessed using a FACScalibur flow cytometer, and data is analyzed according to the manufacturer's instructions.

Cytotoxicity can be assessed by a standard 51Cr-release assay. See, e.g., Milone et al., Molecular Therapy 17(8): 1453-1464 (2009). Briefly, target cells (K562 lines and primary pro-B-ALL cells) are loaded with 51Cr (as NaCrO4, New England Nuclear, Boston, MA) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, MA). Each condition is performed in at least triplicate, and the percentage of lysis is calculated using the formula: % Lysis=(ER−SR)/(TR−SR), where ER represents the average 51Cr released for each experimental condition.

Imaging technologies can be used to evaluate specific trafficking and proliferation of CARs in tumor-bearing animal models. Such assays have been described, for example, in Barrett et al., Human Gene Therapy 22:1575-1586 (2011). Briefly, NOD/SCID/$\gamma c^{-/-}$ (NSG) mice are injected IV with Nalm-6 cells followed 7 days later with T cells 4 hour after electroporation with the CAR constructs. The T cells are stably transfected with a lentiviral construct to express firefly luciferase, and mice are imaged for bioluminescence. Alternatively, therapeutic efficacy and specificity of a single injection of $CAR^+$ T cells in Nalm-6 xenograft model can be measured as the following: NSG mice are injected with Nalm-6 transduced to stably express firefly luciferase, followed by a single tail-vein injection of T cells electroporated with cars of the present invention 7 days later. Animals are imaged at various time points post injection. For example, photon-density heat maps of firefly luciferase positive leukemia in representative mice at day 5 (2 days before treatment) and day 8 (24 hr post CAR$^+$ PBLs) can be generated.

Other assays, including those described in the Example section herein as well as those that are known in the art can also be used to evaluate the CARs described herein.

Therapeutic Application

The modified cells described herein may be included in a composition for therapy. In one aspect, the composition comprises a population of modified T cells comprising a nucleic acid sequence encoding a CAR and a nucleic acid sequence encoding a peptide comprising an amphipathic helix domain and a cluster of basic amino acids, wherein the peptide disrupts PKA and an AKAP association as described herein. In another aspect, the composition comprises the modified T cell comprising a nucleic acid sequence encoding a CAR and a nucleic acid sequence encoding a peptide comprising an amphipathic helix domain and a cluster of basic amino acids, wherein the peptide disrupts PKA and an AKAP association as described herein. In yet another embodiment, the composition includes a modified T cell comprising a CAR and a peptide described herein, e.g., a peptide that disrupts PKA and an AKAP binding. The composition may include a pharmaceutical composition and further include a pharmaceutically acceptable carrier. A therapeutically effective amount of the pharmaceutical composition comprising the modified cells may be administered.

In one aspect, the invention includes a method comprising administering a population of modified T cells to a subject in need thereof to prevent or treat a tumor, wherein the modified T cells comprise a nucleic acid sequence encoding a CAR and a nucleic acid sequence encoding a peptide described herein, e.g., a peptide comprising an amphipathic helix domain and a cluster of basic amino acids, wherein the peptide disrupts PKA and an AKAP association.

In another aspect, the invention includes a method comprising administering a population of modified cells to a subject in need thereof to prevent or treat a tumor that is adverse to the subject, wherein the modified cells comprise a CAR and a peptide described herein, e.g., a peptide that disrupts PKA and an AKAP binding.

In one aspect, the invention provides methods for treating a disease associated with expression of a cancer associated antigen described herein.

In one aspect, the present invention provides methods of treating cancer by providing to the subject in need thereof immune effector cells (e.g., T cells, NK cells) that are engineered to express an XCAR, wherein X represents a tumor antigen as described herein, and wherein the cancer cells express said X tumor antigen.

In one aspect, the present invention provides methods of treating cancer by providing to the subject in need thereof immune effector cells (e.g., T cells, NK cells) that are engineered to express a XCAR described herein, wherein the cancer cells express X. In one embodiment, X is expressed on both normal cells and cancers cells, but is expressed at lower levels on normal cells. In one embodiment, the method further comprises selecting a CAR that binds X with an affinity that allows the XCAR to bind and kill the cancer cells expressing X but less than 30%, 25%, 20%, 15%, 10%, 5% or less of the normal cells expressing X are killed, e.g., as determined by an assay described herein. In one embodiment, the selected CAR has an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In one embodiment, the selected antigen binding domain has a binding affinity that is at least five-fold, 10-fold, 20-fold, 30-fold, 50-fold, 100-fold or 1,000-fold less than a reference antibody, e.g., an antibody described herein.

In one embodiment, the present invention provides methods of treating cancer by providing to the subject in need thereof immune effector cells (e.g., T cells, NK cells) that are engineered to express CD19 CAR, wherein the cancer cells express CD19. In one embodiment, the cancer to be treated is ALL (acute lymphoblastic leukemia), CLL (chronic lymphocytic leukemia), DLBCL (diffuse large B-cell lymphoma), MCL (Mantle cell lymphoma, or MM (multiple myeloma).

In one aspect, the present invention provides methods of treating cancer by providing to the subject in need thereof immune effector cells (e.g., T cells, NK cells) that are engineered to express an EGFRvIIICAR, wherein the cancer cells express EGFRvIII. In one embodiment, the cancer to be treated is glioblastoma.

In one aspect, the present invention provides methods of treating cancer by providing to the subject in need thereof immune effector cells (e.g., T cells, NK cells) that are engineered to express a mesothelin CAR, wherein the cancer cells express mesothelin. In one embodiment, the cancer to be treated is mesothelioma, pancreatic cancer, or ovarian cancer.

In one aspect, the present invention provides methods of treating cancer by providing to the subject in need thereof immune effector cells (e.g., T cells, NK cells) that are engineered to express a CD123CAR, wherein the cancer cells express CD123. In one embodiment, the cancer to be treated is AML.

In one aspect, the present invention provides methods of treating cancer by providing to the subject in need thereof immune effector cells (e.g., T cells, NK cells) that are engineered to express a CD22CAR, wherein the cancer cells express CD22. In one embodiment, the cancer to be treated is B cell malignancies.

In one aspect, the present invention provides methods of treating cancer by providing to the subject in need thereof immune effector cells (e.g., T cells, NK cells) that are engineered to express a CS-1CAR, wherein the cancer cells express CS-1. In one embodiment, the cancer to be treated is multiple myeloma.

In one aspect, the present invention provides methods of treating cancer by providing to the subject in need thereof immune effector cells (e.g., T cells, NK cells) that are engineered to express a CLL-1CAR, wherein the cancer cells express CLL-1. In one embodiment, the cancer to be treated is AML.

In one aspect, the present invention provides methods of treating cancer by providing to the subject in need thereof immune effector cells (e.g., T cells, NK cells) that are engineered to express a CD33CAR, wherein the cancer cells express CD33. In one embodiment, the cancer to be treated is AML.

In one aspect, the present invention provides methods of treating cancer by providing to the subject in need thereof immune effector cells (e.g., T cells, NK cells) that are engineered to express a GD2CAR, wherein the cancer cells express GD2. In one embodiment, the cancer to be treated is neuroblastoma.

In one aspect, the present invention provides methods of treating cancer by providing to the subject in need thereof immune effector cells (e.g., T cells, NK cells) that are engineered to express a BCMACAR, wherein the cancer cells express BCMA. In one embodiment, the cancer to be treated is multiple myeloma.

In one aspect, the present invention provides methods of treating cancer by providing to the subject in need thereof immune effector cells (e.g., T cells, NK cells) that are engineered to express a TnCAR, wherein the cancer cells express Tn antigen. In one embodiment, the cancer to be treated is ovarian cancer.

In one aspect, the present invention provides methods of treating cancer by providing to the subject in need thereof immune effector cells (e.g., T cells, NK cells) that are engineered to express a PSMACAR, wherein the cancer cells express PSMA. In one embodiment, the cancer to be treated is prostate cancer.

In one aspect, the present invention provides methods of treating cancer by providing to the subject in need thereof immune effector cells (e.g., T cells, NK cells) that are engineered to express a ROR1CAR, wherein the cancer cells express ROR1. In one embodiment, the cancer to be treated is B cell malignancies.

In one aspect, the present invention provides methods of treating cancer by providing to the subject in need thereof immune effector cells (e.g., T cells, NK cells) that are engineered to express a FLT3 CAR, wherein the cancer cells express FLT3. In one embodiment, the cancer to be treated is AML.

In one aspect, the present invention provides methods of treating cancer by providing to the subject in need thereof immune effector cells (e.g., T cells, NK cells) that are engineered to express a TAG72CAR, wherein the cancer cells express TAG72. In one embodiment, the cancer to be treated is gastrointestinal cancer.

In one aspect, the present invention provides methods of treating cancer by providing to the subject in need thereof immune effector cells (e.g., T cells, NK cells) that are engineered to express a CD38CAR, wherein the cancer cells express CD38. In one embodiment, the cancer to be treated is multiple myeloma.

In one aspect, the present invention provides methods of treating cancer by providing to the subject in need thereof immune effector cells (e.g., T cells, NK cells) that are engineered to express a CD44v6CAR, wherein the cancer cells express CD44v6. In one embodiment, the cancer to be treated is cervical cancer, AML, or MM.

In one aspect, the present invention provides methods of treating cancer by providing to the subject in need thereof immune effector cells (e.g., T cells, NK cells) that are engineered to express a CEACAR, wherein the cancer cells express CEA. In one embodiment, the cancer to be treated is gastrointestinal cancer, or pancreatic cancer.

In one aspect, the present invention provides methods of treating cancer by providing to the subject in need thereof immune effector cells (e.g., T cells, NK cells) that are engineered to express an EPCAMCAR, wherein the cancer cells express EPCAM. In one embodiment, the cancer to be treated is gastrointestinal cancer.

In one aspect, the present invention provides methods of treating cancer by providing to the subject in need thereof immune effector cells (e.g., T cells, NK cells) that are engineered to express a B7H3CAR, wherein the cancer cells express B7H3.

In one aspect, the present invention provides methods of treating cancer by providing to the subject in need thereof immune effector cells (e.g., T cells, NK cells) that are engineered to express a KITCAR, wherein the cancer cells express KIT. In one embodiment, the cancer to be treated is gastrointestinal cancer.

In one aspect, the present invention provides methods of treating cancer by providing to the subject in need thereof immune effector cells (e.g., T cells, NK cells) that are engineered to express an IL-13Ra2CAR, wherein the cancer cells express IL-13Ra2. In one embodiment, the cancer to be treated is glioblastoma.

In one aspect, the present invention provides methods of treating cancer by providing to the subject in need thereof immune effector cells (e.g., T cells, NK cells) that are engineered to express a PRSS21CAR, wherein the cancer cells express PRSS21. In one embodiment, the cancer to be treated is selected from ovarian, pancreatic, lung and breast cancer.

In one aspect, the present invention provides methods of treating cancer by providing to the subject in need thereof immune effector cells (e.g., T cells, NK cells) that are engineered to express a CD30CAR, wherein the cancer cells express CD30. In one embodiment, the cancer to be treated is lymphomas, or leukemias.

In one aspect, the present invention provides methods of treating cancer by providing to the subject in need thereof immune effector cells (e.g., T cells, NK cells) that are engineered to express a GD3CAR, wherein the cancer cells express GD3. In one embodiment, the cancer to be treated is melanoma.

In one aspect, the present invention provides methods of treating cancer by providing to the subject in need thereof immune effector cells (e.g., T cells, NK cells) that are engineered to express a CD171CAR, wherein the cancer cells express CD171. In one embodiment, the cancer to be treated is neuroblastoma, ovarian cancer, melanoma, breast cancer, pancreatic cancer, colon cancers, or NSCLC (non-small cell lung cancer).

In one aspect, the present invention provides methods of treating cancer by providing to the subject in need thereof immune effector cells (e.g., T cells, NK cells) that are engineered to express an IL-11RaCAR, wherein the cancer cells express IL-11Ra. In one embodiment, the cancer to be treated is osteosarcoma.

In one aspect, the present invention provides methods of treating cancer by providing to the subject in need thereof immune effector cells (e.g., T cells, NK cells) that are engineered to express a PSCACAR, wherein the cancer cells express PSCA. In one embodiment, the cancer to be treated is prostate cancer.

In one aspect, the present invention provides methods of treating cancer by providing to the subject in need thereof immune effector cells (e.g., T cells, NK cells) that are engineered to express a VEGFR2CAR, wherein the cancer cells express VEGFR2. In one embodiment, the cancer to be treated is a solid tumor.

In one aspect, the present invention provides methods of treating cancer by providing to the subject in need thereof immune effector cells (e.g., T cells, NK cells) that are engineered to express a LewisYCAR, wherein the cancer cells express LewisY. In one embodiment, the cancer to be treated is ovarian cancer, or AML.

In one aspect, the present invention provides methods of treating cancer by providing to the subject in need thereof immune effector cells (e.g., T cells, NK cells) that are engineered to express a CD24CAR, wherein the cancer cells express CD24. In one embodiment, the cancer to be treated is pancreatic cancer.

In one aspect, the present invention provides methods of treating cancer by providing to the subject in need thereof immune effector cells (e.g., T cells, NK cells) that are engineered to express a PDGFR-betaCAR, wherein the cancer cells express PDGFR-beta. In one embodiment, the cancer to be treated is breast cancer, prostate cancer, GIST (gastrointestinal stromal tumor), CML, DFSP (dermatofibrosarcoma protuberans), or glioma.

In one aspect, the present invention provides methods of treating cancer by providing to the subject in need thereof immune effector cells (e.g., T cells, NK cells) that are engineered to express a SSEA-4CAR, wherein the cancer cells express SSEA-4. In one embodiment, the cancer to be treated is glioblastoma, breast cancer, lung cancer, or stem cell cancer.

In one aspect, the present invention provides methods of treating cancer by providing to the subject in need thereof immune effector cells (e.g., T cells, NK cells) that are engineered to express a CD20CAR, wherein the cancer cells express CD20. In one embodiment, the cancer to be treated is B cell malignancies.

In one aspect, the present invention provides methods of treating cancer by providing to the subject in need thereof immune effector cells (e.g., T cells, NK cells) that are engineered to express a Folate receptor alphaCAR, wherein the cancer cells express folate receptor alpha.

In one embodiment, the cancer to be treated is ovarian cancer, NSCLC, endometrial cancer, renal cancer, or other solid tumors.

In one aspect, the present invention provides methods of treating cancer by providing to the subject in need thereof immune effector cells (e.g., T cells, NK cells) that are engineered to express an ERBB2CAR, wherein the cancer cells express ERBB2 (Her2/neu). In one embodiment, the cancer to be treated is breast cancer, gastric cancer, colorectal cancer, lung cancer, or other solid tumors.

In one aspect, the present invention provides methods of treating cancer by providing to the subject in need thereof immune effector cells (e.g., T cells, NK cells) that are engineered to express a MUC1CAR, wherein the cancer cells express MUC1. In one embodiment, the cancer to be treated is breast cancer, lung cancer, or other solid tumors.

In one aspect, the present invention provides methods of treating cancer by providing to the subject in need thereof immune effector cells (e.g., T cells, NK cells) that are engineered to express an EGFRCAR, wherein the cancer cells express EGFR. In one embodiment, the cancer to be treated is glioblastoma, SCLC (small cell lung cancer), SCCHN (squamous cell carcinoma of the head and neck), NSCLC, or other solid tumors.

In one aspect, the present invention provides methods of treating cancer by providing to the subject in need thereof immune effector cells (e.g., T cells, NK cells) that are engineered to express a NCAMCAR, wherein the cancer cells express NCAM. In one embodiment, the cancer to be treated is neuroblastoma, or other solid tumors.

In one aspect, the present invention provides methods of treating cancer by providing to the subject in need thereof immune effector cells (e.g., T cells, NK cells) that are engineered to express a CAIXCAR, wherein the cancer cells express CAIX. In one embodiment, the cancer to be treated is renal cancer, CRC, cervical cancer, or other solid tumors.

In one aspect, the present invention provides methods of treating cancer by providing to the subject in need thereof immune effector cells (e.g., T cells, NK cells) that are engineered to express an EphA2CAR, wherein the cancer cells express EphA2. In one embodiment, the cancer to be treated is GBM.

In one aspect, the present invention provides methods of treating cancer by providing to the subject in need thereof immune effector cells (e.g., T cells, NK cells) that are engineered to express a GD3CAR, wherein the cancer cells express GD3. In one embodiment, the cancer to be treated is melanoma.

In one aspect, the present invention provides methods of treating cancer by providing to the subject in need thereof immune effector cells (e.g., T cells, NK cells) that are engineered to express a Fucosyl GM1CAR, wherein the cancer cells express Fucosyl GM In one aspect, the present invention provides methods of treating cancer by providing to the subject in need thereof immune effector cells (e.g., T cells, NK cells) that are engineered to express a sLeCAR, wherein the cancer cells express sLe. In one embodiment, the cancer to be treated is NSCLC, or AML.

In one aspect, the present invention provides methods of treating cancer by providing to the subject in need thereof immune effector cells (e.g., T cells, NK cells) that are engineered to express a GM3CAR, wherein the cancer cells express GM3.

In one aspect, the present invention provides methods of treating cancer by providing to the subject in need thereof immune effector cells (e.g., T cells, NK cells) that are engineered to express a TGS5CAR, wherein the cancer cells express TGS5.

In one aspect, the present invention provides methods of treating cancer by providing to the subject in need thereof immune effector cells (e.g., T cells, NK cells) that are engineered to express a HMWMAACAR, wherein the cancer cells express HMWMAA. In one embodiment, the cancer to be treated is melanoma, glioblastoma, or breast cancer.

In one aspect, the present invention provides methods of treating cancer by providing to the subject in need thereof immune effector cells (e.g., T cells, NK cells) that are engineered to express an o-acetyl-GD2CAR, wherein the cancer cells express o-acetyl-GD2. In one embodiment, the cancer to be treated is neuroblastoma, or melanoma.

In one aspect, the present invention provides methods of treating cancer by providing to the subject in need thereof immune effector cells (e.g., T cells, NK cells) that are engineered to express a CD19CAR, wherein the cancer cells express CD19. In one embodiment, the cancer to be treated is Follicular lymphoma, CLL, ALL, or myeloma.

In one aspect, the present invention provides methods of treating cancer by providing to the subject in need thereof immune effector cells (e.g., T cells, NK cells) that are engineered to express a TEM1/CD248CAR, wherein the cancer cells express TEM1/CD248. In one embodiment, the cancer to be treated is a solid tumor.

In one aspect, the present invention provides methods of treating cancer by providing to the subject in need thereof immune effector cells (e.g., T cells, NK cells) that are engineered to express a TEM7RCAR, wherein the cancer cells express TEM7R. In one embodiment, the cancer to be treated is solid tumor.

In one aspect, the present invention provides methods of treating cancer by providing to the subject in need thereof immune effector cells (e.g., T cells, NK cells) that are engineered to express a CLDN6CAR, wherein the cancer cells express CLDN6. In one embodiment, the cancer to be treated is ovarian cancer, lung cancer, or breast cancer.

In one aspect, the present invention provides methods of treating cancer by providing to the subject in need thereof immune effector cells (e.g., T cells, NK cells) that are engineered to express a TSHRCAR, wherein the cancer cells express TSHR. In one embodiment, the cancer to be treated is thyroid cancer, or multiple myeloma.

In one aspect, the present invention provides methods of treating cancer by providing to the subject in need thereof immune effector cells (e.g., T cells, NK cells) that are engineered to express a GPRC5DCAR, wherein the cancer cells express GPRC5D. In one embodiment, the cancer to be treated is multiple myeloma.

In one aspect, the present invention provides methods of treating cancer by providing to the subject in need thereof immune effector cells (e.g., T cells, NK cells) that are engineered to express a CXORF61CAR, wherein the cancer cells express CXORF61.

In one aspect, the present invention provides methods of treating cancer by providing to the subject in need thereof immune effector cells (e.g., T cells, NK cells) that are engineered to express a CD97CAR, wherein the cancer cells express CD97. In one embodiment, the cancer to be treated is B cell malignancies, gastric cancer, pancreatic cancer, esophageal cancer, glioblastoma, breast cancer, or colorectal cancer.

In one aspect, the present invention provides methods of treating cancer by providing to the subject in need thereof immune effector cells (e.g., T cells, NK cells) that are engineered to express a CD179aCAR, wherein the cancer cells express CD179a. In one embodiment, the cancer to be treated is B cell malignancies.

In one aspect, the present invention provides methods of treating cancer by providing to the subject in need thereof immune effector cells (e.g., T cells, NK cells) that are engineered to express an ALK CAR, wherein the cancer cells express ALK. In one embodiment, the cancer to be treated is NSCLC, ALCL (anaplastic large cell lymphoma), IMT (inflammatory myofibroblastic tumor), or neuroblastoma.

In one aspect, the present invention provides methods of treating cancer by providing to the subject in need thereof immune effector cells (e.g., T cells, NK cells) that are engineered to express a Polysialic acid CAR, wherein the cancer cells express Polysialic acid. In one embodiment, the cancer to be treated is small cell lung cancer.

In one aspect, the present invention provides methods of treating cancer by providing to the subject in need thereof immune effector cells (e.g., T cells, NK cells) that are engineered to express a PLAC1CAR, wherein the cancer cells express PLAC1. In one embodiment, the cancer to be treated is HCC (hepatocellular carcinoma).

In one aspect, the present invention provides methods of treating cancer by providing to the subject in need thereof immune effector cells (e.g., T cells, NK cells) that are engineered to express a GloboHCAR, wherein the cancer cells express GloboH. In one embodiment, the cancer to be treated is ovarian cancer, gastric cancer, prostate cancer, lung cancer, breast cancer, or pancreatic cancer.

In one aspect, the present invention provides methods of treating cancer by providing to the subject in need thereof immune effector cells (e.g., T cells, NK cells) that are engineered to express a NY-BR-1CAR, wherein the cancer cells express NY-BR-1. In one embodiment, the cancer to be treated is breast cancer.

In one aspect, the present invention provides methods of treating cancer by providing to the subject in need thereof immune effector cells (e.g., T cells, NK cells) that are engineered to express a UPK2CAR, wherein the cancer cells express UPK2. In one embodiment, the cancer to be treated is bladder cancer.

In one aspect, the present invention provides methods of treating cancer by providing to the subject in need thereof immune effector cells (e.g., T cells, NK cells) that are engineered to express a HAVCR1CAR, wherein the cancer cells express HAVCR1. In one embodiment, the cancer to be treated is renal cancer.

In one aspect, the present invention provides methods of treating cancer by providing to the subject in need thereof immune effector cells (e.g., T cells, NK cells) that are engineered to express a ADRB3CAR, wherein the cancer cells express ADRB3. In one embodiment, the cancer to be treated is Ewing sarcoma.

In one aspect, the present invention provides methods of treating cancer by providing to the subject in need thereof immune effector cells (e.g., T cells, NK cells) that are engineered to express a PANX3CAR, wherein the cancer cells express PANX3. In one embodiment, the cancer to be treated is osteosarcoma.

In one aspect, the present invention provides methods of treating cancer by providing to the subject in need thereof immune effector cells (e.g., T cells, NK cells) that are engineered to express a GPR20CAR, wherein the cancer cells express GPR20. In one embodiment, the cancer to be treated is GIST.

In one aspect, the present invention provides methods of treating cancer by providing to the subject in need thereof immune effector cells (e.g., T cells, NK cells) that are engineered to express a LY6KCAR, wherein the cancer cells express LY6K. In one embodiment, the cancer to be treated is breast cancer, lung cancer, ovary cancer, or cervix cancer.

In one aspect, the present invention provides methods of treating cancer by providing to the subject in need thereof immune effector cells (e.g., T cells, NK cells) that are engineered to express a OR51E2CAR, wherein the cancer cells express OR51E2. In one embodiment, the cancer to be treated is prostate cancer.

In one aspect, the present invention provides methods of treating cancer by providing to the subject in need thereof immune effector cells (e.g., T cells, NK cells) that are engineered to express a TARPCAR, wherein the cancer cells express TARP. In one embodiment, the cancer to be treated is prostate cancer.

In one aspect, the present invention provides methods of treating cancer by providing to the subject in need thereof immune effector cells (e.g., T cells, NK cells) that are engineered to express a WT1CAR, wherein the cancer cells express WT1.

In one aspect, the present invention provides methods of treating cancer by providing to the subject in need thereof immune effector cells (e.g., T cells, NK cells) that are engineered to express a NY-ESO-1CAR, wherein the cancer cells express NY-ESO-1.

In one aspect, the present invention provides methods of treating cancer by providing to the subject in need thereof immune effector cells (e.g., T cells, NK cells) that are engineered to express a LAGE-1a CAR, wherein the cancer cells express LAGE-1a.

In one aspect, the present invention provides methods of treating cancer by providing to the subject in need thereof immune effector cells (e.g., T cells, NK cells) that are engineered to express a MAGE-A1CAR, wherein the cancer cells express MAGE-A1. In one embodiment, the cancer to be treated is melanoma.

In one aspect, the present invention provides methods of treating cancer by providing to the subject in need thereof immune effector cells (e.g., T cells, NK cells) that are engineered to express a MAGE A1CAR, wherein the cancer cells express MAGE A1.

In one aspect, the present invention provides methods of treating cancer by providing to the subject in need thereof immune effector cells (e.g., T cells, NK cells) that are engineered to express a ETV6-AML CAR, wherein the cancer cells express ETV6-AML.

In one aspect, the present invention provides methods of treating cancer by providing to the subject in need thereof immune effector cells (e.g., T cells, NK cells) that are engineered to express a sperm protein 17 CAR, wherein the cancer cells express sperm protein 17. In one embodiment, the cancer to be treated is ovarian cancer, HCC, or NSCLC.

In one aspect, the present invention provides methods of treating cancer by providing to the subject in need thereof immune effector cells (e.g., T cells, NK cells) that are engineered to express a XAGE1CAR, wherein the cancer cells express XAGE1. In one embodiment, the cancer to be treated is Ewings, or rhabdo cancer.

In one aspect, the present invention provides methods of treating cancer by providing to the subject in need thereof immune effector cells (e.g., T cells, NK cells) that are engineered to express a Tie 2 CAR, wherein the cancer cells express Tie 2. In one embodiment, the cancer to be treated is a solid tumor.

In one aspect, the present invention provides methods of treating cancer by providing to the subject in need thereof immune effector cells (e.g., T cells, NK cells) that are engineered to express a MAD-CT-1CAR, wherein the cancer cells express MAD-CT-1. In one embodiment, the cancer to be treated is prostate cancer, or melanoma.

In one aspect, the present invention provides methods of treating cancer by providing to the subject in need thereof immune effector cells (e.g., T cells, NK cells) that are engineered to express a MAD-CT-2CAR, wherein the cancer cells express MAD-CT-2. In one embodiment, the cancer to be treated is prostate cancer, melanoma.

In one aspect, the present invention provides methods of treating cancer by providing to the subject in need thereof immune effector cells (e.g., T cells, NK cells) that are engineered to express a Fos-related antigen 1 CAR, wherein the cancer cells express Fos-related antigen 1. In one embodiment, the cancer to be treated is glioma, squamous cell cancer, or pancreatic cancer.

In one aspect, the present invention provides methods of treating cancer by providing to the subject in need thereof immune effector cells (e.g., T cells, NK cells) that are engineered to express a p53CAR, wherein the cancer cells express p53.

In one aspect, the present invention provides methods of treating cancer by providing to the subject in need thereof immune effector cells (e.g., T cells, NK cells) that are engineered to express a prostein CAR, wherein the cancer cells express prostein.

In one aspect, the present invention provides methods of treating cancer by providing to the subject in need thereof immune effector cells (e.g., T cells, NK cells) that are engineered to express a survivin and telomerase CAR, wherein the cancer cells express survivin and telomerase.

In one aspect, the present invention provides methods of treating cancer by providing to the subject in need thereof immune effector cells (e.g., T cells, NK cells) that are engineered to express a PCTA-1/Galectin 8 CAR, wherein the cancer cells express PCTA-1/Galectin 8.

In one aspect, the present invention provides methods of treating cancer by providing to the subject in need thereof immune effector cells (e.g., T cells, NK cells) that are engineered to express a MelanA/MART1CAR, wherein the cancer cells express MelanA/MART1.

In one aspect, the present invention provides methods of treating cancer by providing to the subject in need thereof immune effector cells (e.g., T cells, NK cells) that are engineered to express a Ras mutant CAR, wherein the cancer cells express Ras mutant.

In one aspect, the present invention provides methods of treating cancer by providing to the subject in need thereof immune effector cells (e.g., T cells, NK cells) that are engineered to express a p53 mutant CAR, wherein the cancer cells express p53 mutant.

In one aspect, the present invention provides methods of treating cancer by providing to the subject in need thereof immune effector cells (e.g., T cells, NK cells) that are engineered to express a hTERT CAR, wherein the cancer cells express hTERT.

In one aspect, the present invention provides methods of treating cancer by providing to the subject in need thereof immune effector cells (e.g., T cells, NK cells) that are engineered to express a sarcoma translocation breakpoints CAR, wherein the cancer cells express sarcoma translocation breakpoints. In one embodiment, the cancer to be treated is sarcoma.

In one aspect, the present invention provides methods of treating cancer by providing to the subject in need thereof immune effector cells (e.g., T cells, NK cells) that are engineered to express a ML-IAP CAR, wherein the cancer cells express ML-IAP. In one embodiment, the cancer to be treated is melanoma.

In one aspect, the present invention provides methods of treating cancer by providing to the subject in need thereof immune effector cells (e.g., T cells, NK cells) that are engineered to express an ERGCAR, wherein the cancer cells express ERG (TMPRSS2 ETS fusion gene).

In one aspect, the present invention provides methods of treating cancer by providing to the subject in need thereof immune effector cells (e.g., T cells, NK cells) that are engineered to express a NA17CAR, wherein the cancer cells express NA17. In one embodiment, the cancer to be treated is melanoma.

In one aspect, the present invention provides methods of treating cancer by providing to the subject in need thereof immune effector cells (e.g., T cells, NK cells) that are engineered to express a PAX3CAR, wherein the cancer cells express PAX3. In one embodiment, the cancer to be treated is alveolar rhabdomyosarcoma.

In one aspect, the present invention provides methods of treating cancer by providing to the subject in need thereof immune effector cells (e.g., T cells, NK cells) that are engineered to express an androgen receptor CAR, wherein the cancer cells express androgen receptor. In one embodiment, the cancer to be treated is metastatic prostate cancer.

In one aspect, the present invention provides methods of treating cancer by providing to the subject in need thereof immune effector cells (e.g., T cells, NK cells) that are engineered to express a Cyclin B1CAR, wherein the cancer cells express Cyclin B1.

In one aspect, the present invention provides methods of treating cancer by providing to the subject in need thereof immune effector cells (e.g., T cells, NK cells) that are engineered to express a MYCNCAR, wherein the cancer cells express MYCN.

In one aspect, the present invention provides methods of treating cancer by providing to the subject in need thereof immune effector cells (e.g., T cells, NK cells) that are engineered to express a RhoC CAR, wherein the cancer cells express RhoC.

In one aspect, the present invention provides methods of treating cancer by providing to the subject in need thereof immune effector cells (e.g., T cells, NK cells) that are engineered to express a TRP-2CAR, wherein the cancer cells express TRP-2. In one embodiment, the cancer to be treated is melanoma.

In one aspect, the present invention provides methods of treating cancer by providing to the subject in need thereof immune effector cells (e.g., T cells, NK cells) that are engineered to express a CYP1B1CAR, wherein the cancer cells express CYP1B1. In one embodiment, the cancer to be treated is breast cancer, colon cancer, lung cancer, esophagus cancer, skin cancer, lymph node cancer, brain cancer, or testis cancer.

In one aspect, the present invention provides methods of treating cancer by providing to the subject in need thereof immune effector cells (e.g., T cells, NK cells) that are engineered to express a BORIS CAR, wherein the cancer cells express BORIS. In one embodiment, the cancer to be treated is lung cancer.

In one aspect, the present invention provides methods of treating cancer by providing to the subject in need thereof immune effector cells (e.g., T cells, NK cells) that are engineered to express a SART3CAR, wherein the cancer cells express SART3

In one aspect, the present invention provides methods of treating cancer by providing to the subject in need thereof immune effector cells (e.g., T cells, NK cells) that are engineered to express a PAX5CAR, wherein the cancer cells express PAX5.

In one aspect, the present invention provides methods of treating cancer by providing to the subject in need thereof immune effector cells (e.g., T cells, NK cells) that are engineered to express a OY-TES1CAR, wherein the cancer cells express OY-TES1.

In one aspect, the present invention provides methods of treating cancer by providing to the subject in need thereof immune effector cells (e.g., T cells, NK cells) that are engineered to express a LCK CAR, wherein the cancer cells express LCK.

In one aspect, the present invention provides methods of treating cancer by providing to the subject in need thereof immune effector cells (e.g., T cells, NK cells) that are engineered to express a AKAP-4CAR, wherein the cancer cells express AKAP-4.

In one aspect, the present invention provides methods of treating cancer by providing to the subject in need thereof immune effector cells (e.g., T cells, NK cells) that are engineered to express a SSX2CAR, wherein the cancer cells express SSX2.

In one aspect, the present invention provides methods of treating cancer by providing to the subject in need thereof immune effector cells (e.g., T cells, NK cells) that are engineered to express a RAGE-1CAR, wherein the cancer cells express RAGE-1. In one embodiment, the cancer to be treated is RCC (renal cell cancer), or other solid tumors In one aspect, the present invention provides methods of treating cancer by providing to the subject in need thereof immune effector cells (e.g., T cells, NK cells) that are engineered to express a human telomerase reverse transcriptase CAR, wherein the cancer cells express human telomerase reverse transcriptase. In one embodiment, the cancer to be treated is solid tumors.

In one aspect, the present invention provides methods of treating cancer by providing to the subject in need thereof immune effector cells (e.g., T cells, NK cells) that are engineered to express a RU1CAR, wherein the cancer cells express RU1.

In one aspect, the present invention provides methods of treating cancer by providing to the subject in need thereof immune effector cells (e.g., T cells, NK cells) that are engineered to express a RU2CAR, wherein the cancer cells express RU2.

In one aspect, the present invention provides methods of treating cancer by providing to the subject in need thereof immune effector cells (e.g., T cells, NK cells) that are engineered to express an intestinal carboxyl esterase CAR, wherein the cancer cells express intestinal carboxyl esterase. In one embodiment, the cancer to be treated is thyroid cancer, RCC, CRC (colorectal cancer), breast cancer, or other solid tumors.

In one aspect, the present invention provides methods of treating cancer by providing to the subject in need thereof immune effector cells (e.g., T cells, NK cells) that are engineered to express a Prostase CAR, wherein the cancer cells express Prostase.

In one aspect, the present invention provides methods of treating cancer by providing to the subject in need thereof immune effector cells (e.g., T cells, NK cells) that are engineered to express a PAPCAR, wherein the cancer cells express PAP.

In one aspect, the present invention provides methods of treating cancer by providing to the subject in need thereof immune effector cells (e.g., T cells, NK cells) that are engineered to express an IGF-I receptor CAR, wherein the cancer cells express IGF-I receptor.

In one aspect, the present invention provides methods of treating cancer by providing to the subject in need thereof immune effector cells (e.g., T cells, NK cells) that are engineered to express a gp100 CAR, wherein the cancer cells express gp100.

In one aspect, the present invention provides methods of treating cancer by providing to the subject in need thereof immune effector cells (e.g., T cells, NK cells) that are engineered to express a bcr-abl CAR, wherein the cancer cells express bcr-abl.

In one aspect, the present invention provides methods of treating cancer by providing to the subject in need thereof immune effector cells (e.g., T cells, NK cells) that are engineered to express a tyrosinase CAR, wherein the cancer cells express tyrosinase.

In one aspect, the present invention provides methods of treating cancer by providing to the subject in need thereof immune effector cells (e.g., T cells, NK cells) that are engineered to express a Fucosyl GM1CAR, wherein the cancer cells express Fucosyl GME In one aspect, the present invention provides methods of treating cancer by providing to the subject in need thereof immune effector cells (e.g., T cells, NK cells) that are engineered to express a mut hsp70-2CAR, wherein the cancer cells express mut hsp70-2. In one embodiment, the cancer to be treated is melanoma.

In one aspect, the present invention provides methods of treating cancer by providing to the subject in need thereof immune effector cells (e.g., T cells, NK cells) that are engineered to express a CD79a CAR, wherein the cancer cells express CD79a.

In one aspect, the present invention provides methods of treating cancer by providing to the subject in need thereof immune effector cells (e.g., T cells, NK cells) that are engineered to express a CD79b CAR, wherein the cancer cells express CD79b.

In one aspect, the present invention provides methods of treating cancer by providing to the subject in need thereof immune effector cells (e.g., T cells, NK cells) that are engineered to express a CD72 CAR, wherein the cancer cells express CD72.

In one aspect, the present invention provides methods of treating cancer by providing to the subject in need thereof immune effector cells (e.g., T cells, NK cells) that are engineered to express a LAIR1 CAR, wherein the cancer cells express LAIR1.

In one aspect, the present invention provides methods of treating cancer by providing to the subject in need thereof immune effector cells (e.g., T cells, NK cells) that are engineered to express a FCAR CAR, wherein the cancer cells express FCAR.

In one aspect, the present invention provides methods of treating cancer by providing to the subject in need thereof immune effector cells (e.g., T cells, NK cells) that are engineered to express a LILRA2 CAR, wherein the cancer cells express LILRA2.

In one aspect, the present invention provides methods of treating cancer by providing to the subject in need thereof immune effector cells (e.g., T cells, NK cells) that are engineered to express a CD300LF CAR, wherein the cancer cells express CD300LF.

In one aspect, the present invention provides methods of treating cancer by providing to the subject in need thereof immune effector cells (e.g., T cells, NK cells) that are engineered to express a CLEC12A CAR, wherein the cancer cells express CLEC12A.

In one aspect, the present invention provides methods of treating cancer by providing to the subject in need thereof immune effector cells (e.g., T cells, NK cells) that are engineered to express a BST2 CAR, wherein the cancer cells express BST2.

In one aspect, the present invention provides methods of treating cancer by providing to the subject in need thereof immune effector cells (e.g., T cells, NK cells) that are engineered to express an EMR2 CAR, wherein the cancer cells express EMR2.

In one aspect, the present invention provides methods of treating cancer by providing to the subject in need thereof immune effector cells (e.g., T cells, NK cells) that are engineered to express a LY75 CAR, wherein the cancer cells express LY75.

In one aspect, the present invention provides methods of treating cancer by providing to the subject in need thereof immune effector cells (e.g., T cells, NK cells) that are engineered to express a GPC3 CAR, wherein the cancer cells express GPC3.

In one aspect, the present invention provides methods of treating cancer by providing to the subject in need thereof immune effector cells (e.g., T cells, NK cells) that are engineered to express a FCRL5 CAR, wherein the cancer cells express FCRL5.

In one aspect, the present invention provides methods of treating cancer by providing to the subject in need thereof immune effector cells (e.g., T cells, NK cells) that are engineered to express an IGLL1 CAR, wherein the cancer cells express IGLL1.

In one aspect, the present invention relates to treatment of a subject in vivo using an PD1 CAR such that growth of cancerous tumors is inhibited. A PD1 CAR may be used alone to inhibit the growth of cancerous tumors. Alternatively, PD1 CAR may be used in conjunction with other CARs, immunogenic agents, standard cancer treatments, or other antibodies. In one embodiment, the subject is treated with a PD1 CAR and an XCAR described herein. In an embodiment, a PD1 CAR is used in conjunction with another CAR, e.g., a CAR described herein, and a kinase inhibitor, e.g., a kinase inhibitor described herein.

In another aspect, a method of treating a subject, e.g., reducing or ameliorating, a hyperproliferative condition or disorder (e.g., a cancer), e.g., solid tumor, a soft tissue tumor, or a metastatic lesion, in a subject is provided. As used herein, the term "cancer" is meant to include all types of cancerous growths or oncogenic processes, metastatic tissues or malignantly transformed cells, tissues, or organs, irrespective of histopathologic type or stage of invasiveness. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention. Examples of other cancers that can be treated include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. Treatment of metastatic cancers, e.g., metastatic cancers that express PD-L1 (Iwai et al. (2005) Int. Immunol. 17:133-144) can be effected using the antibody molecules described herein.

Exemplary cancers whose growth can be inhibited include cancers typically responsive to immunotherapy. Non-limiting examples of cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, refractory or recurrent malignancies can be treated using the molecules described herein.

In one aspect, the invention pertains to a vector comprising a CAR operably linked to promoter for expression in mammalian immune effector cells (e.g., T cells, NK cells). In one aspect, the invention provides a recombinant immune effector cell expressing a CAR of the present invention for use in treating cancer expressing a cancer associate antigen as described herein. In one aspect, CAR-expressing cells of the invention is capable of contacting a tumor cell with at least one cancer associated antigen expressed on its surface such that the CAR-expressing cell targets the cancer cell and growth of the cancer is inhibited.

In one aspect, the invention pertains to a method of inhibiting growth of a cancer, comprising contacting the cancer cell with a CAR-expressing cell of the present invention such that the CART is activated in response to the antigen and targets the cancer cell, wherein the growth of the tumor is inhibited.

In one aspect, the invention pertains to a method of treating cancer in a subject. The method comprises administering to the subject CAR-expressing cell of the present invention such that the cancer is treated in the subject. In one aspect, the cancer associated with expression of a cancer associate antigen as described herein is a hematological cancer. In one aspect, the hematological cancer is a leukemia or a lymphoma. In one aspect, a cancer associated with expression of a cancer associate antigen as described herein includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of a cancer associate antigen as described herein include, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with a cancer associate antigen as described herein expression include, but not limited to, e.g., atypical and/or non-classical cancers, malignancies, precancerous conditions or proliferative diseases associated with expression of a cancer associate antigen as described herein.

In some embodiments, a cancer that can be treated with CAR-expressing cell of the present invention is multiple myeloma. Multiple myeloma is a cancer of the blood, characterized by accumulation of a plasma cell clone in the bone marrow. Current therapies for multiple myeloma include, but are not limited to, treatment with lenalidomide, which is an analog of thalidomide. Lenalidomide has activities which include anti-tumor activity, angiogenesis inhibition, and immunomodulation. Generally, myeloma cells are thought to be negative for a cancer associate antigen as described herein expression by flow cytometry. Thus, in some embodiments, a CD19 CAR, e.g., as described herein, may be used to target myeloma cells. In some embodiments, cars of the present invention therapy can be used in combination with one or more additional therapies, e.g., lenalidomide treatment.

The invention includes a type of cellular therapy where immune effector cells (e.g., T cells, NK cells) are genetically modified to express a chimeric antigen receptor (CAR) and the CAR-expressing T cell or NK cell is infused to a recipient in need thereof. The infused cell is able to kill tumor cells in the recipient. Unlike antibody therapies, CAR-modified immune effector cells (e.g., T cells, NK cells) are able to replicate in vivo resulting in long-term persistence that can lead to sustained tumor control. In various aspects, the immune effector cells (e.g., T cells, NK cells) administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell or NK cell to the patient.

The invention also includes a type of cellular therapy where immune effector cells (e.g., T cells, NK cells) are modified, e.g., by in vitro transcribed RNA, to transiently express a chimeric antigen receptor (CAR) and the CAR T cell or NK cell is infused to a recipient in need thereof. The infused cell is able to kill tumor cells in the recipient. Thus, in various aspects, the immune effector cells (e.g., T cells, NK cells) administered to the patient, is present for less than one month, e.g., three weeks, two weeks, one week, after administration of the T cell or NK cell to the patient.

Without wishing to be bound by any particular theory, the anti-tumor immunity response elicited by the CAR-modified immune effector cells (e.g., T cells, NK cells) may be an active or a passive immune response, or alternatively may be due to a direct vs indirect immune response. In one aspect, the CAR transduced immune effector cells (e.g., T cells, NK cells) exhibit specific proinflammatory cytokine secretion and potent cytolytic activity in response to human cancer cells expressing the a cancer associate antigen as described herein, resist soluble a cancer associate antigen as described herein inhibition, mediate bystander killing and mediate regression of an established human tumor. For example, antigen-less tumor cells within a heterogeneous field of a cancer associate antigen as described herein-expressing tumor may be susceptible to indirect destruction by a cancer associate antigen as described herein-redirected immune effector cells (e.g., T cells, NK cells) that has previously reacted against adjacent antigen-positive cancer cells.

In one aspect, the fully-human CAR-modified immune effector cells (e.g., T cells, NK cells) of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of immune effector cells (e.g., T cells, NK cells) comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified immune effector cells (e.g., T cells, NK cells) of the invention are used in the treatment of diseases, disorders and conditions associated with expression of a cancer associate antigen as described herein. In certain aspects, the cells of the invention are used in the treatment of patients at risk for developing diseases, disorders and conditions associated with expression of a cancer associate antigen as described herein. Thus, the present invention provides methods for the treatment or prevention of diseases, disorders and conditions associated with expression of a cancer associate antigen as described herein comprising administering to a subject in need thereof, a therapeutically effective amount of the CAR-modified immune effector cells (e.g., T cells, NK cells) of the invention.

In one aspect the CAR-expressing cells of the inventions may be used to treat a proliferative disease such as a cancer or malignancy or is a precancerous condition such as a myelodysplasia, a myelodysplastic syndrome or a preleukemia. Further a disease associated with a cancer associate antigen as described herein expression include, but not limited to, e.g., atypical and/or non-classical cancers, malignancies, precancerous conditions or proliferative diseases expressing a cancer associated antigen as described herein. Non-cancer related indications associated with expression of a cancer associate antigen as described herein include, but are not limited to, e.g., autoimmune disease, (e.g., lupus), inflammatory disorders (allergy and asthma) and transplantation.

The CAR-modified immune effector cells (e.g., T cells, NK cells) of the present invention may be administered either alone, or as a pharmaceutical composition in combination with diluents and/or with other components such as IL-2 or other cytokines or cell populations.

Hematologic Cancer

Hematological cancer conditions are the types of cancer such as leukemia, lymphoma, and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as “preleukemia”) which are a diverse collection of hematological conditions united by ineffective production (or dysplasia) of myeloid blood cells and risk of transformation to AML.

Lymphoma is a group of blood cell tumors that develop from lymphocytes. Exemplary lymphomas include non-Hodgkin lymphoma and Hodgkin lymphoma.

The present invention provides for compositions and methods for treating cancer. In one aspect, the cancer is a hematologic cancer including but is not limited to hematological cancer is a leukemia or a lymphoma. In one aspect, the CAR-expressing cells of the invention may be used to treat cancers and malignancies such as, but not limited to, e.g., acute leukemias including but not limited to, e.g., B-cell acute lymphoid leukemia (“BALL”), T-cell acute lymphoid leukemia (“TALL”), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt’s lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and “preleukemia” which are a diverse collection of hematological conditions united by ineffective production (or dysplasia) of myeloid blood cells, and the like. Further a disease associated with a cancer associate antigen as described herein expression includes, but not limited to, e.g., atypical and/or non-classical cancers, malignancies, precancerous conditions or proliferative diseases expressing a cancer associate antigen as described herein.

The present invention also provides methods for inhibiting the proliferation or reducing a cancer associated antigen as described herein-expressing cell population, the methods comprising contacting a population of cells comprising a cancer associated antigen as described herein-expressing cell with a CAR-expressing T cell or NK cell of the invention that binds to the a cancer associate antigen as described herein-expressing cell. In a specific aspect, the present invention provides methods for inhibiting the proliferation or reducing the population of cancer cells expressing a cancer associated antigen as described herein, the methods comprising contacting a cancer associate antigen as described herein-expressing cancer cell population with a CAR-expressing T cell or NK cell of the invention that binds to a cancer associated antigen as described herein-expressing cell. In one aspect, the present invention provides methods for inhibiting the proliferation or reducing the population of cancer cells expressing a cancer associated antigen as described herein, the methods comprising contacting a cancer associated antigen as described herein-expressing cancer cell population with a CAR-expressing T cell or NK cell of the invention that binds to a cancer associated antigen as described herein-expressing cell. In certain aspects, a CAR-expressing T cell or NK cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with a cancer associated antigen as described herein-expressing cells relative to a negative control. In one aspect, the subject is a human.

The present invention also provides methods for preventing, treating and/or managing a disease associated with a cancer associated antigen as described herein-expressing cells (e.g., a hematologic cancer or atypical cancer expressing a cancer associated antigen as described herein), the methods comprising administering to a subject in need a CAR T cell or NK cell of the invention that binds to a cancer associated antigen as described herein-expressing cell. In one aspect, the subject is a human Non-limiting examples of disorders associated with a cancer associated antigen as described herein-expressing cells include autoimmune disorders (such as lupus), inflammatory disorders (such as allergies and asthma) and cancers (such as hematological cancers or atypical cancers expressing a cancer associated antigen as described herein).

The present invention also provides methods for preventing, treating and/or managing a disease associated with a cancer associated antigen as described herein-expressing cells, the methods comprising administering to a subject in need a CAR T cell or NK cell of the invention that binds to a cancer associated antigen as described herein-expressing cell. In one aspect, the subject is a human.

The present invention provides methods for preventing relapse of cancer associated with a cancer associated antigen as described herein-expressing cells, the methods comprising administering to a subject in need thereof a CAR T cell or NK cell of the invention that binds to a cancer associated antigen as described herein-expressing cell. In one aspect, the methods comprise administering to the subject in need thereof an effective amount of a CAR-expressing T cell or NK cell described herein that binds to a cancer associated antigen as described herein-expressing cell in combination with an effective amount of another therapy.

Combination Therapies

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

The CAR therapy and/or other therapeutic agents, procedures or modalities can be administered during periods of active disorder, or during a period of remission or less active disease. The CAR therapy can be administered before the other treatment, concurrently with the treatment, post-treatment, or during remission of the disorder.

When administered in combination, the CAR therapy and the additional agent (e.g., second or third agent), or all, can be administered in an amount or dose that is higher, lower or the same than the amount or dosage of each agent used individually, e.g., as a monotherapy. In certain embodiments, the administered amount or dosage of the CAR therapy, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the CAR therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, a CAR-expressing cell described herein may be used in a treatment regimen in combination with surgery, chemotherapy, radiation, immunosuppressive agents, such as n, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, a CAR-expressing cell described herein can be used in combination with a chemotherapeutic agent. Exemplary chemotherapeutic agents include an anthracycline (e.g., doxorubicin (e.g., liposomal doxorubicin)). a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzumab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitabine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Triazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednimustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoramide, TESPA and TSPA, Thioplex®); Cyclophosphamide (Endoxan®, Cytoxan®, Neosar®, Procytox®, Revimmune®); and Bendamustine HCl (Treanda®).

In embodiments, a CAR-expressing cell described herein is administered to a subject in combination with fludarabine, cyclophosphamide, and/or rituximab. In embodiments, a CAR-expressing cell described herein is administered to a subject in combination with fludarabine, cyclophosphamide, and rituximab (FCR). In embodiments, the subject has CLL. For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region ($IgV_H$) gene. In other embodiments, the subject does not comprise a leukemic cell comprising a mutation in the immunoglobulin heavy-chain variable-region ($IgV_H$) gene. In embodiments, the fludarabine is administered at a dosage of about 10-50 mg/m² (e.g., about 10-15, 15-20, 20-25, 25-30, 30-35, 35-40, 40-45, or 45-50 mg/m²), e.g., intravenously. In embodiments, the cyclophosphamide is administered at a dosage of about 200-300 mg/m² (e.g., about 200-225, 225-250, 250-275, or 275-300 mg/m²), e.g., intravenously. In embodiments, the rituximab is administered at a dosage of about 400-600 mg/m2 (e.g., 400-450, 450-500, 500-550, or 550-600 mg/m²), e.g., intravenously.

In embodiments, a CAR-expressing cell described herein is administered to a subject in combination with bendamustine and rituximab. In embodiments, the subject has CLL. For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region ($IgV_H$) gene. In other embodiments, the subject does not comprise a leukemic cell comprising a mutation in the immunoglobulin heavy-chain variable-region ($IgV_H$) gene. In embodiments, the bendamustine is administered at a dosage of about 70-110 mg/m2 (e.g., 70-80, 80-90, 90-100, or 100-110 mg/m2), e.g., intravenously. In embodiments, the rituximab is administered at a dosage of about 400-600 mg/m2 (e.g., 400-450, 450-500, 500-550, or 550-600 mg/m²), e.g., intravenously.

In embodiments, a CAR-expressing cell described herein is administered to a subject in combination with rituximab, cyclophosphamide, doxorubicine, vincristine, and/or a corticosteroid (e.g., prednisone). In embodiments, a CAR-expressing cell described herein is administered to a subject in combination with rituximab, cyclophosphamide, doxorubicine, vincristine, and prednisone (R-CHOP). In embodiments, the subject has diffuse large B-cell lymphoma (DLBCL). In embodiments, the subject has nonbulky limited-stage DLBCL (e.g., comprises a tumor having a size/diameter of less than 7 cm). In embodiments, the subject is treated with radiation in combination with the R-CHOP. For example, the subject is administered R-CHOP (e.g., 1-6 cycles, e.g., 1, 2, 3, 4, 5, or 6 cycles of R-CHOP), followed by radiation. In some cases, the subject is administered R-CHOP (e.g., 1-6 cycles, e.g., 1, 2, 3, 4, 5, or 6 cycles of R-CHOP) following radiation.

In embodiments, a CAR-expressing cell described herein is administered to a subject in combination with etoposide, prednisone, vincristine, cyclophosphamide, doxorubicin, and/or rituximab. In embodiments, a CAR-expressing cell described herein is administered to a subject in combination with etoposide, prednisone, vincristine, cyclophosphamide, doxorubicin, and rituximab (EPOCH-R). In embodiments, a CAR-expressing cell described herein is administered to a subject in combination with dose-adjusted EPOCH-R (DA-EPOCH-R). In embodiments, the subject has a B cell lymphoma, e.g., a Myc-rearranged aggressive B cell lymphoma.

In embodiments, a CAR-expressing cell described herein is administered to a subject in combination with rituximab and/or lenalidomide. Lenalidomide ((RS)-3-(4-Amino-1-oxo 1,3-dihydro-2H-isoindol-2-yl)piperidine-2,6-dione) is an immunomodulator. In embodiments, a CAR-expressing cell described herein is administered to a subject in combination with rituximab and lenalidomide. In embodiments, the subject has follicular lymphoma (FL) or mantle cell lymphoma (MCL). In embodiments, the subject has FL and has not previously been treated with a cancer therapy. In embodiments, lenalidomide is administered at a dosage of about 10-20 mg (e.g., 10-15 or 15-20 mg), e.g., daily. In embodiments, rituximab is administered at a dosage of about 350-550 mg/m² (e.g., 350-375, 375-400, 400-425, 425-450, 450-475, or 475-500 mg/m²), e.g., intravenously.

Exemplary mTOR inhibitors include, e.g., temsirolimus; ridaforolimus (formally known as deforolimus, (1R,2R,4S)-4-[(2R)-2[(1R,9S,12S,15R,16E,18R,19R,21R,23S,24E, 26E,28Z,30S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.0$^{4,9}$]hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 112), inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (daunorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In embodiments, a CAR-expressing cell described herein is administered to a subject in combination with brentuximab. Brentuximab is an antibody-drug conjugate of anti-CD30 antibody and monomethyl auristatin E. In embodiments, the subject has Hodgkin's lymphoma (HL), e.g., relapsed or refractory HL. In embodiments, the subject comprises CD30+HL. In embodiments, the subject has undergone an autologous stem cell transplant (ASCT). In embodiments, the subject has not undergone an ASCT. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In embodiments, a CAR-expressing cell described herein is administered to a subject in combination with brentuximab and dacarbazine or in combination with brentuximab and bendamustine. Dacarbazine is an alkylating agent with a chemical name of 5-(3,3-Dimethyl-1-triazenyl)imidazole-4-carboxamide. Bendamustine is an alkylating agent with a chemical name of 4-[5-[Bis(2-chloroethyl)amino]-1-methylbenzimidazol-2-yl]butanoic acid. In embodiments, the subject has Hodgkin's lymphoma (HL). In embodiments, the subject has not previously been treated with a cancer therapy. In embodiments, the subject is at least 60 years of age, e.g., 60, 65, 70, 75, 80, 85, or older. In embodiments, dacarbazine is administered at a dosage of about 300-450 mg/m² (e.g., about 300-325, 325-350, 350-375, 375-400, 400-425, or 425-450 mg/m²), e.g., intravenously. In embodiments, bendamustine is administered at a dosage of about 75-125 mg/m2 (e.g., 75-100 or 100-125 mg/m², e.g., about 90 mg/m²), e.g., intravenously. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In some embodiments, a CAR-expressing cell described herein is administered to a subject in combination with a CD20 inhibitor, e.g., an anti-CD20 antibody (e.g., an anti-CD20 mono- or bispecific antibody) or a fragment thereof. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). See, e.g., Lim et al. Haematologica. 95.1 (2010):135-43.

In some embodiments, the anti-CD20 antibody comprises rituximab. Rituximab is a chimeric mouse/human monoclonal antibody IgG1 kappa that binds to CD20 and causes cytolysis of a CD20 expressing cell, e.g., as described in www.accessdata.fda.gov/drugsatfda_docs/label/2010/103705s53111b1.pdf. In embodiments, a CAR-expressing cell described herein is administered to a subject in combination with rituximab. In embodiments, the subject has CLL or SLL.

In some embodiments, rituximab is administered intravenously, e.g., as an intravenous infusion. For example, each infusion provides about 500-2000 mg (e.g., about 500-550, 550-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, or 1900-2000 mg) of rituximab. In some embodiments, rituximab is administered at a dose of 150 mg/m² to 750 mg/m², e.g., about 150-175 mg/m², 175-200 mg/m², 200-225 mg/m², 225-250 mg/m², 250-300 mg/m², 300-325 mg/m², 325-350 mg/m², 350-375 mg/m², 375-400 mg/m², 400-425 mg/m², 425-450 mg/m², 450-475 mg/m², 475-500 mg/m², 500-525 mg/m², 525-550 mg/m², 550-575 mg/m², 575-600 mg/m², 600-625 mg/m², 625-650 mg/m², 650-675 mg/m², or 675-700 mg/m², where m² indicates the body surface area of the subject. In some embodiments, rituximab is administered at a dosing interval of at least 4 days, e.g., 4, 7, 14, 21, 28, 35 days, or more. For example, rituximab is administered at a dosing interval of at least 0.5 weeks, e.g., 0.5, 1, 2, 3, 4, 5, 6, 7, 8 weeks, or more. In some embodiments, rituximab is administered at a dose and dosing interval described herein for a period of time, e.g., at least 2 weeks, e.g., at least 2, 3, 4, 5, 6, 7, 8, 9, 10, 11, 12, 13, 14, 15, 16, 17, 18, 19, 20 weeks, or greater. For example, rituximab is administered at a dose and dosing interval described herein for a total of at least 4 doses per treatment cycle (e.g., at least 4, 5, 6, 7, 8, 9, 10, 11, 12, 13, 14, 15, 16, or more doses per treatment cycle).

In some embodiments, the anti-CD20 antibody comprises ofatumumab. Ofatumumab is an anti-CD20 IgG1κ human monoclonal antibody with a molecular weight of approximately 149 kDa. For example, ofatumumab is generated using transgenic mouse and hybridoma technology and is expressed and purified from a recombinant murine cell line (NS0). See, e.g., www.accessdata.fda.gov/drugsatfda_docs/label/2009/1253261b1.pdf; and Clinical Trial Identifier number NCT01363128, NCT01515176, NCT01626352, and NCT01397591. In embodiments, a CAR-expressing cell described herein is administered to a subject in combination with ofatumumab. In embodiments, the subject has CLL or SLL.

In some embodiments, ofatumumab is administered as an intravenous infusion. For example, each infusion provides about 150-3000 mg (e.g., about 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1200, 1200-1400, 1400-1600, 1600-1800, 1800-2000, 2000-2200, 2200-2400, 2400-2600, 2600-2800, or 2800-3000 mg) of ofatumumab. In embodiments, ofatumumab is administered at a starting dosage of about 300 mg, followed by 2000 mg, e.g., for about 11 doses, e.g., for 24 weeks. In some embodiments, ofatumumab is administered at a dosing interval of at least 4 days, e.g., 4, 7, 14, 21, 28, 35 days, or more. For example, ofatumumab is administered at a dosing interval of at least 1 week, e.g., 1, 2, 3, 4, 5, 6, 7, 8, 9, 10, 11, 12, 24, 26, 28, 20, 22, 24, 26, 28, 30 weeks, or more. In some embodiments, ofatumumab is administered at a dose and dosing interval described herein for a period of time, e.g., at least 1 week, e.g., 1, 2, 3, 4, 5, 6, 7, 8, 9, 10, 11, 12, 13, 14, 15, 16, 17, 18, 19, 20, 22, 24, 26, 28, 30, 40, 50, 60 weeks or greater, or 1, 2, 3, 4, 5, 6, 7, 8, 9, 10, 11, 12 months or greater, or 1, 2, 3, 4, 5 years or greater. For example, ofatumumab is administered at a dose and dosing interval described herein for a total of at least 2 doses per treatment cycle (e.g., at least 2, 3, 4, 5, 6, 7, 8, 9, 10, 11, 12, 13, 14, 15, 16, 18, 20, or more doses per treatment cycle).

In some cases, the anti-CD20 antibody comprises ocrelizumab. Ocrelizumab is a humanized anti-CD20 monoclonal antibody, e.g., as described in Clinical Trials Identifier Nos. NCT00077870, NCT01412333, NCT00779220, NCT00673920, NCT01194570, and Kappos et al. Lancet. 19.378 (2011):1779-87.

In some cases, the anti-CD20 antibody comprises veltuzumab. Veltuzumab is a humanized monoclonal antibody against CD20. See, e.g., Clinical Trial Identifier No. NCT00547066, NCT00546793, NCT01101581, and Goldenberg et al. Leuk Lymphoma. 51(5)(2010):747-55.

In some cases, the anti-CD20 antibody comprises GA101. GA101 (also called obinutuzumab or RO5072759) is a humanized and glyco-engineered anti-CD20 monoclonal antibody. See, e.g., Robak. Curr. Opin. Investig. Drugs. 10.6 (2009):588-96; Clinical Trial Identifier Numbers: NCT01995669, NCT01889797, NCT02229422, and NCT01414205; and www.accessdata.fda.gov/drugsatfda_docs/label/2013/125486s0001b1.pdf.

In some cases, the anti-CD20 antibody comprises AME-133v. AME-133v (also called LY2469298 or ocaratuzumab) is a humanized IgG1 monoclonal antibody against CD20 with increased affinity for the FcγRIIIa receptor and an enhanced antibody dependent cellular cytotoxicity (ADCC) activity compared with rituximab. See, e.g., Robak et al. BioDrugs 25.1 (2011):13-25; and Forero-Torres et al. Clin Cancer Res. 18.5 (2012):1395-403.

In some cases, the anti-CD20 antibody comprises PRO131921. PRO131921 is a humanized anti-CD20 monoclonal antibody engineered to have better binding to FcγRIIIa and enhanced ADCC compared with rituximab. See, e.g., Robak et al. BioDrugs 25.1 (2011):13-25; and Casulo et al. Clin Immunol. 154.1 (2014):37-46; and Clinical Trial Identifier No. NCT00452127.

In some cases, the anti-CD20 antibody comprises TRU-015. TRU-015 is an anti-CD20 fusion protein derived from domains of an antibody against CD20. TRU-015 is smaller than monoclonal antibodies, but retains Fc-mediated effector functions. See, e.g., Robak et al. BioDrugs 25.1 (2011):13-25. TRU-015 contains an anti-CD20 single-chain variable fragment (scFv) linked to human IgG1 hinge, CH2, and CH3 domains but lacks CH1 and CL domains.

In some embodiments, an anti-CD20 antibody described herein is conjugated or otherwise bound to a therapeutic agent, e.g., a chemotherapeutic agent (e.g., cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein.

In embodiments, a CAR-expressing cell described herein is administered to a subject in combination with a B-cell lymphoma 2 (BCL-2) inhibitor (e.g., venetoclax, also called ABT-199 or GDC-0199) and/or rituximab. In embodiments, a CAR-expressing cell described herein is administered to a subject in combination with venetoclax and rituximab. Venetoclax is a small molecule that inhibits the anti-apoptotic protein, BCL-2. The structure of venetoclax (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) is shown below.

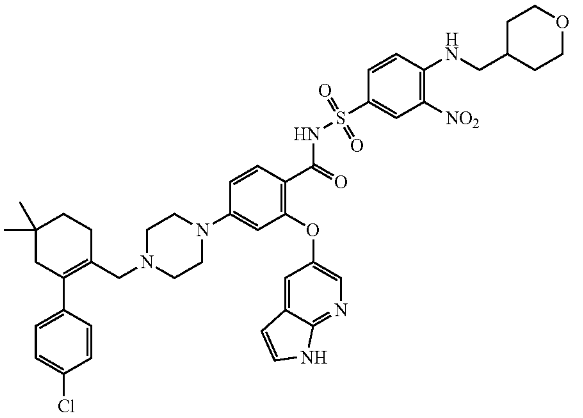 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

In embodiments, the subject has CLL. In embodiments, the subject has relapsed CLL, e.g., the subject has previously been administered a cancer therapy. In embodiments, venetoclax is administered at a dosage of about 15-600 mg (e.g., 15-20, 20-50, 50-75, 75-100, 100-200, 200-300, 300-400, 400-500, or 500-600 mg), e.g., daily. In embodiments, rituximab is administered at a dosage of about 350-550 mg/m2 (e.g., 350-375, 375-400, 400-425, 425-450, 450-475, or 475-500 mg/m2), e.g., intravenously, e.g., monthly In an embodiment, cells expressing a CAR described herein are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse. In one embodiment, cells expressing a CAR described herein are administered to a subject in combination with a molecule targeting GITR and/or modulating GITR functions, such as a GITR agonist and/or a GITR antibody that depletes regulatory T cells (Tregs). In embodiments, cells expressing a CAR described herein are administered to a subject in combination with cyclophosphamide. In one embodiment, the GITR binding molecules and/or molecules modulating GITR functions (e.g., GITR agonist and/or Treg depleting GITR antibodies) are administered prior to administration of the CAR-expressing cell. For example, in one embodiment, the GITR agonist can be administered prior to apheresis of the cells. In embodiments, cyclophosphamide is administered to the subject prior to administration (e.g., infusion or re-infusion) of the CAR-expressing cell or prior to apheresis of the cells. In embodiments, cyclophosphamide and an anti-GITR antibody are administered to the subject prior to administration (e.g., infusion or re-infusion) of the CAR-expressing cell or prior to apheresis of the cells. In one embodiment, the subject has cancer (e.g., a solid cancer or a hematological cancer such as ALL or CLL). In an embodiment, the subject has CLL. In embodiments, the subject has ALL. In embodiments, the subject has a solid cancer, e.g., a solid cancer described herein. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, a CAR expressing cell described herein is administered to a subject in combination with an mTOR inhibitor, e.g., an mTOR inhibitor described herein, e.g., a rapalog such as everolimus. In one embodiment, the mTOR inhibitor is administered prior to the CAR-expressing cell. For example, in one embodiment, the mTOR inhibitor can be administered prior to apheresis of the cells. In one embodiment, the subject has CLL.

In one embodiment, a CAR expressing cell described herein is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells. In one embodiment, the subject has CLL.

In one embodiment, a CAR-expressing cell described herein can be used in combination with a kinase inhibitor. In one embodiment, the kinase inhibitor is a CDK4 inhibitor, e.g., a CDK4 inhibitor described herein, e.g., a CD4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo[3,4-d]pyrimidine. The MNK inhibitor can be, e.g., a MNK1a, MNK1b, MNK2a and/or MNK2b inhibitor. In one embodiment, the kinase inhibitor is a dual PI3K/mTOR inhibitor described herein, such as, e.g., PF-04695102.

In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In embodiments, a CAR-expressing cell described herein is administered to a subject in combination with a cyclin-dependent kinase (CDK) 4 or 6 inhibitor, e.g., a CDK4 inhibitor or a CDK6 inhibitor described herein. In embodiments, a CAR-expressing cell described herein is administered to a subject in combination with a CDK4/6 inhibitor (e.g., an inhibitor that targets both CDK4 and CDK6), e.g., a CDK4/6 inhibitor described herein. In an embodiment, the subject has MCL. MCL is an aggressive cancer that is poorly responsive to currently available therapies, i.e., essentially incurable. In many cases of MCL, cyclin D1 (a regulator of CDK4/6) is expressed (e.g., due to chromosomal translocation involving immunoglobulin and Cyclin D1 genes) in MCL cells. Thus, without being bound by theory, it is thought that MCL cells are highly sensitive to CDK4/6 inhibition with high specificity (i.e., minimal effect on normal immune cells). CDK4/6 inhibitors alone have had some efficacy in treating MCL, but have only achieved partial remission with a high relapse rate. An exemplary CDK4/6 inhibitor is LEE011 (also called ribociclib), the structure of which is shown below.

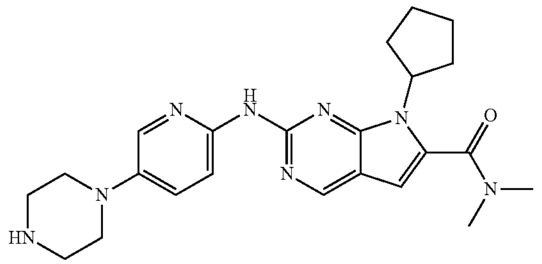 [SMILES: CN(C)C(=O)c1cc2cnc(Nc3ccc(N4CCNCC4)cn3)nc2n1C1CCCC1]

Without being bound by theory, it is believed that administration of a CAR-expressing cell described herein with a CDK4/6 inhibitor (e.g., LEE011 or other CDK4/6 inhibitor described herein) can achieve higher responsiveness, e.g., with higher remission rates and/or lower relapse rates, e.g., compared to a CDK4/6 inhibitor alone.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765). In embodiments, a CAR-expressing cell described herein is administered to a subject in combination with a BTK inhibitor (e.g., ibrutinib). In embodiments, a CAR-expressing cell described herein is administered to a subject in combination with ibrutinib (also called PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

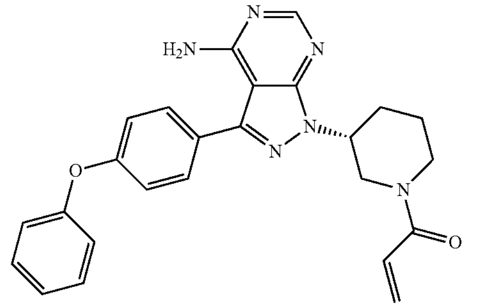 [SMILES: C=CC(=O)N1CCC[C@@H](n2nc(-c3ccc(Oc4ccccc4)cc3)c3c(N)ncnc32)C1]

In embodiments, the subject has CLL, mantle cell lymphoma (MCL), or small lymphocytic lymphoma (SLL). For example, the subject has a deletion in the short arm of chromosome 17 (del(17p), e.g., in a leukemic cell). In other examples, the subject does not have a del(17p). In embodiments, the subject has relapsed CLL or SLL, e.g., the subject has previously been administered a cancer therapy (e.g., previously been administered one, two, three, or four prior cancer therapies). In embodiments, the subject has refractory CLL or SLL. In other embodiments, the subject has follicular lymphoma, e.g., relapse or refractory follicular lymphoma. In some embodiments, ibrutinib is administered at a dosage of about 300-600 mg/day (e.g., about 300-350, 350-400, 400-450, 450-500, 500-550, or 550-600 mg/day, e.g., about 420 mg/day or about 560 mg/day), e.g., orally. In embodiments, the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In one embodiment, 1, 2, 3, 4, 5, 6, 7, 8, 9, 10, 11, 12 or more cycles of ibrutinib are administered. Without being bound by theory, it is thought that the addition of ibrutinib enhances the T cell proliferative response and may shift T cells from a T-helper-2 (Th2) to T-helper-1 (Th1) phenotype. Th1 and Th2 are phenotypes of helper T cells, with Th1 versus Th2 directing different immune response pathways. A Th1 phenotype is associated with proinflammatory responses, e.g., for killing cells, such as intracellular pathogens/viruses or cancerous cells, or perpetuating autoimmune responses. A Th2 phenotype is associated with eosinophil accumulation and anti-inflammatory responses.

In one embodiment, the kinase inhibitor is an mTOR inhibitor selected from temsirolimus; ridaforolimus (1R,2R,4S)-4-[*2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 112), inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo[3,4-d]pyrimidine (CGP57380); cercosporamide; ETC-1780445-2; and 4-amino-5-(4-fluoroanilino)-pyrazolo[3,4-d]pyrimidine.

In embodiments, a CAR-expressing cell described herein is administered to a subject in combination with a phosphoinositide 3-kinase (PI3K) inhibitor (e.g., a PI3K inhibitor described herein, e.g., idelalisib or duvelisib) and/or rituximab. In embodiments, a CAR-expressing cell described herein is administered to a subject in combination with idelalisib and rituximab. In embodiments, a CAR-expressing cell described herein is administered to a subject in combination with duvelisib and rituximab. Idelalisib (also called GS-1101 or CAL-101; Gilead) is a small molecule that blocks the delta isoform of PI3K. The structure of idelalisib (5-Fluoro-3-phenyl-2-[(1 S)-1-(7H-purin-6-ylamino)propyl]-4(3H)-quinazolinone) is shown below.

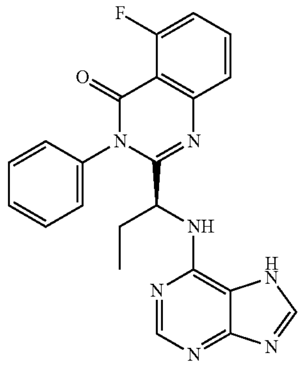 [SMILES: CC[C@H](Nc1ncnc2nc[nH]c12)c1nc2cccc(F)c2c(=O)n1-c1ccccc1]

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

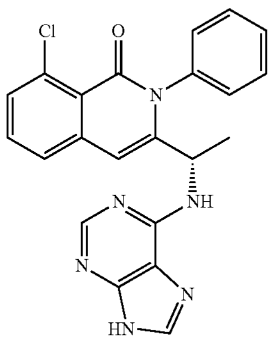 [SMILES: C[C@H](Nc1ncnc2[nH]cnc12)c1cc2cccc(Cl)c2c(=O)n1-c1ccccc1]

In embodiments, the subject has CLL. In embodiments, the subject has relapsed CLL, e.g., the subject has previously been administered a cancer therapy (e.g., previously been administered an anti-CD20 antibody or previously been administered ibrutinib). For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region ($IgV_H$) gene. In other embodiments, the subject does not comprise a leukemic cell comprising a mutation in the immunoglobulin heavy-chain variable-region ($IgV_H$) gene. In embodiments, the subject has a deletion in the long arm of chromosome 11 (del(11q)). In other embodiments, the subject does not have a del(11q). In embodiments, idelalisib is administered at a dosage of about 100-400 mg (e.g., 100-125, 125-150, 150-175, 175-200, 200-225, 225-250, 250-275, 275-300, 325-350, 350-375, or 375-400 mg), e.g., BID. In embodiments, duvelisib is administered at a dosage of about 15-100 mg (e.g., about 15-25, 25-50, 50-75, or 75-100 mg), e.g., twice a day. In embodiments, rituximab is administered at a dosage of about 350-550 $mg/m^2$ (e.g., 350-375, 375-400, 400-425, 425-450, 450-475, or 475-500 $mg/m^2$), e.g., intravenously.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-c]pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In embodiments, a CAR-expressing cell described herein is administered to a subject in combination with an anaplastic lymphoma kinase (ALK) inhibitor. Exemplary ALK kinases include but are not limited to crizotinib (Pfizer), ceritinib (Novartis), alectinib (Chugai), brigatinib (also called AP26113; Ariad), entrectinib (Ignyta), PF-06463922 (Pfizer), TSR-011 (Tesaro) (see, e.g., Clinical Trial Identifier No. NCT02048488), CEP-37440 (Teva), and X-396 (Xcovery). In some embodiments, the subject has a solid cancer, e.g., a solid cancer described herein, e.g., lung cancer.

The chemical name of crizotinib is 3-[(1R)-1-(2,6-dichloro-3-fluorophenyl)ethoxy]-5-(1-piperidin-4-ylpyrazol-4-yl)pyridin-2-amine. The chemical name of ceritinib is 5-Chloro-$N^2$-[2-isopropoxy-5-methyl-4-(4-piperidinyl)phenyl]-$N^4$-[2-(isopropylsulfonyl)phenyl]-2,4-pyrimidinediamine. The chemical name of alectinib is 9-ethyl-6,6-dimethyl-8-(4-morpholinopiperidin-1-yl)-11-oxo-6,11-dihydro-5H-benzo[b]carbazole-3-carbonitrile. The chemical name of brigatinib is 5-Chloro-$N^2$-{4-[4-(dimethylamino)-1-piperidinyl]-2-methoxyphenyl}-$N^4$-[2-(dimethylphosphoryl)phenyl]-2,4-pyrimidinediamine. The chemical name of entrectinib is N-(5-(3,5-difluorobenzyl)-1H-indazol-3-yl)-4-(4-methylpiperazin-1-yl)-2-((tetrahydro-2H-pyran-4-yl)amino)benzamide. The chemical name of PF-06463922 is (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile. The chemical structure of CEP-37440 is (S)-2-((5-chloro-2-((6-(4-(2-hydroxyethyl)piperazin-1-yl)-1-methoxy-6,7,8,9-tetrahydro-5H-benzo[7]annulen-2-yl)amino)pyrimidin-4-yl)amino)-N-methylbenzamide. The chemical name of X-396 is (R)-6-amino-5-(1-(2,6-dichloro-3-fluorophenyl)ethoxy)-N-(4-(4-methylpiperazine-1-carbonyl)phenyl)pyridazine-3-carboxamide.

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In embodiments, a CAR-expressing cell described herein is administered to a subject in combination with an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. pDCs, macrophages, and dendritic cells (DCs) can express IDO. Without being bound by theory, it is thought that a decrease in L-tryptophan (e.g., catalyzed by IDO) results in an immunosuppressive milieu by inducing T-cell anergy and apoptosis. Thus, without being bound by theory, it is thought that an IDO inhibitor can enhance the efficacy of a CAR-expressing cell described herein, e.g., by decreasing the suppression or death of a CAR-expressing immune cell. In embodiments, the subject has a solid tumor, e.g., a solid tumor described herein, e.g., prostatic, colorectal, pancreatic, cervical, gastric, ovarian, head, or lung cancer. Exemplary inhibitors of IDO include but are not limited to 1-methyl-tryptophan, indoximod (NewLink Genetics) (see, e.g., Clinical Trial Identifier Nos. NCT01191216; NCT01792050), and INCB024360 (Incyte Corp.) (see, e.g., Clinical Trial Identifier Nos. NCT01604889; NCT01685255).

In embodiments, a CAR-expressing cell described herein is administered to a subject in combination with a modulator of myeloid-derived suppressor cells (MDSCs). MDSCs accumulate in the periphery and at the tumor site of many solid tumors. These cells suppress T cell responses, thereby hindering the efficacy of CAR-expressing cell therapy. Without being bound by theory, it is thought that administration of a MDSC modulator enhances the efficacy of a CAR-expressing cell described herein. In an embodiment, the subject has a solid tumor, e.g., a solid tumor described herein, e.g., glioblastoma. Exemplary modulators of MDSCs include but are not limited to MCS110 and BLZ945. MCS110 is a monoclonal antibody (mAb) against macrophage colony-stimulating factor (M-CSF). See, e.g., Clinical Trial Identifier No. NCT00757757. BLZ945 is a small molecule inhibitor of colony stimulating factor 1 receptor (CSF1R). See, e.g., Pyonteck et al. Nat. Med. 19(2013): 1264-72. The structure of BLZ945 is shown below.

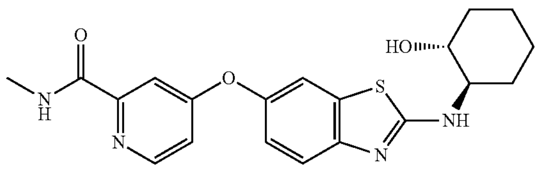 [SMILES: CNC(=O)c1cc(Oc2ccc3nc(N[C@@H]4CCCC[C@H]4O)sc3c2)ccn1]

In embodiments, a CAR-expressing cell described herein is administered to a subject in combination with a CD19 CART cell (e.g., CTL019, e.g., as described in WO2012/079000, incorporated herein by reference). In embodiments, the subject has a CD19+ lymphoma, e.g., a CD19+ Non-Hodgkin's Lymphoma (NHL), a CD19+FL, or a CD19+ DLBCL. In embodiments, the subject has a relapsed or refractory CD19+ lymphoma. In embodiments, a lymphodepleting chemotherapy is administered to the subject prior to, concurrently with, or after administration (e.g., infusion) of CD19 CART cells. In an example, the lymphodepleting chemotherapy is administered to the subject prior to administration of CD19 CART cells. For example, the lymphodepleting chemotherapy ends 1-4 days (e.g., 1, 2, 3, or 4 days) prior to CD19 CART cell infusion. In embodiments, multiple doses of CD19 CART cells are administered, e.g., as described herein. For example, a single dose comprises about $5\times10^8$ CD19 CART cells. In embodiments, a lymphodepleting chemotherapy is administered to the subject prior to, concurrently with, or after administration (e.g., infusion) of a CAR-expressing cell described herein, e.g., a non-CD19 CAR-expressing cell. In embodiments, a CD19 CART is administered to the subject prior to, concurrently with, or after administration (e.g., infusion) of a non-CD19 CAR-expressing cell, e.g., a non-CD19 CAR-expressing cell described herein.

In some embodiments, a CAR-expressing cell described herein is administered to a subject in combination with a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. In embodiments, het-IL-15 is administered subcutaneously. In embodiments, the subject has a cancer, e.g., solid cancer, e.g., melanoma or colon cancer. In embodiments, the subject has a metastatic cancer.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthralgias, nausea, vomiting, and headache. CRS may include clinical skin signs and symptoms such as rash. CRS may include clinical gastrointestinal signs and symptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardiac output (early) and potentially diminished cardiac output (late). CRS may include clinical coagulation signs and symptoms such as elevated d-dimer, hypofibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures.

Accordingly, the methods described herein can comprise administering a CAR-expressing cell described herein to a subject and further administering one or more agents to manage elevated levels of a soluble factor resulting from treatment with a CAR-expressing cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antigen binding fragment thereof. Examples of such agents include, but are not limited to a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitors of TNFα include, but are not limited to, xanthine derivatives (e.g. pentoxifylline) and bupropion. An example of an IL-6 inhibitor is an anti-IL-6 antibody molecule or an anti-IL-6 receptor antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 receptor antibody molecule is tocilizumab. An example of an IL-1R based inhibitor is anakinra.

In one embodiment, the subject can be administered an agent which enhances the activity of a CAR-expressing cell. For example, in one embodiment, the agent can be an agent which inhibits an inhibitory molecule. Inhibitory molecules, e.g., Programmed Death 1 (PD-1), can, in some embodiments, decrease the ability of a CAR-expressing cell to mount an immune effector response. Examples of inhibitory molecules include PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used to inhibit expression of an inhibitory molecule in the CAR-expressing cell. In an embodiment the inhibitor is an shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR. In one embodiment, the inhibitor of an inhibitory signal can be, e.g., an antibody or antibody fragment that binds to an inhibitory molecule. For example, the agent can be an antibody or antibody fragment that binds to PD-1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206)). In an embodiment, the agent is an antibody or antibody fragment that binds to TIM3. In an embodiment, the agent is an antibody or antibody fragment that binds to CEACAM (CEACAM-1, CEACAM-3, and/or CEACAM-5). In an embodiment, the agent is an antibody or antibody fragment that binds to LAGS.

PD-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094) Immune suppression can be reversed by inhibiting the local interaction of PD-1 with PD-L1. Antibodies, antibody fragments, and other inhibitors of PD-1, PD-L1 and PD-L2 are available in the art and may be used combination with a cars of the present invention described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. Pembrolizumab (formerly known as lambrolizumab, and also referred to as MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. MEDI4736 (Medimmune) is a human monoclonal antibody that binds to PDL1, and inhibits interaction of the ligand with PD1. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.570 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

TIM-3 (T cell immunoglobulin-3) also negatively regulates T cell function, particularly in IFN-g-secreting CD4+ T helper 1 and CD8+ T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In other embodiments, the agent that enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10:1371/journal-.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG-3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG-3 and its ligands are available in the art and may be used combination with a CD19 CAR described herein. For example, BMS-986016 (Bristol-Myers Squib) is a monoclonal antibody that targets LAG3. IMP701 (Immutep) is an antagonist LAG-3 antibody and IMP731 (Immutep and GlaxoSmithKline) is a depleting LAG-3 antibody. Other LAG-3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an intracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell that does not express a CAR of the present invention.

In one embodiment, the agent which enhances activity of a CAR-expressing cell described herein is miR-17-92.

In one embodiment, the agent which enhances activity of a CAR-described herein is a cytokine. Cytokines have important functions related to T cell expansion, differentiation, survival, and homeostasis. Cytokines that can be administered to the subject receiving a CAR-expressing cell described herein include: IL-2, IL-4, IL-7, IL-9, IL-15, IL-18, and IL-21, or a combination thereof. In preferred embodiments, the cytokine administered is IL-7, IL-15, or IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days.

In embodiments, the cytokine is administered in combination with CAR-expressing T cells. The cytokine can be administered simultaneously or concurrently with the CAR-expressing T cells, e.g., administered on the same day. The cytokine may be prepared in the same pharmaceutical composition as the CAR-expressing T cells, or may be prepared in a separate pharmaceutical composition. Alternatively, the cytokine can be administered shortly after administration of the CAR-expressing T cells, e.g., 1 day, 2 days, 3 days, 4 days, 5 days, 6 days, or 7 days after administration of the CAR-expressing T cells. In embodiments where the cytokine is administered in a dosing regimen that occurs over more than one day, the first day of the cytokine dosing regimen can be on the same day as administration with the CAR-expressing T cells, or the first day of the cytokine dosing regimen can be 1 day, 2 days, 3 days, 4 days, 5 days, 6 days, or 7 days after administration of the CAR-expressing T cells. In one embodiment, on the first day, the CAR-expressing T cells are administered to the subject, and on the second day, a cytokine is administered once a day for the next 7 days. In a preferred embodiment, the cytokine to be administered in combination with CAR-expressing T cells is IL-7, IL-15, or IL-21.

In other embodiments, the cytokine is administered a period of time after administration of CAR-expressing cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells. In one embodiment, the cytokine is administered after assessment of the subject's response to the CAR-expressing cells. For example, the subject is administered CAR-expressing cells according to the dosage and regimens described herein. The response of the subject to CAR-expressing cell therapy is assessed at 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells, using any of the methods described herein, including inhibition of tumor growth, reduction of circulating tumor cells, or tumor regression. Subjects that do not exhibit a sufficient response to CAR-expressing cell therapy can be administered a cytokine. Administration of the cytokine to the subject that has sub-optimal response to the CAR-expressing cell therapy improves CAR-expressing cell efficacy or anti-cancer activity. In a preferred embodiment, the cytokine administered after administration of CAR-expressing cells is IL-7.

Combination with a Low Dose of an mTOR Inhibitor

In one embodiment, the cells expressing a CAR molecule, e.g., a CAR molecule described herein, are administered in combination with a low, immune enhancing dose of an mTOR inhibitor.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, or at least 70 but no more than 90%.

In an embodiment, a dose of an mTOR inhibitor is associated with, or provides, mTOR inhibition of at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, or at least 60 but no more than 80%.

In an embodiment, a dose of an mTOR inhibitor is associated with, or provides, mTOR inhibition of at least 5 but no more than 70%, at least 10 but no more than 70%, at least 15, but no more than 70%, at least 20 but no more than 70%, at least 30 but no more than 70%, at least 40 but no more than 70%, or at least 50 but no more than 70%.

In an embodiment, a dose of an mTOR inhibitor is associated with, or provides, mTOR inhibition of at least 5 but no more than 60%, at least 10 but no more than 60%, at least 15, but no more than 60%, at least 20 but no more than 60%, at least 30 but no more than 60%, or at least 40 but no more than 60%.

In an embodiment, a dose of an mTOR inhibitor is associated with, or provides, mTOR inhibition of at least 5 but no more than 50%, at least 10 but no more than 50%, at least 15, but no more than 50%, at least 20 but no more than 50%, at least 30 but no more than 50%, or at least 40 but no more than 50%.

In an embodiment, a dose of an mTOR inhibitor is associated with, or provides, mTOR inhibition of at least 5 but no more than 40%, at least 10 but no more than 40%, at least 15, but no more than 40%, at least 20 but no more than 40%, at least 30 but no more than 40%, or at least 35 but no more than 40%.

In an embodiment, a dose of an mTOR inhibitor is associated with, or provides, mTOR inhibition of at least 5 but no more than 30%, at least 10 but no more than 30%, at least 15, but no more than 30%, at least 20 but no more than 30%, or at least 25 but no more than 30%.

In an embodiment, a dose of an mTOR inhibitor is associated with, or provides, mTOR inhibition of at least 1, 2, 3, 4 or 5 but no more than 20%, at least 1, 2, 3, 4 or 5 but no more than 30%, at least 1, 2, 3, 4 or 5, but no more than 35, at least 1, 2, 3, 4 or 5 but no more than 40%, or at least 1, 2, 3, 4 or 5 but no more than 45%.

In an embodiment, a dose of an mTOR inhibitor is associated with, or provides, mTOR inhibition of at least 1, 2, 3, 4 or 5 but no more than 90%.

As is discussed herein, the extent of mTOR inhibition can be expressed as the extent of P70 S6 kinase inhibition, e.g., the extent of mTOR inhibition can be determined by the level of decrease in P70 S6 kinase activity, e.g., by the decrease in phosphorylation of a P70 S6 kinase substrate. The level of mTOR inhibition can be evaluated by a method described herein, e.g. by the Boulay assay, or measurement of phosphorylated S6 levels by western blot.

Exemplary mTOR Inhibitors

As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by *Streptomyces hygroscopicus* having the structure shown in Formula A.

(A)

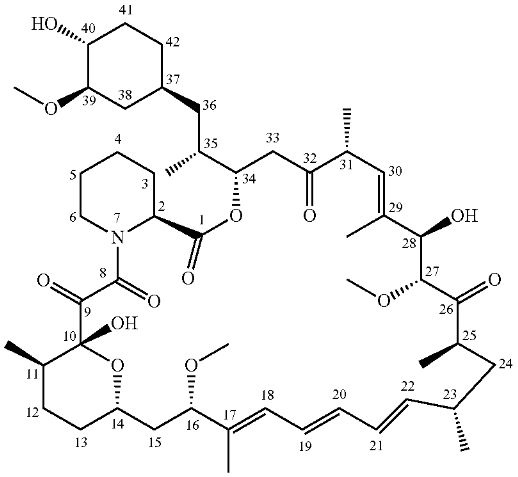

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, O-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'- yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(25)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the methoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demethoxy-16-(pent-2-ynyl)oxy-rapamycin, 16-demethoxy-16-(but-2-ynyl)oxy-rapamycin, 16-demethoxy-16-(propargyl)oxy-rapamycin, 16-demethoxy-16-(4-hydroxy-but-2-ynyl)oxy-rapamycin, 16-demethoxy-16-benzyloxy-40-O-(2-hydroxyethyl)-rapamycin, 16-demethoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

RAD001, otherwise known as everolimus (Afinitor®), has the chemical name (1R,9S,12S,15R,16E,18R,19R,21R,23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-azatricyclo[30.3.1.04,9]hexatriaconta-16,24,26,28-tetraene-2,3,10,14,20-pentaone Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTor inhibitors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more effective inhibitors of mTORC1 than such allosteric mTOR inhibitors as rapamycin, because they modulate rapamycin-resistant mTORC1 outputs such as 4EBP1-T37/46 phosphorylation and cap-dependent translation.

Catalytic inhibitors include: BEZ235 or 2-methyl-2-[4-(3-methyl-2-oxo-8-quinolin-3-yl-2,3-dihydro-imidazo[4,5-c]quinolin-1-yl)-phenyl]-propionitrile, or the monotosylate salt form. the synthesis of BEZ235 is described in WO2006/122806; CCG168 (otherwise known as AZD-8055, Chresta, C. M., et al., Cancer Res, 2010, 70(1), 288-298) which has the chemical name {5-[2,4-bis-((S)-3-methyl-morpholin-4-yl)-pyrido[2,3d]pyrimidin-7-yl]-2-methoxy-phenyl}-methanol; 3-[2,4-bis[(3S)-3-methylmorpholin-4-yl]pyrido[2,3-d]pyrimidin-7-yl]-N-methylbenzamide (WO09104019); 3-(2-aminobenzo[d]oxazol-5-yl)-1-isopropyl-1H-pyrazolo[3,4-d]pyrimidin-4-amine (WO10051043 and WO2013023184); A N-(3-(N-(3-((3,5-dimethoxyphenyl)amino)quinoxaline-2-yl)sulfamoyl)phenyl)-3-methoxy-4-methylbenzamide (WO07044729 and WO12006552); PKI-587 (Venkatesan, A. M., J. Med. Chem., 2010, 53, 2636-2645) which has the chemical name 1-[4-[4-(dimethylamino)piperidine-1-carbonyl]phenyl]-3-[4-(4,6-dimorpholino-1,3,5-triazin-2-yl)phenyl]urea; GSK-2126458 (ACS Med. Chem. Lett., 2010, 1, 39-43) which has the chemical name 2,4-difluoro-N-{2-methoxy-5-[4-(4-pyridazinyl)-6-quinolinyl]-3-pyridinyl}benzenesulfonamide; 5-(9-isopropyl-8-methyl-2-morpholino-9H-purin-6-yl)pyrimidin-2-amine (WO10114484); (E)-N-(8-(6-amino-5-(trifluoromethyl)pyridin-3-yl)-1-(6-(2-cyanopropan-2-yl)pyridin-3-yl)-3-methyl-1H-imidazo quinolin-2(3H)-ylidene)cyanamide (WO12007926).

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTor inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof of any of the foregoing.

mTOR inhibitors, such as RAD001, may be formulated for delivery based on well-established methods in the art based on the particular dosages described herein. In particular, U.S. Pat. No. 6,004,973 (incorporated herein by reference) provides examples of formulations useable with the mTOR inhibitors described herein.

Evaluation of mTor Inhibition mTOR phosphorylates the kinase P70 S6, thereby activating P70 S6 kinase and allowing it to phosphorylate its substrate. The extent of mTOR inhibition can be expressed as the extent of P70 S6 kinase inhibition, e.g., the extent of mTOR inhibition can be determined by the level of decrease in P70 S6 kinase activity, e.g., by the decrease in phosphorylation of a P70 S6 kinase substrate. One can determine the level of mTOR inhibition, by measuring P70 S6 kinase activity (the ability of P70 S6 kinase to phosphorylate a substrate), in the absence of inhibitor, e.g., prior to administration of inhibitor, and in the presences of inhibitor, or after the administration of inhibitor. The level of inhibition of P70 S6 kinase gives the level of mTOR inhibition. Thus, if P70 S6 kinase is inhibited by 40%, mTOR activity, as measured by P70 S6 kinase activity, is inhibited by 40%. The extent or level of inhibition referred to herein is the average level of inhibition over the dosage interval. By way of example, if the inhibitor is given once per week, the level of inhibition is given by the average level of inhibition over that interval, namely a week.

Boulay et al., *Cancer Res,* 2004, 64:252-61, hereby incorporated by reference, teaches an assay that can be used to assess the level of mTOR inhibition (referred to herein as the Boulay assay). In an embodiment, the assay relies on the measurement of P70 S6 kinase activity from biological samples before and after administration of an mTOR inhibitor, e.g., RAD001. Samples can be taken at preselected times after treatment with an mTOR inhibitor, e.g., 24, 48, and 72 hours after treatment. Biological samples, e.g., from skin or peripheral blood mononuclear cells (PBMCs) can be used. Total protein extracts are prepared from the samples. P70 S6 kinase is isolated from the protein extracts by immunoprecipitation using an antibody that specifically recognizes the P70 S6 kinase. Activity of the isolated P70 S6 kinase can be measured in an in vitro kinase assay. The isolated kinase can be incubated with 40S ribosomal subunit substrates (which is an endogenous substrate of P70 S6 kinase) and gamma-$^{32}P$ under conditions that allow phosphorylation of the substrate. Then the reaction mixture can be resolved on an SDS-PAGE gel, and $^{32}P$ signal analyzed using a PhosphorImager. A $^{32}P$ signal corresponding to the size of the 40S ribosomal subunit indicates phosphorylated substrate and the activity of P70 S6 kinase. Increases and decreases in kinase activity can be calculated by quantifying the area and intensity of the $^{32}P$ signal of the phosphorylated substrate (e.g., using ImageQuant, Molecular Dynamics), assigning arbitrary unit values to the quantified signal, and comparing the values from after administration with values from before administration or with a reference value. For example, percent inhibition of kinase activity can be calculated with the following formula: 1−(value obtained after administration/value obtained before administration)×100. As described above, the extent or level of inhibition referred to herein is the average level of inhibition over the dosage interval.

Methods for the evaluation of kinase activity, e.g., P70 S6 kinase activity, are also provided in U.S. Pat. No. 7,727,950, hereby incorporated by reference.

The level of mTOR inhibition can also be evaluated by a change in the ration of PD1 negative to PD1 positive T cells. T cells from peripheral blood can be identified as PD1 negative or positive by art-known methods.

Low-Dose mTOR Inhibitors

Methods described herein use low, immune enhancing, dose mTOR inhibitors, doses of mTOR inhibitors, e.g., allosteric mTOR inhibitors, including rapalogs such as RAD001. In contrast, levels of inhibitor that fully or near fully inhibit the mTOR pathway are immunosuppressive and are used, e.g., to prevent organ transplant rejection. In addition, high doses of rapalogs that fully inhibit mTOR also inhibit tumor cell growth and are used to treat a variety of cancers (See, e.g., Antineoplastic effects of mammalian target of rapamycine inhibitors. Salvadori M. World J Transplant. 2012 Oct. 24; 2(5):74-83; Current and Future Treatment Strategies for Patients with Advanced Hepatocellular Carcinoma: Role of mTOR Inhibition. Finn R S. Liver Cancer. 2012 November; 1(3-4):247-256; Emerging Signaling Pathways in Hepatocellular Carcinoma. Moeini A, Cornellà H, Villanueva A. Liver Cancer. 2012 September; 1(2):83-93; Targeted cancer therapy—Are the days of systemic chemotherapy numbered? Joo W D, Visintin I, Mor G. Maturitas. 2013 Sep. 20*; Role of natural and adaptive immunity in renal cell carcinoma response to VEGFR-TKIs and mTOR inhibitor*. Santoni M, Berardi R, Amantini C, Burattini L, Santini D, Santoni G, Cascinu S. Int J Cancer. 2013 Oct. 2).

The present invention is based, at least in part, on the surprising finding that doses of mTOR inhibitors well below those used in current clinical settings had a superior effect in increasing an immune response in a subject and increasing the ratio of PD-1 negative T cells/PD-1 positive T cells. It was surprising that low doses of mTOR inhibitors, producing only partial inhibition of mTOR activity, were able to effectively improve immune responses in human subjects and increase the ratio of PD-1 negative T cells/PD-1 positive T cells.

Alternatively, or in addition, without wishing to be bound by any theory, it is believed that low, a low, immune enhancing, dose of an mTOR inhibitor can increase naive T cell numbers, e.g., at least transiently, e.g., as compared to a non-treated subject. Alternatively or additionally, again while not wishing to be bound by theory, it is believed that treatment with an mTOR inhibitor after a sufficient amount of time or sufficient dosing results in one or more of the following:

- an increase in the expression of one or more of the following markers: $CD62L^{high}$, $CD127^{high}$, $CD27^{+}$, and BCL2, e.g., on memory T cells, e.g., memory T cell precursors;
- a decrease in the expression of KLRG1, e.g., on memory T cells, e.g., memory T cell precursors; and
- an increase in the number of memory T cell precursors, e.g., cells with any one or combination of the following characteristics: increased $CD62L^{high}$ increased $CD127^{high}$, increased $CD27^{+}$, decreased KLRG1, and increased BCL2;
- and wherein any of the changes described above occurs, e.g., at least transiently, e.g., as compared to a non-treated subject (Araki, K et al. (2009) *Nature* 460:108-112). Memory T cell precursors are memory T cells that are early in the differentiation program. For example, memory T cells have one or more of the following characteristics: increased $CD62L^{high}$, increased $CD127^{high}$ increased $CD27^{+}$, decreased KLRG1, and/or increased BCL2.

In an embodiment, the invention relates to a composition, or dosage form, of an mTOR inhibitor, e.g., an allosteric mTOR inhibitor, e.g., a rapalog, rapamycin, or RAD001, or a catalytic mTOR inhibitor, which, when administered on a selected dosing regimen, e.g., once daily or once weekly, is associated with: a level of mTOR inhibition that is not associated with complete, or significant immune suppression, but is associated with enhancement of the immune response.

An mTOR inhibitor, e.g., an allosteric mTOR inhibitor, e.g., a rapalog, rapamycin, or RAD001, or a catalytic mTOR inhibitor, can be provided in a sustained release formulation. Any of the compositions or unit dosage forms described herein can be provided in a sustained release formulation. In some embodiments, a sustained release formulation will have lower bioavailability than an immediate release formulation. E.g., in embodiments, to attain a similar therapeutic effect of an immediate release formulation a sustained release formulation will have from about 2 to about 5, about 2.5 to about 3.5, or about 3 times the amount of inhibitor provided in the immediate release formulation.

In an embodiment, immediate release forms, e.g., of RAD001, typically used for one administration per week, having 0.1 to 20, 0.5 to 10, 2.5 to 7.5, 3 to 6, or about 5, mgs per unit dosage form, are provided. For once per week administrations, these immediate release formulations correspond to sustained release forms, having, respectively, 0.3 to 60, 1.5 to 30, 7.5 to 22.5, 9 to 18, or about 15 mgs of an mTOR inhibitor, e.g., an allosteric mTOR inhibitor, e.g., rapamycin or RAD001. In embodiments both forms are administered on a once/week basis.

In an embodiment, immediate release forms, e.g., of RAD001, typically used for one administration per day, having 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs per unit dosage form, are provided. For once per day administrations, these immediate release forms correspond to sustained release forms, having, respectively, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of an mTOR inhibitor, e.g., an allosteric mTOR inhibitor, e.g., rapamycin or RAD001. For once per week administrations, these immediate release forms correspond to sustained release forms, having, respectively, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of an mTOR inhibitor, e.g., an allosteric mTOR inhibitor, e.g., rapamycin or RAD001.

In an embodiment, immediate release forms, e.g., of RAD001, typically used for one administration per day, having 0.01 to 1.0 mgs per unit dosage form, are provided. For once per day administrations, these immediate release forms correspond to sustained release forms, having, respectively, 0.03 to 3 mgs of an mTOR inhibitor, e.g., an allosteric mTOR inhibitor, e.g., rapamycin or RAD001. For once per week administrations, these immediate release forms correspond to sustained release forms, having, respectively, 0.2 to 20 mgs of an mTOR inhibitor, e.g., an allosteric mTOR inhibitor, e.g., rapamycin or RAD001.

In an embodiment, immediate release forms, e.g., of RAD001, typically used for one administration per week, having 0.5 to 5.0 mgs per unit dosage form, are provided. For once per week administrations, these immediate release forms correspond to sustained release forms, having, respectively, 1.5 to 15 mgs of an mTOR inhibitor, e.g., an allosteric mTOR inhibitor, e.g., rapamycin or RAD001.

As described above, one target of the mTOR pathway is the P70 S6 kinase. Thus, doses of mTOR inhibitors which are useful in the methods and compositions described herein are those which are sufficient to achieve no greater than 80% inhibition of P70 S6 kinase activity relative to the activity of the P70 S6 kinase in the absence of an mTOR inhibitor, e.g., as measured by an assay described herein, e.g., the Boulay assay. In a further aspect, the invention provides an amount of an mTOR inhibitor sufficient to achieve no greater than 38% inhibition of P70 S6 kinase activity relative to P70 S6 kinase activity in the absence of an mTOR inhibitor.

In one aspect the dose of mTOR inhibitor useful in the methods and compositions of the invention is sufficient to achieve, e.g., when administered to a human subject, 90+/−5% (i.e., 85-95%), 89+/−5%, 88+/−5%, 87+/−5%, 86+/−5%, 85+/−5%, 84+/−5%, 83+/−5%, 82+/−5%, 81+/−5%, 80+/−5%, 79+/−5%, 78+/−5%, 77+/−5%, 76+/−5%, 75+/−5%, 74+/−5%, 73+/−5%, 72+/−5%, 71+/−5%, 70+/−5%, 69+/−5%, 68+/−5%, 67+/−5%, 66+/−5%, 65+/−5%, 64+/−5%, 63+/−5%, 62+/−5%, 61+/−5%, 60+/−5%, 59+/−5%, 58+/−5%, 57+/−5%, 56+/−5%, 55+/−5%, 54+/−5%, 54+/−5%, 53+/−5%, 52+/−5%, 51+/−5%, 50+/−5%, 49+/−5%, 48+/−5%, 47+/−5%, 46+/−5%, 45+/−5%, 44+/−5%, 43+/−5%, 42+/−5%, 41+/−5%, 40+/−5%, 39+/−5%, 38+/−5%, 37+/−5%, 36+/−5%, 35+/−5%, 34+/−5%, 33+/−5%, 32+/−5%, 31+/−5%, 30+/−5%, 29+/−5%, 28+/−5%, 27+/−5%, 26+/−5%, 25+/−5%, 24+/−5%, 23+/−5%, 22+/−5%, 21+/−5%, 20+/−5%, 19+/−5%, 18+/−5%, 17+/−5%, 16+/−5%, 15+/−5%, 14+/−5%, 13+/−5%, 12+/−5%, 11+/−5%, or 10+/−5%, inhibition of P70 S6 kinase activity, e.g., as measured by an assay described herein, e.g., the Boulay assay.

P70 S6 kinase activity in a subject may be measured using methods known in the art, such as, for example, according to the methods described in U.S. Pat. No. 7,727,950, by immunoblot analysis of phosphoP70 S6K levels and/or phosphoP70 S6 levels or by in vitro kinase activity assays.

As used herein, the term "about" in reference to a dose of mTOR inhibitor refers to up to a +/−10% variability in the amount of mTOR inhibitor, but can include no variability around the stated dose.

In some embodiments, the invention provides methods comprising administering to a subject an mTOR inhibitor, e.g., an allosteric inhibitor, e.g., RAD001, at a dosage within a target trough level. In some embodiments, the trough level is significantly lower than trough levels associated with dosing regimens used in organ transplant and cancer patients. In an embodiment mTOR inhibitor, e.g., RAD001, or rapamycin, is administered to result in a trough level that is less than ½, ¼, ⅒, or 1/20 of the trough level that results in immunosuppression or an anticancer effect. In an embodiment mTOR inhibitor, e.g., RAD001, or rapamycin, is administered to result in a trough level that is less than ½, ¼, ⅒, or 1/20 of the trough level provided on the FDA approved packaging insert for use in immunosuppression or an anticancer indications.

In an embodiment a method disclosed herein comprises administering to a subject an mTOR inhibitor, e.g., an allosteric inhibitor, e.g., RAD001, at a dosage that provides a target trough level of 0.1 to 10 ng/ml, 0.1 to 5 ng/ml, 0.1 to 3 ng/ml, 0.1 to 2 ng/ml, or 0.1 to 1 ng/ml.

In an embodiment a method disclosed herein comprises administering to a subject an mTOR inhibitor, e.g., an allosteric inhibitor, e.g., RAD001, at a dosage that provides a target trough level of 0.2 to 10 ng/ml, 0.2 to 5 ng/ml, 0.2 to 3 ng/ml, 0.2 to 2 ng/ml, or 0.2 to 1 ng/ml.

In an embodiment a method disclosed herein comprises administering to a subject an mTOR inhibitor, e.g. an, allosteric inhibitor, e.g., RAD001, at a dosage that provides a target trough level of 0.3 to 10 ng/ml, 0.3 to 5 ng/ml, 0.3 to 3 ng/ml, 0.3 to 2 ng/ml, or 0.3 to 1 ng/ml.

In an embodiment a method disclosed herein comprises administering to a subject an mTOR inhibitor, e.g., an allosteric inhibitor, e.g., RAD001, at a dosage that provides a target trough level of 0.4 to 10 ng/ml, 0.4 to 5 ng/ml, 0.4 to 3 ng/ml, 0.4 to 2 ng/ml, or 0.4 to 1 ng/ml.

In an embodiment a method disclosed herein comprises administering to a subject an mTOR inhibitor, e.g., an allosteric inhibitor, e.g., RAD001, at a dosage that provides a target trough level of 0.5 to 10 ng/ml, 0.5 to 5 ng/ml, 0.5 to 3 ng/ml, 0.5 to 2 ng/ml, or 0.5 to 1 ng/ml.

In an embodiment a method disclosed herein comprises administering to a subject an mTOR inhibitor, e.g., an allosteric inhibitor, e.g., RAD001, at a dosage that provides a target trough level of 1 to 10 ng/ml, 1 to 5 ng/ml, 1 to 3 ng/ml, or 1 to 2 ng/ml.

As used herein, the term "trough level" refers to the concentration of a drug in plasma just before the next dose, or the minimum drug concentration between two doses.

In some embodiments, a target trough level of RAD001 is in a range of between about 0.1 and 4.9 ng/ml. In an embodiment, the target trough level is below 3 ng/ml, e.g., is between 0.3 or less and 3 ng/ml. In an embodiment, the target trough level is below 3 ng/ml, e.g., is between 0.3 or less and 1 ng/ml.

In a further aspect, the invention can utilize an mTOR inhibitor other than RAD001 in an amount that is associated with a target trough level that is bioequivalent to the specified target trough level for RAD001. In an embodiment, the target trough level for an mTOR inhibitor other than RAD001, is a level that gives the same level of mTOR inhibition (e.g., as measured by a method described herein, e.g., the inhibition of P70 S6) as does a trough level of RAD001 described herein.

Pharmaceutical Compositions: mTOR Inhibitors

In one aspect, the present invention relates to pharmaceutical compositions comprising an mTOR inhibitor, e.g., an mTOR inhibitor as described herein, formulated for use in combination with CAR cells described herein.

In some embodiments, the mTOR inhibitor is formulated for administration in combination with an additional, e.g., as described herein.

In general, compounds of the invention will be administered in therapeutically effective amounts as described above via any of the usual and acceptable modes known in the art, either singly or in combination with one or more therapeutic agents.

The pharmaceutical formulations may be prepared using conventional dissolution and mixing procedures. For example, the bulk drug substance (e.g., an mTOR inhibitor or stabilized form of the compound (e.g., complex with a cyclodextrin derivative or other known complexation agent) is dissolved in a suitable solvent in the presence of one or more of the excipients described herein. The mTOR inhibitor is typically formulated into pharmaceutical dosage forms to provide an easily controllable dosage of the drug and to give the patient an elegant and easily handleable product.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Where an mTOR inhibitor is administered in combination with (either simultaneously with or separately from) another agent as described herein, in one aspect, both components can be administered by the same route (e.g., parenterally). Alternatively, another agent may be administered by a different route relative to the mTOR inhibitor. For example, an mTOR inhibitor may be administered orally and the other agent may be administered parenterally.

Sustained Release mTOR inhibitors, e.g., allosteric mTOR inhibitors or catalytic mTOR inhibitors, disclosed herein can be provided as pharmaceutical formulations in form of oral solid dosage forms comprising an mTOR inhibitor disclosed herein, e.g., rapamycin or RAD001, which satisfy product stability requirements and/or have favorable pharmacokinetic properties over the immediate release (IR) tablets, such as reduced average plasma peak concentrations, reduced inter- and intra-patient variability in the extent of drug absorption and in the plasma peak concentration, reduced $C_{max}/C_{min}$ ratio and/or reduced food effects. Provided pharmaceutical formulations may allow for more precise dose adjustment and/or reduce frequency of adverse events thus providing safer treatments for patients with an mTOR inhibitor disclosed herein, e.g., rapamycin or RAD001.

In some embodiments, the present disclosure provides stable extended release formulations of an mTOR inhibitor disclosed herein, e.g., rapamycin or RAD001, which are multi-particulate systems and may have functional layers and coatings.

The term "extended release, multi-particulate formulation as used herein refers to a formulation which enables release of an mTOR inhibitor disclosed herein, e.g., rapamycin or RAD001, over an extended period of time e.g. over at least 1, 2, 3, 4, 5 or 6 hours. The extended release formulation may contain matrices and coatings made of special excipients, e.g., as described herein, which are formulated in a manner as to make the active ingredient available over an extended period of time following ingestion.

The term "extended release" can be interchangeably used with the terms "sustained release" (SR) or "prolonged release". The term "extended release" relates to a pharmaceutical formulation that does not release active drug substance immediately after oral dosing but over an extended in accordance with the definition in the pharmacopoeias Ph. Eur. ($7^{th}$ edition) monograph for tablets and capsules and USP general chapter <1151> for pharmaceutical dosage forms. The term "Immediate Release" (IR) as used herein refers to a pharmaceutical formulation which releases 85% of the active drug substance within less than 60 minutes in accordance with the definition of "Guidance for Industry: "Dissolution Testing of Immediate Release Solid Oral Dosage Forms" (FDA CDER, 1997). In some embodiments, the term "immediate release" means release of everolimus from tablets within the time of 30 minutes, e.g., as measured in the dissolution assay described herein.

Stable extended release formulations of an mTOR inhibitor disclosed herein, e.g., rapamycin or RAD001, can be characterized by an in-vitro release profile using assays known in the art, such as a dissolution assay as described herein: a dissolution vessel filled with 900 mL phosphate buffer pH 6.8 containing sodium dodecyl sulfate 0.2% at 37° C. and the dissolution is performed using a paddle method at 75 rpm according to USP by according to USP testing monograph 711, and Ph.Eur. testing monograph 2.9.3. respectively.

In some embodiments, stable extended release formulations of an mTOR inhibitor disclosed herein, e.g., rapamycin or RAD001, release the mTOR inhibitor in the in-vitro release assay according to following release specifications:

0.5 h: <45%, or <40, e.g., <30%

1 h: 20-80%, e.g., 30-60%

2 h: >50%, or >70%, e.g., >75%

3 h: >60%, or >65%, e.g., >85%, e.g., >90%.

In some embodiments, stable extended release formulations of an mTOR inhibitor disclosed herein, e.g., rapamycin or RAD001, release 50% of the mTOR inhibitor not earlier than 45, 60, 75, 90, 105 min or 120 min in the in-vitro dissolution assay.

Biopolymer Delivery Methods

In some embodiments, one or more CAR-expressing cells as disclosed herein can be administered or delivered to the subject via a biopolymer scaffold, e.g., a biopolymer implant. Biopolymer scaffolds can support or enhance the delivery, expansion, and/or dispersion of the CAR-expressing cells described herein. A biopolymer scaffold comprises a biocompatible (e.g., does not substantially induce an inflammatory or immune response) and/or a biodegradable polymer that can be naturally occurring or synthetic.

Examples of suitable biopolymers include, but are not limited to, agar, agarose, alginate, alginate/calcium phosphate cement (CPC), beta-galactosidase (β-GAL), (1,2,3,4, 6-pentaacetyl a-D-galactose), cellulose, chitin, chitosan, collagen, elastin, gelatin, hyaluronic acid collagen, hydroxyapatite, poly(3-hydroxybutyrate-co-3-hydroxy-hexanoate) (PHBHHx), poly(lactide), poly(caprolactone) (PCL), poly(lactide-co-glycolide) (PLG), polyethylene oxide (PEO), poly(lactic-co-glycolic acid) (PLGA), polypropylene oxide (PPO), polyvinyl alcohol) (PVA), silk, soy protein, and soy protein isolate, alone or in combination with any other polymer composition, in any concentration and in any ratio. The biopolymer can be augmented or modified with adhesion- or migration-promoting molecules, e.g., collagen-mimetic peptides that bind to the collagen receptor of lymphocytes, and/or stimulatory molecules to enhance the delivery, expansion, or function, e.g., anti-cancer activity, of the cells to be delivered. The biopolymer scaffold can be an injectable, e.g., a gel or a semi-solid, or a solid composition.

In some embodiments, CAR-expressing cells described herein are seeded onto the biopolymer scaffold prior to delivery to the subject. In embodiments, the biopolymer scaffold further comprises one or more additional therapeutic agents described herein (e.g., another CAR-expressing cell, an antibody, or a small molecule) or agents that enhance the activity of a CAR-expressing cell, e.g., incorporated or conjugated to the biopolymers of the scaffold. In embodiments, the biopolymer scaffold is injected, e.g., intratumorally, or surgically implanted at the tumor or within a proximity of the tumor sufficient to mediate an anti-tumor effect. Additional examples of biopolymer compositions and methods for their delivery are described in Stephan et al., *Nature Biotechnology,* 2015, 33:97-101; and WO2014/110591.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, *mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the immune effector cells (e.g., T cells, NK cells) described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated immune effector cells (e.g., T cells, NK cells) to a subject and then subsequently redraw blood (or have an apheresis performed), activate immune effector cells (e.g., T cells, NK cells) therefrom according to the present invention, and reinfuse the patient with these activated and expanded immune effector cells (e.g., T cells, NK cells). This process can be carried out multiple times every few weeks. In certain aspects, immune effector cells (e.g., T cells, NK cells) can be activated from blood draws of from 10 cc to 400 cc. In certain aspects, immune effector cells (e.g., T cells, NK cells) are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the T cell compositions of the present invention are administered by i.v. injection. The compositions of immune effector cells (e.g., T cells, NK cells) may be injected directly into a tumor, lymph node, or site of infection.

In a particular exemplary aspect, subjects may undergo leukopheresis, wherein leukocytes are collected, enriched, or depleted ex vivo to select and/or isolate the cells of interest, e.g., T cells. These T cell isolates may be expanded by methods known in the art and treated such that one or more CAR constructs of the invention may be introduced, thereby creating a CAR T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the CAR is introduced into immune effector cells (e.g., T cells, NK cells), e.g., using in vitro transcription, and the subject (e.g., human) receives an initial administration of CAR immune effector cells (e.g., T cells, NK cells) of the invention, and one or more subsequent administrations of the CAR immune effector cells (e.g., T cells, NK cells) of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR immune effector cells (e.g., T cells, NK cells) of the invention are administered to the subject (e.g., human) per week, e.g., 2, 3, or 4 administrations of the CAR immune effector cells (e.g., T cells, NK cells) of the invention are administered per week. In one embodiment, the subject (e.g., human subject) receives more than one administration of the CAR immune effector cells (e.g., T cells, NK cells) per week (e.g., 2, 3 or 4 administrations per week) (also referred to herein as a cycle), followed by a week of no CAR immune effector cells (e.g., T cells, NK cells) administrations, and then one or more additional administration of the CAR immune effector cells (e.g., T cells, NK cells) (e.g., more than one administration of the CAR immune effector cells (e.g., T cells, NK cells) per week) is administered to the subject. In another embodiment, the subject (e.g., human subject) receives more than one cycle of CAR immune effector cells (e.g., T cells, NK cells), and the time between each cycle is less than 10, 9, 8, 7, 6, 5, 4, or 3 days. In one embodiment, the CAR immune effector cells (e.g., T cells, NK cells) are administered every other day for 3 administrations per week. In one embodiment, the CAR immune effector cells (e.g., T cells, NK cells) of the invention are administered for at least two, three, four, five, six, seven, eight or more weeks.

In one aspect, CAR-expressing cells of the present inventions are generated using lentiviral viral vectors, such as lentivirus. Cells, e.g., CARTs, generated that way will have stable CAR expression.

In one aspect, CAR-expressing cells, e.g., CARTs, are generated using a viral vector such as a gammaretroviral vector, e.g., a gammaretroviral vector described herein. CARTs generated using these vectors can have stable CAR expression.

In one aspect, CARTs transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the T cell by electroporation.

A potential issue that can arise in patients being treated using transiently expressing CAR immune effector cells (e.g., T cells, NK cells) (particularly with murine scFv bearing CARTs) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CART infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: PD-1 CAR

In one embodiment, the extracellular domain (ECD) of inhibitory molecules, e.g., Programmed Death 1 (PD-1), can be fused to a transmembrane domain and intracellular signaling domains such as 4-1BB and CD3 zeta. In one embodiment, the PD-1 CAR can be used alone. In one embodiment, the PD-1 CAR can be used in combination with another CAR, e.g., CD19CAR. In one embodiment, the PD-1 CAR improves the persistence of the T cell. In one embodiment, the CAR is a PD-1 CAR comprising the extracellular domain of PD-1 indicated as underlined in SEQ ID NO: 26 (PD-1 domain is underlined)

SEQ ID NO: 26

```
Malpvtalllplalllhaarppgwfldspdrpwnpptfspallvvtegdn
atftcsfsntsesfvlnwyrmspsnqtdklaafpedrsqpgqdcrfrvtq
lpngrdfhmsvvrarrndsgtylcgaislapkaqikeshaelrvterrae
vptahpspsprpagqfqtlvtttpaprpptpaptiasqplslrpeacrpa
aggavhtrgldfacdiyiwaplagtcgvlllslvitlyckrgrkkllyif
kqpfmrpvqttqeedgcscrfpeeeeggcelrvkfsrsadapaykqgqnq
lynelnlgrreeydvldlargrdpemggkprrknpqeglynelqkdkmae
ayseigmkgerrrgkghdglyqglstatkdtydalhmqalppr
```

The corresponding nucleotide sequence for the PD-1 CAR is shown below, with the PD-1 ECD underlined below in SEQ ID NO: 27 (PD-1 domain is underlined)

SEQ ID NO: 27

```
Atggccctccctgtcactgccctgatctcccctcgcactcctgctccac
gccgctagaccacccggatggtactggactctccggatcgcccgtggaat
cccccaaccactcaccggcactcaggagtgactgagggcgataatgcgac
```

-continued

```
cacacgtgctcgactccaacacctccgaatcattcgtgctgaactggtac

cgcatgagcccgtcaaaccagaccgacaagctcgccgcgtaccggaagat

cggtcgcaaccgggacaggattgtcggttccgcgtgactcaactgccgaa

tggcagagacttccacatgagcgtggtccgcgctaggcgaaacgactccg

ggacctacctgtgcggagccatctcgctggcgcctaaggcccaaatcaaa

gagagcttgagggccgaactgagagtgaccgagcgcagagctgaggtgcc

aactgcacatccatccccatcgcctcggcctgcggggcagtttcagaccc

tggtcacgaccactccggcgccgcgcccaccgactccggccccaactatc

gcgagccagcccctgtcgctgaggccggaagcatgccgccctgccgccgg

aggtgctgtgcatacccggggattggacttcgcatgcgacatctacatag

ggctcctctcgccggaacttgtggcgtgctccactgtccctggtcatcac

cctgtactgcaagcggggtcggaaaaagatctgtacattacaagcagcca

tcatgaggcccgtgcaaaccacccaggaggaggacggagctcctgccgga

ccccgaagaggaagaaggaggagcgagctgcgcgtgaagactcccggagc

gccgacgcccccgcctataagcagggccagaaccagctgtacaacgaact

gaacctgggacggcgggaagagtacgatgtgctggacaagcggcgcggcc

gggaccccgaaatgggcgggaagcctagaagaaagaaccctcaggaaggc

ctgtataacgagctgcagaaggacaagatggccgaggcctactccgaaat

tgggatgaagggagagcggcggaggggaaaggggcacgacggcctgtacc

aaggactgtccaccgccaccaaggacacatacgatgccctgcacatgcag

gccatccccctcgc
```

Other examples of inhibitory molecules in include PD1, CTLA4, TIM3, LAG3, VISTA, BTLA, TIGIT, LAIR1, CD160, 2B4 and TGFR beta. PD1 is an inhibitory member of the CD28 family of receptors that also includes CD28, CTLA-4, ICOS, and BTLA. PD-1 is expressed on activated B cells, T cells and myeloid cells (Agata et al. 1996 Int Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

Example 2: Decreasing the Affinity of CAR Increases Therapeutic Efficacy

Adoptive cell therapy (ACT) with CAR engineered 1' cells can target and kill widespread malignant cells thereby inducing durable clinical responses in treating some hematopoietic malignancies (Kochenderfer, J. N., et al. (2010) *Blood* 116:4099-4102; Porter, D. L., et al. (2011) *N Engl J Med* 365:725-733; and Brentjens, R. J., et al. (2013) *Sci Transl Med* 5:177ra138). However, many commonly targeted tumor antigens are also expressed by healthy tissues and on target off tumor toxicity from T cell-mediated destruction of normal tissue has limited the development and adoption of this otherwise promising type of cancer therapy. Recent reports on severe adverse events associated with treatment of cancer patients with CAR- or TCR-engineered T lymphocytes further illustrate the importance of target selection for safe and efficient therapy (Lamers et al., 2006, *J Clin Oncol.* 24:e20; Parkhurst et al., 2011, *Molecular therapy: the journal of the American Society of Gene Therapy.* 19:620-6; Morgan et al., 2013, *J Immunotherapy.* 36:133-151; Linette et al., 2013, *Blood.* 122:863-71). In specific, the targeting of ErbB2 (Her2/neu or CD340) with high affinity CARTs led to serious toxicity due to target recognition on normal cardiopulmonary tissue (Morgan et al., 2013, *Mol Therapy.* 18:843-851), and similarly, the presence of relatively high levels of EGFR in healthy skin leads to dose-limiting skin toxicity (Perez-Soler et al., 2010, *J Clin Oncol.* 23:5235-46).

Selecting highly tissue-restricted antigens, cancer testis antigens, mutated gene products or viral proteins as targets could significantly improve the safety profile of using CART cells. However, none of these antigens is present with high frequency in common cancers, constitutively expressed exclusively by malignant cells, functionally important for tumor growth, and targetable with CART. Most of the top-ranked target antigens that could be targeted by CART are expressed in potentially important normal tissues, such as ErbB, EGFR, MUC1, PSMA, and GD2 (Cheever et al., 2009, *Clinical Cancer Research.* 15:5323-37). Current strategies for generating CARs consist of selecting scFv with high affinity, as previous studies have shown that the activation threshold inversely correlated with the affinity of the scFv (Chmielewski et al., 2004, *J Clin Oncol.* 173:7647-53; and Hudecek et al., 2013, *Clinical Cancer Research.* 19:3153-64. Studies indicate that the costimulatory domain of CARs does not influence the activation threshold (Chmielewski et al., 2011, *Gene Therapy.* 18:62-72). After TCR stimulation there is a narrow window of affinity for optimal T cell activation, and increasing the affinity of the TCRs does not necessarily improve treatment efficacy (Zhong et al., 2013, *Proc Natl Acad Sci USA.* 110:6973-8; and Schmid et al., 2010, *J Immunol.* 184:4936-46).

In this example, it was determined whether equipping T cells with high affinity scFv may limit the utility of CARs, due to poor discrimination of the CART for tumors and normal tissues that express the same antigen at lower levels. It was also determined whether fine-tuning the affinity of the scFv could increase the ability of CART cells to discriminate tumors from normal tissues expressing the same antigen at lower levels. CARs with affinities against two validated targets, ErbB2 and EGFR, which are amplified or overexpressed in variety of cancers but are also expressed, at lower levels by normal tissues, were tested extensively against multiple tumor lines, as well as primary cell lines from normal tissues and organs. It was found that decreasing the affinity of the scFv could significantly increase the therapeutic index of CARs while maintaining robust antitumor efficacy.

The following materials and methods were used in the experiments described in this example:

Cell Lines and Primary Human Lymphocytes

SK-BR3, SK-OV3, BT-474, MCF7, MDA231, MDA468, HCC2281, MDA-361, MDA-453, HCC-1419, HCC-1569, UACC-812, LnCap, MDA-175, MCF-10A, HCC38 and HG261 cell lines were purchased from American Type Culture Collection and cultured as instructed. Seven primary cell lines (keratinocytes, osteoblast, renal epithelial, pulmonary artery endothelial cells, pulmonary artery smooth muscle, neural progenitor, CD34+ enriched PBMC) were obtained from Promocell and cultured according to their protocols. Primary lymphocytes were isolated from normal donors by the University of Pennsylvania Human Immunology Core and cultured in R10 medium (RPMI 1640 supplemented with 10% fetal calf serum; Invitrogen). Primary lymphocytes were stimulated with microbeads coated with CD3 and CD28 stimulatory antibodies (Life Technologies, Grand Island, NY, Catalog) as described (Barrett et al., 2009, *Proc Nat Acad Sci USA,* 106:3360). T cells were cryopreserved at day 10 in a solution of 90% fetal calf serum and 10% dimethylsulfoxide (DMSO) at $1\times10^8$ cells/vial.

Generation of CAR Constructs for mRNA Electroporation and Lentiviral Transduction.

CAR scFv domains against ErbB2 or EGFR were synthesized and/or amplified by PCR, based on sequencing information provided by the relevant publications (Carter et al., 1992, *Proc Nat Acad Sci USA,* 89:4285; Zhou et al., 2007, *J Mol Bio,* 371:934), linked to CD8 transmembrane domain and 4-1BB and CD3Z intracellular signaling domains, and subcloned into pGEM.64A RNA based vector (Zhao et al., 2010, *Cancer Res,* 70:9053) or pTRPE lentiviral vectors (Carpenito et al., 2009, *Proc Nat Acad Sci USA,* 106:3360.

Biacore Assay

Biotinylated ErbB2 was mobilized to a streptavidin coated sensor chip at a density of 200 RU. Binding affinity of the parental 4D5 antibody (Carter et al., 1992, *Proc Nat Acad Sci USA,* 89:4285) were compared to recombinant scFv. The purity and atomic mass of the scFv were verified by liquid chromatography-mass spectrometry. ScFv samples were serial diluted 3-fold and injected over the chip at a constant flow rate. Association and dissociation rates of the protein complex were monitored for 270 s and 400 s, respectively. Double referencing was performed against a blank immobilized flow cell and a buffer blank and the data was fit using a 1:1 Langmuir model or steady state affinity where appropriate with the Biacore T200 evaluation software.

mRNA In Vitro Transcription and T Cell Electroporation

T7 mScript systems kit (CellScript) was used to generate IVT RNA. CD3/CD28 bead stimulated T cells were electroporated with IVT RNA using BTX EM830 (Harvard Apparatus BTX) as previously described (Zhao et al., 2010, *Cancer Res,* 70:9053). Briefly, T cells were washed three times and resuspended in OPTI-MEM (Invitrogen) at a final concentration of $1\text{-}3\times10^8$ cells/ml. Subsequently, 0.1 ml of cells were mixed with 10 ug IVT RNA (or as indicated) and electroporated in a 2 mm cuvette.

Flow Cytometry Analysis

Antibodies were obtained from the following suppliers: anti-human CD3 (BD Biosciences, 555335), anti-human CD8 (BD Biosciences 555366), anti-human CD107a (BD Biosciences 555801), anti-human CD137 (BD Biosciences 555956). Cell surface expression of ErbB2 was detected by biotinylated anti-ErbB2 Affibody (Abcam, ab31890), and EGFR by FITC conjugated anti-EGFR affibody (Abcam, ab81872). ErbB2, EGFR and CD19 specific CAR T cell expression were detected by ErbB2-Fc fusion protein (R&D system, 1129-ER), EGFR-Fc fusion protein and biotin-labeled polyclonal goat anti-mouse F(ab)2 antibodies (Jackson Immunoresearch, 115-066-072) respectively, incubated at 4° C. for 25 minutes and washed twice (PBS with 2% FBS). Samples were then stained with PE-conjugated anti-human IgG Fc Ab (eBioscience, 12-4998-82) or phycoerythrin-labeled streptavidin (eBioscience, 17-4317-82), incubated at 4° C. for 25 minutes and washed once. Flow cytometry acquisition was performed on either a BD FacsCalibur or Accuri C6 Cytometer (BD Biosciences). Analysis was performed using FlowJo software (Treestar).

ELISA Assays

Target cells were washed and suspended at $1\times10^6$ cells/ml in R10 medium (RPMI 1640 supplemented with 10% fetal calf serum; Invitrogen). 100 ul each target cell type were added in duplicate to a 96 well round bottom plate (Corning). Effector T cells were washed, and re-suspended at $1\times10^6$ cells/ml in R10 medium and then 100 ul of T cells were combined with target cells in the indicated wells. In addition, wells containing T cells alone were prepared. The plates were incubated at 37° C. for 18 to 20 hours. After the incubation, supernatant was harvested and subjected to an ELISA assay (eBioscience, 88-7316-77; 88-7025-77).

CD107a Staining

Cells were plated at an E:T of 1:1 ($1\times10^5$ effectors: $1\times10^5$ targets) in 160 μl of complete RPMI medium in a 96 well plate. 20 μl of phycoerythrin-labeled anti-CD107a Ab (BD Biosciences, 555801) was added and the plate was incubated at 37° C. for 1 hour before adding Golgi Stop (2 ul Golgi Stop in 3 ml RPMI medium, 20 ul/well; BD Biosciences, 51-2092KZ) and incubating for another 2.5 hours. Then 5 μl FITC-anti-CD8 and 5 ul APC-anti-CD3 were added and incubated at 37° C. for 30 min. After incubation, the samples were washed with FACS buffer and analyzed by flow cytometry.

CFSE Based T Cells Proliferation Assay

Resting CD4 T cells were washed and suspended at a concentration of $1\times10^7$ cells/ml in PBS. Then 120 ul CFSE working solution (25 μM CFSE) was added to $1\times10^7$ cells for 3.5 min at 25° C. The labeling was stopped with 5% FBS (in PBS), washed twice with 5% FBS and cultured in R10 with 10 IU/ml IL2. After overnight culture, the CFSE labeled T cells were electroporated with different affinity ErbB2 CAR RNA. Two to four hours after electroporation, T cells were suspended at concentration of $1\times10^6$/ml in R10 medium (with 10 IU/ml IL2). Tumor or K562 cell lines were irradiated and suspended at $1\times10^6$/mL in R10 medium. Cells were plated at an E:T of 1:1 ($5\times10^5$ effectors: $5\times10^5$ targets) in 1 ml of complete RPMI medium in a 48 well plate. T cells were then counted and fed every 2 days from day 3. CFSE dilution was monitored by flow cytometry at day 3, day 5 and day 7.

Luciferase Based CTL Assay.

Nalm6-CBG tumor cells were generated and employed in a modified version of a luciferase based CTL assay as follows: Click beetle green luciferase (CBG) was cloned into the pELNS vector, packaged into lentivirus, transduced into NALM6 tumor cells and sorted for CBG expression. Resulting Nalm6-CBG cells were washed and resuspended at $1\times10^5$ cells/ml in R10 medium, and 100 ul of CBG-labeled cells were incubated with different ratios of T cells (e.g. 30:1, 15:1, etc) overnight at 37° C. 100 μl of the mixture was transferred to a 96 well white luminometer-plate, 100 ul of substrate was added and the luminescence was immediately determined.

Mouse Xenograft Studies

Studies were performed as previously described with certain modifications (Barrett et al., 2011, *Human Gene Therapy,* 22:1575; and Carpenito et al., 2009, *PNAS,* 106:336). Briefly, 6-10 week old NOD scid gamma (NSG) mice were injected subcutaneously with $1\times10^6$ PC3-CBG tumors cells on the right flank at day 0 and the same mice were given SK-OV3-CBG tumor cells ($5\times10^6$ cells/mouse, s.c.) on the left flank at day 5. The mice were treated with T cells via the tail vein at day 23 post PC3-CBG tumor inoculation such that both tumors were approximately 200 $mm^3$ in volume. Lentivirally transduced T cells were given at $1\times10^7$ cells/mouse (10 M), or $3\times10^6$ cells/mouse (3 M). RNA electroporated T cells were given at $5\times10^7$ cells/mouse for the 1st treatment, followed by 3 treatments at days 26, 30 and 33 in the dose of $1\times10^7$ RNA electroporated T cells/mouse.

Results

Lowering the Affinity of the Anti-ErbB2 scFv Improves the Therapeutic Index of ErbB2 CAR T Cells In Vitro A panel of tumor lines with a wide range of ErbB2 expression as measured by flow cytometry was compiled. SK-OV3 (ovarian cancer), SK-BR3 (breast cancer), BT-474 (breast cancer) over-express ErbB2, while EM-Meso (mesothelioma), MCF7 (breast cancer), 293T (embryonic kidney 293 cell), A549 (lung cancer), 624me1 (melanoma), PC3 (prostate cancer), MDA231 (breast cancer) express ErbB2 at lower levels and ErbB2 was not detected in MDA468 (breast cancer). ErbB2 mRNA levels were also measured by real time PCR and there was a strong correlation between the two techniques.

A panel of ErbB2 CARs was constructed making use scFv derived from the published mutations of the parental 4D5 antibody (Carter et al. (1992) *Proc Natl Acad Sci USA* 89:4285-4289). The sequences encoding the CARs against ErbB2 are provided in Table 2.

TABLE 2

Nucleic acid sequences encoding CARs against ErbB2

| CAR Designation | Nucleic Acid Sequence | SEQ ID NO: |
|---|---|---|
| 4D5-BZZ | atg gac ttc cag gtt cag atc ttt tcg ttc ctg ctg atc agc gcc tct gtt atc atg<br>tcg cgc ggc gac atc cag atg acc cag tcc cct tcc tcc ctc tct gcc tct gtg<br>gga gac cgc gtt acc atc aca tgc cga gct tcc cag gac gtg aac aca gcc<br>gtg gcc tgg tac cag cag aag ccc ggg aag gca ccc aaa ctc ctc atc tac<br>tcc gcc tcc ttc cta tac agt ggc gtg cct tcc cga ttc tcc ggc tcc agg agt<br>ggc acg gac ttt acg ctc acc att agt agc ctg cag ccc gaa gac ttc gcg acc<br>tac tat tgt cag caa cac tac acg acg cca cca act ttc ggc cag ggt acc aag<br>gtc gag att aag cga acc ggc agt acc agt ggg tct ggc aag ccc ggc agc<br>ggc gag gga tcc gag gtc cag ctg gtc gag tcc ggc ggg ggc ctg gtg cag<br>ccg ggc ggc tcg ctg agg tta tct tgc gcc gcc agt ggc ttc aac atc aag gat<br>act tac atc cac tgg gtg agg cag gct ccg ggc aag ggc ctg gaa tgg gtg<br>gct agg atc tac cct act aac ggg tac aca cgc tac gca gat tcg gtg aaa ggc<br>cgc ttc act atc tcc gcc gac acc tcg aag aac act gct tac ctg cag atg aac<br>tcc ctc agg gcc gaa gat act gca gtc tac tac tgc tcc cgc tgg ggt ggg gac<br>ggc ttc tac gcc atg gac gtg tgg ggt cag ggc act cta gtt aca gtg tca tcc<br>acc acg acg cca gcg ccg cga cca cca aca ccg gcg ccc acc atc gcg tcg<br>cag ccc ctg tcc ctg cgc cca gag gcg tgc cgg cca gcg gcg ggg ggc gca<br>gtg cac acg agg ggg ctg gac ttc gcc tgt gat atc tac atc tgg gcg ccc ttg<br>gcc ggg act tgt ggg gtc ctt ctc ctg tca ctg gtt atc acc ctt tac tgc aaa<br>cgg ggc aga aag aaa ctc ctg tat ata ttc aaa caa cca ttt atg aga cca gta<br>caa act act caa gag gaa gat ggc tgt agc tgc cga ttt cca gaa gaa gaa gaa<br>gga gga tgt gaa ctg aga gtg aag ttc agc agg agc gca gac gcc ccc gcg<br>tac aag cag ggc cag aac cag ctc tat aac gag ctc aat cta gga cga aga<br>gag gag tac gac gtt ttg gac aag aga cgt ggc cgg gac cct gag atg ggg<br>gga aag ccg aga agg aag aac cct cag gaa ggc ctg tac aat gaa ctg cag<br>aaa gat aag atg gcg gag gcc tac agt gag att ggg atg aaa ggc gag cgc<br>cgg agg ggc aag ggg cac gat ggc ctt tac cag ggt ctc agt aca gcc acc<br>aag gac acc tac gac gcc ctt cac atg cag gcc ctg ccc cct cgc taa | 40 |
| 4D5-1-BBZ | atg gac ttc cag gtt cag atc ttt tcg ttc ctg ctg atc agc gcc tct gtt atc atg<br>tcg cgc ggc gac atc cag atg acc cag tcc cct tcc tcc ctc tct gcc tct gtg<br>gga gac cgc gtt acc atc aca tgc cga gct tcc cag gac gtg aac aca gcc<br>gtg gcc tgg tac cag cag aag ccc ggg aag gca ccc aaa ctc ctc atc tac<br>tcc gcc tcc ttc cta gag agt ggc gtg cct tcc cga ttc tcc ggc tcc ggc agt<br>ggc acg gac ttt acg ctc acc att agt agc ctg cag ccc gaa gac ttc gcg acc<br>tac tat tgt cag caa cac tac acg acg cca cca act ttc ggc cag ggt acc aag<br>gtc gag att aag cga acc ggc agt acc agt ggg tct ggc aag ccc ggc agc<br>ggc gag gga tcc gag gtc cag ctg gtc gag tcc ggc ggg ggc ctg gtg cag<br>ccg ggc ggc tcg ctg agg tta tct tgc gcc gcc agt ggc ttc aac atc aag gat<br>act tac atc cac tgg gtg agg cag gct ccg ggc aag ggc ctg gaa tgg gtg<br>gct agg atc tac cct act aac ggg tac aca cgc tac gca gat tcg gtg aaa ggc<br>cgc ttc act atc tcc agg gac gac tcg aag aac act ctg tac ctg cag atg aac<br>tcc ctc agg gcc gaa gat act gca gtc tac tac tgc gcc cgc tgg ggt ggg gac<br>ggc ttc gta gcc atg gac gtg tgg ggt cag ggc act cta gtt aca gtg tca tcc<br>acc acg acg cca gcg ccg cga cca cca aca ccg gcg ccc acc atc gcg tcg<br>cag ccc ctg tcc ctg cgc cca gag gcg tgc cgg cca gcg gcg ggg ggc gca<br>gtg cac acg agg ggg ctg gac ttc gcc tgt gat atc tac atc tgg gcg ccc ttg<br>gcc ggg act tgt ggg gtc ctt ctc ctg tca ctg gtt atc acc ctt tac tgc aaa<br>cgg ggc aga aag aaa ctc ctg tat ata ttc aaa caa cca ttt atg aga cca gta<br>caa act act caa gag gaa gat ggc tgt agc tgc cga ttt cca gaa gaa gaa gaa<br>gga gga tgt gaa ctg aga atg gac ttc cag gtt cag atc ttt tcg ttc ctg ctg<br>atc agc gcc tct gtt atc atg tcg cgc ggc gac atc cag atg acc cag tcc cct<br>tcc tcc ctc tct gcc tct gtg gga gac cgc gtt acc atc aca tgc cga gct tcc<br>cag gac gtg aac aca gcc gtg gcc tgg tac cag cag aag ccc ggg aag gca<br>ccc aaa ctc ctc atc tac tcc gcc tcc ttc cta gag agt ggc gtg cct tcc cga<br>ttc tcc ggc tcc ggc agt ggc acg gac ttt acg ctc acc att agt agc ctg cag<br>ccc gaa gac ttc gcg acc tac tat tgt cag caa cac tac acg acg cca cca act<br>ttc ggc cag ggt acc aag gtc gag att aag cga acc ggc agt acc agt ggg tct | 41 |

TABLE 2-continued

Nucleic acid sequences encoding CARs against ErbB2

| CAR Designation | Nucleic Acid Sequence | SEQ ID NO: |
|---|---|---|
| | ggc aag ccc ggc agc ggc gag gga tcc gag gtc cag ctg gtc gag tcc ggc<br>ggg ggc ctg gtg cag ccg ggc ggc tcg ctg agg tta tct tgc gcc gcc agt<br>ggc ttc aac atc aag gat act tac atc cac tgg gtg agg cag gct ccg ggc aag<br>ggc ctg gaa tgg gtg gct agg atc tac cct act aac ggg tac aca cgc tac gca<br>gat tcg gtg aaa ggc cgc ttc act atc tcc agg gac gac tcg aag aac act ctg<br>tac ctg cag atg aac tcc ctc agg gcc gaa gat act gca gtc tac tac tgc gcc<br>cgc tgg ggt ggg gac ggc ttc gta gcc atg gac gtg tgg ggt cag ggc act<br>cta gtt aca gtg tca tcc gtg aag ttc agc agg agc gca gac gcc ccc gcg tac<br>aag cag ggc cag aac cag ctc tat aac gag ctc aat cta gga cga aga gag<br>gag tac gac gtt ttg gac aag aga cgt ggc cgg gac cct gag atg ggg gga<br>aag ccg aga agg aag aac cct cag gaa ggc ctg tac aat gaa ctg cag aaa<br>gat aag atg gcg gag gcc tac agt gag att ggg atg aaa ggc gag cgc cgg<br>agg ggc aag ggg cac gat ggc ctt tac cag ggt ctc agt aca gcc acc aag<br>gac acc tac gac gcc ctt cac atg cag gcc ctg ccc cct cgc taa | |
| 4D5-3-BBZ | acc acg acg cca gcg ccg cga cca cca aca ccg gcg ccc acc atc gcg tcg<br>cag ccc ctg tcc ctg cgc cca gag gcg tgc cgg cca gcg gcg ggg ggc gca<br>gtg cac acg agg ggg ctg gac ttc gcc tgt gat atc tac atc tgg gcg ccc ttg<br>gcc ggg act tgt ggg gtc ctt ctc ctg tca ctg gtt atc acc ctt tac tgc aaa<br>cgg ggc aga aag aaa ctc ctg tat ata ttc aaa caa cca ttt atg aga cca gta<br>caa act act caa gag gaa gat ggc tgt agc tgc cga ttt cca gaa gaa gaa atg<br>gac ttc cag gtt cag atc ttt tcg ttc ctg ctg atc agc gcc tct gtt atc atg tcg<br>cgc ggc gac atc cag atg acc cag tcc cct tcc tcc ctc tct gcc tct gtg gga<br>gac cgc gtt acc atc aca tgc cga gct tcc cag gac gtg aac aca gcc gtg<br>gcc tgg tac cag cag aag ccc ggg aag gca ccc aaa ctc ctc atc tac tcc<br>gcc tcc ttc cta gag agt ggc gtg cct tcc cga ttc tcc ggc tcc ggc agt ggc<br>acg gac ttt acg ctc acc att agt agc ctg cag ccc gaa gac ttc gcg acc tac<br>tat tgt cag caa cac tac acg acg cca cca act ttc ggc cag ggt acc aag gtc<br>gag att aag cga acc ggc agt acc agt ggg tct ggc aag ccc ggc agc ggc<br>gag gga tcc gag gtc cag ctg gtc gag tcc ggc ggg ggc ctg gtg cag ccg<br>ggc ggc tcg ctg agg tta tct tgc gcc gcc agt ggc ttc aac atc aag gat act<br>tac atc cac tgg gtg agg cag gct ccg ggc aag ggc ctg gaa tgg gtg gct<br>agg atc tac cct act aac ggg tac aca cgc tac gca gat tcg gtg aaa ggc cgc<br>ttc act atc tcc gcc gac acc tcg aag aac act gct tac ctg cag atg aac tcc<br>ctc agg gcc gaa gat act gca gtc tac tac tgc tcc cgc tgg ggt ggg gac<br>ggc ttc gta gcc atg gac gtg tgg ggt cag ggc act cta gtt aca gtg tca tcc<br>gaa gga gga tgt gaa ctg aga gtg aag ttc agc agg agc gca gac gcc ccc<br>gcg tac aag cag ggc cag aac cag ctc tat aac gag ctc aat cta gga cga<br>aga gag gag tac gac gtt ttg gac aag aga cgt ggc cgg gac cct gag atg<br>ggg gga aag ccg aga agg aag aac cct cag gaa ggc ctg tac aat gaa ctg<br>cag aaa gat aag atg gcg gag gcc tac agt gag att ggg atg aaa ggc gag<br>cgc cgg agg ggc aag ggg cac gat ggc ctt tac cag ggt ctc agt aca gcc<br>acc aag gac acc tac gac gcc ctt cac atg cag gcc ctg ccc cct cgc taa | 42 |
| 4D5-5-BBZ | atg gac ttc cag gtt cag atc ttt tcg ttc ctg ctg atc agc gcc tct gtt atc atg<br>tcg cgc ggc gac atc cag atg acc cag tcc cct tcc tcc ctc tct gcc tct gtg<br>gga gac cgc gtt acc atc aca tgc cga gct tcc cag gac gtg aac aca gcc<br>gtg gcc tgg tac cag cag aag ccc ggg aag gca ccc aaa ctc ctc atc tac<br>tcc gcc tcc ttc cta gag agt ggc gtg cct tcc cga ttc tcc ggc tcc agg agt<br>ggc acg gac ttt acg ctc acc att agt agc ctg cag ccc gaa gac ttc gcg acc<br>tac tat tgt cag caa cac tac acg acg cca cca act ttc ggc cag ggt acc aag<br>gtc gag att aag cga acc ggc agt acc agt ggg tct ggc aag ccc ggc agc<br>ggc gag gga tcc gag gtc cag ctg gtc gag tcc ggc ggg ggc ctg gtg cag<br>ccg ggc ggc tcg ctg agg tta tct tgc gcc gcc agt ggc ttc aac atc aag gat<br>act tac atc cac tgg gtg agg cag gct ccg ggc aag ggc ctg gaa tgg gtg<br>gct agg atc tac cct act aac ggg tac aca cgc tac gca gat tcg gtg aaa ggc<br>cgc ttc act atc tcc gcc gac acc tcg aag aac act gct tac ctg cag atg aac<br>tcc ctc agg gcc gaa gat act gca gtc tac tac tgc tcc cgc tgg ggt ggg gac<br>ggc ttc gta gcc atg gac gtg tgg ggt cag ggc act cta gtt aca gtg tca tcc<br>acc acg acg cca gcg ccg cga cca cca aca ccg gcg ccc acc atc gcg tcg<br>cag ccc ctg tcc ctg cgc cca gag gcg tgc cgg cca gcg gcg ggg ggc gca<br>gtg cac acg agg ggg ctg gac ttc gcc tgt gat atc tac atc tgg gcg ccc ttg<br>gcc ggg act tgt ggg gtc ctt ctc ctg tca ctg gtt atc acc ctt tac tgc aaa<br>cgg ggc aga aag aaa ctc ctg tat ata ttc aaa caa cca ttt atg aga cca gta<br>caa act act caa gag gaa gat ggc tgt agc tgc cga ttt cca gaa gaa gaa gaa<br>gga gga tgt gaa ctg aga gtg aag ttc agc agg agc gca gac gcc ccc gcg<br>tac aag cag ggc cag aac cag ctc tat aac gag ctc aat cta gga cga aga<br>gag gag tac gac gtt ttg gac aag aga cgt ggc cgg gac cct gag atg ggg<br>gga aag ccg aga agg aag aac cct cag gaa ggc ctg tac aat gaa ctg cag<br>aaa gat aag atg gcg gag gcc tac agt gag att ggg atg aaa ggc gag cgc<br>cgg agg ggc aag ggg cac gat ggc ctt tac cag ggt ctc agt aca gcc acc<br>aag gac acc tac gac gcc ctt cac atg cag gcc ctg ccc cct cgc taa | 43 |

TABLE 2-continued

Nucleic acid sequences encoding CARs against ErbB2

| CAR Designation | Nucleic Acid Sequence | SEQ ID NO: |
|---|---|---|
| 4D5-7-BBZ | atg gac ttc cag gtt cag atc ttt tcg ttc ctg ctg atc agc gcc tct gtt atc atg<br>tcg cgc ggc gac atc cag atg acc cag tcc cct tcc tcc ctc tct gcc tct gtg<br>gga gac cgc gtt acc atc aca tgc cga gct tcc cag gac gtg aac aca gcc<br>gtg gcc tgg tac cag cag aag ccc ggg aag gca ccc aaa ctc ctc atc tac<br>tcc gcc tcc ttc cta gag agt ggc gtg cct tcc cga ttc tcc ggc tcc agg agt<br>ggc acg gac ttt acg ctc acc att agt agc ctg cag ccc gaa gac ttc gcg acc<br>tac tat tgt cag caa cac tac acg acg cca cca act ttc ggc cag ggt acc aag<br>gtc gag att aag cga acc ggc agt acc agt ggg tct ggc aag ccc ggc agc<br>ggc gag gga tcc gag gtc cag ctg gtc gag tcc ggc ggg ggc ctg gtg cag<br>ccg ggc ggc tcg ctg agg tta tct tgc gcc gcc agt ggc ttc aac atc aag gat<br>act tac atc cac tgg gtg agg cag gct ccg ggc aag ggc ctg gaa tgg gtg<br>gct agg atc tac cct act aac ggg tac aca cgc tac gca gat tcg gtg aaa ggc<br>cgc ttc act atc tcc gcc gac acc tcg aag aac act gct tac ctg cag atg aac<br>tcc ctc agg gcc gaa gat act gca gtc tac acc acg acg cca gcg ccg cga<br>cca cca aca ccg gcg ccc acc atc gcg tcg cag ccc ctg tcc ctg cgc cca<br>gag gcg tgc cgg cca gcg gcg ggg ggc gca gtg cac acg agg ggg ctg<br>gac ttc gcc tgt gat atc tac atc tgg gcg ccc ttg gcc ggg act tgt ggg gtc<br>ctt ctc ctg tca ctg gtt atc acc ctt tac tgc aaa cgg ggc aga aag aaa ctc<br>ctg tat ata ttc aaa caa cca ttt atg aga cca gta caa act act caa gag gaa<br>gat ggc tgt agc tgc cga ttt cca gaa gaa gaa gaa gga gga tgt gaa ctg<br>aga gtg aag ttc agc agg agc gca gac gcc ccc gcg tac aag cag ggc cag<br>aac cag ctc tat aac gag ctc aat cta gga cga aga gag gag tac gac gtt ttg<br>gac aag aga cgt ggc cgg gac cct gag atg ggg gga aag ccg aga agg aag<br>aac cct cag gaa ggc ctg tac aat gaa ctg cag aaa gat aag atg gcg gag<br>gcc tac agt gag att ggg atg aaa ggc gag cgc cgg agg ggc aag ggg cac<br>gat ggc ctt tac cag ggt ctc agt aca gcc acc aag gac acc tac gac gcc ctt<br>cac atg cag gcc ctg ccc cct cgc taa | 44 |

The monovalent affinities of the ErbB2 scFvs varied by approximately 3 orders of magnitude (Table 3), in contrast to the corresponding mutant antibodies that retained binding affinities within 10-fold of each other (Carter, P., et al. 1992).

TABLE 3

Comparison of measured affinities of the wild type 4D5 and mutated antibody with the corresponding scFv

| Sample | Mutation | Antibody KD (nM) | scFv KD (nM) |
|---|---|---|---|
| 4D5 | Wild Type | 0.3 | 0.58 |
| 4D5-7 | 1 in CDR2 | 0.62 | 3.2 |
| 4D5-5 | 1 in CDR3, 1 in CDR2 | 1.1 | 1119 |
| 4D5-3 | 1 in framework, 1 in CDR3, 1 in CDR2 | 4.4 | 3910 |

CARs were constructed by linking the various scFv to the CD8 alpha hinge and transmembrane domain followed by the 4-1BB and CD3ζ intracellular signaling domains. The CARs were expressed by lentiviral vector technology or by cloning into an RNA-based vector (Zhao et al., 2010, *Cancer Res,* 70:9053). After production of mRNA by in vitro transcription and electroporation into T cells, the surface expression of the panel of affinity-modified ErbB2 RNA CARs was similar. To compare recognition thresholds, the panel of ErbB2 CAR T cells was stimulated with ErbB2 high expressing (SK-BR3, SK-OV3 and BT-474) or low expressing tumor cell lines (MCF7, 293T, A549, 624 Mel, PC3, MDA231 and MDA468) and T cell activation was assessed by upregulation of CD137 (4-1BB), secretion of IFN-γ and IL-2 and induction of surface CD107a expression. T cells expressing a CD19-specific CAR served as control for allogeneic reactivity. Lower affinity CAR T cells (4D5-5 and 4D5-3) were strongly reactive to tumors with amplified ErbB2 expression and exhibited undetectable or low reactivity to the tumor lines that expressed ErbB2 at lower levels. In contrast, higher affinity CAR T cells (4D5 and 4D5-7) showed strong reactivity to tumor lines expressing high and low levels of ErbB2, as evidenced by CD137 up-regulation, cytokine secretion and CD107a translocation. These results were extended by assaying additional ErbB2-expressing cell lines. Interestingly, higher affinity CAR T cells secreted greater levels of IFN-γ and IL-2 when exposed to targets expressing low levels of ErbB2, while lower affinity CAR T cells secreted more cytokines when exposed to cells expressing high levels of target. As expected, the CD19-BBζ CAR was not reactive against ErbB2-expressing cell lines. In summary, higher affinity 4D5-BBζ T cells recognized all the ErbB2 expressing lines tested, whereas CARs with lower affinity scFvs, 4D5-5-BBζ or 4D5-3-BBζ, were highly reactive to all tumor lines with overexpressed ErbB2, but displayed negligible reactivity to cell lines expressing low or undetectable levels of ErbB2.

ErbB2 CARS with Lower Affinity scFvs Discriminate Between Tumor Cells Expressing Low and High Levels of ErbB2.

To exclude any tumor-specific effects that might contribute to the above results, the activity of the panel of ErbB2-BBζ CAR T cells was assayed against a single tumor line expressing varying levels of ErbB2 (K562 cells electroporated with varying amounts of ErbB2 RNA). In agreement, it was observed that T cells expressing higher affinity scFvs (4D5 and 4D5-7) recognized K562 cells electroporated with ErbB2 RNA at doses as low as 0.001 μg, which is 100 fold lower than the flow cytometrically detectable level of 0.1 μg mRNA. In contrast the CARs with lower affinity scFvs (4D5-5 and 4D5-3) only recognized K562 electroporated ErbB2 RNA at doses of 0.5 μg (4D5-5; 10) or higher, indicating that CAR T cell sensitivity was decreased by 2000-(4D5-3) to 500-fold (4D5-5) compared to the high affinity 4D5 CAR T cells. Moreover, the antigen dose associated reactivity observed with lower affinity ErbB2 CARs (4D5-5 and 4D5-3), was confirmed by performing a CFSE-based proliferation assay. Interestingly, decreasing the CAR RNA dose 5 fold (from 10 μg RNA/100 μl T cells to 2 μg RNA/100 μl T cells), further increased the antigen recognition threshold of the T cells with lower and high affinity CARs as assessed by cytokine secretion, suggesting that fine tuning of CAR density on the surface of the T cells is an important variable, or that doses above 2 μg of mRNA may have some toxicity on overall T cell activity.

A luciferase based cytolytic T cell (CTL) assay was used to determine whether T cells with affinity decreased CARs could maintain potent killing activity against ErbB2 over expressing targets while sparing cells expressing lower ErbB2 levels. When Nalm6 target cells were transfected with 10 μg ErbB2 RNA, T cells with either higher or lower affinity ErbB2 CARs effectively lysed target cells. CARs with higher affinity scFv (4D5 and 4D5-7) exhibit potent lytic activity against target cells transfected with 1 μg ErbB2 RNA, but lower affinity scFvs (4D5-5 and 4D5-3) showed decreased killing activity. Finally, only CARs with higher affinity scFvs were able to kill target cells expressing very low amounts of target after electroporation with 0.1 μg ErbB2 RNA. Since Nalm6 is a CD19 positive cell line, CART19 maintained cytolytic activity independent of levels of transfected ErbB2 RNA. These data indicate that that fine-tuning the affinity of ErbB2 CAR T cells enhances discrimination of ErbB2 over-expressing tumor from tumor cells that have low or undetectable levels of ErbB2 expression.

Affinity Decreased ErbB2 CAR T Cells Fail to Recognize Physiological Levels of ErbB2

Given the previous serious adverse event which occurred upon administration of the high affinity ErbB2 CAR that incorporated the scFv from the parental 4D5 trastuzumab antibody (Morgan et al., 2010, *Mol Therapy,* 18:843), it is of paramount importance to evaluate potential reactivity of the reduced affinity ErbB2 CAR T cells to physiological levels of ErbB2 expression. To address this, seven primary cell lines isolated from different organs were tested for ErbB2 expression. Most of the primary lines had detectable levels of surface ErbB2, with the neural progenitor line expressing the highest levels of ErbB2. T cells expressing the high affinity 4D5 CAR were strongly reactive to all primary lines tested, as evidenced by levels of CD107a up-regulation. However, T cells expressing the affinity decreased ErbB2 CARs 4D5-5 and 4D5-3 exhibited no reactivity to the primary lines with the exception of weak reactivity to the neural progenitor line. These results were confirmed by analysis of a larger panel of cell lines that had low or undetectable levels of ErbB2 by flow cytometry.

Comparable Effects with Affinity-Tuned ErbB2 CARs Expressed Using Lentiviral Transduction or RNA Electroporation To establish comparability between T cells permanently expressing CARs by lentiviral transduction with mRNA electroporated CAR T cells, the panel of affinity-tuned CARs was expressed in T cells from the same normal donor using either lentiviral transduction or mRNA electroporation. T cells were stimulated with tumor cell lines, or K562 cells, expressing varying amounts of ErbB2. CAR T cell recognition and activation was monitored by CD107a upregulation, CD137 upregulation and IFN-γ secretion. In agreement with the previous ErbB2 mRNA CAR T cell results, T cells that constitutively expressed high affinity CARs showed strong reactivity to all cell lines expressing ErbB2; no correlation was observed between antigen expression levels and T cell-activity. In contrast, T cells with low affinity CARs expressed by lentiviral technology demonstrated a robust correlation between target antigen expression and activation. These results confirm that the sensitivity of ErbB2 antigen recognition is dependent on scFv affinity using both mRNA electroporated and lentiviral transduced CAR T cells.

Affinity Decreased ErbB2 CAR T Cells Eliminate Tumor In Vivo and Ignore Tissues Expressing Physiological Levels of ErbB2

To extend the above in vitro results, a series of experiments were conducted in NSG mice with advanced vascularized tumor xenografts. The human ovarian cancer cell line SK-OV3 was selected as a representative ErbB2 over-expressing tumor and PC3, a human prostate cancer line, was chosen to model normal tissue ErbB2 levels. The antitumor efficacy of ErbB2 CAR T cells expressing either the high affinity 4D5 scFv or the low affinity 45D-5 scFv in NSG mice was compared with day 18 established flank SK-OV3 tumors. Serial bioluminescence imaging revealed that both the high and low affinity CAR T cells resulted in the rapid elimination of the tumors.

To further evaluate the therapeutic index of the low affinity ErbB2 CAR T cells in vivo, a mouse model was designed to simultaneously compare the efficacy and normal tissue toxicity of the high affinity (4D5:BBζ) and low affinity (4D5-5:BBζ) ErbB2 CARs. SK-OV3 and PC3 tumor cell lines were injected subcutaneously into opposite flanks of the same NSG mouse and T cells were administered when tumor volumes reached approximately 200 $mm^3$. Mice were injected (i.v.) with either $3\times10^6$ or $1\times10^7$ CAR T cells on day 22 and serial bioluminescence imaging and tumor size assessments were conducted. Mice treated with either dose of the CAR T cells exhibited nearly complete regression of the ErbB2 overexpressing SK-OV3 tumor. In addition, almost complete regression of the PC3 tumor expressing ErbB2 at low levels on the opposite flank was also seen for the mice treated with high affinity 4D5-based CAR T cells. In contrast, the progressive tumor growth of PC3 was observed in the mice treated with low affinity 4D5-5-based CAR T cells, indicating that whereas the lower affinity CAR T cells were efficacious against ErbB2 overexpressing tumor, they show limited or no detectable reactivity against cells expressing ErbB2 at physiological levels. Moreover, the selective tumor elimination was observed in mice treated at both high and low doses of CAR T cells. The above effects were not due to allorecognition because progressive tumor growth of both tumors was observed in mice treated with mock transduced T cells.

Affinity-Tuning of scFv Increases the Therapeutic Index of EGFR CAR T Cells

To test the broader applicability the strategy to fine tune the affinity of the scFv, we evaluated a panel of EGFR CARs. EGFR:BBζ CARs were constructed from scFvs derived from the parental human anti-EGFR antibody C10 (Heitner et al., 2001, *J Immunol Methods,* 248:17-30. The nucleic acid sequences encoding the EGFR CARs are provided in Table 4.

TABLE 4

| Nucleic Acid Sequences of Exemplary EGFR CARs | | |
|---|---|---|
| CAR designation | Nucleic Acid Sequence | SEQ ID NO: |
| C10-BBZ | atg ggt tgg tcg tgc att atc ctc ttc ctc gtc gca acc gct acc ggc gtt cac<br>tcg gat tac aag gat gac gac gac aaa gag gta cag ctg gtg cag agc ggg<br>gcc gag gtt aag aag ccc ggg tct tcc gta aag gtg tcc tgc aag gcc tcg<br>ggg ggc aca ttc tca tcg tac gca ata tcg tgg gtg cgg cag gcc ccc ggg<br>cag ggg ctg gaa tgg atg ggc gga att atc cca atc ttc ggg acc gcc aac<br>tat gcc cag aag ttt cag ggt cgt gtg acc att act gcc gac gag tcc acc agt<br>acg gcc tac atg gag ctg agt agt ctg cgt agc gag gat act gcc gtt tat tat<br>tgc gcc cgg gaa gag gga ccg tac tgc tcg tcg acc tca tgt tac ggc gcc<br>ttc gac atc tgg ggc caa ggc acc ctg gtg acg gtg tcc tcc ggt ggt ggc<br>gga agt ggc ggc ggg ggg tcc ggc ggg ggc ggt tca cag tcc gtc ctg acc<br>cag gat ccc gcg gtg tcg gtc gcg ctg ggt cag aca gta aag ata aca tgc<br>cag ggc gat tct ctg cgc agt tat ttc gcc tcg tgg tac cag cag aaa ccc ggc<br>cag gct cct acc ctt gtt atg tac gcg cgc aat gac aga ccc gcg ggc gtg<br>ccc gac cgc ttc tcc ggc tca aag agc ggg acc tcc gcc tcc ctg gcc atc<br>tcc ggg ctc cag tct gag gat gag gcc gat tac tac tgc gct gct tgg gac<br>gac tcc ctc aat ggc tat ctg ttt ggc gca ggc aca aag ctg acc gtg ctc acc<br>acg acg cca gcg ccg cga cca cca aca ccg gcg ccc acc atc gcg tcg cag<br>ccc ctg tcc ctg cgc cca gag gcg tgc cgg cca gcg gcg ggg ggc gca gtg<br>cac acg agg ggg ctg gac ttc gcc tgt gat atc tac atc tgg gcg ccc ttg gcc<br>ggg act tgt ggg gtc ctt ctc ctg tca ctg gtt atc acc ctt tac tgc aaa cgg<br>ggc aga aag aaa ctc ctg tat ata ttc aaa caa cca ttt atg aga cca gta caa<br>act act caa gag gaa gat ggc tgt agc tgc cga ttt cca gaa gaa gaa gaa<br>gga gga tgt gaa ctg aga gtg aag ttc agc agg agc gca gac gcc ccc gcg<br>tac aag cag ggc cag aac cag ctc tat aac gag ctc aat cta gga cga aga<br>gag gag tac gac gtt ttg gac aag aga cgt ggc cgg gac cct gag atg ggg<br>gga aag ccg aga agg aag aac cct cag gaa ggc ctg tac aat gaa ctg cag<br>aaa gat aag atg gcg gag gcc tac agt gag att ggg atg aaa ggc gag cgc<br>cgg agg ggc aag ggg cac gat ggc ctt tac cag ggt ctc agt aca gcc acc<br>aag gac acc tac gac gcc ctt cac atg cag gcc ctg ccc cct cgc taa | 45 |
| 2224-BBZ | atg ggt tgg tcg tgc att atc ctc ttc ctc gtc gca acc gct acc ggc gtt cac<br>tcg gat tac aag gat gac gac gac aaa gag gta cag ctg gtg cag agc ggg<br>gcc gag gtt aag aag ccc ggg tct tcc gta aag gtg tcc tgc aag gcc tcg<br>ggg ggc aca ttc tca tcg tac gca ata ggt tgg gtg cgg cag gcc ccc ggg<br>cag ggg ctg gaa tgg atg ggc gga att atc cca atc ttc ggg atc gcc aac tat<br>gcc cag aag ttt cag ggt cgt gtg acc att act gcc gac gag tcc acc agt agt<br>gcc tac atg gag ctg agt agt ctg cgt agc gag gat act gcc gtt tat tat tgc<br>gcc cgg gaa gag gga ccg tac tgc tcg tcg acc tca tgt tac gca gcc ttc<br>gac atc tgg ggc caa ggc acc ctg gtg acg gtg tcc tcc ggt ggt ggc gga<br>agt ggc ggc ggg ggg tcc ggc ggg ggc ggt tca cag tcc gtc ctg acc cag<br>gat ccc gcg gtg tcg gtc gcg ctg ggt cag aca gta aag ata aca tgc cag<br>ggc gat tct ctg cgc agt tat ttc gcc tcg tgg tac cag cag aaa ccc ggc cag<br>gct cct acc ctt gtt atg tac gcg cgc aat gac aga ccc gcg ggc gtg ccc<br>gac cgc ttc tcc ggc tca aag agc ggg acc tcc gcc tcc ctg gcc atc tcc<br>ggg ctc cag ccc gag gat gag gcc gat tac tac tgc gct gct tgg gac gac<br>tcc ctc aat ggc tat ctg ttt ggc gca ggc aca aag ctg acc gtg ctc acc acg<br>acg cca gcg ccg cga cca cca aca ccg gcg ccc acc atc gcg tcg cag ccc<br>ctg tcc ctg cgc cca gag gcg tgc cgg cca gcg gcg ggg ggc gca gtg cac<br>acg agg ggg ctg gac ttc gcc tgt gat atc tac atc tgg gcg ccc ttg gcc<br>ggg act tgt ggg gtc ctt ctc ctg tca ctg gtt atc acc ctt tac tgc aaa cgg<br>ggc aga aag aaa ctc ctg tat ata ttc aaa caa cca ttt atg aga cca gta caa<br>act act caa gag gaa gat ggc tgt agc tgc cga ttt cca gaa gaa gaa gaa<br>gga gga tgt gaa ctg aga gtg aag ttc agc agg agc gca gac gcc ccc gcg<br>tac aag cag ggc cag aac cag ctc tat aac gag ctc aat cta gga cga aga<br>gag gag tac gac gtt ttg gac aag aga cgt ggc cgg gac cct gag atg ggg<br>gga aag ccg aga agg aag aac cct cag gaa ggc ctg tac aat gaa ctg cag<br>aaa gat aag atg gcg gag gcc tac agt gag att ggg atg aaa ggc gag cgc<br>cgg agg ggc aag ggg cac gat ggc ctt tac cag ggt ctc agt aca gcc acc<br>aag gac acc tac gac gcc ctt cac atg cag gcc ctg ccc cct cgc taa | 46 |
| 3524-BBZ | atg ggt tgg tcg tgc att atc ctc ttc ctc gtc gca acc gct acc ggc gtt cac<br>tcg gat tac aag gat gac gac gac aaa gag gta cag ctg gtg cag agc ggg<br>gcc gag gtt aag aag ccc ggg tct tcc gta aag gtg tcc tgc aag gcc tcg<br>ggg ggc aca ttc tca tcg tac gca ata tcg tgg gtg cgg cag gcc ccc ggg<br>cag ggg ctg gaa tgg gtc ggc gga att atc cca atc ttc ggg acc gcc aac<br>tat gcc cag aag ttt cag ggt cgt gtg aag att act gcc gac gag tcc gca agt<br>acg gcc tac atg gag ctg agt agt ctg cgt agc gag gat act gcc gtt tat tat<br>tgc gcc cgg gaa gag gga ccg tac tgc tcg tcg acc tca tgt tac gca gcc<br>ttc gac atc tgg ggc caa ggc acc ctg gtg acg gtg tcc tcc ggt ggt ggc<br>gga agt ggc ggc ggg ggg tcc ggc ggg ggc ggt tca cag tcc gtc ctg acc<br>cag gat ccc gcg gtg tcg gtc gcg ctg ggt cag aca gta aag ata aca tgc<br>cag ggc gat tct ctg cgc agt tat ctg gcc tcg tgg tac cag cag aaa ccc<br>ggc cag gct cct acc ctt gtt acc tac gcg cgc aat gac aga ccc gcg ggc<br>gtg ccc gac cgc ttc tcc ggc tca aag agc ggg acc tcc gcc tcc ctg gcc<br>atc tcc ggg ctc cag tct gag gat gag gcc gat tac tac tgc gct gct tgg gac | 47 |

TABLE 4-continued

Nucleic Acid Sequences of Exemplary EGFR CARs

| CAR designation | Nucleic Acid Sequence | SEQ ID NO: |
| --- | --- | --- |
| | gac tcc ctc aat ggc tat ctg ttt ggc gca ggc aca aag ctg acc gtg ctc acc<br>acg acg cca gcg ccg cga cca cca aca ccg gcg ccc acc atc gcg tcg cag<br>ccc ctg tcc ctg cgc cca gag gcg tgc cgg cca gcg gcg ggg ggc gca gtg<br>cac acg agg ggg ctg gac ttc gcc tgt gat atc tac atc tgg gcg ccc ttg gcc<br>ggg act tgt ggg gtc ctt ctc ctg tca ctg gtt atc acc ctt tac tgc aaa cgg<br>ggc aga aag aaa ctc ctg tat ata ttc aaa caa cca ttt atg aga cca gta caa<br>act act caa gag gaa gat ggc tgt agc tgc cga ttt cca gaa gaa gaa gaa<br>gga gga tgt gaa ctg aga gtg aag ttc agc agg agc gca gac gcc ccc gcg<br>tac aag cag ggc cag aac cag ctc tat aac gag ctc aat cta gga cga aga<br>gag gag tac gac gtt ttg gac aag aga cgt ggc cgg gac cct gag atg ggg<br>gga aag ccg aga agg aag aac cct cag gaa ggc ctg tac aat gaa ctg cag<br>aaa gat aag atg gcg gag gcc tac agt gag att ggg atg aaa ggc gag cgc<br>cgg agg ggc aag ggg cac gat ggc ctt tac cag ggt ctc agt aca gcc acc<br>aag gac acc tac gac gcc ctt cac atg cag gcc ctg ccc cct cgc taa | |
| P3-5BBZ | atg ggt tgg tcg tgc att atc ctc ttc ctc gtc gca acc gct acc ggc gtt cac<br>tcg gat tac aag gat gac gac gac aaa gag gta cag ctg gtg cag agc ggg<br>gcc gag gtt aag aag ccc ggg tct tcc gta aag gtg tcc tgc aag gcc tcg<br>ggg ggc aca ttc tca tcg tac gca ata tcg tgg gtg cgg cag gcc ccc ggg<br>cag ggg ctg gaa tgg gtc ggc gga att atc cca atc ttc ggg acc gcc aac<br>tat gcc cag aag ttt cag ggt cgt gtg aag att act gcc gac gag tcc gca agt<br>acg gcc tac atg gag ctg agt agt ctg cgt agc gag gat act gcc gtt tat tat<br>tgc gcc cgg gaa gag gga ccg tac tgc tcg tcg acc tca tgt tac ggc gcc<br>ttc gac atc tgg ggc caa ggc acc ctg gtg acg gtg tcc tcc ggt ggt ggc<br>gga agt ggc ggc ggg ggg tcc ggc ggg ggc ggt tca cag tcc gtc ctg acc<br>cag gat ccc gcg gtg tcg gtc gcg ctg ggt cag aca gta aag ata aca tgc<br>cag ggc gat tct ctg cgc agt tat ctg gcc tcg tgg tac cag cag aaa ccc<br>ggc cag gct cct acc ctt gtt acc tac gcg cgc aat gac aga ccc gcg ggc<br>gtg ccc gac cgc ttc tcc ggc tca aag agc ggg acc tcc gcc tcc ctg gcc<br>atc tcc ggg ctc cag tct gag gat gag gcc gat tac tac tgc gct gct tgg gac<br>gac tcc ctc aat ggc tat ctg ttt ggc gca ggc aca aag ctg acc gtg ctc acc<br>acg acg cca gcg ccg cga cca cca aca ccg gcg ccc acc atc gcg tcg cag<br>ccc ctg tcc ctg cgc cca gag gcg tgc cgg cca gcg gcg ggg ggc gca gtg<br>cac acg agg ggg ctg gac ttc gcc tgt gat atc tac atc tgg gcg ccc ttg gcc<br>ggg act tgt ggg gtc ctt ctc ctg tca ctg gtt atc acc ctt tac tgc aaa cgg<br>ggc aga aag aaa ctc ctg tat ata ttc aaa caa cca ttt atg aga cca gta caa<br>act act caa gag gaa gat ggc tgt agc tgc cga ttt cca gaa gaa gaa gaa<br>gga gga tgt gaa ctg aga gtg aag ttc agc agg agc gca gac gcc ccc gcg<br>tac aag cag ggc cag aac cag ctc tat aac gag ctc aat cta gga cga aga<br>gag gag tac gac gtt ttg gac aag aga cgt ggc cgg gac cct gag atg ggg<br>gga aag ccg aga agg aag aac cct cag gaa ggc ctg tac aat gaa ctg cag<br>aaa gat aag atg gcg gag gcc tac agt gag att ggg atg aaa ggc gag cgc<br>cgg agg ggc aag ggg cac gat ggc ctt tac cag ggt ctc agt aca gcc acc<br>aag gac acc tac gac gcc ctt cac atg cag gcc ctg ccc cct cgc taa | 48 |
| P2-4BBZ | atg ggt tgg tcg tgc att atc ctc ttc ctc gtc gca acc gct acc ggc gtt cac<br>tcg gat tac aag gat gac gac gac aaa gag gta cag ctg gtg cag agc ggg<br>gcc gag gtt aag aag ccc ggg tct tcc gta aag gtg tcc tgc aag gcc tcg<br>ggg ggc aca ttc tca tcg tac gca ata tcg tgg gtg cgg cag gcc ccc ggg<br>cag ggg ctg gaa tgg atg ggc gga att atc cca atc ttc ggg acc gcc aac<br>tat gcc cag aag ttt cag ggt cgt gtg acc att act gcc gac gag tcc acc agt<br>acg gcc tac atg gag ctg agt agt ctg cgt agc gag gat act gcc gtt tat tat<br>tgc gcc cgg gaa gag gga ccg tac tgc tcg tcg acc tca tgt tac gca gcc<br>ttc gac atc tgg ggc caa ggc acc ctg gtg acg gtg tcc tcc ggt ggt ggc<br>gga agt ggc ggc ggg ggg tcc ggc ggg ggc ggt tca cag tcc gtc ctg acc<br>cag gat ccc gcg gca tcg gtc gcg ctg ggt cag aca gta aag ata aca tgc<br>cag ggc gat tct ctg cgc agt tat ttc gcc tcg tgg tac cag cag aaa ccc ggc<br>cag gct cct acc ctt gtt atg tac gcg cgc aat gac aga ccc gcg ggc gtg<br>ccc gac cgc ttc tcc ggc tca aag agc ggg acc tcc gcc tcc ctg gcc atc<br>tcc ggg ctc cag tct gag gat gag gcc gat tac tac tgc gct gct tgg gac<br>gac tcc ctc aat ggc tat ctg ttt ggc gca ggc aca aag ctg acc gtg ctc acc<br>acg acg cca gcg ccg cga cca cca aca ccg gcg ccc acc atc gcg tcg cag<br>ccc ctg tcc ctg cgc cca gag gcg tgc cgg cca gcg gcg ggg ggc gca gtg<br>cac acg agg ggg ctg gac ttc gcc tgt gat atc tac atc tgg gcg ccc ttg gcc<br>ggg act tgt ggg gtc ctt ctc ctg tca ctg gtt atc acc ctt tac tgc aaa cgg<br>ggc aga aag aaa ctc ctg tat ata ttc aaa caa cca ttt atg aga cca gta caa<br>act act caa gag gaa gat ggc tgt agc tgc cga ttt cca gaa gaa gaa gaa<br>gga gga tgt gaa ctg aga gtg aag ttc agc agg agc gca gac gcc ccc gcg<br>tac aag cag ggc cag aac cag ctc tat aac gag ctc aat cta gga cga aga<br>gag gag tac gac gtt ttg gac aag aga cgt ggc cgg gac cct gag atg ggg<br>gga aag ccg aga agg aag aac cct cag gaa ggc ctg tac aat gaa ctg cag<br>aaa gat aag atg gcg gag gcc tac agt gag att ggg atg aaa ggc gag cgc<br>cgg agg ggc aag ggg cac gat ggc ctt tac cag ggt ctc agt aca gcc acc<br>aag gac acc tac gac gcc ctt cac atg cag gcc ctg ccc cct cgc taa | 49 |

The monovalent affinities of the panel of EGFR-specific scFvs varied over a range of approximately 300-fold (Zhoe et al., 2007, *J Mol Biol,* 371:934). The 2224, P2-4, P3-5 and C10 scFvs were cloned into an RNA-based vector and in vitro transcribed for T cell mRNA electroporation. Levels of CAR surface expression were assayed and found to be similar among the EGFR constructs. To compare reactivities of the panel of EGFR CARs, CAR T cells were stimulated with EGFR-expressing tumor cell lines that have a broad range of EGFR expression at the cell surface. CAR T cell activation was evaluated by levels of CD107a up-regulation. Higher affinity EGFR CARs (2224:BBζ and P2-4:BBζ) responded to all EGFR positive tumor lines (MDA468, MDA231 and SK-OV3) regardless of EGFR expression levels. However, the reactivity exhibited by lower affinity EGFR CARs (P3-5.BBZ and C10.BBZ) against EGFR-expressing tumor lines did correlate with the levels of EGFR expression. Furthermore, lower affinity EGFR CARs displayed more potent reactivity to the EGFR overexpressing tumor, MDA468, than the higher affinity EGFR CARs, while provoking a much weaker response to EGFR low expressing cells. None of the EGFR CAR T cells reacted to the EGFR negative tumor line K562.

To confirm that the level of response was related to scFv affinity and the level of EGFR expression, and to exclude tumor-specific effects, the panel of EGFR CAR T cells was co-cultured with K562 cells expressing varying levels of EGFR after electroporation with EGFR mRNA. The higher affinity EGFR CARs did not discriminate between target cells with different levels of EGFR expression. For example, T cells expressing CAR 2224 responded equally well to K562 cells electroporated with a 200-fold difference in EGFR mRNA (0.1 μg to 20 μg). However in agreement with the above ErbB2 CAR results, the lower affinity EGFR CARs (P3-5 and C10) exhibited a high correlation between T cell responses and EGFR expression levels.

To confirm the increased safety profile of the lower affinity EGFR CARs, we tested the reactivities of EGFR CARs against primary cells derived from different organs. Five primary cell lines and five tumor cell lines were tested for both surface levels of EGFR and ability to trigger CAR T cell reactivity. Three of the primary cell lines examined express detectable levels of EGFR and two did not (pulmonary artery smooth muscle and PBMC). Two of the tumor cell lines (MCF7 and Raji) did not express detectable EGFR on the cell surface. Comparing EGFR CAR T cells to CD19 CAR T cells, T cells with higher EGFR affinity CARs (2224 and P2-4) reacted to all the primary lines tested and all of the tumors except Raji. However, T cells with the affinity decreased EGFR CAR T cells P3-5 and C10 were not reactive to any of the five primary cells tested. CD19 specific CAR T cells reacted to the CD19+ line Raji, and to PBMCs, presumably to the B cells in PBMC, but did not respond to any of the tumor lines or other primary cell lines. These data demonstrate that affinity tuning of scFv can increase the therapeutic index for CAR T cells that target either ErbB2 or EGFR.

Example 3: Optimizing CAR Therapy with Administration of Exogenous Cytokines

Cytokines have important functions related to T cell expansion, differentiation, survival and homeostasis. One of the most important cytokine families for clinical use is the common γ-chain ($\gamma_c$) family cytokines, which includes interleukin (IL)-2, IL-4, IL-7, IL-9, IL-15 and IL-21 (Liao et al., 2013, *Immunity,* 38:13-25). IL-2 has been widely studied as an immunotherapeutic agent for cancer. The supplement of IL-2 enhanced the antitumor ability of anti-CD19 CAR-T cells in the clinical trials (Xu et al., 2013, *Lymphoma,* 54:255-60). However, the administration of IL-2 is limited by side effects and a propensity for expansion of regulatory T cells and the effect of activated induced cell death (AICD) (Malek et al., 2010, *Immunity,* 33:153-65; and Lenardo et al., 1999, *Annu Rev Immunol,* 17:221-53). IL-7, IL-15, and IL-21 each can enhance the effectiveness of adoptive immunotherapies and seems to be less toxicity compared with IL-2 (Alves et al., 2007, *Immunol Lett,* 108:113-20). Despite extensive preclinical and clinical studies on the role of the above cytokines, multi-parameter comparative studies on the roles of various exogenous $\gamma_c$ cytokines on CAR-T cell adoptive therapy are lacking.

Besides γ-chain cytokines, IL-18 is another immunostimulatory cytokine regulating immune responses, which enhances the production of IFN-γ by T cells and augments the cytolytic activity of CTLs (Srivastava et al., 2010, *Curr Med Chem,* 17:3353-7). Administration of IL-18 is safe and well tolerated, even when the dose reaching as high as 1000 μg/kg (Robertson et al., 2006, *Clin Cancer Res,* 12:4265-73). Therefore, IL-18 could be another candidate used to boost the antitumor of CAR-T cells.

To further enhance the efficacy of adoptive therapy with CAR engineered T (CAR-T) cells, optimization of CAR therapy with administration of exogenous cytokines was examined. To compare the roles of different cytokines administrated exogenously during CAR-T cell immunotherapy and find the optimal cytokine for clinical use, the in vivo antitumor ability of CAR-T cells was tested using ovarian cancer animal models.

The following materials and methods were used in the experiments described in this example.

CAR Construction and Lentivirus Preparation

The pELNS-C4-27z CAR vector was constructed as described previously (manuscript under review), Briefly, the pHEN2 plasmid containing the anti-FRα C4/AFRA4 scFv was used as a template for PCR amplification of C4 fragment using the primers of 5'-ataggatcccagctggtggagtctgggg-gaggc-3' (SEQ ID NO: 50) and 5'-atagctagcacctaggacggtcagcttggtccc-3' (SEQ ID NO: 51) (BamHI and NheI were underlined). The PCR product and the third generation self-inactivating lentiviral expression vectors pELNS were digested with BamHI and NheI. The digested PCR products were then inserted into the pELNS vector containing CD27-CD3z T-cell signaling domain in which transgene expression is driven by the elongation factor-1α (EF-1α) promoter.

High-titer replication-defective lentivirus was generated by transfection of human embryonic kidney cell line 293T (293T) cells with four plasmids (pVSV-G, pRSV.REV, pMDLg/p.RRE and pELNS-C4-27z CAR) by using Express In (Open Biosystems) as described previously (manuscript under review). Supernatants were collected and filtered at 24 h and 48 h after transfection. The media was concentrated by ultracentrifugation. Alternatively, a single collection was done 30 hr after media change. Virus containing media was alternatively used unconcentrated or concentrated by Lenti-X concentrator (Clontech, Cat #631232). The virus titers were determined based on the transduction efficiency of lentivirus to SupT1 cells by using limiting dilution method.

T Cells and Cell Lines

Peripheral blood lymphocytes were obtained from healthy donors after informed consent under a protocol approved by University Institutional Review Board at the University of Pennsylvania. The primary T cells were purchased from the Human Immunology Core after purified by negative selection. T cells were cultured in complete media (RPMI 1640 supplemented with 10% FBS, 100 U/mL penicillin, 100 μg/mL streptomycin sulfate) and stimulated with anti-CD3 and anti-CD28 mAbs-coated beads (Invitrogen) at a ratio of 1:1 following the instruction. Twenty-four hours after activation, cells were transduced with lentivirus at MOI of 5. Indicated cytokines were added to the transduced T cells from the next day with a final concentration of 10 ng/mL. The cytokines were replaced every 3 days.

The 293T cell used for lentivirus packaging and the SupT1 cell used for lentiviral titration were obtained from ATCC. The established ovarian cancer cell lines SKOV3 (FRα+) and C30 (FRα−) was used as target cell for cytokine-secreting and cytotoxicity assay. For bioluminescence assays, SKOV3 was transduced with lentivirus to express firefly luciferase (fLuc).

Flow Cytometric Analysis and Cell Sorting

Flow cytometry was performed on a BD FACSCanto. Anti-human CD45 (HI30), CD3 (HIT3a), CD8 (HIT8a), CD45RA (HI100), CD62L (DREG-56), CCR7 (G043H7), IL-7Rα (A019D5), CD27 (M-T271), CD28 (CD28.2), CD95 (DX2), TNF-α (MAb11), IFN-γ (4S.B3), IL-2 (MQ1-17H12), perforin (B-D48), granzym-B (GB11) were obtained from Biolegend. Biotin-SP-conjugated rabbit anti-human IgG (H+L) was purchased from Jackson Immunoresearch and APC conjugated streptavidin was purchased from Biolegand. Anti-human Bcl-xl (7B2.5) was purchased from SouhernBiotech. Apoptosis kit and TruCount tubes were obtained from BD Bioscience. For peripheral blood T cell count, blood was obtained via retro-orbital bleeding and stained for the presence of human CD45, CD3, CD4 and CD8 T cells. Human CD45+-gated, CD3+, CD4+ and CD8+ subsets were quantified with the TruCount tubes following the manufacturer's instructions.

In Vivo Study of Adoptive Cell Therapy

Female non-obese diabetic/severe combined immunodeficiency/γ-chain$^{-/-}$ (NSG) mice 8 to 12 weeks of age were obtained from the Stem Cell and Xenograft Core of the Abramson Cancer Center, University of Pennsylvania. The mice were inoculated subcutaneously with $3\times10^6$ fLuc$^+$ SKOV3 cells on the flank on day 0. Four or Five mice were randomized per group before treatment. After tumors became palpable, human primary T cells were activated and transduced as described previously. T cells were expanded in the presence of IL-2 (5 ng/mL) for about 2 weeks. When the tumor burden was ~250-300 mm$^3$, the mice were injected with $5\times10^6$ CAR-T cells or 100 μl saline intravenously and then received daily intraperitoneal injection of 5 μg of IL-2, IL-7, IL-15, IL-18, IL-21 or phosphate buffer solution (PBS) for 7 days. Tumor dimensions were measured with calipers and tumor volumes were calculated with the following formula: tumor volume=(length×width$^2$)/2. The number and phenotype of transferred T cells in recipient mouse blood was determined by flow cytometry after retro-orbital bleeding. The mice were euthanized when the tumor volumes were more than 2000 mm$^3$ and tumors were resected immediately for further analysis.

Statistical Analysis

Statistical analysis was performed with Prism 5 (GraphPad software) and IBM SPSS Statistics 20.0 software. The data were shown as mean±SEM unless clarified. Paired sample t-tests or nonparametric Wilcoxon rank tests were used for comparison of two groups and repeated measures ANOVA or Friedman test were used to test statistical significance of differences among three or more groups. Findings were considered as statistically significant when P-values were less than 0.05.

Results

Construction and Expression of Anti-FRα C4 CAR

The pELNS-C4-27z CAR comprised of the anti-FRα C4 scFv linked to a CD8α hinge and transmembrane region, followed by a CD3ζ signaling moiety in tandem with the CD27 intracellular signaling motif. Primary human T cells were efficiently transduced with C4 CAR lentiviral vectors with transduction efficiencies of 43%~65% when detected at 48 h after transduction. The CAR expression levels were comparable between CD4+ and CD8+ T cells (52.6±10.2% vs. 49.5±17.1%, P=0.713).

Different Anti-Tumor Efficacy of Various Cytokines in Animal Models

This study examined whether the in vivo cytokine administration in combination with CAR-T cell injection could enhance the anti-tumor activity of CAR-T cells. Mice bearing subcutaneous SKOV3 tumors received either saline or $5\times10^6$ C4-27z CAR-T cell intravenously injection on day 39. Compared with saline group, mice receiving CAR-T cell therapy underwent short-time tumor regression and the tumor began to rebounded from day 56. Of the various cytokine groups, mice receiving IL-15 and IL-21 injection presented best tumor suppression, followed by IL-2 and IL-7, whereas IL-18 and PBS treated mice had the heaviest tumor burden. The persistence of transferred T cells in the peripheral blood was determined 15 days after adoptive transfer and when termination. Highest numbers of CD4+ and CD8+ T cells were detected in mice treated with IL-15, followed by IL-21. The day+15 CD4+ and CD8+ T-cell count were consistent with the tumor regression and predicted the final tumor weight. The mice were killed 73 days after tumor challenge and the tumors were analyzed for the presence of human T cells. Similarly with peripheral blood, mice treated with IL-15 presented highest T cell number in the tumor, followed by IL-21, IL-2, IL-7, PBS and IL-18. The ratios of CD4 to CD8 were comparable among different cytokine groups, with a predomination of CD4+ T cells both in blood and tumor in all cytokine groups. The CAR expression in CD8+ T cells were comparable among the above groups (45.1%~62.4%), while IL-15 and IL-21 groups had higher proportions of CAR+ CD4 T cells than IL-2 and IL-18 groups. As to the phenotype, all the CAR-T cells in the tumor were CD62L$^-$ and CCR7$^-$, while 35%~60% of them expressed CD45RA+ (Temra) (data not shown). CD8+ T cells were more likely to retained CD27 expression while the CD28 expression was comparable between CD4+ and CD8+ T cells.

Example 4: Improvement in the Efficacy of Adoptively Transferred T Cells by the Genetic Blockade of Protein Kinase A (PKA) Function The protein kinase A (PKA) holoenzyme is a heterotetramer consisting of 2 regulatory subunits (RI and RII) and 2 catalytic subunits (CI and CII). Upon activation by cAMP, the R subunits dissociate, and the C subunits proceed to phosphorylate a large myriad of target substrates; the cAMP-PKA signaling cascade is one of the most ubiquitous and well-established second messenger systems to date. Hence, it follows that the attenuation of cAMP signaling in T cells may represent a means to prolong TCR-mediated signaling and better killing capacity.

In order for PKA to elicit its functions, it is tethered to lipid rafts in close proximity to adenylyl cyclase, the enzyme that metabolizes ATP to generate cAMP. The tethering and subsequent compartmentalization of PKA and its effects are mediated by A-kinase anchoring proteins (AKAP). AKAP therefore serve as a platform on which cAMP and PKA signaling converge, and provide temporal and spatial regulation of these entities. With regard to T cell signaling PKA is directed to the TCR by binding to a protein called Ezrin, which inserts into the membrane and serves as the AKAP.

The RIAD or RISR-RIAD peptide binds to the RI subunit of PKA with high affinity and disrupts PKA anchoring to Ezrin, thereby neutralizing PKA signaling (Carlson et al., 2006). Normally, cAMP binds to PKA, which activates it. The PKA binds to Ezrin and is brought in contact with the kinase Csk. Csk is activated which then phosphorylates and inactivates Lck which stops TCR signaling. With RIAD or RISR-RIAD around, the PKA-cAMP complex cannot localize to Ezrin and thus does not have access to Csk. The RIAD-mediated displacement of PKA ultimately diminishes phosphorylation of Tyr-505 on Lck, and hence upregulates TCR signaling.

An additional peptide sequence enhances RIAD binding to PKA, thereby augmenting the release of T cell inhibition by cAMP; this additional peptide is designated RISR (RI specifier region). A transgenic mouse model expressed RISR-RIAD in T cells under the control of the lck distal promoter displaced PKA from lipid rafts of T cells. These mice showed heightened TCR signaling and interleukin 2 (IL2) secretion, and resistance to PGE2. Impressively, these mice were also more resistant to murine AIDS.

The approach described herein was to couple T cell anti-tumor activity with RISR-RIAD. MesoCAR-expressing viral vectors with RISR-RIAD were generated to test the efficacy of these constructs against tumor cells in vitro and in vivo (FIG. 1).

Figure 2:
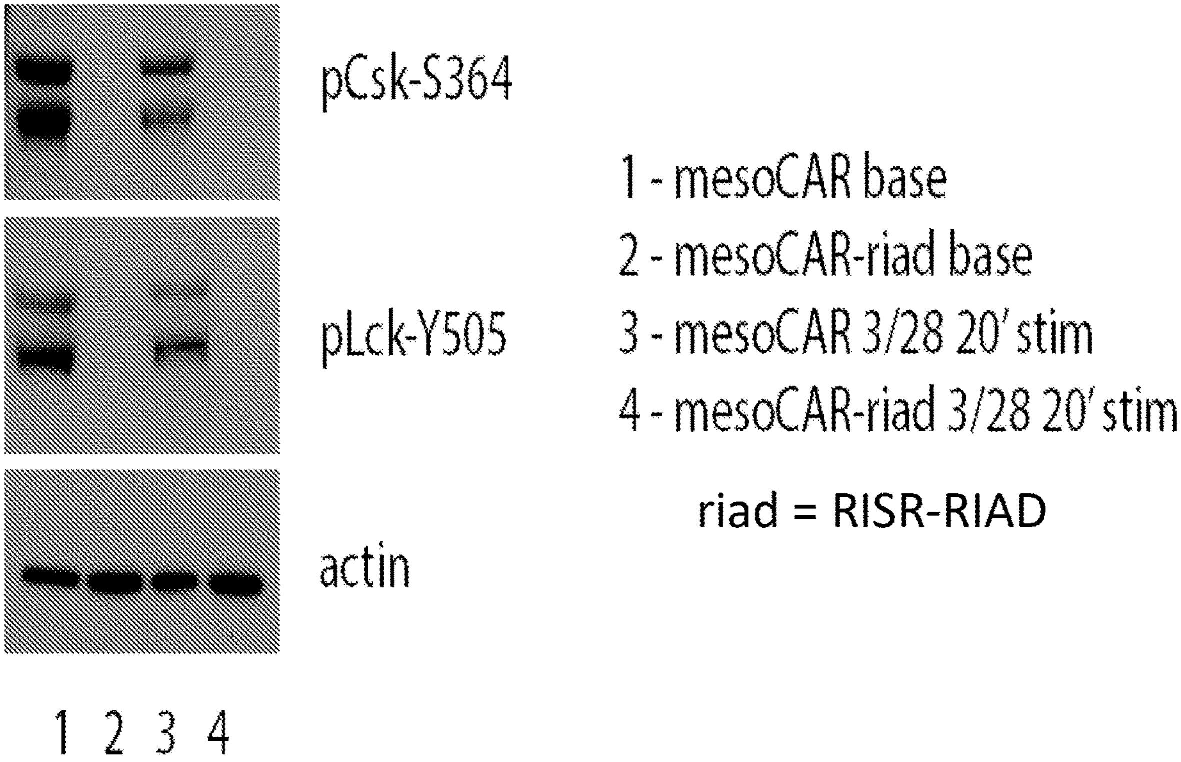
FIG. 2 is a blot showing that RISR-RIAD expression prevented protein kinase A (PKA) from inhibiting Lck and thus prevented immunosuppression.
Figure 3:
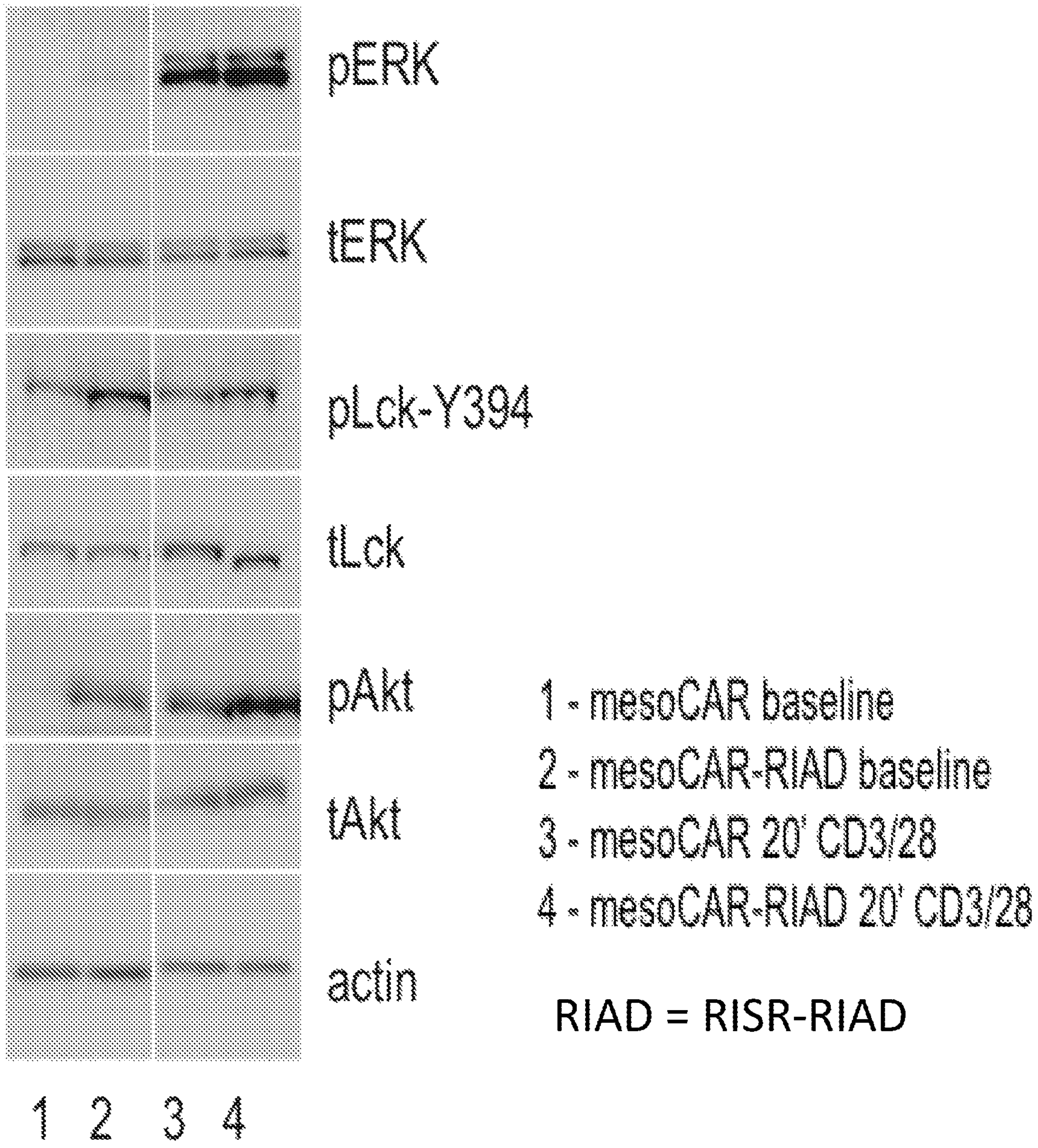
FIG. 3 is a blot showing that RISR-RIAD expression resulted in more active signaling at baseline and after TCR stimulation.

PKA regulates T cell signaling by phosphorylating the kinase Csk at S364, which activates this kinase, resulting in phosphorylation of the key TCR proximal signaling molecule Lck at Y505, which inhibits its activity. FIG. 2 is a blot showing RISR-RIAD expression prevented phosphorylation of Csk-S364 and Lck-Y505. RISR-RIAD expression resulted in more active signaling at baseline and after TCR stimulation (FIG. 3).

Figure 4:
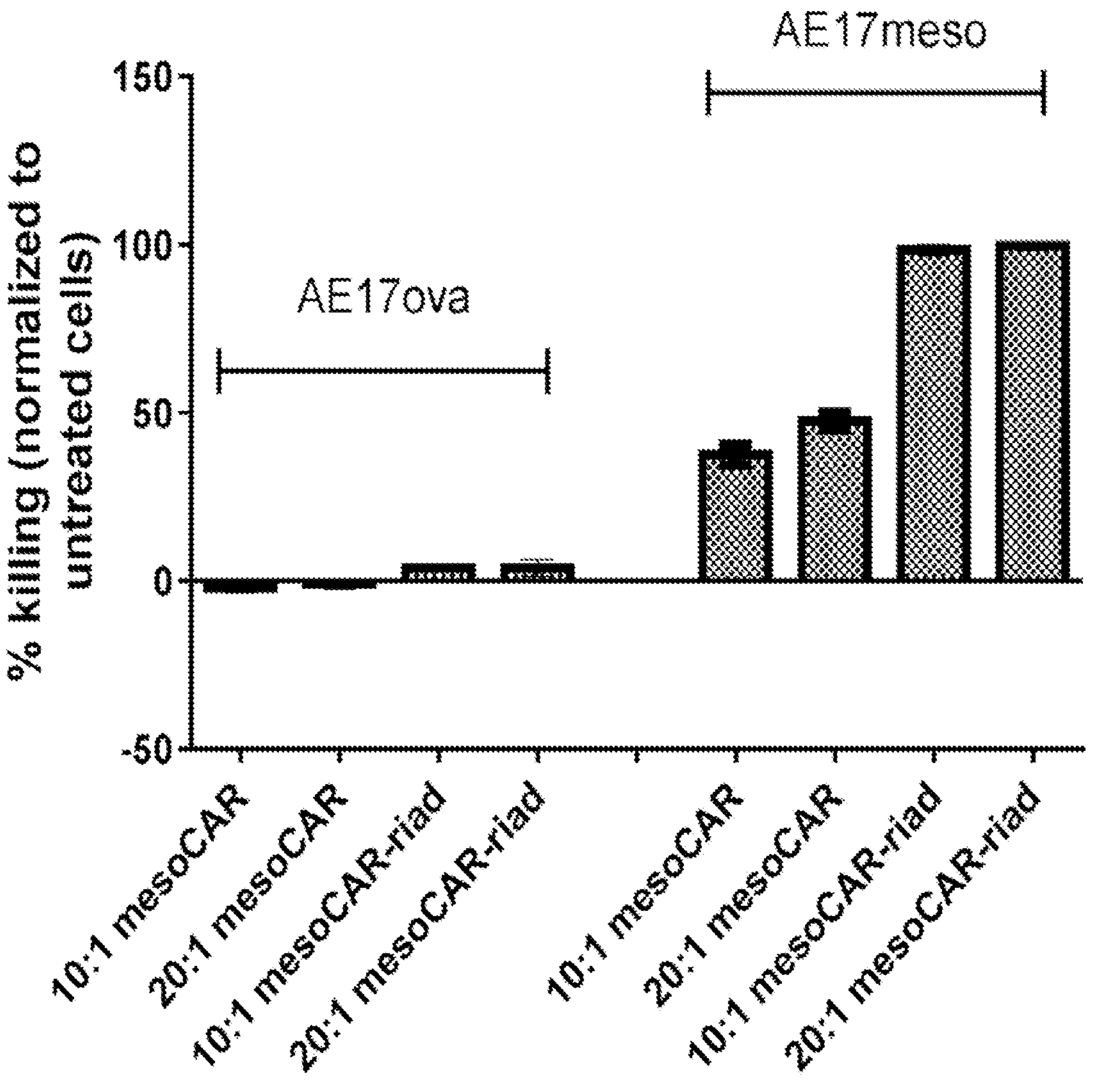
FIG. 4 is a graph showing killing of antigen-expressing cells (AE17meso) and control cells (AE17ova) that were incubated overnight in the presence of varying effector-to-target ratios (E:T); e.g., 10 CAR-expressing T cells to 1 tumor cell. Cytolytic ability of these T cells was then quantified.

Example 5: Retroviral Transduction of Activated Murine T Cells with the mesoCAR-RISR-RIAD Construct LED to Better Killing of Tumor Cells In Vitro and In Vivo Compared to MesoCAR T Cells A technique to successfully transduce murine T cells with CARs using modified retroviruses was developed. In the case of the mesoCAR-RISR-RIAD construct, the RISR-RIAD transgene was tagged by myc and flag, which allowed for simultaneous detection with mesoCAR. Compared to T cells transduced with mesoCAR, mesoCAR-RISR-RIAD-transduced T cells exhibited higher killing ability as demonstrated by an overnight in vitro killing assay of mesothelin-expressing AE17 murine mesothelioma cells (AE17meso) in differing effector-to-target ratios (E:T) shown in FIG. 4. Both constructs were shown to be target-specific as little to no killing was observed in the ova-expressing cell line (AE17ova).

Figure 5A:
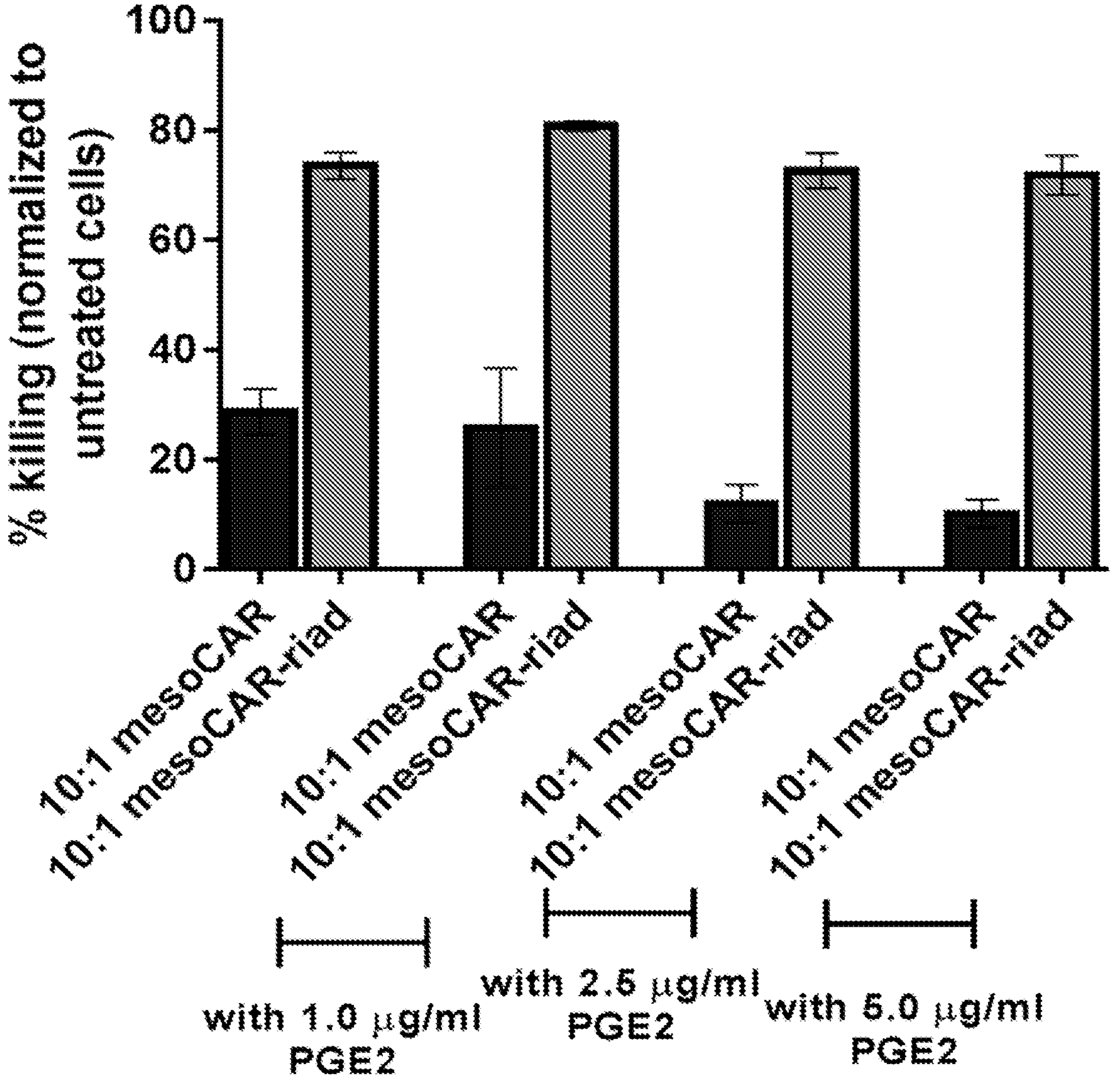
FIG. 5A is a graph showing suppression of killing of AE17meso cells that were incubated overnight with both CAR T cells at the indicated E:T in the presence of varying concentrations of PGE2. A dose-dependent suppression of killing by mesoCAR T cells was observed, but not by mesoCAR-RISR-RIAD T cells.
Figure 5B:
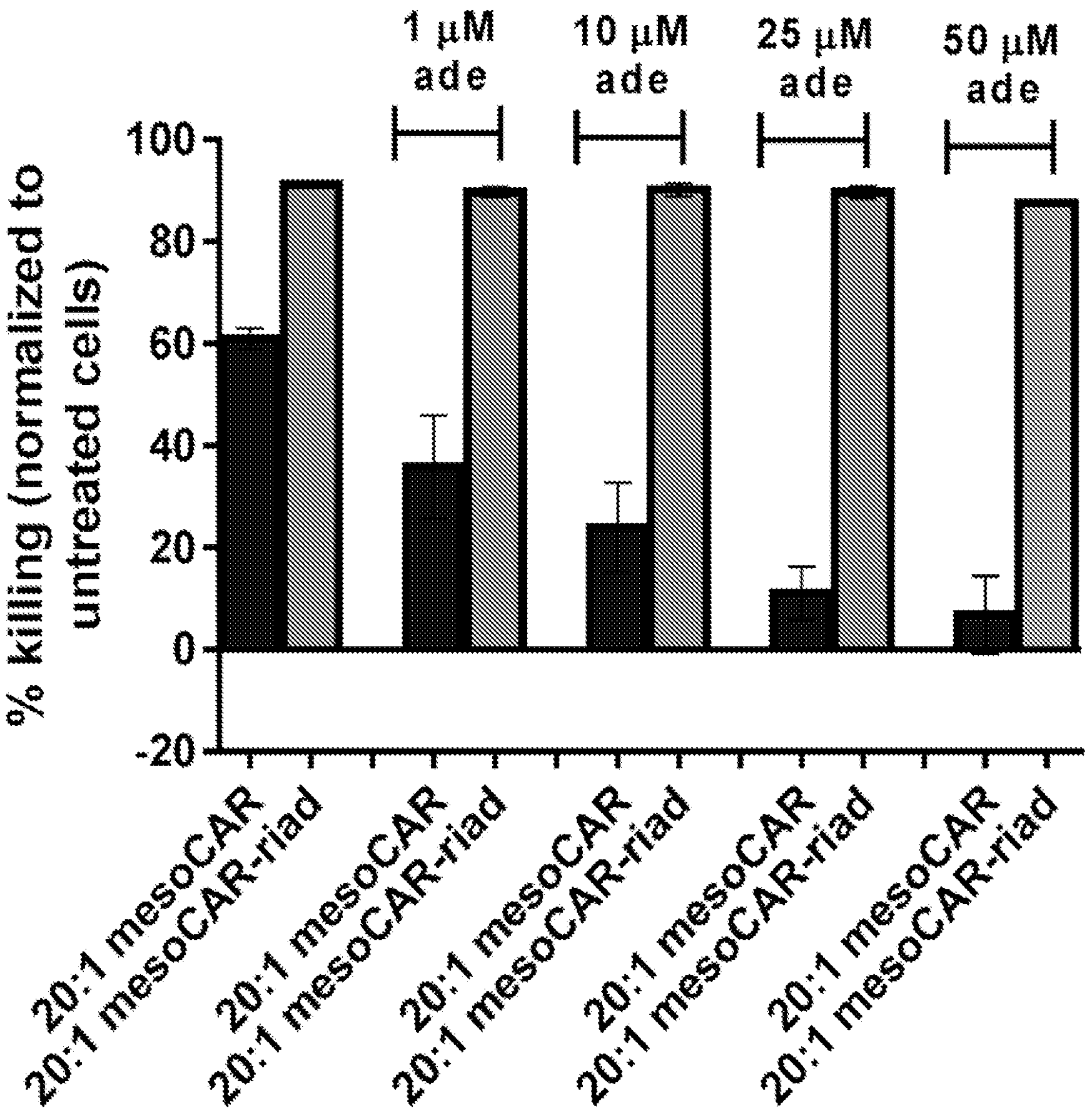
FIG. 5B is a graph showing suppression of killing of AE17meso cells that were incubated overnight with both CAR T cells at the indicated E:T in the presence of varying concentrations of adenosine. A dose-dependent suppression of killing by mesoCAR T cells was observed, but not by mesoCAR-RISR-RIAD T cells.

MesoCAR-expressing T cells exhibited modest killing ability and were susceptible to suppression by adenosine and PGE2; two agents were shown to exert their inhibitory effects in a cAMP-dependent manner FIGS. 5A and 5B substantiated that observation. FIGS. 5A and 5B further showed that the killing ability of mesoCAR-RISR-RIAD construct was unaffected by these inhibitory molecules, adenosine and PGE2.

Given the key role of PKA signaling in the inhibition of T cell function, it was hypothesized that cloning the RISR-RIAD transgene into T cells expressing chimeric antigen receptors or transgenic T cells would enhance their function within the tumor microenvironment, and result in superior tumoricidal ability as compared to CAR T cells, or transgenic TCR T cells alone. The hypothesis was tested in mouse models of mesothelioma and lung cancer treatment. Both murine and human CAR T cells were used, and two different tumor antigens were targeted, mesothelin and the stromal antigen fibroblast activation protein (FAP), see FIG. 6. The effect of RISR-RIAD in human transgenic Ly95 TCR-transduced T cells targeted to the tumor antigen NY-ESO1 expressed on HLA-A2-expressing lung cancer cells was also tested. RISR-RIAD transgene in T cells expressing chimeric antigen receptors or transgenic T cells enhanced their function within the tumor microenvironment, and resulted in superior tumoricidal ability as compared to CAR T cells, or transgenic TCR T cells alone. This hypothesis was tested in mouse models of mesothelioma and lung cancer treatment.

Figure 7A:
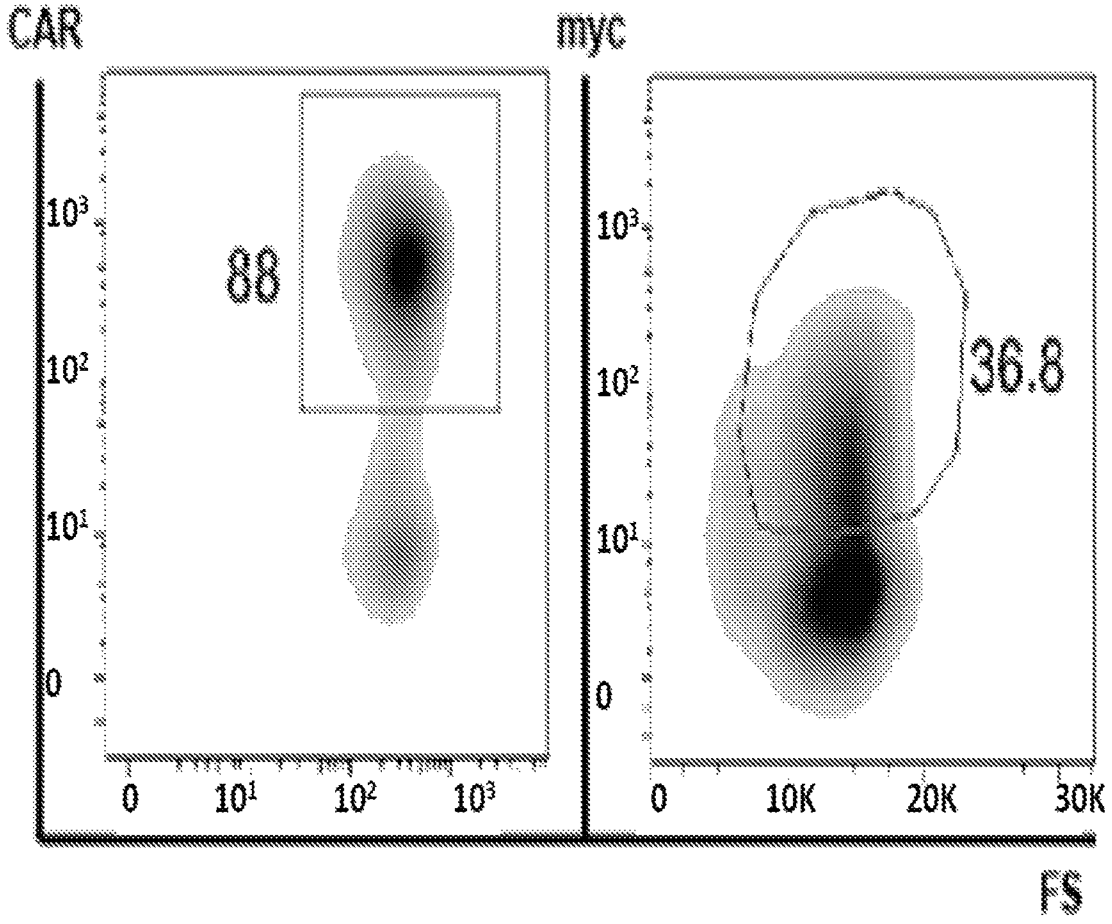
FIG. 7A is a flow plot showing that primary murine T cells transduced with mesoCAR-RISR-RIAD resisted immunosuppression and killed more effectively in vitro. Primary murine T cells isolated and transduced with mesoCAR-RISR-RIAD; transduction efficiency was determined by primary staining using a biotinylated goat anti-mouse IgG recognizing the $F(ab')_2$ fragment, followed by a secondary PE-conjugated streptavidin antibody, along with detection of myc-tagged RISR-RIAD.
Figure 7B:
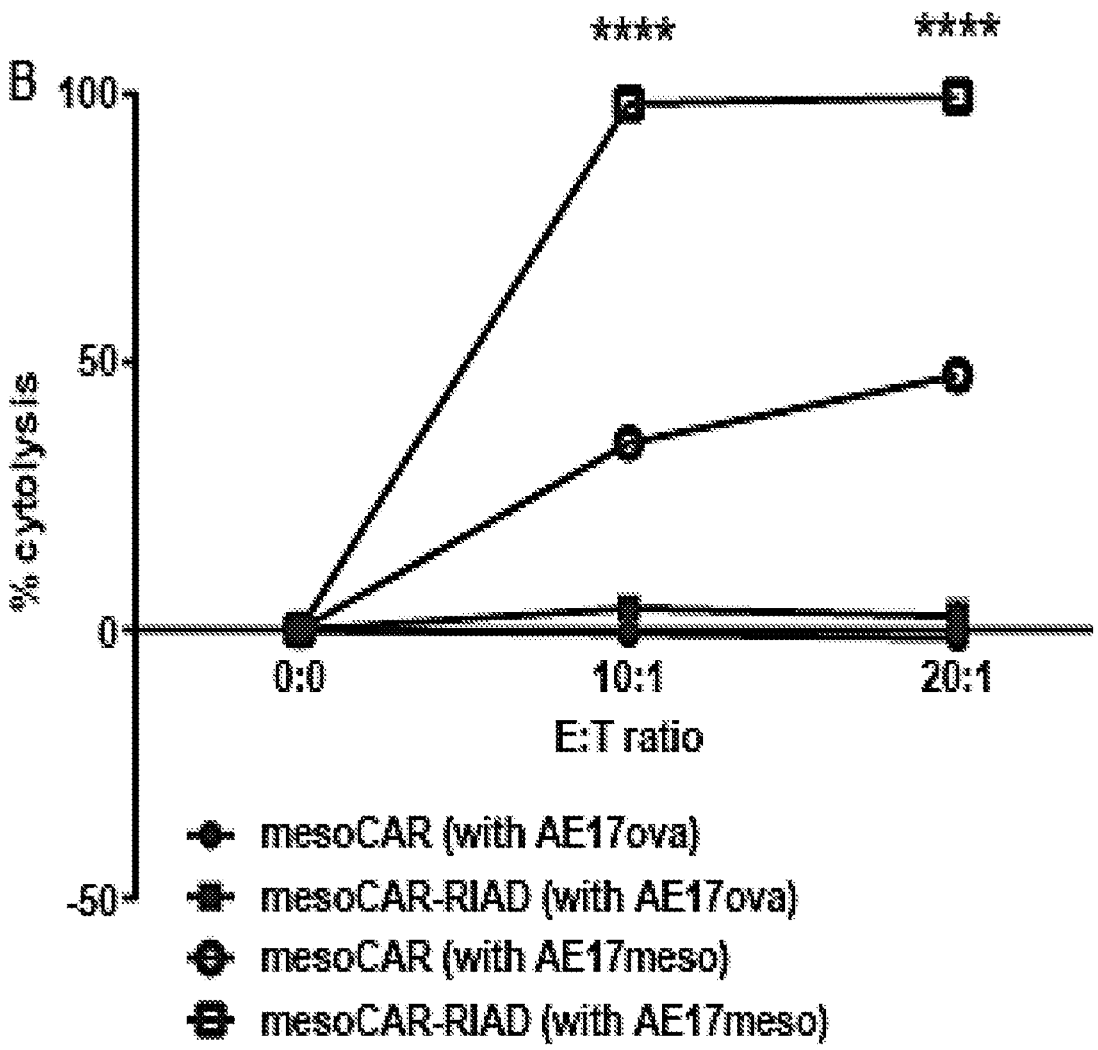
FIG. 7B is a graph showing various effector-to-target (E:T) ratios of mesoCAR and mesoCAR-RISR-RIAD T cells co-cultured with either ova-expressing AE17 (AE17ova) or mesothelin-expressing AE17 (AE17meso) cells overnight. Statistical analysis was performed using two-way ANOVA comparing the percent cytolysis of AE17meso cells by mesoCAR versus mesoCAR-RISR-RIAD T cells.
Figure 7C:
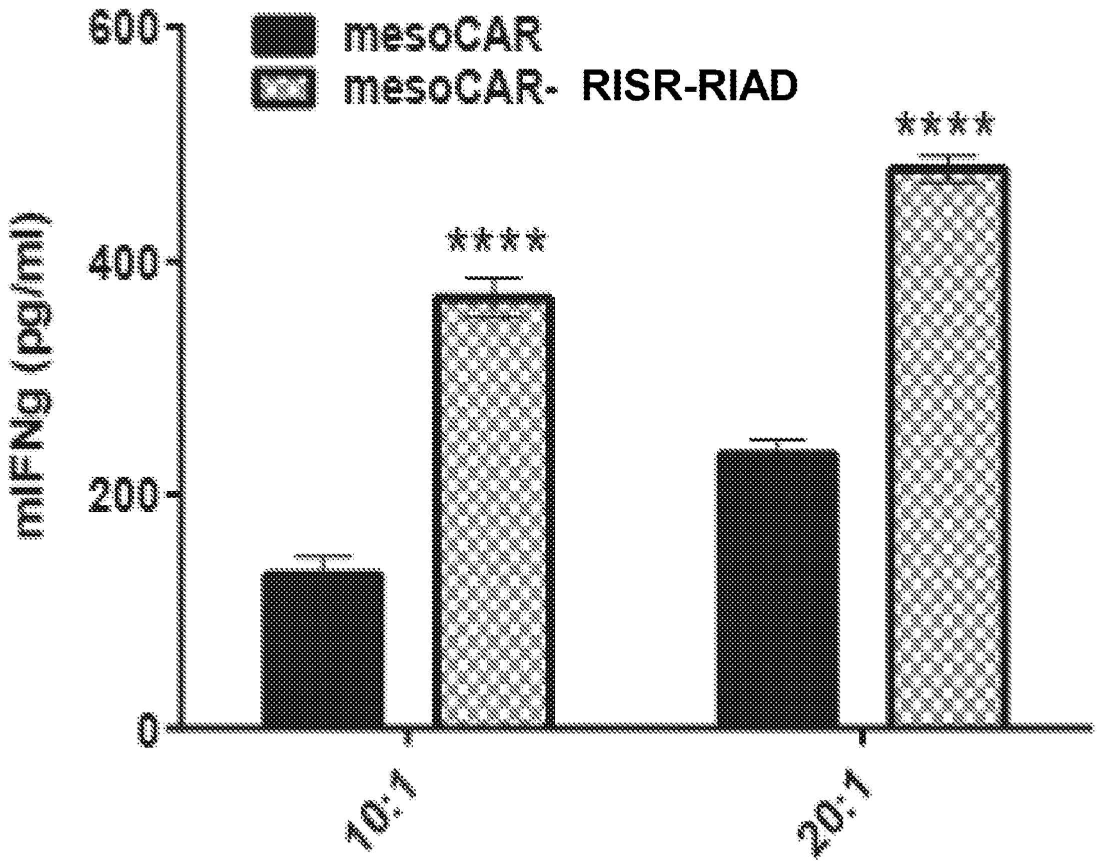
FIG. 7C is a graph showing cell culture supernatant from the overnight cytolysis assay measured for IFNγ production via ELISA, and quantified to compare production by mesoCAR and mesoCAR-RISR-RIAD T cells.
Figure 23:
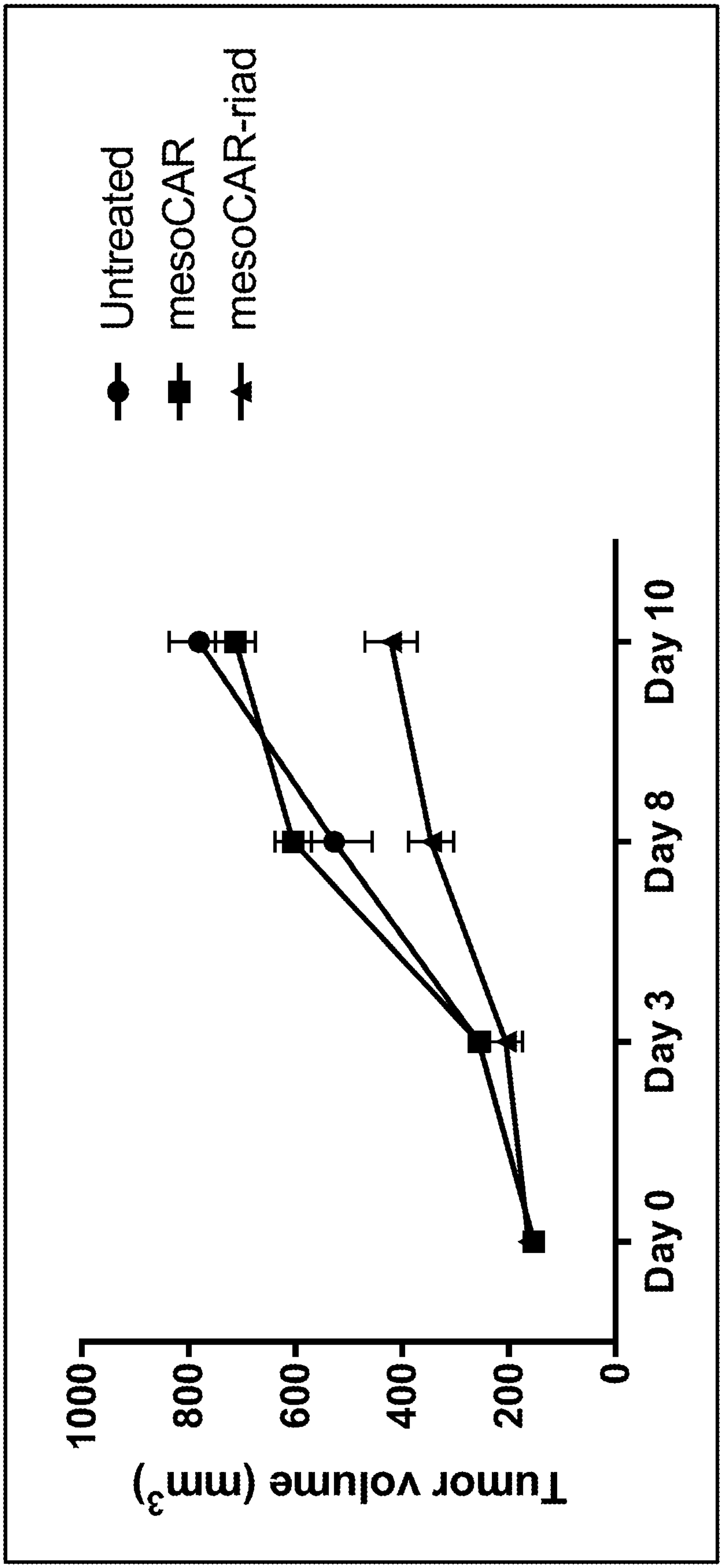
FIG. 23 is a graph showing tumor volume as a function of time in AE17meso-bearing mice were treated with meso-CAR and mesoCAR-riad T cells.
Figure 24:
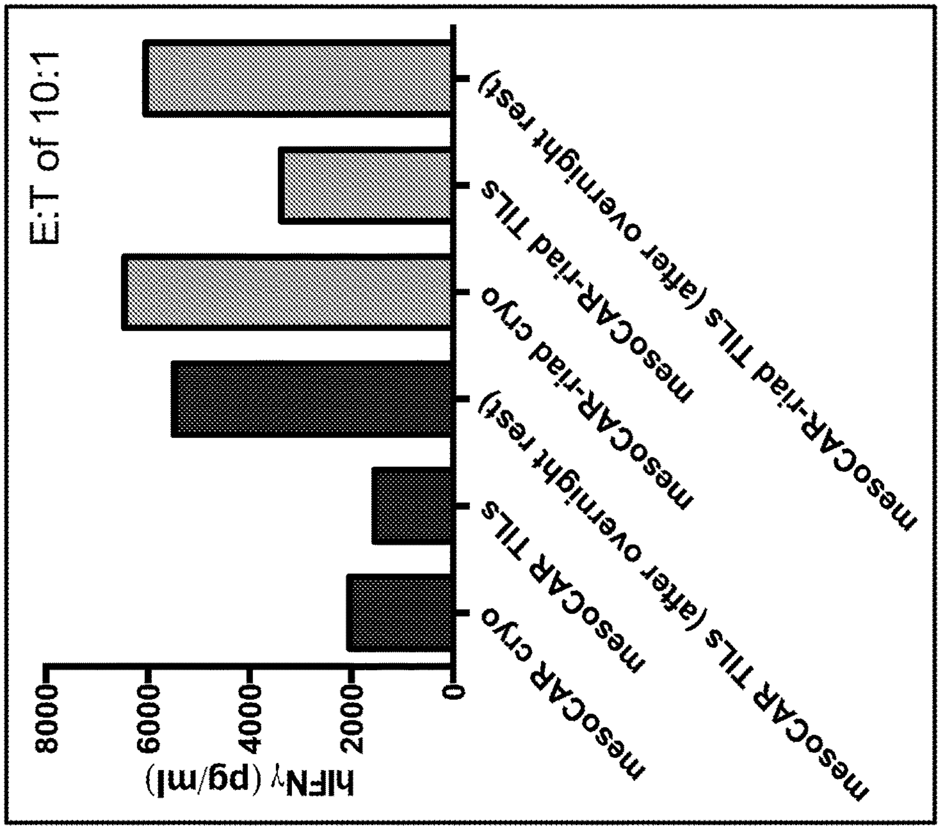
FIG. 24 is a graph showing human interferon expression in cells treated with the indicated constructs. ELISA depicting interferon-γ production from mesoCAR and mesoCAR-riad TILs co-cultured with EMM tumor cells overnight at a E:T of 10:1.

Example 6: Retroviral Transduction of Activated Murine T Cells with the mesoCAR-RISR-RIAD Construct Leads to Enhanced Killing of Tumor Cells In Vitro Due to Dampened PKA-Mediated Signaling The effect of the RISR-RIAD construct in CAR T cells that was generated from murine lymphocytes was studied. Using modified retroviruses expressing mesoCAR, with and without the RISR-RIAD transgene, activated mouse T cells were successfully transduced with over 50% transduction efficiency. The detection of the RISR-RIAD transgene was accomplished using antibodies to detect either the myc or ddk tag (FIG. 7A). Their effector functions were assessed at differing effector-to-target (E:T) ratios of transduced T cells by co-culturing them overnight with ova-expressing and mesothelin-expressing AE17 murine mesothelioma cells (AE17ova and AE17meso, respectively). Compared to murine T cells transduced with mesoCAR alone, mesoCAR-RISR-RIAD T cells showed increased killing ability (FIG. 7B) and IFNγ production with little effect on AE17ova cells (FIG. 7C). Additionally, mesoCAR-RIAD T cells were markedly more effective in reducing tumor volume as compared to mesoCAR T cells (FIG. 23).

Figure 7D:
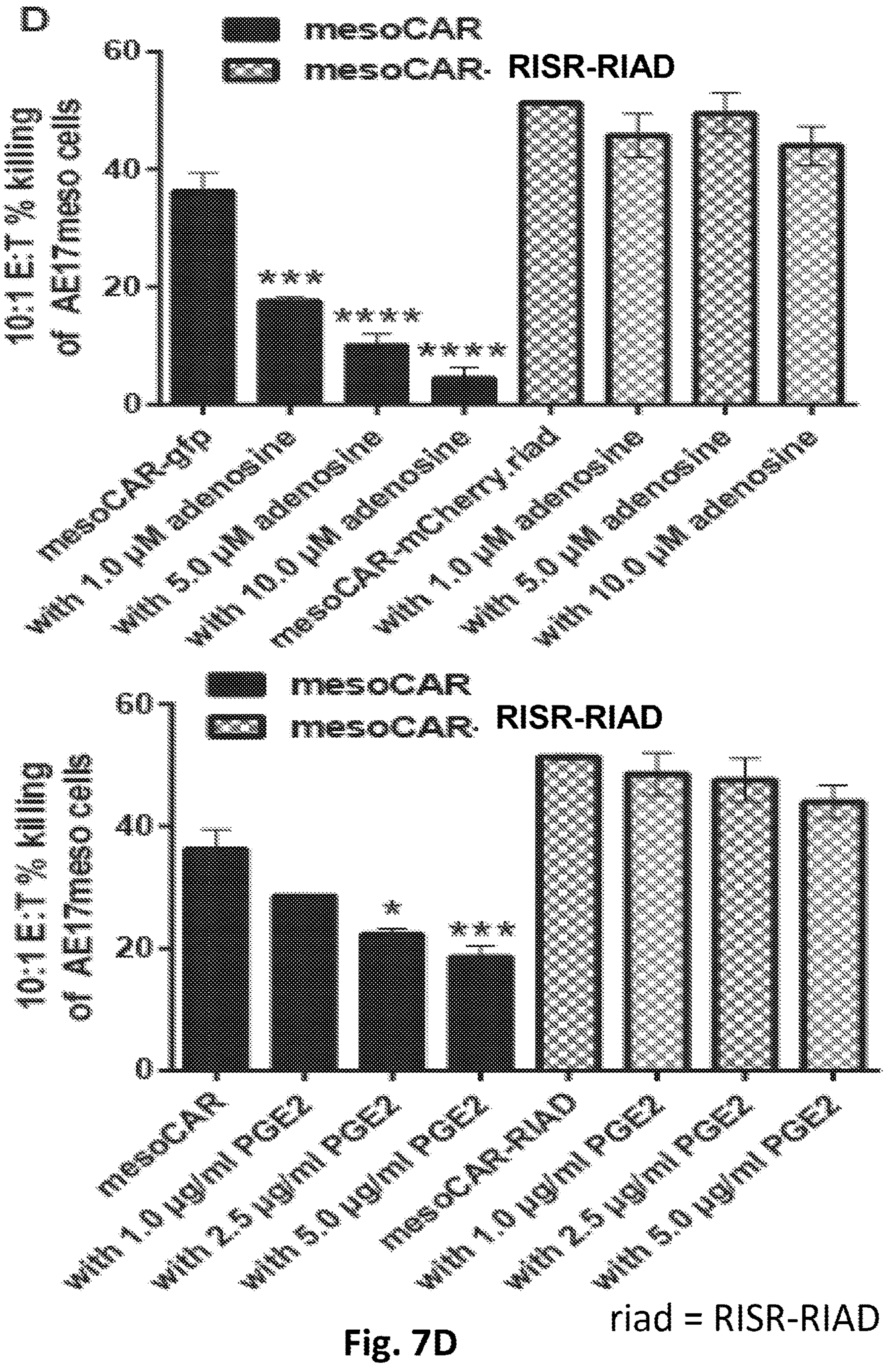
FIG. 7D is a panel of graphs showing an overnight cytolysis assay against AE17meso to assess resistance of mesoCAR and mesoCAR-RISR-RIAD T cells to increasing doses of adenosine (upper graph) shown at 10:1 E:T and increasing doses of PGE2 (lower graph) shown at the E:T of 10:1. Statistics were performed using one-way ANOVA comparing the extent of cytolysis inhibition in the presence of adenosine versus no inhibitor.

The resistance of mesoCAR-RISR-RIAD T cells to immunosuppression mediated by adenosine and PGE2 was tested. The expected dose-dependent inhibition of the killing ability of mesoCAR T cells in the presence of immunosuppressive adenosine and PGE2 was observed, but not mesoCAR-RISR-RIAD T cells (FIG. 7D).

Figure 8A:
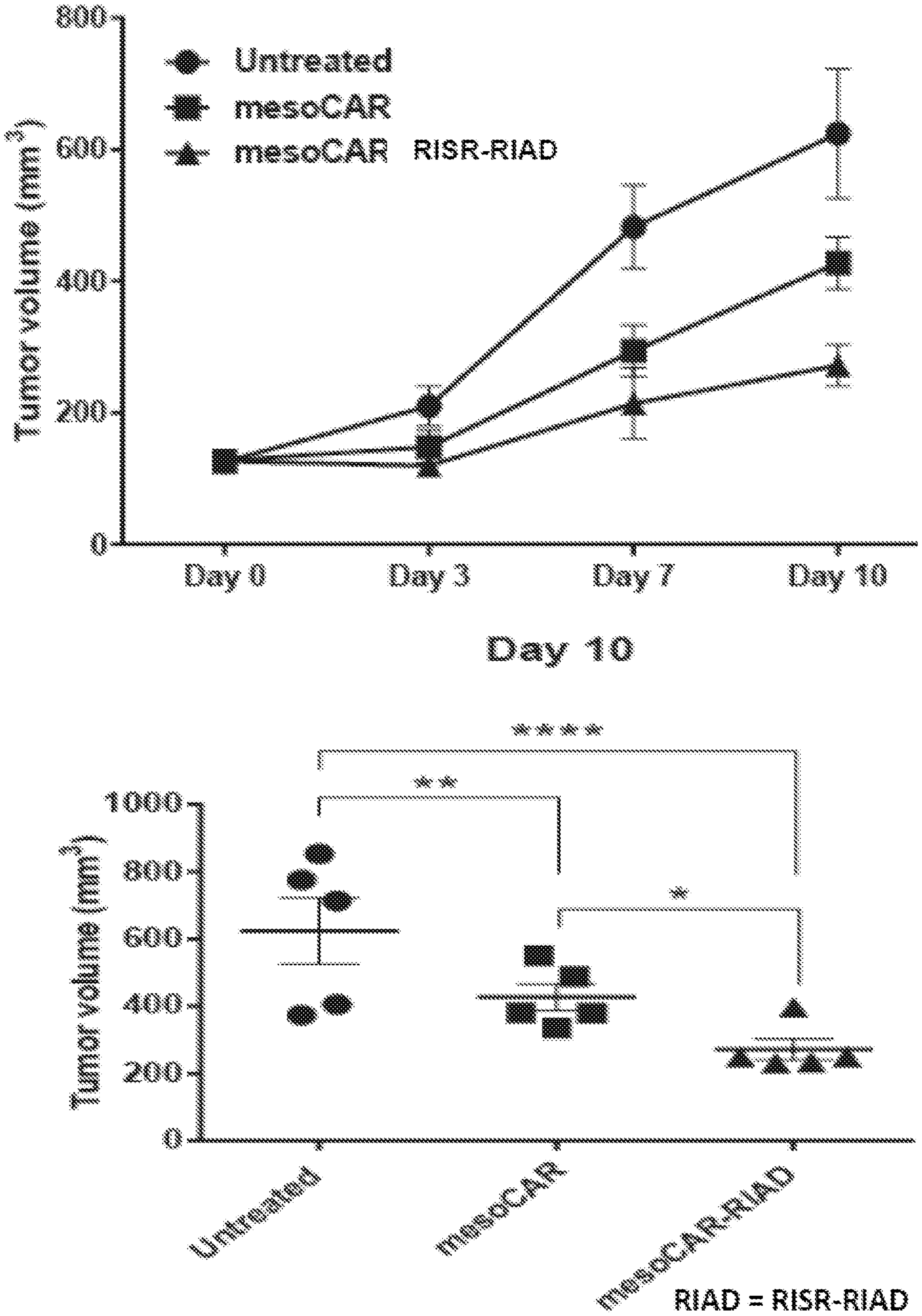
FIG. 8A is a panel of graphs showing enhanced therapeutic responses of murine mesoCAR-RISR-RIAD T cells. Two million AE17meso cells were subcutaneously injected into the right flanks of wild-type C57Bl/6 mice. When tumors were approximately 200 $mm^3$ in volume, 10 million mesoCAR- and mesoCAR-RISR-RIAD-expressing T cells were injected via the tail vein, and tumor development was monitored using calipers. At Day 10 after T cell injections, animals were sacrificed for ex vivo analysis.

Example 7: Intravenous Administration of Murine mesoCAR-RISR-RIAD T Cells Controls Tumor Progression More Efficiently than mesoCAR T Cells Two million AE17meso cells were injected subcutaneously in the flanks of wild-type C57Bl/6 mice, and after tumors were established (about 7-10 days after inoculation), $10^7$ mesoCAR or mesoCAR-RISR-RIAD murine T cells were administered intravenously. Tumor growth was monitored for the next 10-14 days using caliper measurements. The tumor control was observed with mesoCAR T cells;

however, mesoCAR-RISR-RIAD T cells had significantly reduced growth of AE17meso tumors compared to meso-CAR T cells, p≤0.01 (FIG. 8A).

Figure 8B:
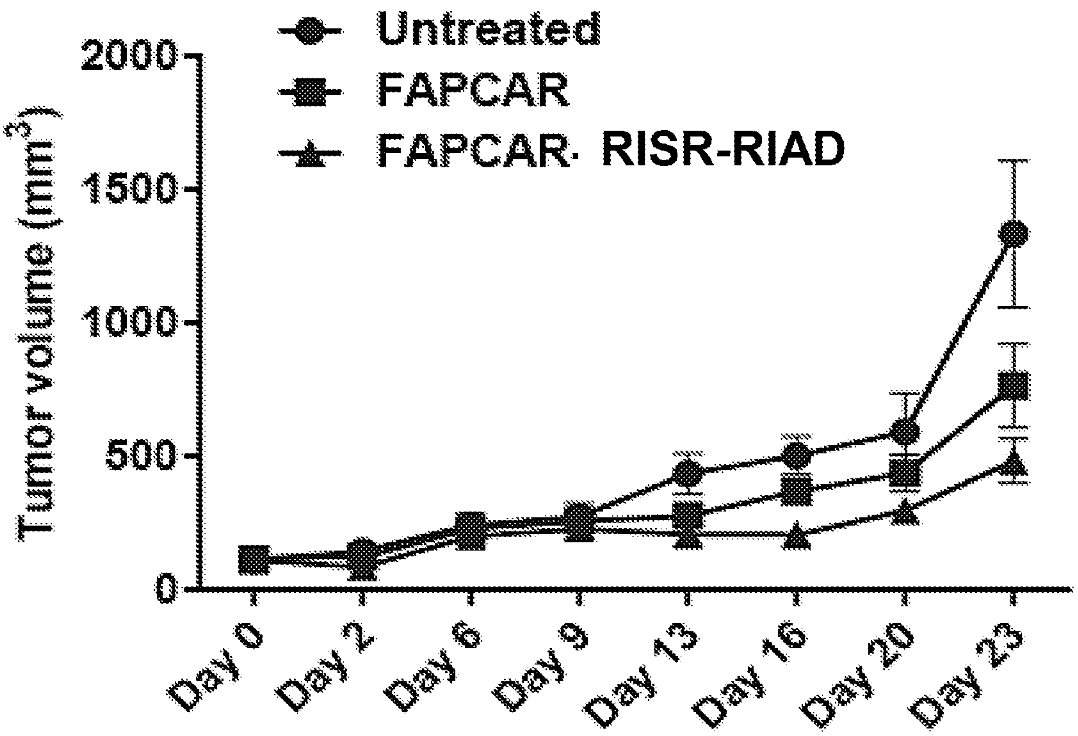
FIG. 8B is a panel of graphs showing enhanced therapeutic responses of murine mesoCAR-RISR-RIAD T cells. One million PDA4662 cells were subcutaneously injected into wild-type mice, and 10 million FAPCAR- and FAPCAR-RISR-RIAD-expressing T cells were injected via the tail vein. Mice were monitored and sacrificed at Day 23 post-T cell administration.
Figure 8B:
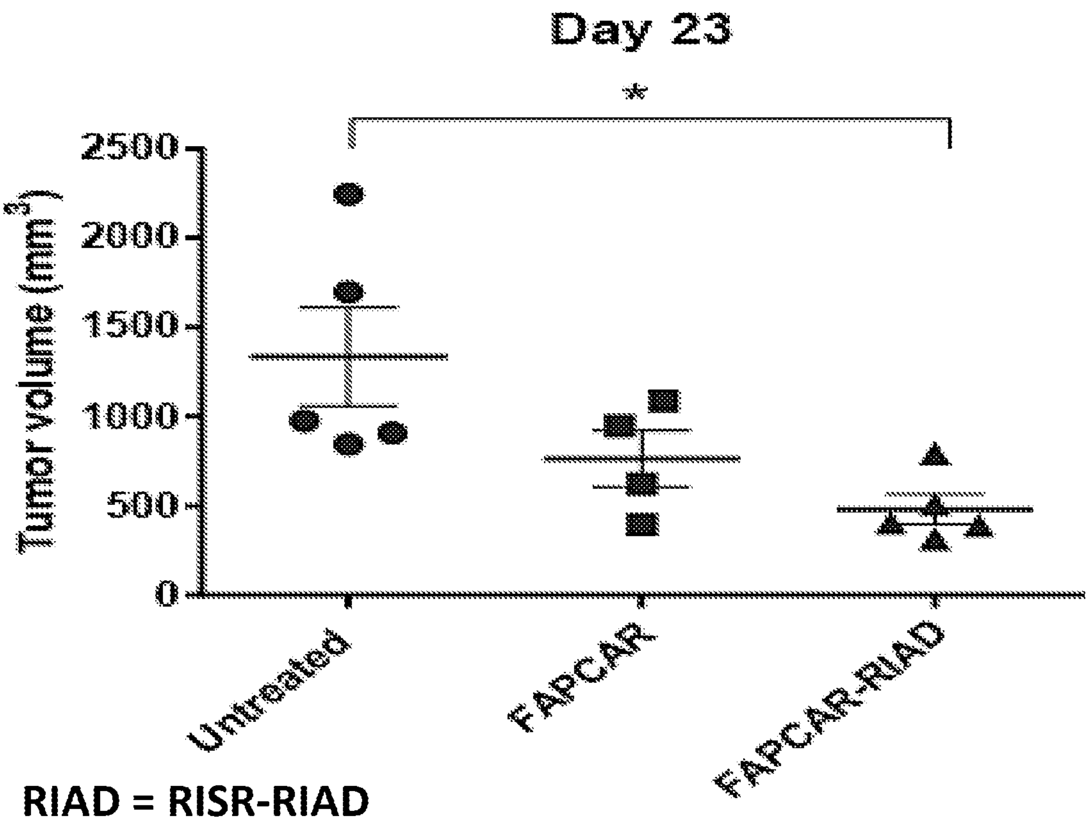

To evaluate the efficacy of RISR-RIAD in a completely different CAR system, a construct that targets fibroblast activation protein (FAP) present on stromal cells surrounding the tumor was used. C57Bl/6 wild-type mice were inoculated with the pancreatic cell line, PDA4662; this cell line induces a highly dense stromal environment. PDA4662-bearing mice were subsequently treated with $10^7$ FAPCAR or FAPCAR-RISR-RIAD T cells when the tumor burden was approximately 200 $mm^3$. Fourteen days post-adoptive transfer, FAPCAR-RISR-RIAD T cells showed significantly enhanced anti-tumor activity in this model (FIG. 8B).

Figure 9A:
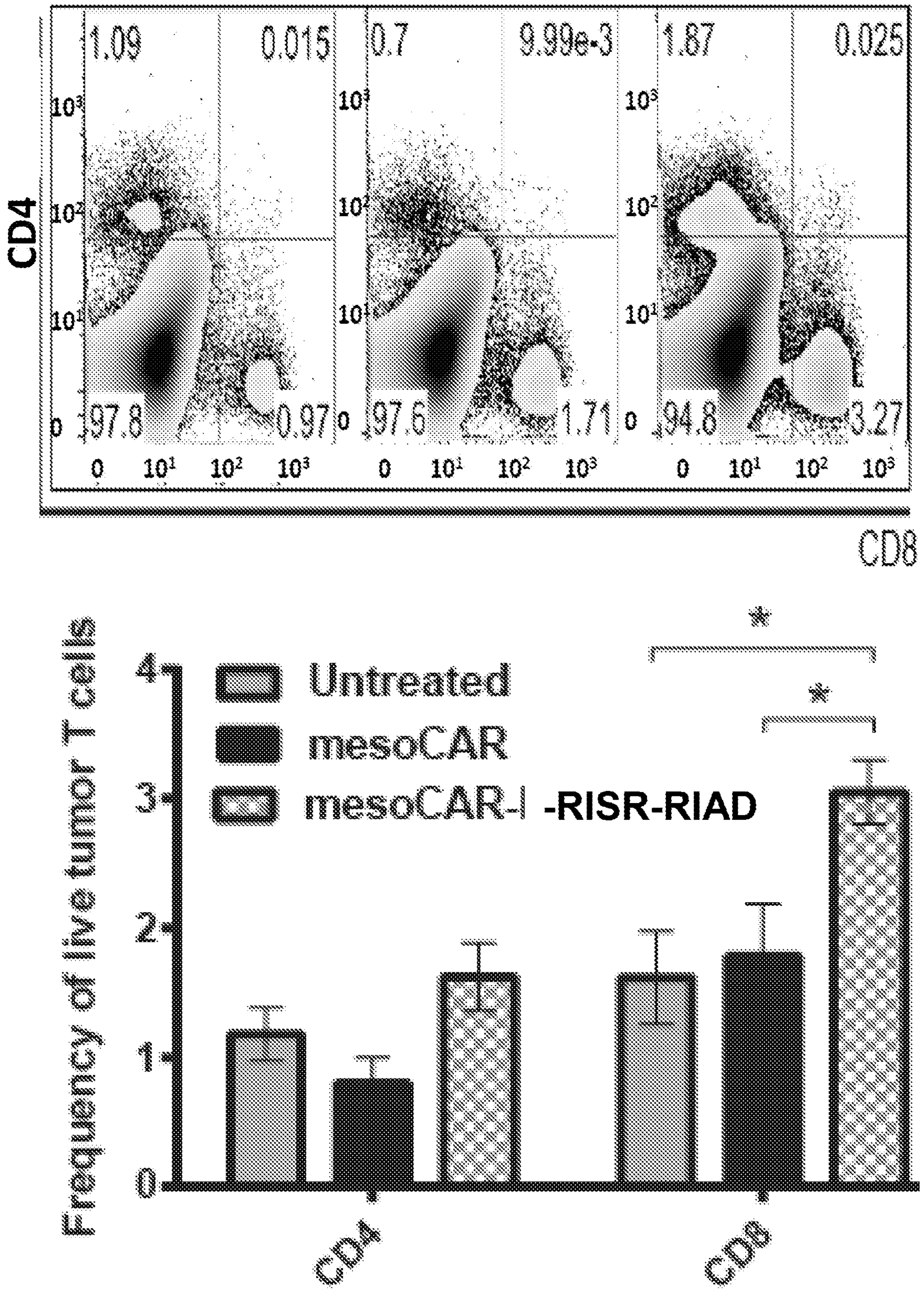
FIG. 9A is a panel of images showing that mesoCAR-RISR-RIAD T cells exhibited superior tumor infiltration capacity in an integrin-mediated manner. AE17meso tumors harvested from mice at Day 10 were digested, and single cell suspensions were prepared for flow cytometry analyses. Total tumor digest were stained for CD4 and CD8.
Figure 9B:
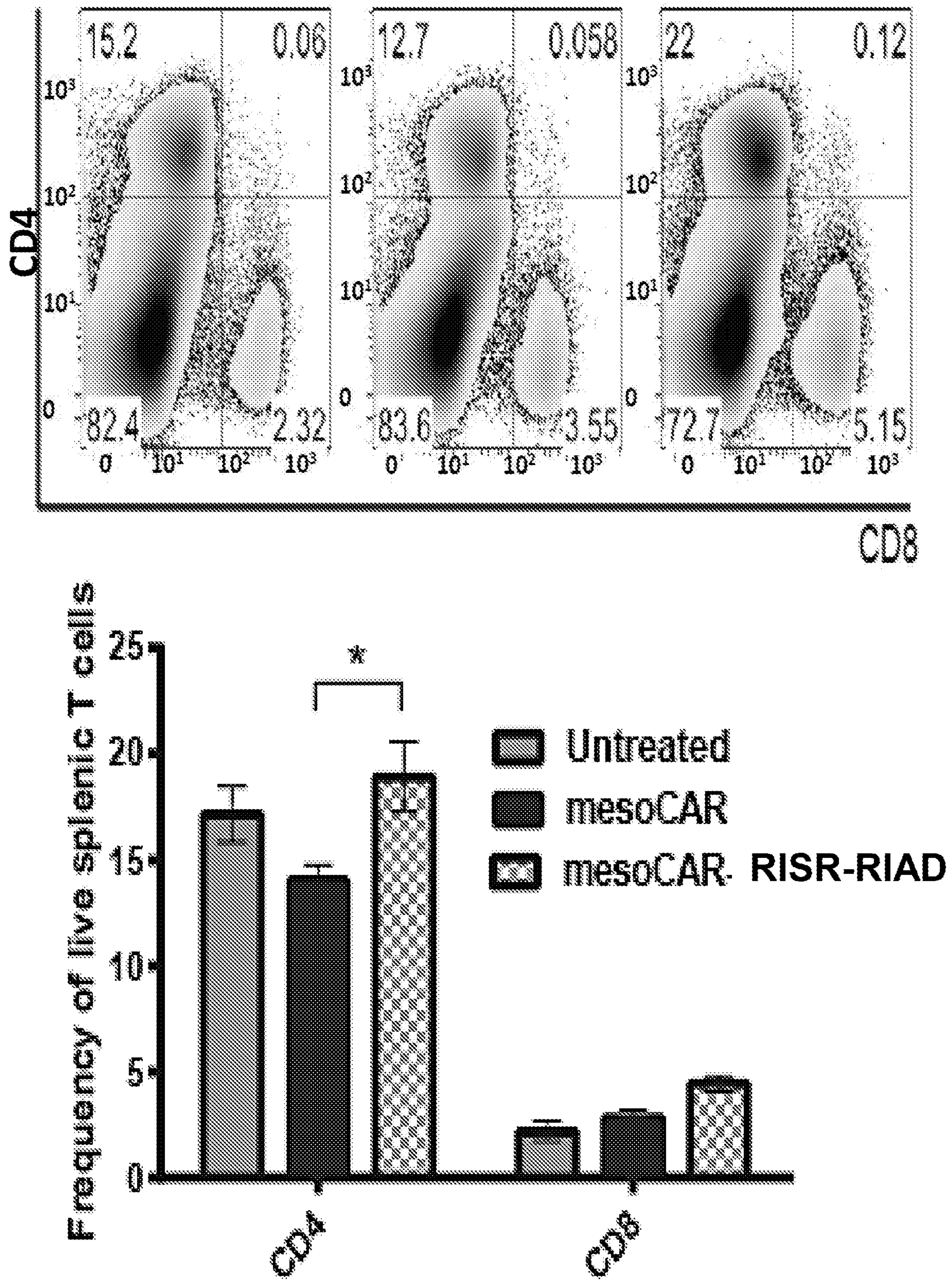
FIG. 9B is a panel of images showing spleens isolated from AE17meso-bearing mice, and processed for flow cytometry analyses. Single cell suspensions were stained for CD4 and CD8 cells.
Figure 9C:
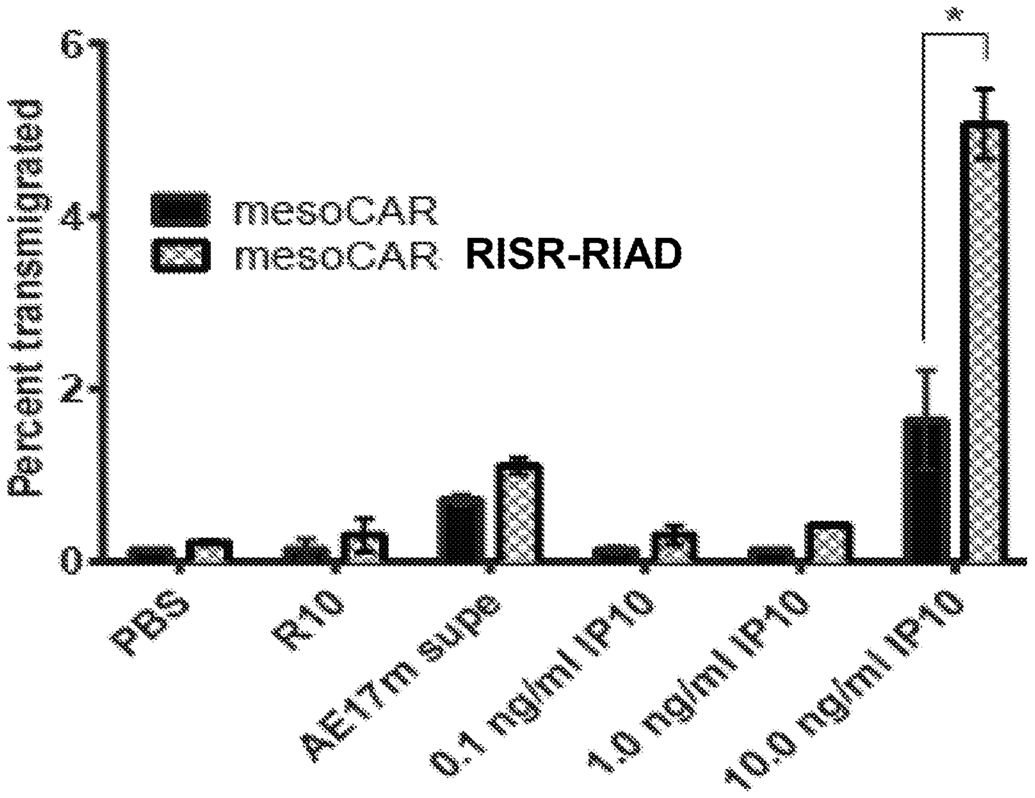
FIG. 9C is a graph showing equal number of both CAR T cells placed in transwell inserts, and allowed to migrate toward the indicated stimulants placed in the bottom well. After 4 hours, migrated cells, and cells that remained in the transwells were collected, counted, and stained for different adhesion and migration markers.
Figure 9D:
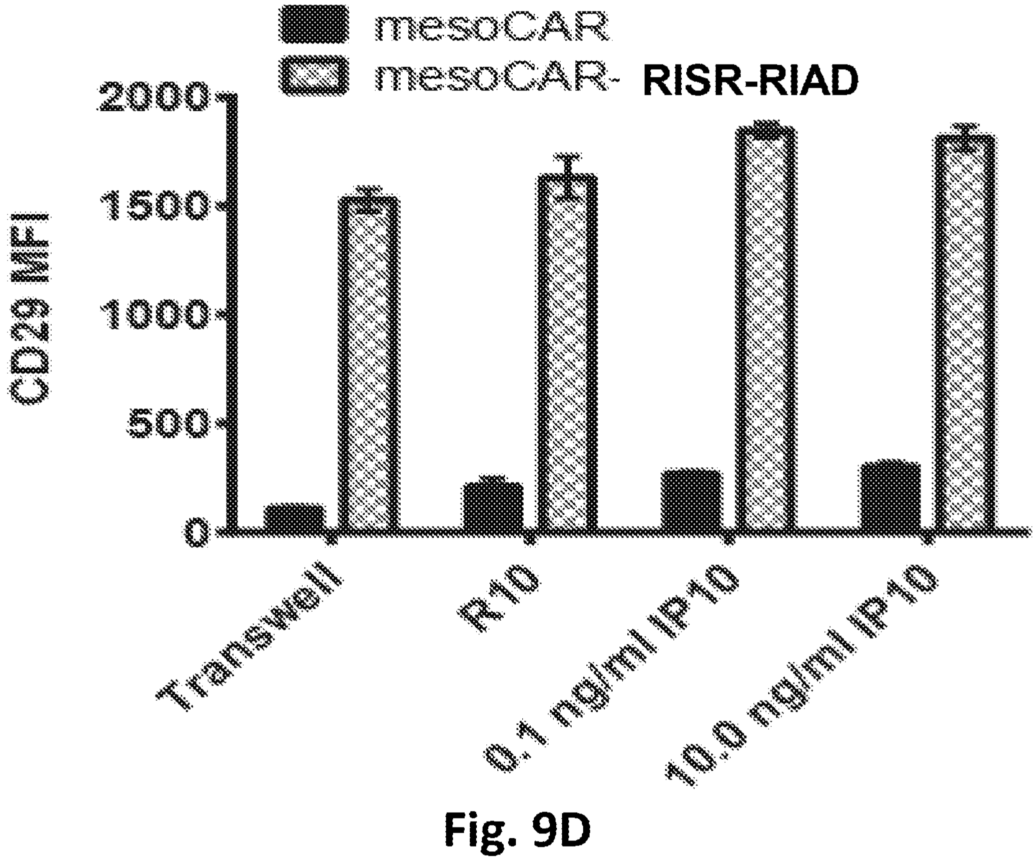
FIG. 9D is a graph showing that mesoCAR-RISR-RIAD T cells exhibited much higher integrin ß1 (CD29) expression compared to mesoCAR T cells.
Figure 16:
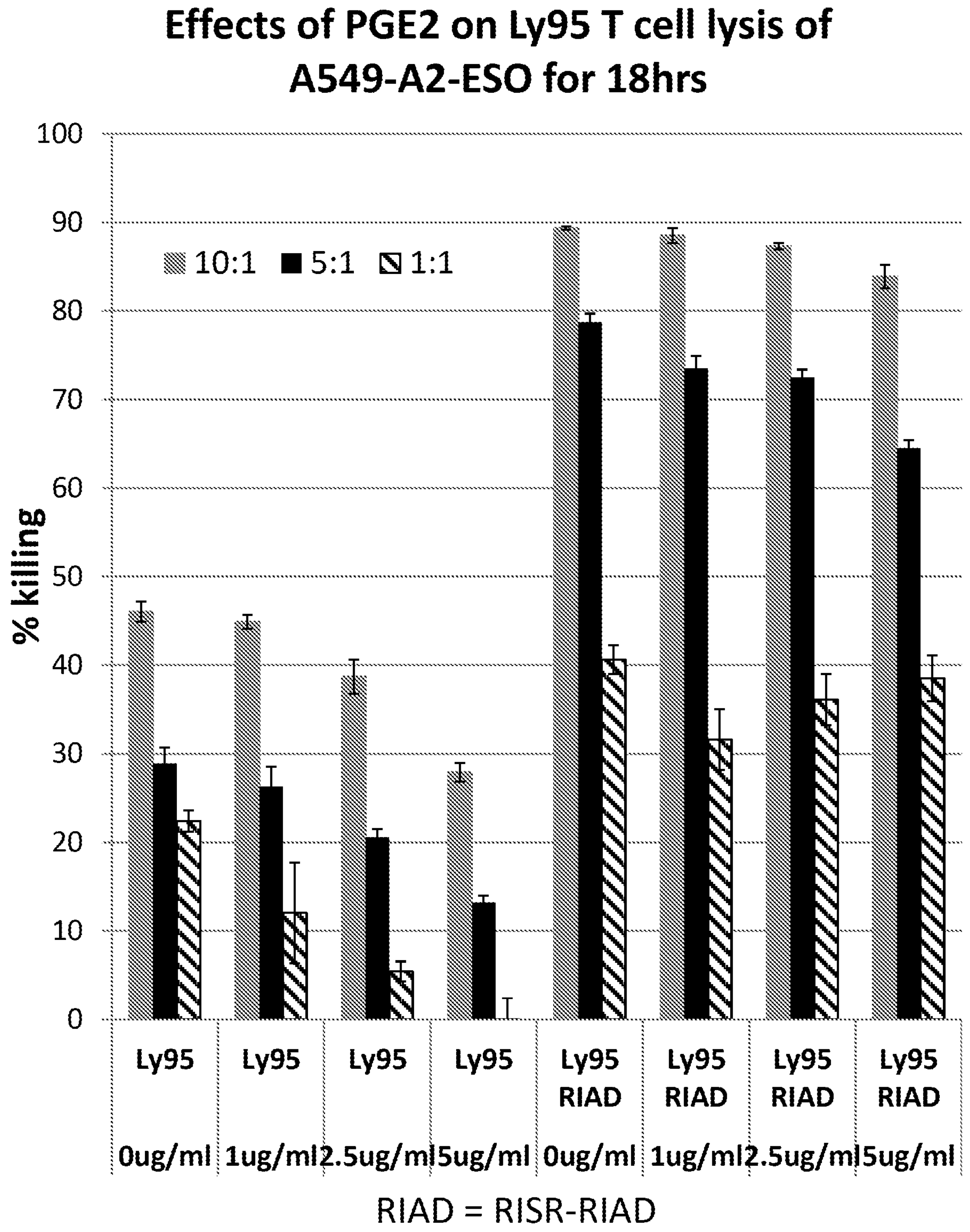
FIG. 16 is a graph showing that the Ly95-RISR-RIAD construct was less susceptible to inhibition by low dose PGE2 than the Ly95 T cells.

Example 8: MesoCAR-RISR-RIAD T Cells Show Increased Migration In Vitro and Enhanced Trafficking into Tumors In Vivo In order to determine the mechanisms involved in the enhanced anti-tumor effects of murine mesoCAR-RISR-RIAD T cells, flow cytometry analysis of spleen- and tumor-infiltrating lymphocytes at Day 3 post-adoptive transfer was performed. The analysis of murine CAR T cells freshly isolated from AE17meso tumors in mice revealed that in comparison with mesoCAR-treated tumors, meso-CAR-RISR-RIAD-treated tumors showed an increased influx of CD8 cells (FIG. 9A), while analysis of spleens from tumor-bearing mice showed an increase in CD4 number in the mesoCAR-RISR-RIAD treatment group (FIG. 9B). Since this observation recapitulates what was observed in human mesoCAR-RISR-RIAD T cells (FIGS. 16A-16C), i.e., they appeared to migrate to tumor sites much more efficiently than mesoCAR T cells, transmigration assays were performed using 0.5 μm transwell inserts in which transduced T cells were allowed to traffic toward the chemokine IP10 in the lower well. Higher chemotaxis and IP10-mediated migration rate was consistently observed in meso-CAR-RISR-RIAD T cells compared to mesoCAR T cells (FIG. 9C), which likely contributes to more robust tumor control. This increased efficiency in migration is attributed to integrin 131-mediated signaling as denoted by the high expression of CD29 in mesoCAR-RISR-RIAD T cells (FIG. 9D). No changes in CXCR3 or CD11A expression was observed.

Figure 10:
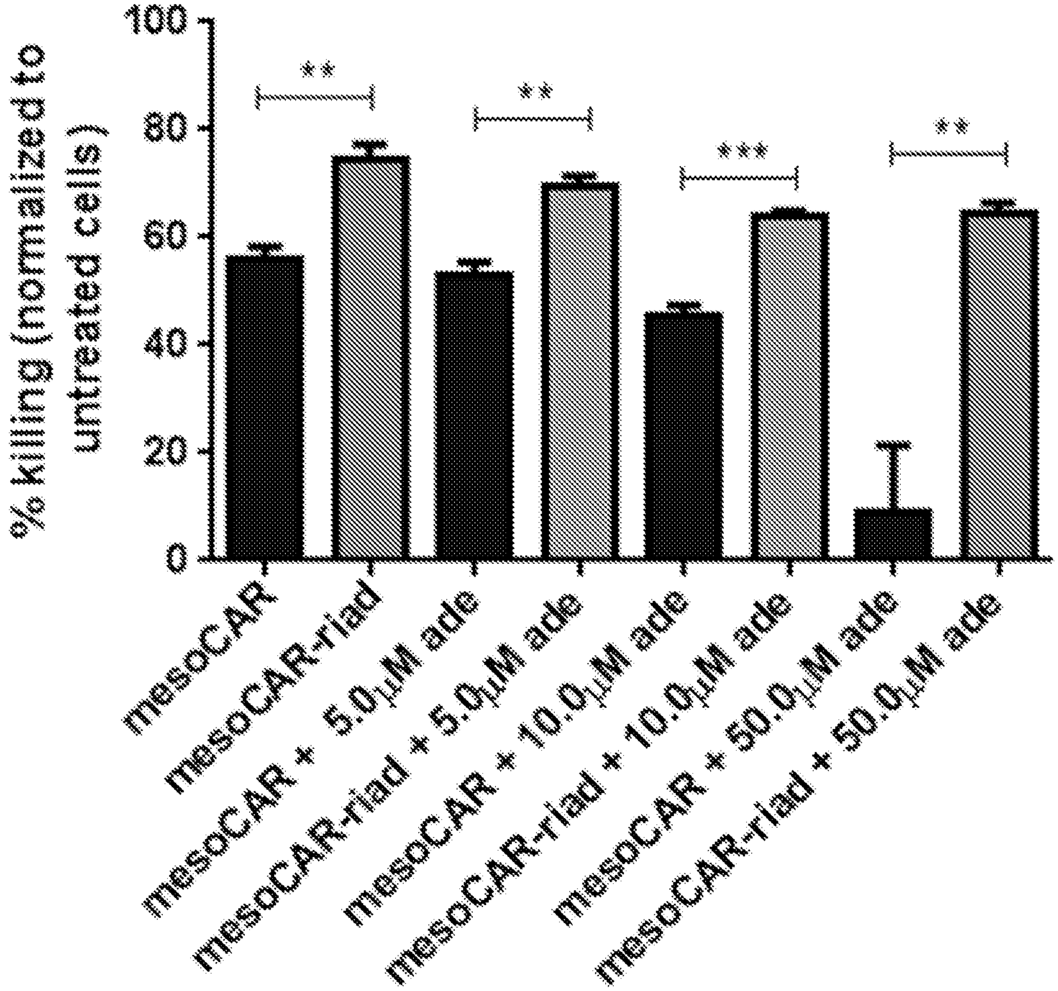
FIG. 10 is a graph showing suppression of killing of EM-meso cells that were incubated overnight with both CAR T cells at the indicated E:T in the presence of varying concentrations of adenosine. A dose-dependent suppression of killing by mesoCAR T cells was observed, but not by mesoCAR-RISR-RIAD T cells.

Example 9: Lentiviral Transduction of Activated Human T Cells with the mesoCAR-RISR-RIAD Construct LED to Better Killing of Tumor Cells In Vitro and In Vivo Compared to MesoCAR T Cells In a similar manner, human T cells with lentiviruses expressing mesoCAR and mesoCAR-RISR-RIAD were transduced to compare their killing efficiencies both alone and in the presence of immunosuppressive agents such as adenosine. Both T cells were incubated with mesothelin-transduced human mesothelioma cells (EM-meso) at varying E:T. FIG. 10 shows that at a E:T of 10:1, mesoCAR-RISR-RIAD T cells have more activity at baseline and possess far superior killing ability in vitro in spite of the presence of adenosine.

Example 10: Lentiviral Transduction of Activated Human T Cells with the mesoCAR-RISR-RIAD Construct Leads to Enhanced Killing of Tumor Cells In Vitro The development and use of CAR constructs expressing the scFv from anti-human mesothelin, along with the human CD3ζ and 4-1BB cytoplasmic domains (mesoCAR) has previously been reported; T cells transduced with this construct cured some mesothelioma cell lines in mice, but not others due to T cell hypofunction exerted by an immunosuppressive solid tumor microenvironment.

Figure 11A:
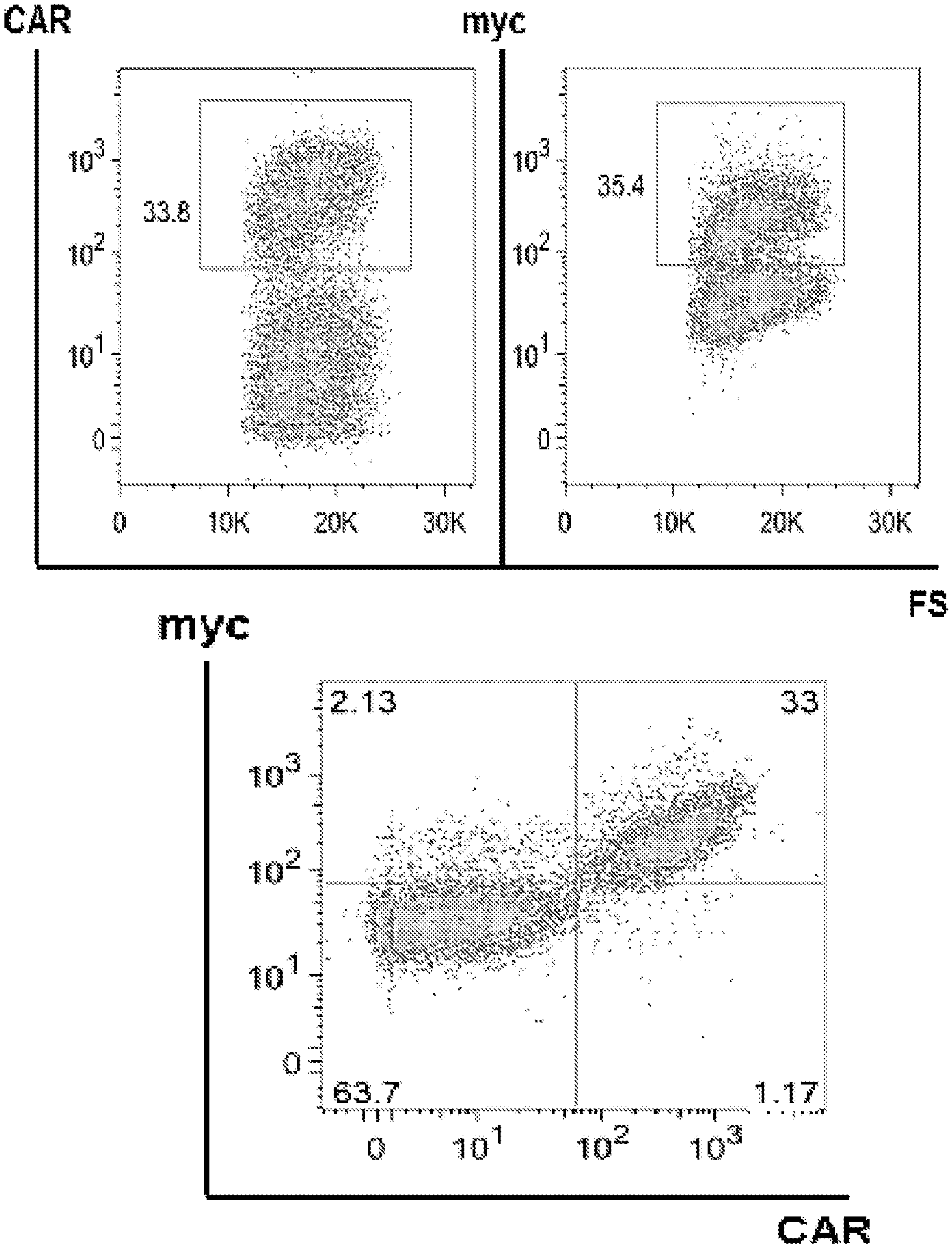
FIG. 11A is a panel of graphs showing that human T cells transduced with mesoCAR-RISR-RIAD exhibit superior killing ability and robust IFNγ production in vitro. Lentiviral-transduced primary human T cells as detected by a primary biotinylated goat anti-mouse IgG recognizing the $F(ab')_2$ fragment, followed by a secondary APC-Cy7-conjugated streptavidin antibody, along with detection of myc-tagged RISR-RIAD.

In an attempt to overcome this issue, one of the inhibitory elements was disarmed, namely the cAMP-PKA pathway. Using modified lentiviruses expressing mesoCAR, with and without the RISR-RIAD transgene, activated human T cells were successfully transduced with over 30% transduction efficiency; the detection of the RISR-RIAD transgene was accomplished using antibodies to detect either the myc or ddk tag (FIG. 11A). In order to assess the effector functions of these T cells, differing effector-to-target (E:T) ratios of transduced T cells were co-cultured overnight with human mesothelioma cells expressing mesothelin and luciferase (EMmeso-luc). Compared to T cells transduced with meso-CAR alone, mesoCAR-RISR-RIAD T cells showed enhanced killing ability (FIG. 11B) and higher interferon-γ (IFNγ) production in a dose-dependent manner (FIG. 11C); both constructs are target-specific as little to no killing was observed with EM parental (EMP) cells not expressing mesothelin.

Figure 12:
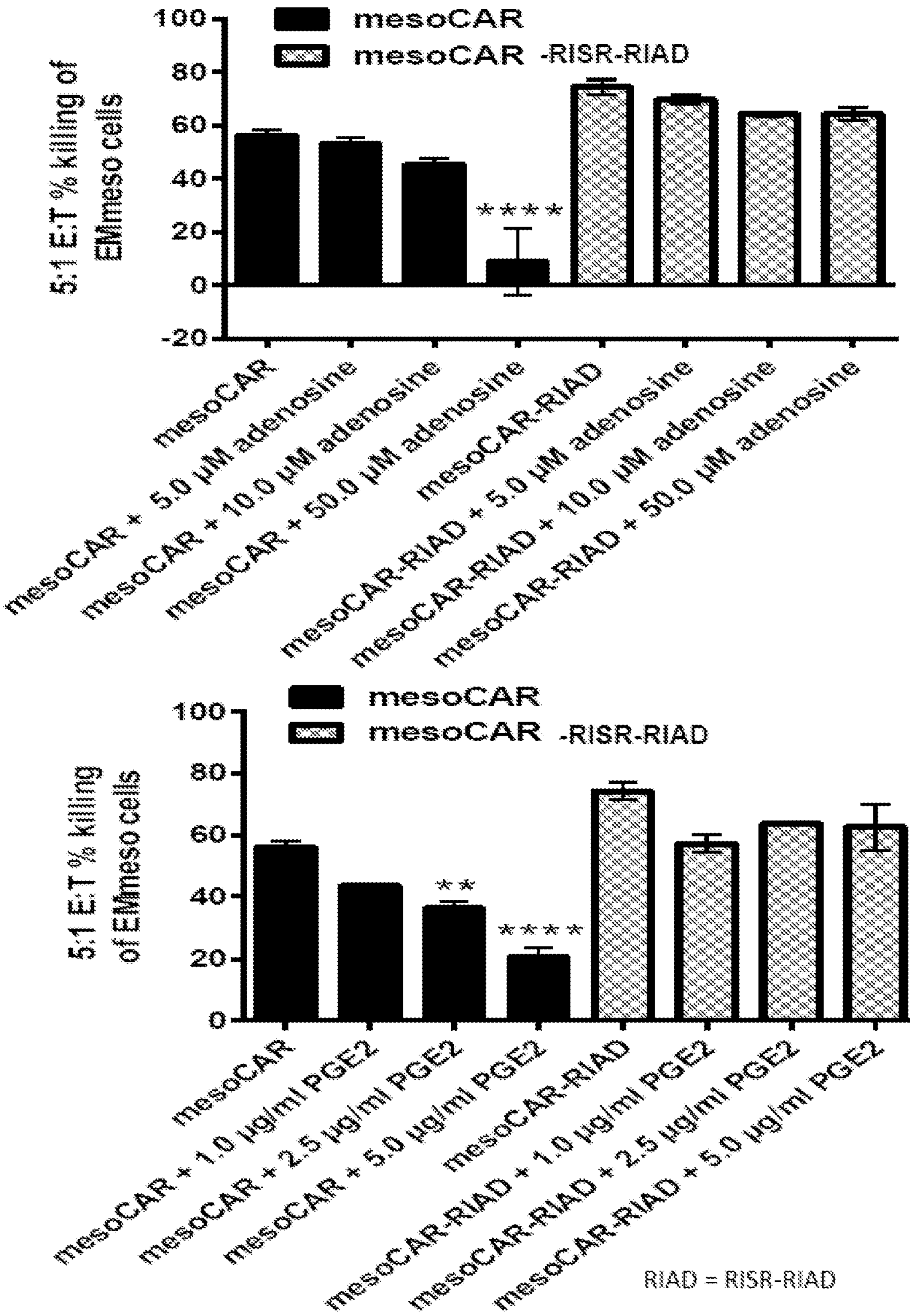
FIG. 12 is panel of graphs showing resistance of mesoCAR-RISR-RIAD T cells to immunosuppression. The upper graph shows the contribution of the RISR-RIAD transgene against immunosuppression of the effector T cell population, mesoCAR and mesoCAR-RISR-RIAD human T cells when co-cultured with EMmeso cells overnight in the presence of increasing doses of adenosine; shown is the E:T at 5:1. Statistics were performed using one-way ANOVA comparing the extent of mesoCAR immunosuppression in the presence of adenosine versus no inhibitor. The lower graph shows the killing of EMmeso cells by mesoCAR and mesoCAR-RISR-RIAD T cells when challenged with the addition of increasing doses of PGE2; shown is the E:T at 5:1.

Example 11: Primary Human T Cells Transduced with mesoCAR-RISR-RIAD are More Resistant to Immunosuppression and Hypofunction Compared to mesoCAR T Cells The resistance of mesoCAR-RISR-RIAD T cells to immunosuppression mediated by adenosine and PGE2 was tested. An overnight co-culture assay (at differing E:T ratios) was set up in the presence/absence of varying doses of adenosine and PGE2. As expected, a dose-dependent inhibition of the killing ability of mesoCAR T cells was observed in the presence of adenosine and PGE2, but mesoCAR-RISR-RIAD T cells were virtually unaffected by these inhibitory molecules (FIG. 12 shown at 5:1 E:T), as well as having enhanced activity in the absence of these inhibitors (FIG. 12).

Figure 13A:
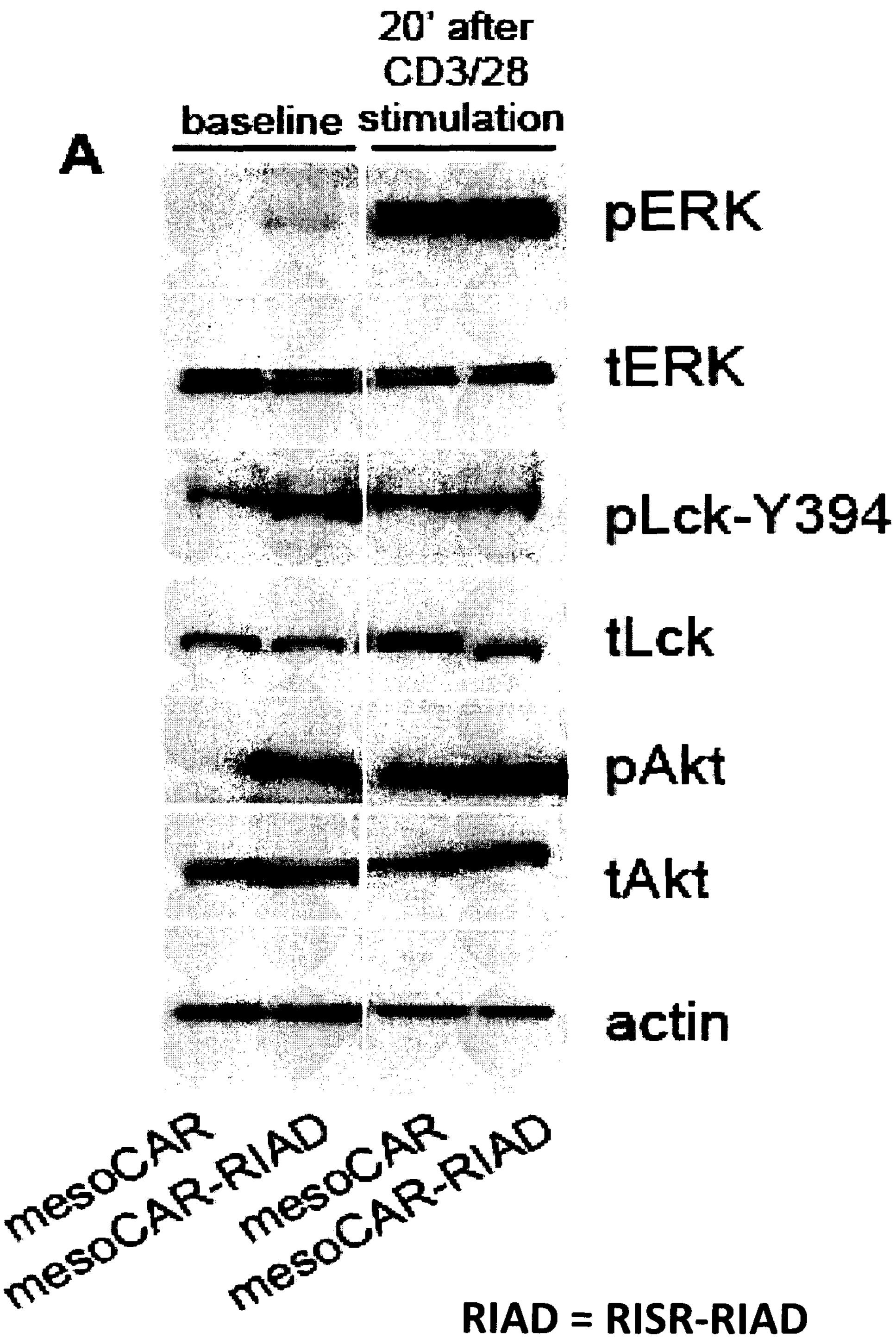
FIG. 13A is a panel of images showing signaling in mesoCAR and mesoCAR-RISR-RIAD human T cells. Equal numbers of mesoCAR- and mesoCAR-RISR-RIAD-expressing T cells were exposed to immobilized CD3 and CD28 antibodies for 5 and 20 minutes. Lysates were prepared and immunoblotted for phospho-ERK (pERK), phospho-Lck at tyrosine-394 (pLck-Y394), and phospho-Akt (pAkt), along with their respective loading controls, including actin. Bar charts show densitometry quantification of the indicated protein.

Example 12: TCR Signaling is Enhanced at Baseline and after Stimulation in mesoCAR-RISR-RIAD T Cells To evaluate signaling, T cells were examined at baseline and after 20 minutes of exposure to plate-bound CD3 and CD28 antibodies. At baseline, compared with mesoCAR T cells, mesoCAR-RISR-RIAD T cells showed some evidence of activation with increased phosphorylation of Erk, $Lck^{Y394}$, and Akt. After stimulation, the expected increases in Erk, $Lck^{Y394}$, and Akt phosphorylation in mesoCAR T cells were observed, but in mesoCAR-RISR-RIAD T cells, higher levels of phosphorylation were observed (FIG. 13A).

Example 13: PKA Signaling is Attenuated in mesoCAR-RISR-RIAD T Cells

Figure 13B:
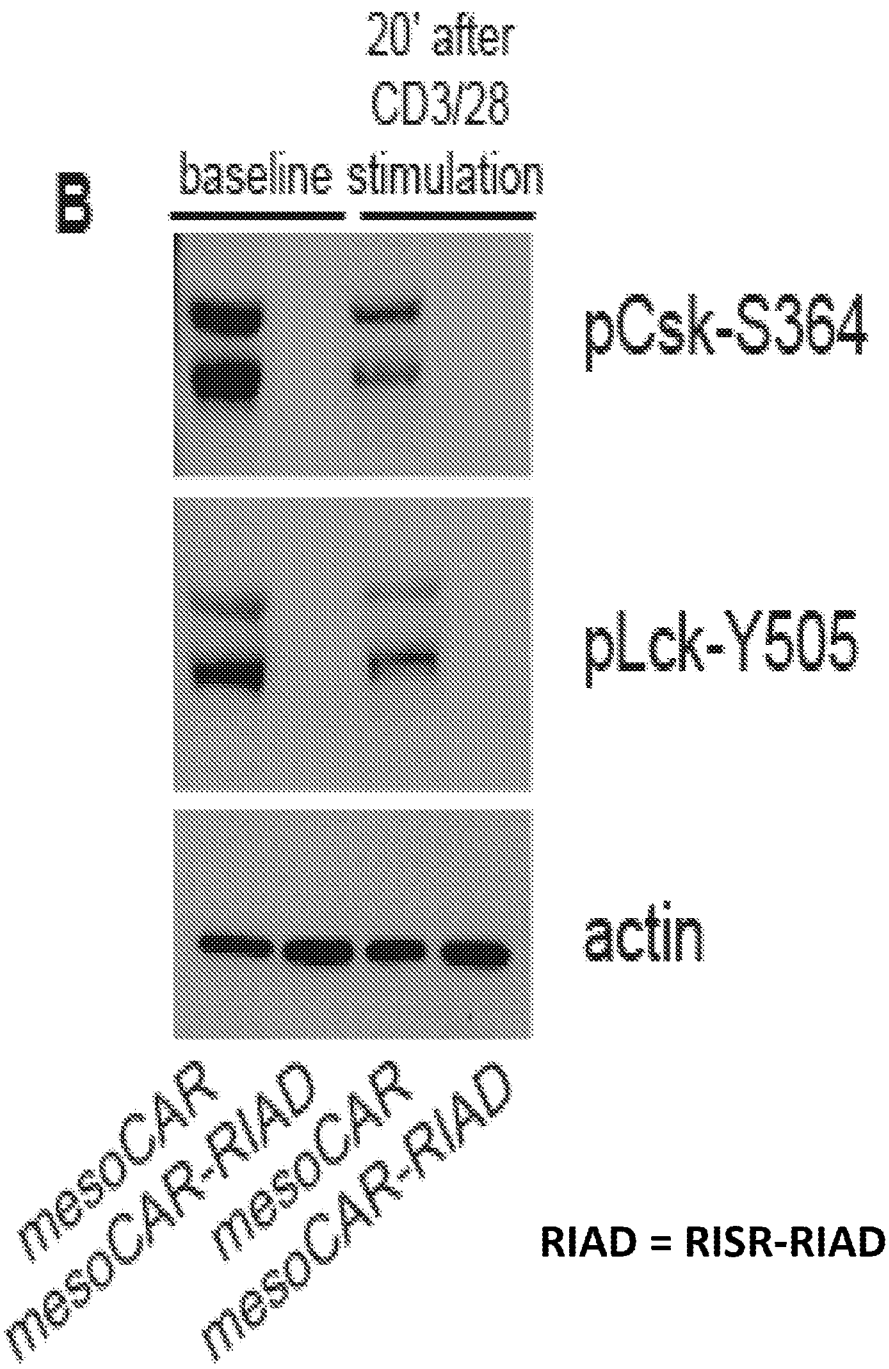
FIG. 13B is a blot showing lysates of human T cells immunoblotted for phospho-Csk at serine 364 (pCsk-S364), and pLck at tyrosine 505 (pLck-Y505) with actin as loading control.

As described herein, one way in which PKA regulates T cell signaling is by phosphorylating the kinase Csk at S364, which activates it and results in phosphorylation of the key TCR proximal signaling molecule Lck at Y505, which inhibits its activity. To confirm that this mechanism of RISR-RIAD inactivation was operative in the cells, the phosphorylation status of $Csk^{S364}$, and $Lck^{Y505}$ was assessed. The loss of phosphorylation was observed at both these residues at baseline and after CD3/28 stimulation in mesoCAR-RISR-RIAD T cells compared to mesoCAR T cells (FIG. 13B).

Figure 14A:
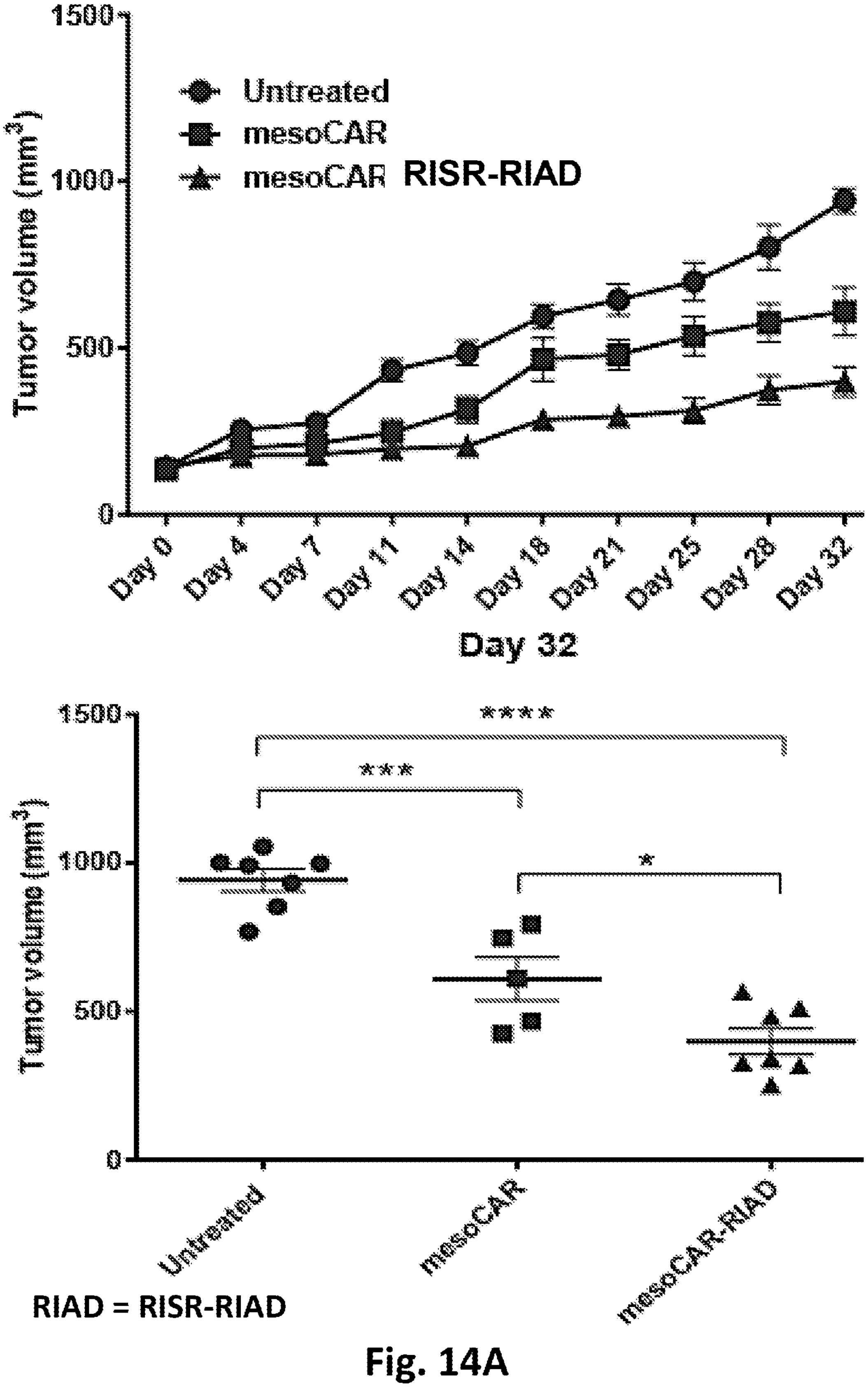
FIG. 14A is a panel of graphs showing tumor control of primary human mesoCAR and mesoCAR-RISR-RIAD T cells in vivo. Two million EMmeso cells were injected subcutaneously into the right flanks of immunodeficient NSG mice, and after they were established (around 200 $mm^3$ in volume), 10 million mesoCAR- or mesoCAR-RISR-RIAD-expressing T cells were administered via tail vein injections. Tumor development was monitored using calipers for the next 32 days after T cell administration, and animals were then sacrificed for ex vivo analyses.

Example 14: Human T Cells with the mesoCAR-RISR-RIAD Construct have Enhanced Ability to Kill Tumors In Vivo To compare the ability of human mesoCAR-RISR-RIAD T cells in controlling tumor burden to that of mesoCAR T cells, EMmeso cells were subcutaneously inoculated on the flanks of immunodeficient NSG mice, and when tumors were around 200 $mm^3$ in volume, $10^7$ mesoCAR- or meso-CAR-RISR-RIAD-expressing primary human T cells were intravenously administered. EMmeso-bearing NSG mice treated with mesoCAR T cells showed significantly slower tumor progression by approximately 40% ($p \leq 0.001$) compared to untreated tumors; however, injection of mesoCAR-RISR-RIAD T cells significantly enhanced the mesoCAR anti-tumor effect ($p \leq 0.0001$), resulting in tumors that were 60% smaller compared to untreated tumors (FIG. 14A).

Figure 14B:
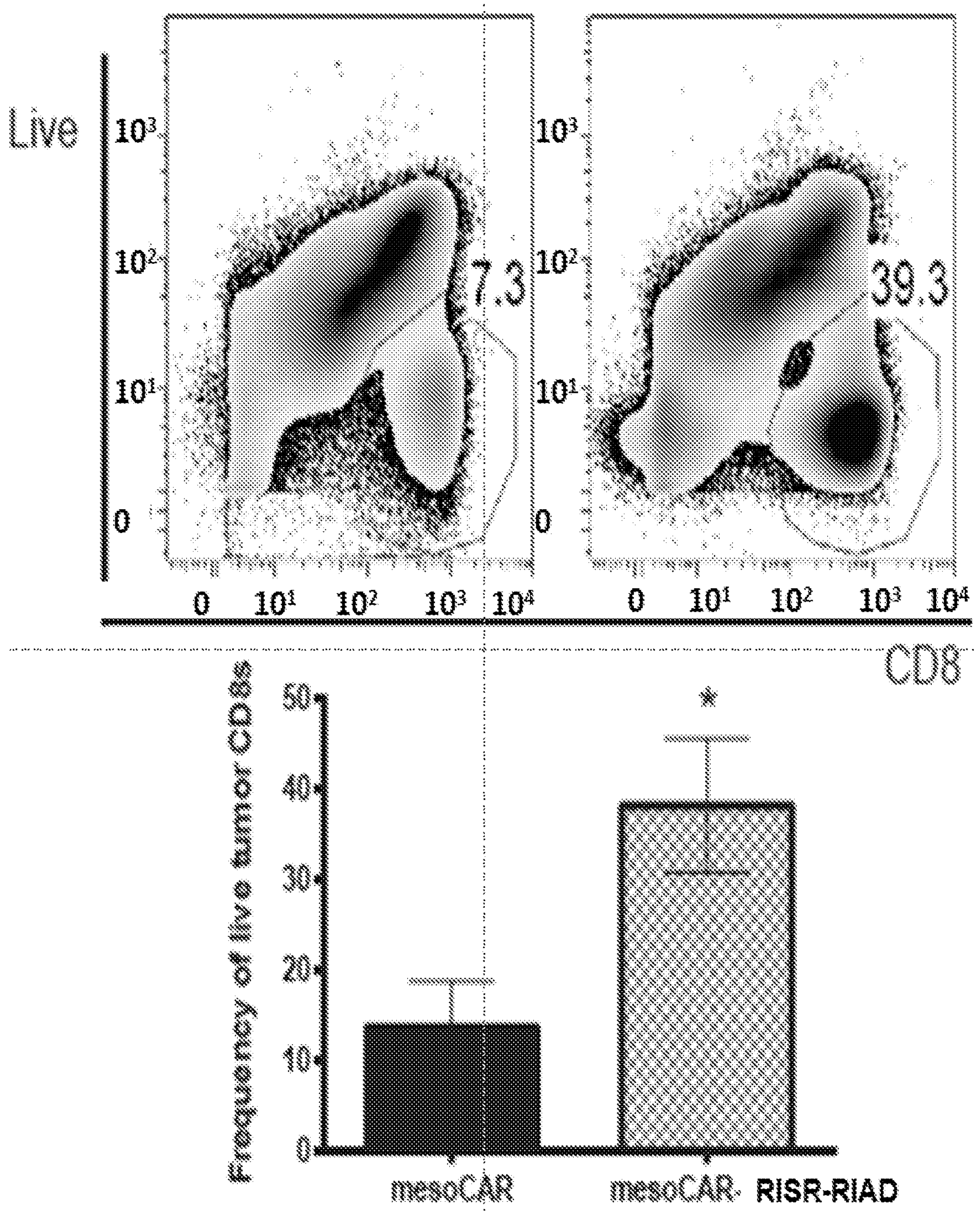
FIG. 14B is a panel of images showing analysis of tumors harvested from mice at Day 32. The tumors were digested, and single cell suspension for flow cytometry analysis was prepared. Cells were stained with anti-CD8 and live/dead antibodies to determine the frequency of live CD8 cells within the tumors.
Figure 14C:
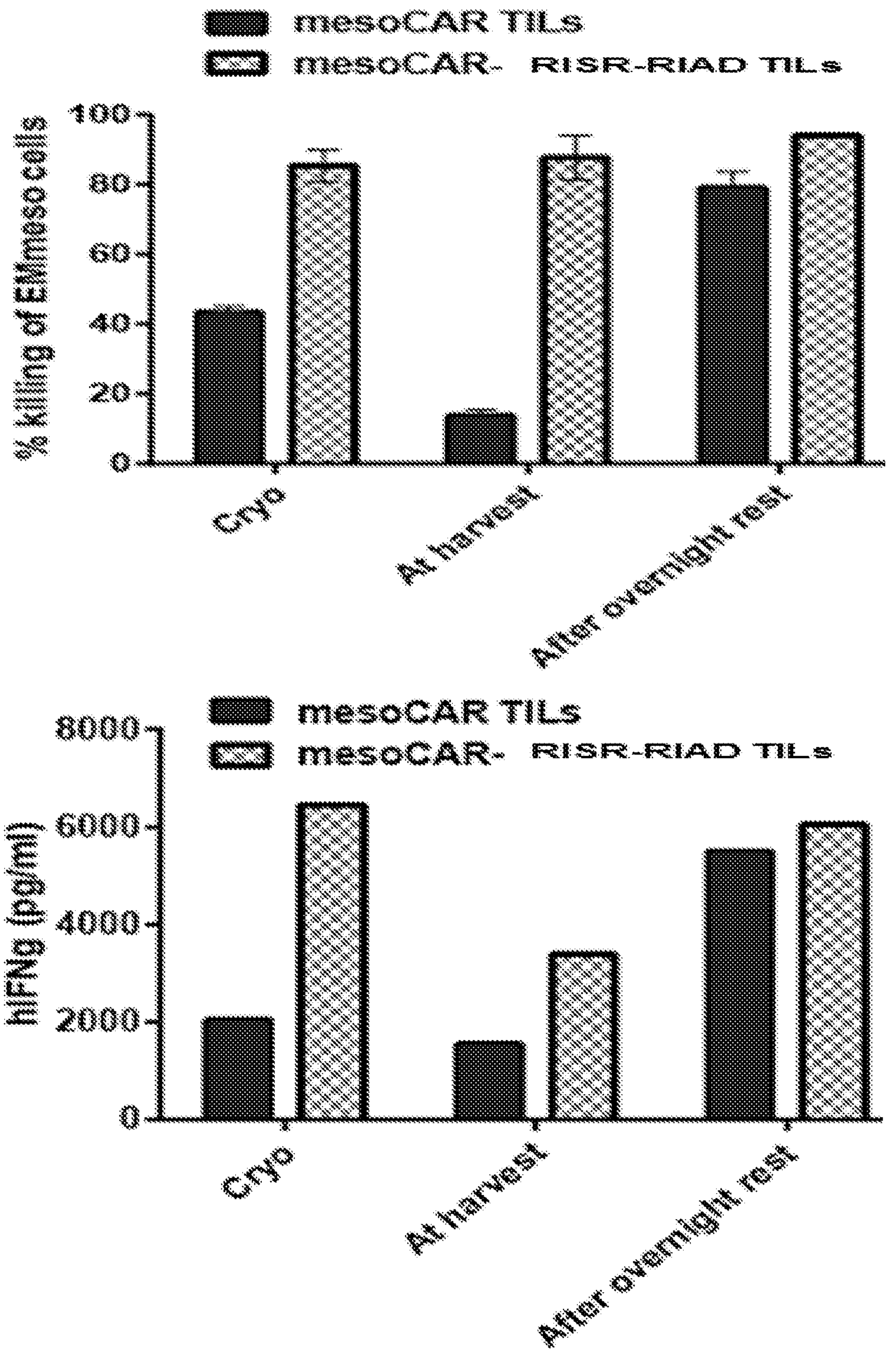
FIG. 14C is a panel of graphs showing tumor-infiltrating lymphocytes (TILs) isolated from mesoCAR- and mesoCAR-RISR-RIAD-treated tumors subjected to an overnight cytolysis assay at a 10:1 E:T ratio against EMmeso cells. The upper graph shows mesoCAR and mesoCAR-RISR-RIAD T cells prepared from the same batch that had been frozen away ("cryo"). The cytolysis assay was performed immediately after TIL isolation ("at harvest"), and "after overnight rest" in cell culture medium. The lower graph shows cell culture supernatant from the overnight cytolysis assay and assayed for IFNγ production via ELISA, and quantification of IFNγ was performed comparing mesoCAR and mesoCAR-RISR-RIAD T cells.

Example 15: Human mesoCAR-RISR-RIAD Tumor-Infiltrating T Cells Show Increased Persistence and Increased Activity To better understand the mechanisms of the enhanced anti-tumor effects observed with mesoCAR-RISR-RIAD T cells, EMmeso-bearing mice were sacrificed on Day 32 after T cell administration, and their tumors were pooled and processed as described herein. Flow cytometry analysis of tumors at this time point showed increased numbers of CD8 cells within the tumors of mesoCAR-RISR-RIAD-treated mice compared to mesoCAR-treated mice (FIG. 14B). Adoptively transferred human T cells were isolated from these tumors and reacted them with freshly plated tumor cells in culture. This was done to determine the ex vivo ability of these T cells ("at harvest") to kill tumor cells and secrete IFNγ as compared with the T cells that were originally administered at Day 0 ("cryo"). As shown in FIG. 14C (Cryo group in both graphs), mesoCAR-RISR-RIAD T cells had higher baseline killing activity and secreted more IFNγ than mesoCAR T cells. MesoCAR tumor-infiltrating lymphocytes (TILs) developed hypofunction with respect to both killing and IFNγ secretion (FIG. 14C, At harvest in both graphs); in marked contrast, mesoCAR-RISR-RIAD TILs retained almost full cytolytic and IFNγ production capacity. Again, after mesoCAR TILs were allowed to rest in culture medium for 24 hours ("after overnight rest"), they recovered almost full activity while mesoCAR-RISR-RIAD T cells remained active (FIG. 14C, After overnight rest in both graphs). ELISA showed that mesoCAR-RIAD T cells, either freshly isolated from these tumor-bearing mice, or after overnight culture in medium, produced more interferon-γ compared to mesoCAR T cells alone (FIG. 23).

Example 16: In Vitro Killing of Tumor by Ly95-RISR-RIAD T Cells

Figure 15:
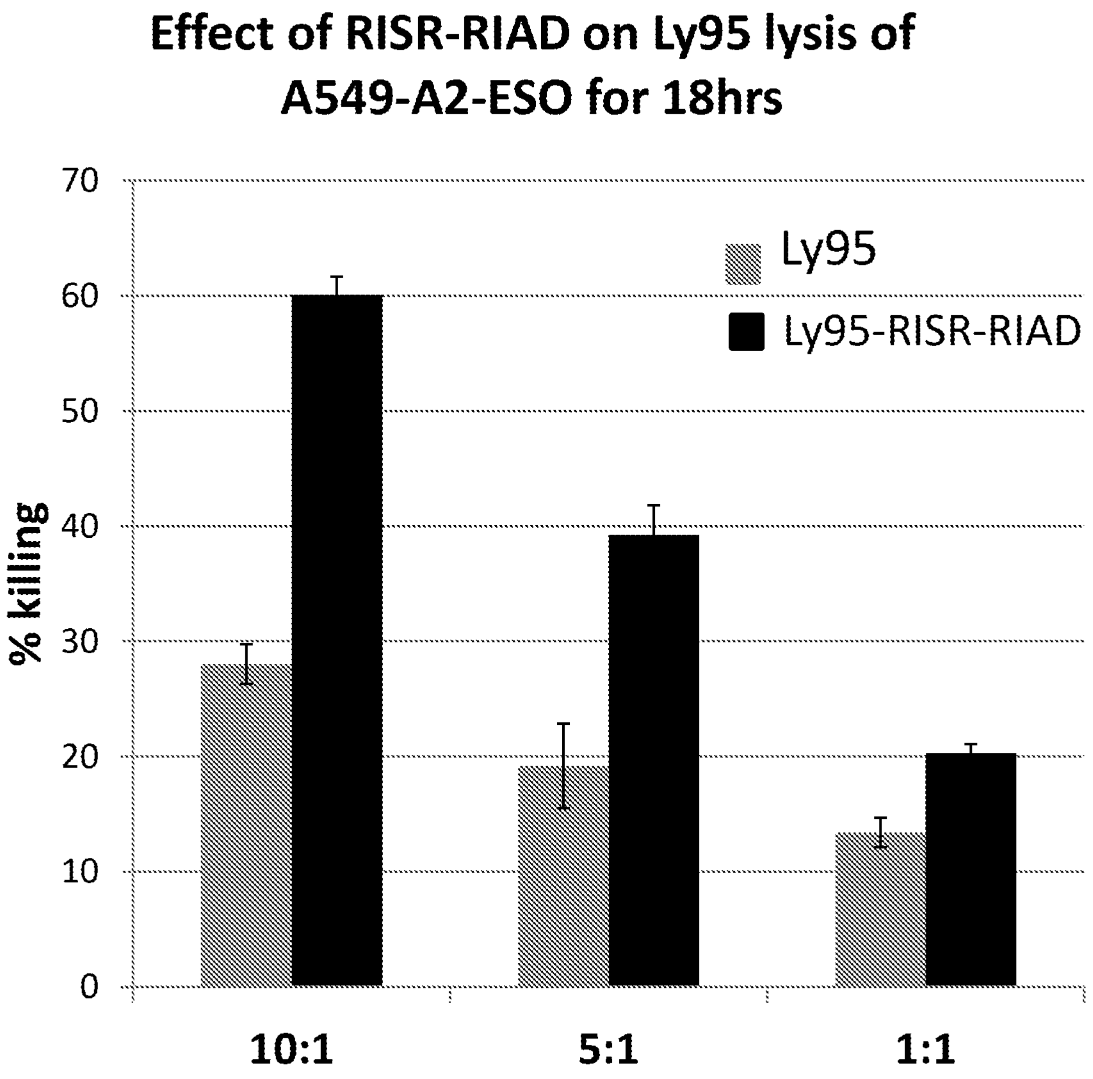
FIG. 15 is a graph showing the ability of the Ly95-RISR-RIAD construct to kill tumor cells was enhanced at each E:T ratio.
Figure 17:
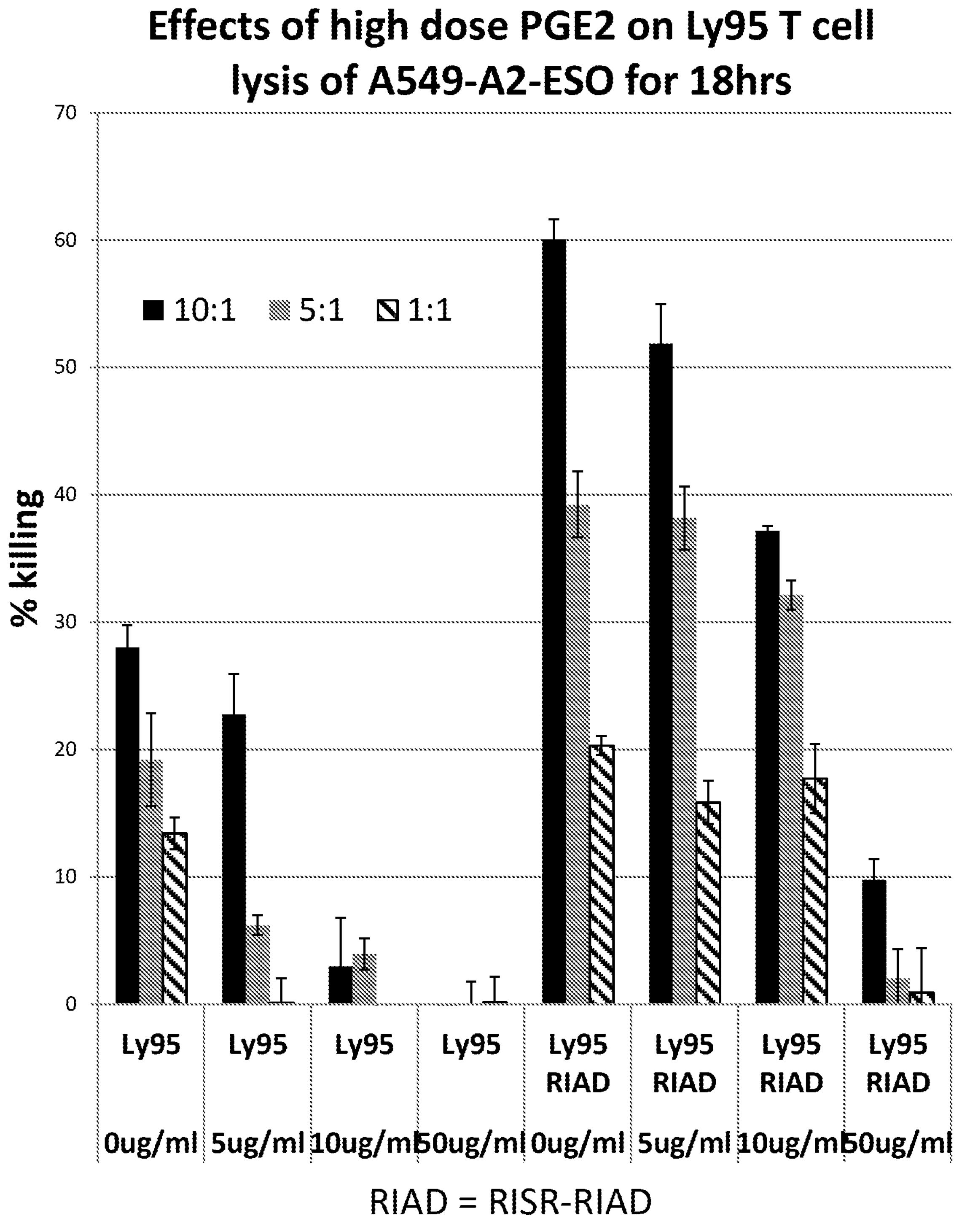
FIG. 17 is a graph showing that the Ly95-RISR-RIAD construct was less susceptible to inhibition by high dose PGE2 than the Ly95 T cells
Figure 18:
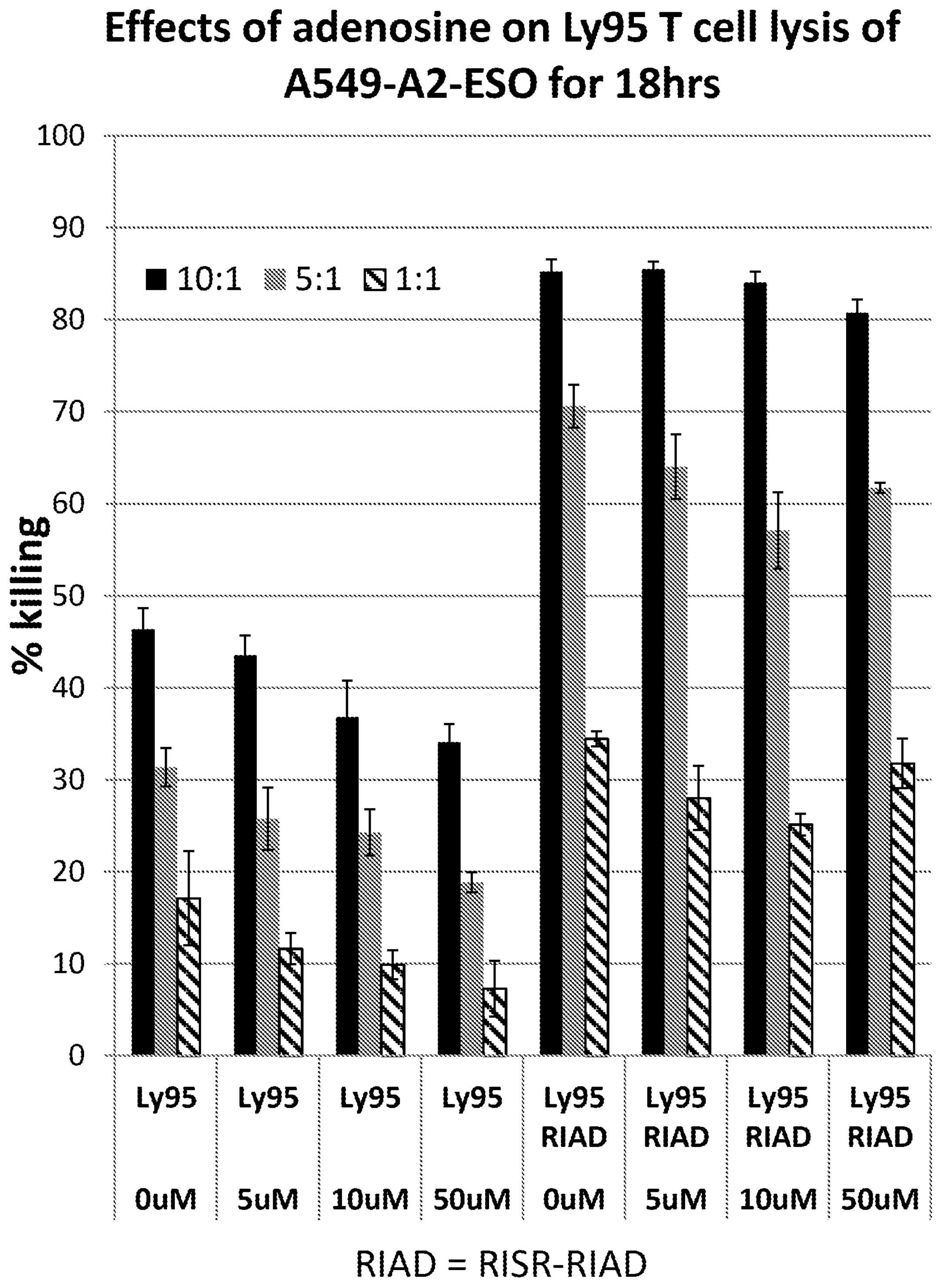
FIG. 18 is a graph showing that the Ly95-RISR-RIAD construct was less susceptible to inhibition by adenosine than the Ly95 T cells.

To evaluate the efficacy of RISR-RIAD in a CAR-free system, the NY-ESO1-reactive Ly95 TCR construct, an affinity-enhanced variant of the wild-type IG4 TCR, was expressed in human T cells with and without RISR-RIAD. The Ly95-RISR-RIAD T cells demonstrated enhanced tumor killing at each E:T ratio (FIG. 15). The Ly95-RISR-RIAD T cells were also less susceptible to inhibition by low (FIG. 16) and high dose (FIG. 17) PGE2 and adenosine (FIG. 18).

Figure 19:
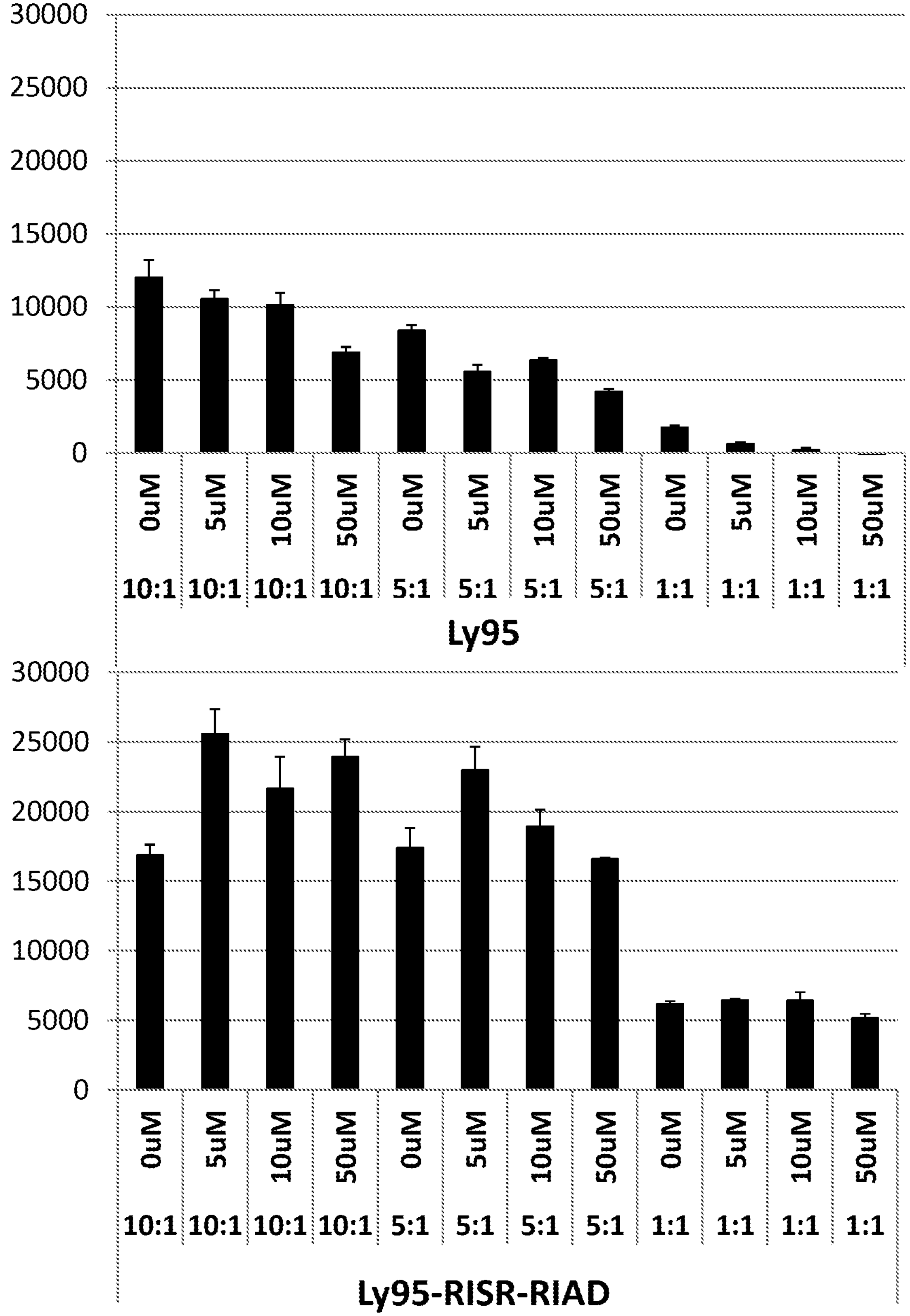
FIG. 19 is a graph showing that Ly95-RISR-RIAD (lower graph) produced more IFNgamma than Ly95 T cells (upper graph) under adenosine suppression conditions.
Figure 20:
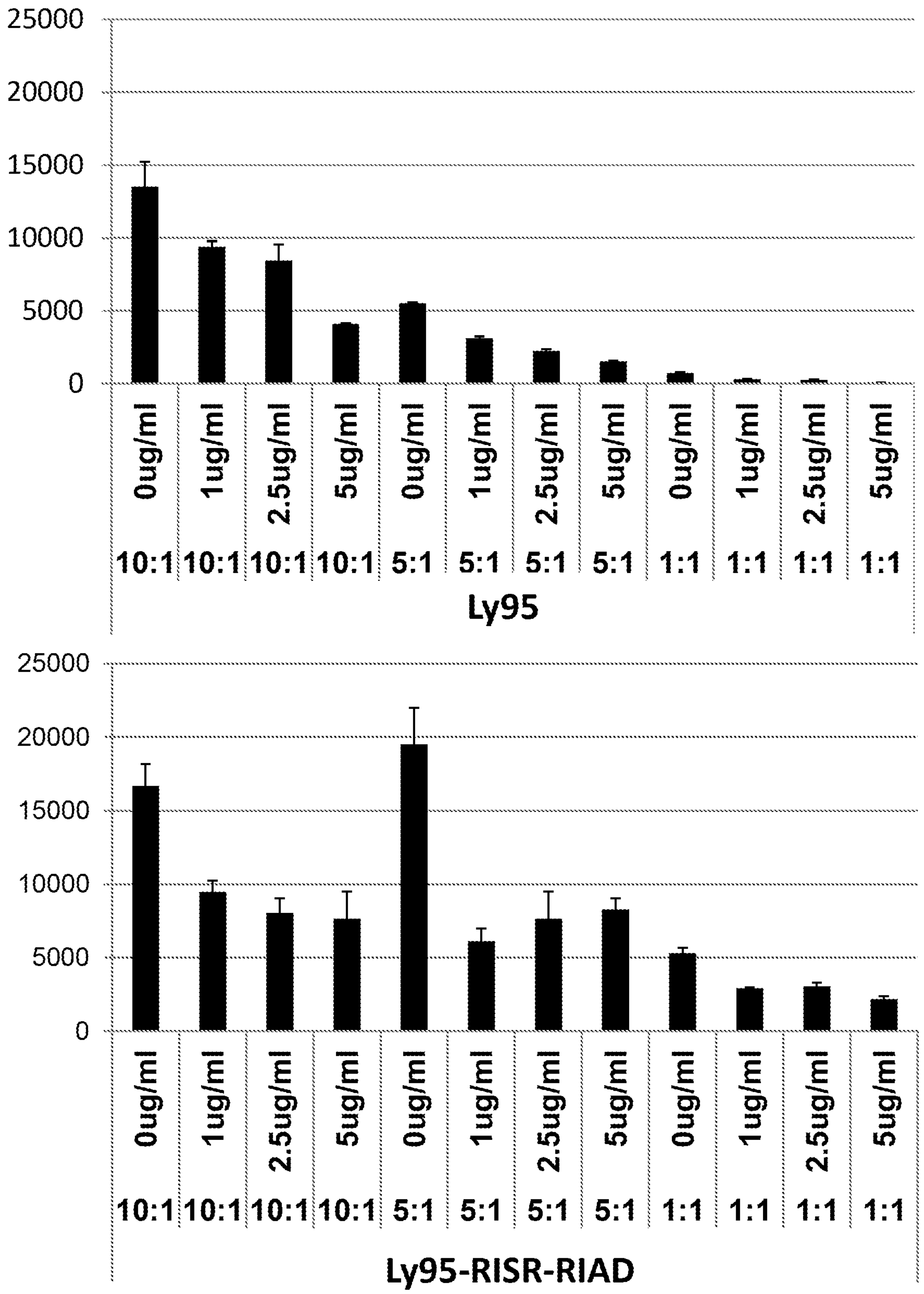
FIG. 20 is a graph showing that Ly95-RISR-RIAD (lower graph) produced more IFNgamma than Ly95 T cells (upper graph) under low dose PGE2 suppression conditions.
Figure 21:
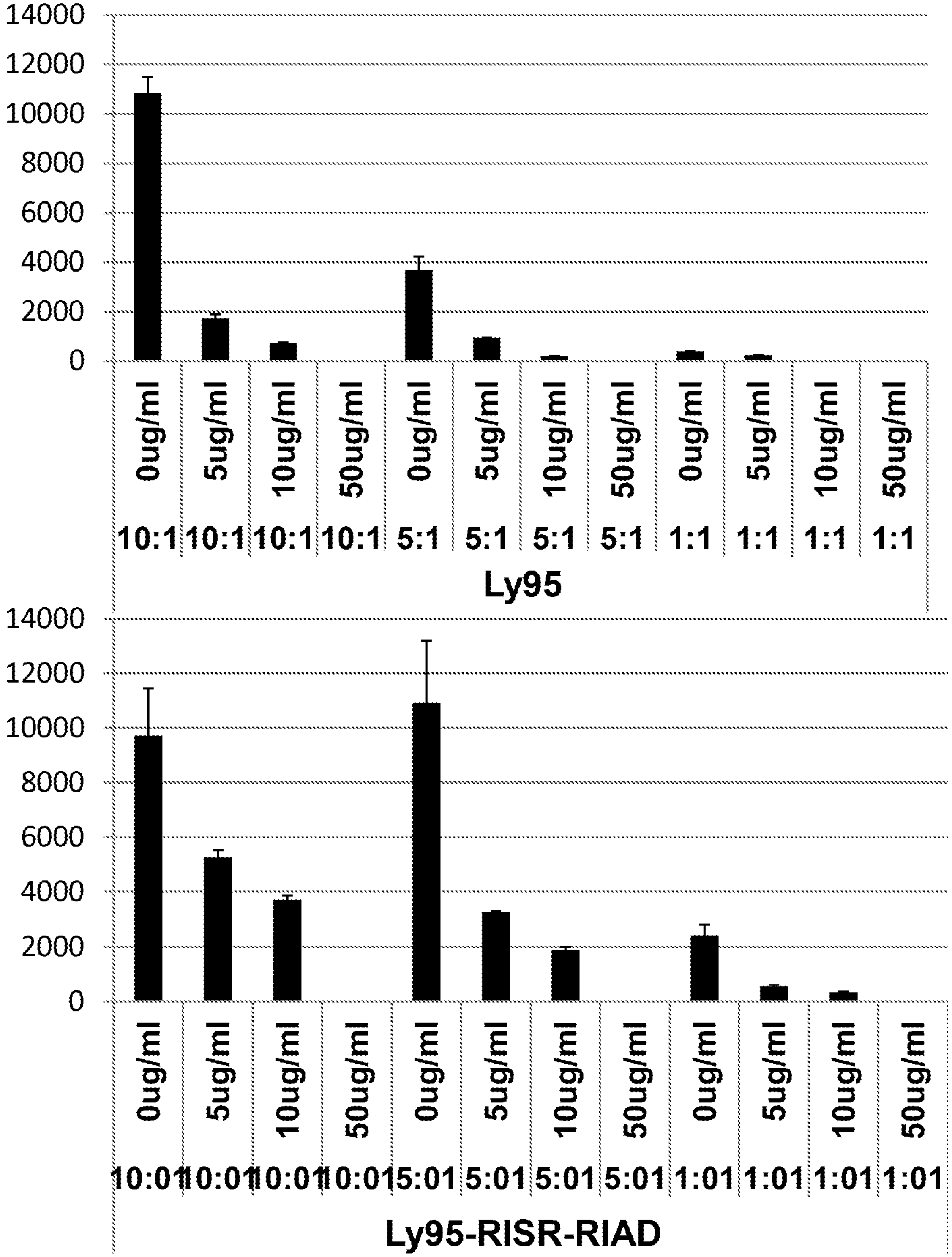
FIG. 21 is a graph showing that Ly95-RISR-RIAD (lower graph) produced more IFNgamma than Ly95 T cells (upper graph) under high dose PGE2 suppression conditions.

Ly95-RISR-RIAD T cells also produced more IFNgamma than Ly95 T cells under adenosine (FIG. 19), low dose (FIG. 20), and high dose (FIG. 21) PGE2 suppression conditions.

Example 17: Use of a Modified RIAD/RISR Based on the Endogenous Ezrin Sequence

Depending on the HLA type of the donor, the RIAD-RISR protein could contain epitopes that might be presented on the surface of the T cells and induce CD4 or CD8 host responses resulting in a potential loss of the T cells by immune attack. In silico analysis of the RISR/RIAD construct of this invention showed no immunogenic neoepitopes for common HLA types. To preclude any chance of immune reaction, another form of the RIAD-RISR construct was designed based upon the sequence of the endogenous protein Ezrin. The sequence of this alternate form of the RIAD-RISR is highly similar to the above described RISR-RIAD protein (SEQ ID NOs: 63-65) but has lower chance, if any, to be immunogenic as it comprises an identical sequence to the endogenous Ezrin sequence.

The sequence of the RISR-RIAD alternate construct is described herein below.

In one aspect, the fundamental part of the construct is an Ezrin sequence (Black bolded, highlighted in light and dark grey, in a box), having an amino acid sequence of QMMREKEELMLRLQDYEEKTKKAERELSEQIQRALQLEEERKRAQEEAERLEADR MAALRAKEELERQAVDQIKSQEQLAAELAEYTAKIALL (SEQ ID NO: 114) and a nucleic acid sequence of CAGATGATGCGCGAAAAAGAAGAACTGATGCTGCG CCTGCAGGATTATGAAGA AAAAACCAAAAAAGCGGAACGCGAACTGAGCGAACAGATTCAGCGCG CGCTG CAGCTGGAAGAAGAACGCAAACGC GCGCAGGAAGAAGCGGAACGCCTGGAAG CGGATCGCATGGCGGCGCTGCGCGCGAAAGAAGAACTGGAACGCCAGGCGGTG GATCAGATTAAAAGCCAGGAACAGCTGGCGGCGGAACTGGCGGAATATACCGC GAAAATTGCGCTGCTG (SEQ ID NO: 115). In some embodiments, the construct comprises some specific enzyme restriction sites such as Xba1 (Grey color) and BSpe1 (Grey color and underlined). In other embodiments, the construct comprises other suitable enzyme restriction sites known in the art. In some embodiments, tag sequences are inserted in order to permit tracking the alternate RISR-RIAD protein. Non limiting examples of tag sequences for tracking a protein are Myc Tag (Black color and inclined), "Flag" (DDK) tag (Black color and underlined) and Human influenza hemagglutinin (HA) tag.

In another aspect, similar to the RIAD-RISR construct described previously herein (SEQ ID NOs: 63-65), the nucleic acid sequences of this alternate RIAD-RISR construct (SEQ ID NO: 116) are cloned into a CAR or TCR expressing vector and augment efficacy of adoptive transferred T cells therapy as described previously herein.

The detailed nucleic acid and amino acid sequences for the RISR-RIAD alternate construct is listed below herein:

(SEQ ID NO: 117)

TCTAGAGCCACC*ATG*CAGATGATGCGCGAAAAAGAAGAACTGATGCTGCGCCT

GCAGGATTATGAAGAAAAAACCAAAAAAGCGGAACGCGAACTGAGCGAAC

AGATTCAGCGCGCGCTGCAGCTGGAAGAAGAACGCAAACGCGCGCAGGAA

GAAGCGGAACGCCTGGAAGCGGATCGCATGGCGGCGCTGCGCGCGAAAGAAG

AACTGGAACGCCAGGCGGTGGATCAGATTAAAAGCCAGGAACAGCTGGCGG

CGGAACTGGCGGAATATACCGCGAAAATTGCGCTGCTG*GCAGAACTCATCTC*

*AGAAGAGGATCTGGCAGCAAATGATATCCTGGATTACAAGGATGACGACGATAAG*T

CCGGA*TAA*

XbaI (TCTAGA)
Kozak sequence (GCCACC)
Start codon (italics and bolded ATG)
Myc tag (italics only)
DDK tag, “Flag-Tag” (dashed box, bold, italics)
BSpeI (TCCGGA)
Stop codon (italics only TAA)
Linker (dashed box, italics only)

(SEQ ID NO: 118)

MQMMREKEELMLRLQDYEEKTKKAERELSEQIQRALQLEEERKRAQEEAERL

EADRMAALRAKEELERQAVDQIKSQEQLAAELAEYTAKIALL*AELISEEDLAAND*

*ILDYKDDDDK**SG-*

RISR (solid box)
RISR sequence for RI binding on peptide array
(solid box, bold)

Nucleic acid sequence of the entire RISR, SEQ ID NO: 119
CAGATGATGCGCGAAAAAGAAGAACTGATGCTGCGCCTGCAGGATTATGAAGA

AAAAACCAAAAAAGCGGAACGCGAACTGAGCGAACAGATTCAGCGCGCGCTG

CAGCTGGAAGAAGAACGCAAACGCGCGCAGGAAGAAGCGGAACGCCTGGAAG

CGGATCGCATGGCGGCGCTGCGCGCGAAAGAAGAACTGGAACGCCAGGCGGTG

GATCAGATT

Amino acid sequence of the entire RISR, SEQ ID NO: 120
QMMREKEELMLRLQDYEEKTKKAERELSEQIQRALQLEEERKRAQEEAERLEADR

MAALRAKEELERQAVDQI

RIAD (dashed box, bold)

Nucleic acid sequence of RIAD, SEQ ID NOs: 121
TAAAAGCCAGGAACAGCTGGCGGCGGAACTGGCGGAATATACCGCGAAAATTG

CGCTGCTG

Amino acid sequence of RIAD, SEQ ID NO: 122
KSQEQLAAELAEYTAKIALL

Nucleic acid sequence of RISR-RIAD (Ezrin), SEQ ID NO: 123
CAGATGATGCGCGAAAAAGAAGAACTGATGCTGCGCCTGCAGGATTATGAAGA

AAAAACCAAAAAAGCGGAACGCGAACTGAGCGAACAGATTCAGCGCGCGCTG

CAGCTGGAAGAAGAACGCAAACGCGCGCAGGAAGAAGCGGAACGCCTGGAAG

CGGATCGCATGGCGGCGCTGCGCGCGAAAGAAGAACTGGAACGCCAGGCGGTG

-continued

GATCAGATTAAAAGCCAGGAACAGCTGGCGGCGGAACTGGCGGAATATACCGC

GAAAATTGCGCTGCTG

Amino acid sequence of RISR-RIAD (Ezrin), SEQ ID NO: 124
QMMREKEELMLRLQDYEEKTKKAERELSEQIQRALQLEEERKRAQEEAERLEADR

MAALRAKEELERQAVDQIKSQEQLAAELAEYTAKIALL

Example 18

Adoptive T cell therapy utilizing chimeric antigen receptors (CARs) has been used to treat hematologic malignancies and solid tumors. Loss of T cell effector function occurs in endogenous T cells, and the same phenomenon with intravenously-administered human CAR T cells has been observed. The data described herein highlight the importance of bolstering adoptively transferred T cell resistance to immunosuppression encountered within the tumor microenvironment.

To address immunosuppression mediated by adenosine and PGE2, two important well-established inhibitory factors within the tumor microenvironment that dampen the anti-tumor response, were analyzed herein. Like many other molecules in the tumor microenvironment, both these entities facilitate signal transduction through their cognate G-protein coupled receptors that culminate in the accumulation of cAMP, a potent mediator of immunosuppression via the effector protein PKA.

The discovery and development of RISR and RIAD brought forth the hypothesis that the co-expression of the RISR-RIAD transgene with a CAR- and transgenic TCR-transduced T cells may protect them from cAMP-mediated immunosuppression. Therefore in this study, the anti-tumor efficacy of CAR and transgenic TCR T cells co-transduced with the transgene RISR-RIAD in murine and human TILs was investigated.

Figure 11B:
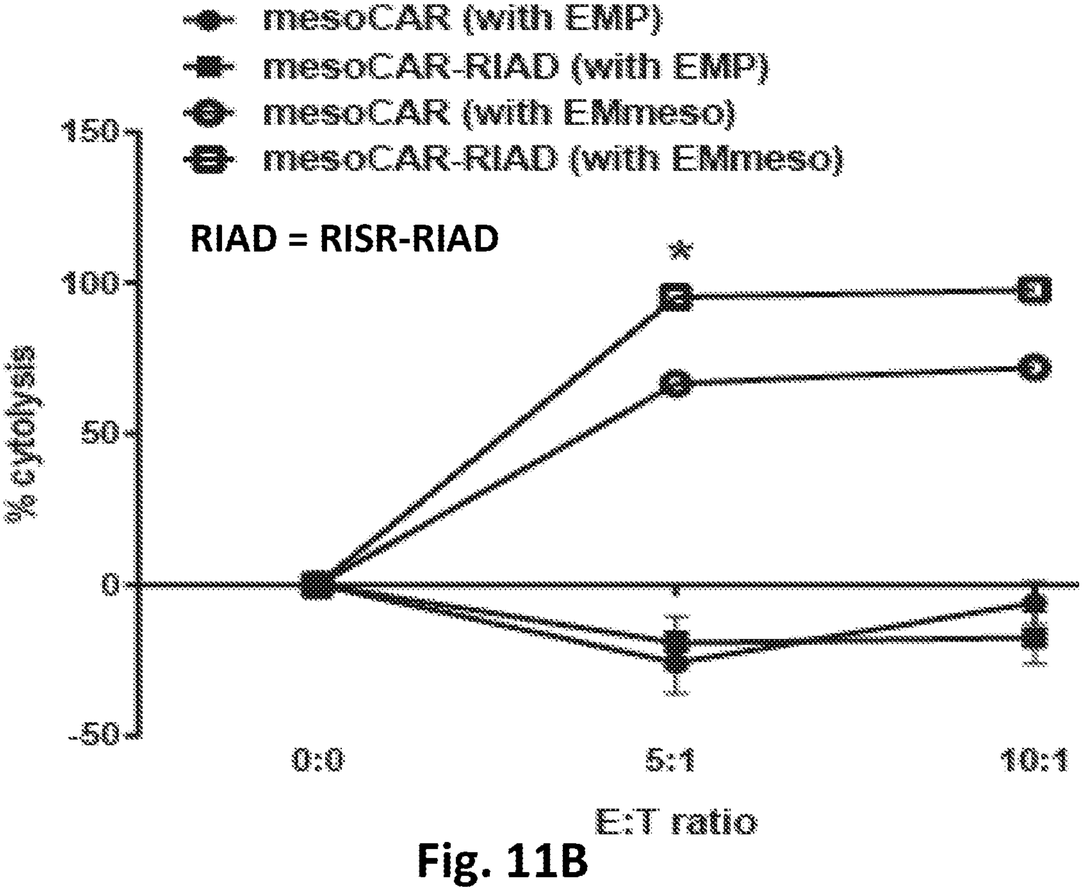
FIG. 11B is a graph showing various effector-to-target (E:T) ratios of mesoCAR and mesoCAR-RISR-RIAD T cells that were co-cultured with either parental EM (EMP) or mesothelin-expressing EM (EMmeso) cells overnight. Statistical analysis was performed using two-way ANOVA comparing the percent cytolysis of EMmeso cells by mesoCAR versus mesoCAR-RISR-RIAD T cells.
Figure 11C:
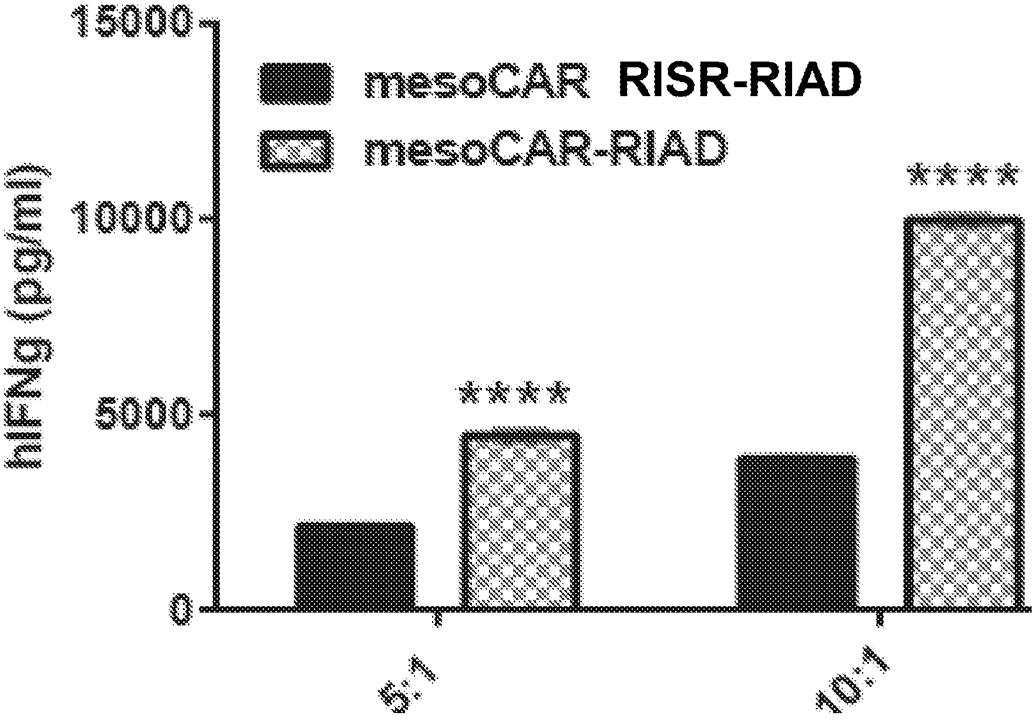
FIG. 11C is a graph showing IFNγ production via ELISA from cell culture supernatant taken from the overnight cytolysis assay, and quantification of IFNγ performed by comparing mesoCAR and mesoCAR-RISR-RIAD T cells.

Using activated human T cells that were transduced with mesoCAR-RISR-RIAD using modified lentiviruses, it was demonstrated in vitro that human mesoCAR-RISR-RIAD T cells exhibited antigen-specific cytotoxicity against EMmeso cells, leaving the parental EM cell line relatively unaffected (FIG. 11B). Moreover, the extent of EMmeso cytolysis by mesoCAR-RISR-RIAD T cells was greater than that of mesoCAR T cells alone (FIG. 11B); this corresponded to the heightened generation of IFNγ by mesoCAR-RISR-RIAD T cells (FIG. 11C). In order to evaluate the contribution of the RISR-RIAD transgene to the system, the in vitro cytolysis assay was challenged with the addition of adenosine and PGE2, and observed the superior resistance of mesoCAR-RISR-RIAD T cells to these immunosuppressive entities in comparison to the dose-dependent inhibition of mesoCAR killing of EMmeso cells (FIG. 12). Since RISR-RIAD was reported to specifically disrupt PKA anchoring to the membrane, and hence abrogate inhibitory PKA signaling, The effect of RISR-RIAD on the two key TCR-related, PKA-affected proximal signaling molecules, Csk and Lck, was assessed. The loss of inhibitory PKA signaling in mesoCAR-RISR-RIAD T cells—the loss of phosphorylation of Csk at S364—was observed, and hence its inability to phosphorylate (and activate) Lck at Y505 confer resistance of human mesoCAR-RISR-RIAD T cells to inhibitory cAMP signaling (FIG. 13B).

The status of actual T cell signaling components ($pLck^{Y394}$, pERK, and pAkt) after engagement of the TCR by CD3/CD28-mediated activation was assessed. As expected, increased signaling after TCR stimulation was observed. However, somewhat surprisingly, even at baseline, mesoCAR-RISR-RIAD T cells showed greater activity compared to mesoCAR T cells, as evidenced by increased pERK, $pLck^{Y394}$, and pAkt phosphorylation. This suggests that there is tonic inhibitory PKA activity in the system, even in resting effector T cells. Overall, these data suggest that mesoCAR-RISR-RIAD T cells would show improved function in an immunosuppressive microenvironment.

To test this theory, immunodeficient NSG mice bearing established EMmeso tumors with both mesoCAR and mesoCAR T cells were treated, and superior tumor volume reduction upon treatment with mesoCAR-RISR-RIAD T cells was observed in comparison with mesoCAR T cells (FIG. 14A). To delineate this effect, TILs were evaluated at Day 32 after T cell administration, and saw a large increase in mesoCAR-RISR-RIAD T cell number within the tumor when compared to mesoCAR T cells (FIG. 14B). The lack of mesoCAR T cell efficacy ex vivo was due to hypofunction acquired within the tumor microenvironment as these T cells encounter a myriad of inhibitory factors; this hypofunction phenomenon is reversible as upon overnight recovery (and removal of inhibitory factors) in complete cell culture medium, mesoCAR T cells regain their cytolytic ability against antigen-expressing tumor cells (FIG. 14C). However, mesoCAR-RISR-RIAD T cells, in accordance with RISR-RIAD-conferred protection against immunosuppression, continued to kill EMmeso cells and generate high levels of IFNγ even at time of harvest (FIG. 14C).

The application of the RISR-RIAD transgene in murine mesoCAR T cells was extended both in vitro and in vivo, and observed similar effects as in the human system—enhanced cytolysis, along with increased murine IFNγ generation, and resistance to adenosine- and PGE2-facilitated suppression in cytolysis (FIGS. 7A-7D). In vivo, the expression of the RISR-RIAD transgene in both mesoCAR- and FAPCAR-transduced murine T cells successfully slowed tumor growth to a greater extent as compared to non-RISR-RIAD-expressing CAR T cells (FIGS. 8A-8B). Flow cytometry analysis of murine TILs similarly denoted an increased influx of mesoCAR-RISR-RIAD T cells within the spleen and tumor (FIGS. 9A and 9B) as previously seen in the human system (FIGS. 7A-7D). Given these observations, the possibility that mesoCAR-RISR-RIAD cells may possess superior migration ability over mesoCAR cells, and hence, can better infiltrate and kill tumors was investigated. Transmigration assays using the chemokine IP10 revealed better mesoCAR-RISR-RIAD trafficking in a CD29 (integrin β1)-dependent fashion (FIGS. 9C and 9D).

Taken together, the study showed that CAR-RISR-RIAD T cells were specifically activated, killed target antigen-expressing tumor cells in vitro and in vivo with no obvious toxicity, and were far superior in their cytolysis ability compared to CAR T cells alone. This additional boon was due to the RISR-RIAD-conferred protection against cAMP-mediated immunosuppression within the tumor microenvironment, and can therefore be used to inhibit tumor growth as a monotherapy, and may possess additive or synergistic anti-tumor effects when combined with other tumor cell-directed therapies; adoptive T cell use in the treatment of solid tumors must be resistant to the immunosuppressive milieu. The insertion of the RISR-RIAD transgene can be easily accomplished into any CAR or T cells with transgenic TCRs in a bicistronic fashion.

The materials and methods employed in these experiments are now described.

Figure 6:
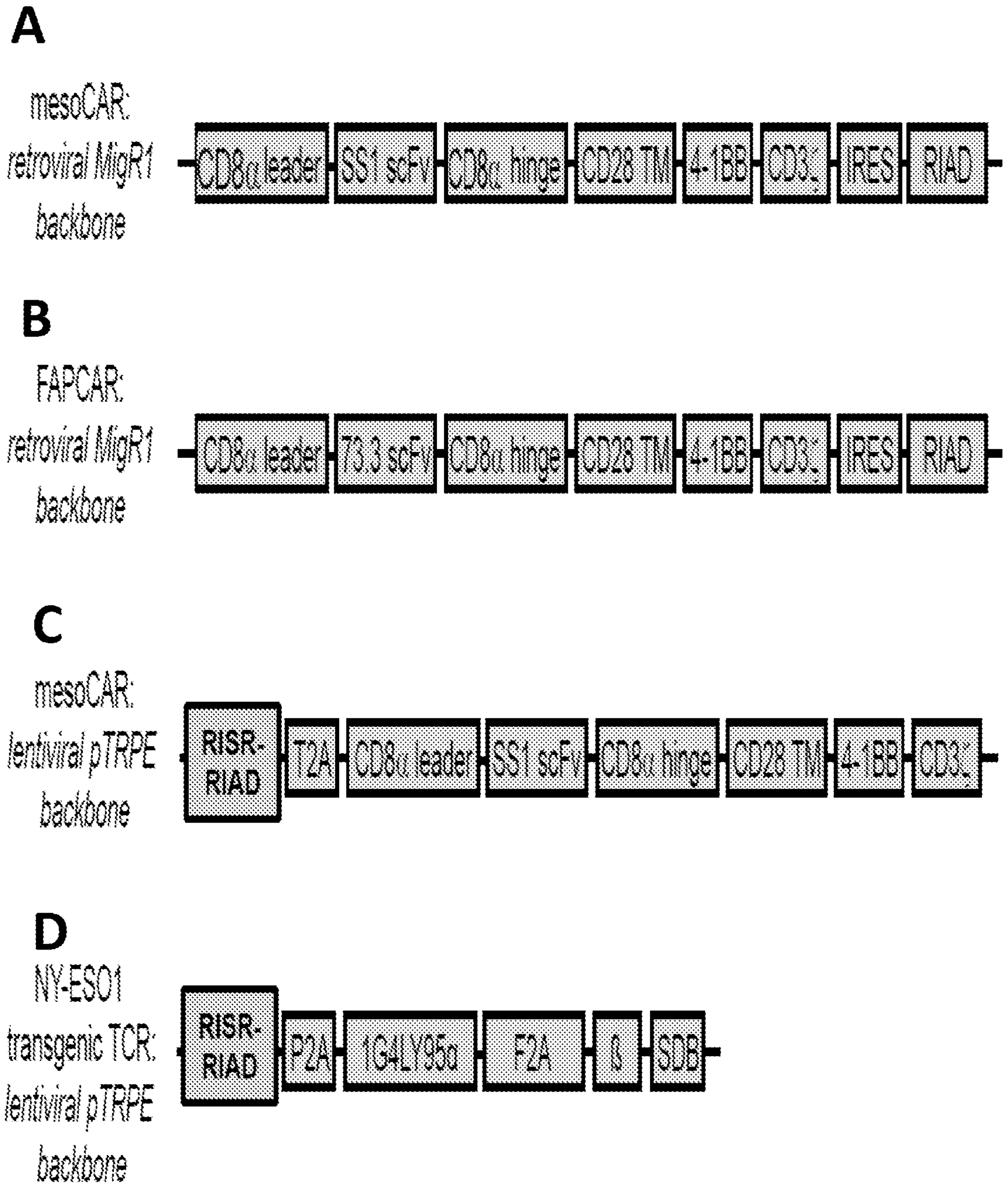
FIG. 6 is a series of schematic representations of viral-engineered constructs for transduction of T cells. A) The previously described murine mesothelin (SS1)-binding chimeric receptor, along with 4-1BB (CD137) and CD3ζ intracellular signaling domains of human origin, or mesoCAR, and RISR-RIAD were cloned into the retroviral MigR1 vector for transduction of primary murine T cells. B) Similarly, anti-FAP scFv, intracellular 4-1BB and CD3ζ of murine origin, and RISR-RIAD were cloned into the MigR1 vector for transduction of primary murine T cells. C) For transduction of primary human T cells, mesoCAR and RISR-RIAD (separated by a T2A sequence for stoichiometric protein expression) were cloned into the lentiviral pTRPE backbone. D) NY-ESO1 LY95 transgenic TCR construct as expressed in the lentiviral pTRPE backbone.

Generation of RISR-RIAD-Expressing mesoCAR, FAP-CAR, and Transgenic Ly95 TCR Constructs, and T Cell Generation The RISR-RIAD construct, incorporated with myc and ddk (FLAG) tags, was synthesized by Integrated DNA Technologies in the pIDT.SMART cloning plasmid. It was then subcloned into a human mesoCAR-expressing MigR1 retroviral vector, dubbed MigR1.mesoCAR-RISR-RIAD (FIG. 6), and murine FAPCAR-expressing MigR1 retroviral vector, dubbed MigR1.FAPCAR-RISR-RIAD (FIG. 6). Primary murine T cells were isolated and transduced with these retroviral particles as previously described (Riese, et al., Canc. Cell, 2013, 3566-3577). Similarly, RISR-RIAD and mesoCAR cDNA were subcloned into the lentiviral vector pTRPE (dubbed pTRPE.mesoCAR and pTRPE.mesoCAR-RISR-RIAD, shown in FIG. 1C). The isolation, bead activation, transduction using pTRPE.mesoCAR and pTRPE.mesoCAR-RISR-RIAD, and subsequent expansion of primary human T cells were carried out as previously described (Moon, et al., Clin. Canc. Res., 2014, 20:4262-4273). The RISR-RIAD transgene was also inserted into the NY-ESO1-reactive Ly95 transgenic TCR construct.

Generation of the Target Lung Cancer Cell Line

The human lung cancer cell line A549-CBG was generated by stably transducing the A549 cell line (ATCC CCL185) with a lentiviral vector encoding Click Beetle Green (CBG) and GFP (CBG-T2A-GFP) and flow-sorted to 100% GFP positivity. The sorted A549-CBG cell line was then transduced by a retroviral vector encoding NY-ESO-1-T2A-HLA-A2. The transduced A549-CBG cells were subjected to limiting dilution at 0.5 cell per well in 96-well plates. Resulting clones were tested by flow cytometry for HLA-A2 expression. HLA-A2 positive clones were selected and tested by co-culture with T cells expressing the NY-ESO-1 TCR. The clones expressing HLA-A2 that could stimulate NY-ESO-1 TCR-expressing T cells to secrete IFNγ were pooled to generate the A549-NY-ESO-1-A2-CBG (A549-A2-ESO) cell line.

Animals

Studies using retroviral MigR1-transduced T cells were carried out in wild-type C57Bl/6 mice obtained from Charles River Laboratories. Studies using lentiviral pTRPE-transduced human T cells were conducted in NOD/scid/IL2rγ$^{-/-}$ (NSG) mice bred at the Children's Hospital of Philadelphia. All test animals used were females at 10-12 weeks of age.

Cell Lines

All cell lines used were cultured as previously described (Moon, et al., Clin. Canc. Res., 2014, 20:4262-4273), and routinely examined for *Mycoplasma* infection using the MycoAlert kit (Lonza #LT07-318). AE17 murine mesothelioma cells expressing chicken ovalbumin (dubbed AE17ova) were obtained from the University of Western Australia, while EM human mesothelioma cells were derived from a patient's tumor (dubbed EMparental, or EMP). These cell lines, stably transduced with mesothelin (AE17meso and EMmeso, respectively), were used for in vivo studies with mesoCAR T cells. Murine 3T3Balb/c cells (3T3parental, or 3T3P) were purchased from American Type Culture Collection, and stably transduced with FAP (Riese, et al., Canc. Cell, 2013, 3566-3577); these were used for studies with FAPCAR T cells. In vitro studies were also performed using these cell lines that were additionally transduced to express firefly luciferase, named AE17ova-luc, AE17meso-luc, EMP-luc, EMmeso-luc, 3T3P-luc, and 3T3FAP-luc. The murine 4662 pancreatic ductal carcinoma cell line (PDA4662) were derived from an autochthonous pancreatic tumor isolated from a fully backcrossed C57BL/6 Kras$^{G12D}$:Trp53$^{R172H}$:Pdx-1 Cre (KPC) mouse.

Antibodies

The detection of RISR-RIAD was carried out using anti-myc antibodies (Cell Signaling Technologies #3739 for flow cytometry, and #2722 for western blotting) and anti-ddk antibodies (Biolegend #637307 for flow cytometry and Origene #TA50011 for western blotting). The following conjugated antibodies for flow cytometric detection of murine cells were purchased from Biolegend: CD206 (#141720), CD8 (#100762), CD4 (#100406), IFNγ (#505825), IL2 (#503808), and anti-GFP (#338008); BD Biosciences: Ly6G (#551480), CD19 (#561739), B220 (#553091), CD69 (#552879), and CD44 (#553135); and eBiosciences: F4/80 (#17-4801-82), CD11B (#12-0112-82), CD3 (#48-0031-82), FOXP3 (#12-5773-80), and 4-1BB (#17-1371-80). For the detection of human cells, the following conjugated antibodies for flow cytometry were purchased from Biolegend: FOXP3 (#320106); BD Biosciences: CD25 (#555432), CD45 (#555483), CD8 (#555367), IL2 (#340448), CD69 (#555530), and TNFα (#340511); and R&D Biosystems: human mesothelin (FAB32652P).

Assessment of T Cell Effector Functions

Functional assays performed to characterize persistence and activity of endogenous and genetically modified T cells in vitro, in vivo, and ex vivo are outlined below. All assays are performed at least thrice in an independent fashion, unless otherwise noted.

In vitro cytotoxicity and interferon-γ (IFNγ) ELISA

Triplicates of luciferase-expressing parental and antigen-expressing cell lines were co-cultured with differing ratios of CAR-expressing T cells to tumor cells as previously described in 96-well plates overnight; cytotoxicity of T cells were evaluated the following day, and culture supernatants were collected for IFNγ ELISA. In order to evaluate the resistance of RISR-RIAD-expressing T cells to immunosuppression, in vitro cytotoxicity assays were also performed in the presence of PGE2 (Enzo Life Sciences #BML-PG007), and adenosine (Sigma #A9251).

In vivo studies

For mesoCAR and FAPCAR studies in wild-type C57Bl/6 mice, 2 million AE17meso and PDA4662 cells were subcutaneously inoculated as previously described (Riese, et al., Canc. Cell, 2013, 3566-3577: Wang, et al., Canc. Cell Immunol. Res., 2014, 2:154-166). Similarly, for mesoCAR and Ly95 transgenic TCR T cell studies in immunodeficient NSG mice, 2 million EMmeso and A549-A2-ESO cells were subcutaneously inoculated. When tumors were approximately 200 mm$^3$, mice were given $10^7$ CAR-expressing, or Ly95-expressing T cells via intravenous administration. Tumor volume was monitored by caliper measurement of tumor diameter twice weekly, and at different time points, tumor-bearing mice were sacrificed for mechanistic studies using immunoblotting and/or flow cytometry.

Immunoblotting

The phosphorylation status of various proximal T cell signaling entities were assessed by western blotting (pERK, pAkt, pLck) using a 1:3 ratio of CAR-expressing T cells and plate-bound CD3/CD28 antibodies as previously described (Riese, et al., Canc. Cell, 2013, 3566-3577). Additionally, antibodies for the detection of CD3z were purchased from Santa Cruz Biotechnologies (#sc-1239), $pLck^{Y505}$ from Cell Signaling Technologies (#2751S), and $pCsk^{S364}$ from Abcam (#ab61782).

Ex vivo T cell analysis

Tumors were harvested from mice, micro-dissected, and digested in a mixture containing collagenase I, II, and IV, DNAse I, and elastase in Leibovitz-L15 medium (Sigma #L1518) for 2 hours at 37° C. in a shaker incubator with 15-minute vortexing intervals before filtering through 70-μm nylon mesh cell strainers. Following this, procedures for red blood cell lysis, and tumor single cell suspension isolation, along with spleen processing, were carried out.

Flow cytometry (FACS)

Single cell suspensions were stained for surface and intracellular markers using the previously listed antibodies based on the manufacturers' recommendations. For intracellular cytokine staining, cells were stimulated for 4-6 hours at 37° C. in the presence of 0.7 μg/ml GolgiStop (BD Biosciences #554724) with plate-bound 1 μg/ml anti-CD3 and 2 μg/ml anti-CD28 antibodies, and 30 ng/ml PMA and 1 μM ionomycin. Acquisition was performed on a CyAn-ADP Analyzer (Beckman Coulter) or a BD LSRFortessa (BD Biosciences). Data was analyzed using FlowJo (TreeStar).

Transwell migration studies

Equal number of mesoCAR-GFP- and mesoCAR-mCherry-RISR-RIAD-expressing cells were placed in 0.5 μm polycarbonate transwell membranes, and allowed to migrate toward PBS, cell culture medium alone, or with different concentrations of the chemokine IP10, or tumor cell supernatant in tissue culture plates. After 4 hours, remaining cells in the transwell inserts and migrated cells in the bottom wells were collected, counted, and stained for adhesion and migration markers for analysis by flow cytometry.

Cell Culture Conditions

Tumor cells and T cells were cultured in RPMI 1640 (Gibco 11875-085) supplemented with 10% heat inactivated fetal calf serum (FCS), 100 U/ml penicillin, 100 ug/ml streptomycin sulfate, and 1% L-glutamine (complete cell culture medium).

Lentivirus Preparation

The NY-ESO1-reactive Ly95 TCR construct is an affinity-enhanced variant of the wild-type IG4 TCR identified from T cells recognizing the HLA-A2 restricted NY-ESO-1:157-165 peptide antigen. In the mutant form, the threonine at residue position 95 is substituted by leucine and the serine at residue position 96 is substituted by tyrosine. It was constructed using an overlapping PCR method based on the description and sequences published previously and incorporated into the lentiviral expression vector pELNS bearing the EF1α promoter. Packaging of each plasmid into lentivirus has been previously described. Titering of lentiviral concentration was performed by transduction of Sup-T1 cells (ATCC CRL-1942) at different virus dilutions and measurement of transgenic TCR expression by flow cytometric analysis using an anti-human Vβ13.1 TCR chain antibody (Beckman Coulter, CA).

Isolation, Bead Activation, Transduction, and Expansion of Primary Human T Lymphocytes Primary human $CD4^+$ T and $CD8^+$ T cells were isolated from healthy volunteer donors following leukopheresis by negative selection using RosetteSep kits (Stem Cell Technologies, Vancouver, Canada). $CD4^+$ and $CD8^+$ T cells were mixed at a 1:1 ratio, and cultured in complete cell culture medium. They were stimulated with magnetic beads coated with anti-CD3/anti-CD28 at a 1:3 cell to bead ratio without the addition of exogenous IL-2. T cells were transduced with lentiviral vectors at an MOI of approximately 5. Cells were counted and fed with complete cell culture medium every 2 days. Once they appeared to become quiescent as determined by both decreased growth kinetics and cell size, they were used either for functional assays or cryopreserved. A small portion of expanded cells were stained for flow cytometry confirmation of successful Ly95 transduction using the Vβ13.1 TCR chain antibody.

Generation of the Target Lung Cancer Cell Line

The human lung cancer cell line A549-CBG was generated by stably transducing the A549 cell line (ATCC CCL185) with a lentiviral vector encoding Click Beetle Green (CBG) and GFP (CBG-T2A-GFP) and flow-sorted to 100% GFP positivity. The sorted A549-CBG cell line was then transduced by a retroviral vector encoding NY-ESO-1-T2A-HLA-A2. The transduced A549-CBG cells were subjected to limiting dilution at 0.5 cell per well in 96-well plates. Resulting clones were tested by flow cytometry for HLA-A2 expression. HLA-A2 positive clones were selected and tested by co-culture with T cells expressing the NY-ESO-1 TCR. The clones expressing HLA-A2 that could stimulate NY-ESO-1 TCR-expressing T cells to secrete IFNγ were pooled to generate the A549-NY-ESO-1-A2-CBG (A549-A2-ESO) cell line.

FACS Analysis

Analysis of target tumor cells was conducted using APC-conjugated antibody against HLA-A2 (BD Biosciences, CA), and a primary monoclonal antibody against NY-ESO-1 (Life Technologies, NY), followed by a PE-conjugated goat anti-mouse secondary antibody (BD Biosciences, CA). Analysis of expression of T cell surface markers was conducted using fluorochrome-conjugated antibodies against CD45, CD8, CD4, PD-1 (BD Biosciences, CA), Tim-3 (eBioscience, CA), and Lag-3 (R&D systems, MN). Cells were stained in standard 5 ml round-bottom Falcon FACS tubes (BD Biosciences, CA) and analyzed on a 9-channel CyAn™ ADP Analyzer (Beckman Coulter, CA).

Flow Cytometric T Cell Activation Assay

Analysis of T cell activation upon stimulation by target tumor cells was performed by plating Ly95 T cells with A549-A2-ESO or control A549-A2 cells at 1:2 E:T ratio in round-bottom 96-well plates. Fluorochrome-conjugated antibodies against CD107a, granzyme B, and CD25 (BD Biosciences, CA) were added to wells and incubated for 1 hour at 37° C. and 5% CO2 in the dark prior to the addition of Golgi Stop™ (BD Biosciences, CA). Measurement of IFNγ was performed using standard intracellular cytokine staining protocols.

In Vitro Testing of Tumor Cell Killing by Ly95 TCR T Cells

Control tumor cells and A549-A2-ESO cells were plated in a flat-bottom 96-well plate at 5000 cells per well in triplicates. After overnight incubation at 37° C. and 5% CO2, Ly95 T cells were co-cultured at different effector: target (E:T) ratios. After 18 hrs of incubation at 37° C. and 5% CO2, supernatant from the wells were aspirated for cytokine analysis by ELISA, wells were washed, the remaining tumor cells were lysed, and luminescence was read in a Modulus II Microplate Multimode Plate Reader after addition of 100 ul of luciferin reagent (Promega E1501, Madison, WI). The same assay was used to examine the tumor killing ability of tumor-infiltrating lymphocytes obtained from the in vivo experiments.

Measurement of Ly95 T Cell IFNγ Secretion by ELISA

Supernatants from 18 hr tumor killing co-culture assays were prepared at different dilutions and measured for levels of IFNγ by standard ELISA protocol. (Biolegend, CA).

Animals

NOD/scid/IL2rγ$^{-/-}$ (NSG) mice were bred in the Animal Services Unit of the Wistar Institute and the Children's Hospital of Philadelphia. Female mice were used for experiments at 10 to 16 weeks of age.

In Vivo Xenograft Experiments

A total of $5\times10^6$ A549-A2-ESO tumor cells were injected in the flanks of NSG mice in a solution of X-Vivo media (Lonza, NJ) and Matrigel (BD Biosciences, CA). After tumors were established (100-200 mm$^3$), the mice were randomly assigned to one of three intravenous (tail-vein) treatment groups: (i) saline, ii) $10\times10^6$ non-transduced but expanded (NTD) T cells, and iii) $10\times10^6$ Ly95 T cells. In the experiments combining anti-PD-1 antibody with T cells, two additional groups were included: (iv) every 5-day intraperitoneal (IP) injection of 10 mg/kg anti-PD1 antibody (Ultra-LEAF™, Biolegend, CA), and (v) $10\times10^6$ Ly95 T cells IV plus every 5-day IP injection of 10 mg/kg anti-PD1 antibody. Tumors were measured using calipers and tumor volumes were calculated using the formula $(\pi/6)$ (length)×(width)$^2$. When predefined protocol endpoints were reached, tumors were harvested, micro-dissected, and digested in a solution of 1:2 DNase:collagenase in a shaker incubator at 37° C. for 2 hours. Digested tumors were then filtered through 70-μm nylon mesh cell strainers, and red blood cells were lysed if needed (BD Pharm Lyse; BD Biosciences, CA). Spleens harvested from the same mice were also filtered through 70-μm nylon mesh cells trainers with red blood cell lysis. $1\times10^6$ cells from single-cell suspensions were placed in standard FACS tubes and were stained with anti-human CD45, CD8, CD4, and TCRVβ13.1 antibodies to assess degree of infiltration of adoptively transferred T cells. Additionally, cells were also stained with anti-PD1, anti-TIM3, and anti-LAGS antibodies to measure expression of IRs on TILs. The in vivo experiments were repeated three times in independent fashion. Groups contained 5-10 mice each.

Ex Vivo TIL Analysis

After digestion of harvested tumors, necrotic debris was first removed by processing the single cell suspension using a Dead Cell Removal Kit (Miltenyi Biotech, CA). TILs were subsequently isolated using an anti-human CD45-PE antibody (BD Biosciences, CA) with the EasySEP PE Selection Kit (STEMCELL Technologies, Vancouver, Canada). Once isolated, functional analyses for TILs were performed in two different ways: (i) luciferase-based killing assays, and (ii) measurement of antigen-induced T cell IFNγ secretion by ELISA (see above).

Animals

All animal experiment protocols were approved and conducted in accordance with the Institutional Animal Care and Use Committee. NOD/scid/IL2rγ$^{-/-}$ (NSG) mice were bred in the Animal Services Unit of the Wistar Institute and the Children's Hospital of Philadelphia. Female mice were used for experiments at 10 to 16 weeks of age.

Statistical Analysis

All results were reported as means±SEM. For studies comparing 2 groups, the Student's t test was used, while for studies comparing more than 2 groups, one- or two-way ANOVA with the appropriate post hoc testing was used, with $*p\leq0.05$, $p\leq0.01$, $*p\leq0.001$, and $****p\leq0.0001$.

Methods for the Ly95-RISR-RIAD

A construct was made fusing the RISR-RIAD construct to the Ly95 transgenic TCR. This was inserted into a lentivirus and used to transduce T cells using the standard approach.

T cells were evaluated by FACS to confirm the transfection efficiency of the CAR. The T cells were then exposed at three different T cell to tumor ratios to A549 cells expressing HLA-2 and NYESO. Their ability to kill the tumor cells was assessed. The efficacy of the Ly95 vs Ly95-RISR-RIAD cells were compared.

To study the ability of RISR-RIAD to prevent immunosuppression, the T cells were then exposed at three different T cell to tumor ratios to A549 cells expressing HLA-2 and NYESO. This was done with normal media or with different concentrations of adenosine or PGE2. Their ability to kill the tumor cells over an 18 hrs period was assessed. The efficacy of the Ly95 vs Ly95-RISR-RIAD cells were compared.

Supernatants were collected from each well and used an ELISA to measure Interferon-gamma as a measure of T cell activation.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A composition comprising a nucleic acid molecule comprising a polynucleotide sequence encoding a chimeric antigen receptor and a RIAD polypeptide or a chimeric antigen receptor and an Ezrin polypeptide, wherein expression of the polynucleotide sequence in a cell yields stoichiometric expression of both said chimeric antigen receptor and said RIAD polypeptide, or said chimeric antigen receptor and said Ezrin polypeptide, and wherein said chimeric antigen receptor and said RIAD polypeptide, or said chimeric antigen receptor and said Ezrin polypeptide, are encoded by a single nucleic molecule and are expressed as a single polypeptide separated by one or more peptide cleavage sites.

2. The composition of claim 1, wherein said RIAD polypeptide comprises a RISR subunit or an Ezrin-derived RISR subunit.

3. The composition of claim 2, wherein said RIAD polypeptide comprises a RISR subunit and said RISR subunit comprises a polypeptide having an amino acid sequence having at least 90% identity to SEQ ID NO: 64.

4. The composition of claim 3, wherein said RISR subunit comprises a polypeptide having an amino acid sequence having at least 95% identity to SEQ ID NO: 64.

5. The composition of claim 4, wherein said RISR subunit comprises a polypeptide having an amino acid sequence having SEQ ID NO: 64.

6. The composition of claim 1, wherein said RIAD polypeptide comprises an amino acid sequence having at least 90% identity to the sequence of SEQ ID NO: 63.

7. The composition of claim 6, wherein said RIAD polypeptide comprises an amino acid sequence having at least 95% identity to the sequence of SEQ ID NO: 63.

8. The composition of claim 7, wherein said RIAD polypeptide comprises an amino acid sequence having the sequence of SEQ ID NO: 63.

9. The composition of claim 2, wherein said RIAD polypeptide comprises an amino acid sequence having the sequence of SEQ ID NO: 65.

10. The composition of claim 1, wherein said chimeric antigen receptor comprises an antigen binding domain, a transmembrane domain, and an intracellular domain comprising a costimulatory domain and/or a primary signaling domain.

11. The composition of claim 10, wherein said antigen binding domain binds a tumor antigen.

12. The composition of claim 11, wherein said tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8) aNeu5Ac(2-3)bDGalp(1-4)bDGlcp(1-1)Cer); TNF receptor family member B cell maturation (BCMA); Tn antigen ((Tn Ag) or (GalNAcaSer/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL11Ra); prostate stem cell antigen (PSCA); Protease Serine 21 (Testisin or PRSS21); vascular endothelial growth factor receptor 2 (VEGFR2); Lewis(Y) antigen; CD24; Platelet derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2 M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp 100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NYBR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ES0-1); Cancer/testis antigen 2 (LAGE-1a); Melanoma associated antigen 1 (MAGE-A1); ETS translocation-variant gene 6, located on chromosome 12p (ETV6-AML); sperm protein 17 (SP A1 7); X Antigen Family, Member IA (XAGE1); angiopoietin-binding cell surface receptor 2 (Tie 2); melanoma cancer testis antigen-I (MAD-CT-1); melanoma cancer testis antigen-2 (MAD-CT-2); Fas-related antigen 1; tumor protein p53 (p53); p53 mutant; prostein; surviving; telomerase; prostate carcinoma tumor antigen-I (PCT A-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); NAcetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B 1 (CYPIB 1); CCCTC-Binding Factor (Zinc Finger Protein)Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1);

Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (L Y75); Glypican-3 (GPC3); Fe receptor-like 5 (FCRL5); and immunoglobulin lambda-like polypeptide 1 (IGLL1).

13. The composition of claim 10, wherein said intracellular domain comprises a primary signaling domain and a costimulatory domain.

14. The composition of claim 10, wherein said intracellular domain comprises a primary signaling domain comprising a functional signaling domain of one or more proteins selected from the group consisting of CD3 zeta, CD3 gamma, CD3 delta, CD3 epsilon, common FcR gamma (FCER1G), FcR beta (Fc Epsilon R1b), CD79a, CD79b, Fcgamma RIIa, DAP10, and DAP12.

15. The composition of claim 10, wherein said intracellular domain comprises a costimulatory domain comprising a functional domain of one or more proteins selected from the group consisting of CD27, CD28, 4-1BB (CD137), OX40, CD30, CD40, PD-1, ICOS, lymphocyte function-associated antigen-I (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

16. The composition of claim 10, wherein the antigen binding domain comprises an antibody, an antibody fragment, an scFv, a Fv, a Fab, a (Fab')2, a single domain antibody (SDAB), a VH or VL domain, or a camelid VHH domain.

17. The composition of claim 10, wherein the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7Ra, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

18. The composition of claim 10, wherein the encoded transmembrane domain comprises: an amino acid sequence having at least one, two or three modifications but not more than 20, 10 or 5 modifications of an amino acid sequence of SEQ ID NO: 12, or a sequence with 95-99% identity to an amino acid sequence of SEQ ID NO: 12; or the amino acid sequence of SEQ ID NO: 12.

19. The composition of claim 10, wherein the nucleic acid sequence encoding the transmembrane domain comprises a nucleotide sequence of SEQ ID NO: 13, or a sequence with 95-99% identity thereof.

20. The composition of claim 10, wherein the antigen binding domain is connected to the transmembrane domain by a hinge region, wherein said hinge region nucleic acid encodes an amino acid sequence comprising SEQ ID NO: 6, or a sequence with 95-99% identity thereof; or said hinge region comprises the nucleotide sequence of SEQ ID NO: 7, or a nucleotide sequence with 95-99% identity thereof; or wherein the chimeric antigen receptor comprises a leader region, wherein said leader region encodes an amino acid sequence comprising SEQ ID NO: 2, or a sequence with 95-99% identity thereof, or said leader region comprises the nucleotide sequence of SEQ ID NO: 3, or a nucleotide sequence with 95-99% identity thereof.

21. The composition of claim 10, wherein the encoded intracellular domain comprises the sequence of SEQ ID NO: 14 or SEQ ID NO: 16, and the sequence of SEQ ID NO: 18 or SEQ ID NO: 20, wherein the sequences comprising the intracellular signaling domain are expressed in the same frame and as a single polypeptide chain.

22. The composition of claim 10, wherein the nucleic acid sequence encoding the intracellular signaling domain comprises a sequence of SEQ ID NO:15 or SEQ ID NO: 17, or a sequence with 95-99% identity thereof, and a sequence of SEQ ID NO: 19 or SEQ ID NO:21, or a sequence with 95-99% identity thereof.

23. The composition of claim 1, wherein the encoded chimeric antigen receptor further comprises a leader sequence comprising SEQ ID NO: 2.

24. The composition of claim 1, wherein said chimeric antigen receptor and RIAD polypeptide are encoded by a single nucleic molecule in the same frame and as a single polypeptide chain.

25. The composition of claim 24, wherein said RIAD polypeptide is attached to the N-terminus of said chimeric antigen receptor.

26. The composition of claim 1, wherein said peptide cleavage site is an autocleavage site or a substrate for an intracellular protease.

27. The composition of claim 26, wherein said peptide cleavage site is a T2A site.

28. A vector comprising a polynucleotide sequence encoding a chimeric antigen receptor and a RIAD polypeptide or a chimeric antigen receptor and an Ezrin polypeptide, wherein expression of the polynucleotide sequence in a cell yields stoichiometric expression of both said chimeric antigen receptor and said RIAD polypeptide, or said chimeric antigen receptor and said Ezrin polypeptide, wherein the vector is a DNA vector, an RNA vector, a plasmid, a lentivirus vector, adenoviral vector, or a retrovirus vector, and wherein said chimeric antigen receptor and said RIAD polypeptide, or said chimeric antigen receptor and said Ezrin polypeptide, are encoded by a single nucleic molecule and are expressed as a single polypeptide separated by one or more peptide cleavage sites.

29. The vector of claim 28, wherein the common promoter is a CMV IE gene promoter, an EF-1α promoter, an ubiquitin C promoter, or a phosphoglycerate kinase (PGK) promoter.

30. The vector of claim 29, wherein the EF-1α promoter comprises the sequence of SEQ ID NO: 1.

31. The vector of claim 28, wherein the vector is an in vitro transcribed vector, or the vector further comprises a poly(A) tail or a 3'UTR.

32. An immune effector cell comprising the nucleic acid molecule of claim 1.

33. The cell of claim 32, wherein the immune effector cell is a human T cell or a human NK cell.

34. A method of making a chimeric antigen receptor and RIAD polypeptide-expressing or Ezrin polypeptide-expressing immune effector cell, comprising introducing the vector of claim 28, into an immune effector cell, under conditions such that the chimeric antigen receptor molecule is expressed.

35. The method of claim 34, further comprising:

providing a population of immune effector cells; and removing T regulatory cells from the population, thereby providing a population of T regulatory-depleted cells;

wherein steps a) and b) are performed prior to introducing the vector to the population.

36. The method of claim 35, wherein the T regulatory cells are removed from the cell population using an anti-CD25 antibody, or an anti-GITR antibody.

37. A method of providing anti-tumor immunity in a subject comprising administering to the subject an effective amount of the immune effector cell of claim 32, wherein the cell is an autologous T cell or an allogeneic T cell, or an autologous T cell or an allogeneic NK cell.

38. The method of claim 37, wherein the allogeneic T cell or allogeneic NK cell lacks expression or has low expression of a functional TCR or a functional HLA.

39. A method of treating a subject having a disease associated with expression of a tumor antigen, comprising administering to the subject an effective amount of an immune effector cell of claim 32, thereby treating the subject.

40. The method of claim 39, said method further comprising administering an agent that increases the efficacy of the immune effector cell, thereby treating the subject.

41. The method of claim 40, wherein said agent is one or more of:

a protein phosphatase inhibitor;

a kinase inhibitor;

a cytokine;

an inhibitor of an immune inhibitory molecule; or an agent that decreases the level or activity of a TREG cell.

42. The method of claim 39, wherein the disease associated with expression of the tumor antigen is selected from the group consisting of a proliferative disease, a precancerous condition, a cancer, and a non-cancer related indication associated with expression of the tumor antigen.

43. The method of claim 42, wherein the cancer is a hematologic cancer, wherein the cancer is one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia.

44. The method of claim 43, wherein the cancer is selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

45. The composition of claim 1, wherein said RIAD polypeptide comprises a polypeptide having an amino acid sequence of SEQ ID NO: 77.

46. The composition of claim 1, wherein said Ezrin polypeptide comprises an amino acid sequence having at least 90% identity to the sequence of SEQ ID NO: 108, or an amino acid sequence having the sequence of SEQ ID NO: 108.

* * * * *

SEQUENCE LISTING

```
<160> NUMBER OF SEQ ID NOS: 112

<210> SEQ ID NO 1
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
```

-continued

```
cgtgaggctc cggtgcccgt cagtgggcag agcgcacatc gcccacagtc cccgagaagt     60

tggggggagg ggtcggcaat tgaaccggtg cctagagaag gtggcgcggg gtaaactggg    120

aaagtgatgt cgtgtactgg ctccgccttt ttcccgaggg tgggggagaa ccgtatataa    180

gtgcagtagt cgccgtgaac gttctttttc gcaacgggtt tgccgccaga acacaggtaa    240

gtgccgtgtg tggttcccgc gggcctggcc tctttacggg ttatggccct tgcgtgcctt    300

gaattacttc cacctggctg cagtacgtga ttcttgatcc cgagcttcgg gttggaagtg    360

ggtgggagag ttcgaggcct tgcgcttaag gagccccttc gcctcgtgct tgagttgagg    420

cctggcctgg gcgctggggc cgccgcgtgc gaatctggtg gcaccttcgc gcctgtctcg    480

ctgctttcga taagtctcta gccatttaaa atttttgatg acctgctgcg acgctttttt    540

tctggcaaga tagtcttgta aatgcgggcc aagatctgca cactggtatt tcggtttttg    600

gggccgcggg cggcgacggg gcccgtgcgt cccagcgcac atgttcggcg aggcggggcc    660

tgcgagcgcg gccaccgaga atcggacggg ggtagtctca agctggccgg cctgctctgg    720

tgcctggcct cgcgccgccg tgtatcgccc cgccctgggc ggcaaggctg gcccggtcgg    780

caccagttgc gtgagcggaa agatggccgc ttcccggccc tgctgcaggg agctcaaaat    840

ggaggacgcg gcgctcggga gagcgggcgg gtgagtcacc cacacaaagg aaaagggcct    900

ttccgtcctc agccgtcgct tcatgtgact ccacggagta ccgggcgccg tccaggcacc    960

tcgattagtt ctcgagcttt tggagtacgt cgtctttagg ttggggggag gggttttatg   1020

cgatggagtt tccccacact gagtgggtgg agactgaagt taggccagct tggcacttga   1080

tgtaattctc cttggaattt gccctttttg agtttggatc ttggttcatt ctcaagcctc   1140

agacagtggt tcaaagtttt tttcttccat ttcaggtgtc gtga                    1184
```

<210> SEQ ID NO 2
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 2

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 3
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3

```
atggccctgc ctgtgacagc cctgctgctg cctctggctc tgctgctgca tgccgctaga     60

ccc                                                                   63
```

<210> SEQ ID NO 4
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 5
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5

```
accacgacgc cagcgccgcg accaccaaca ccggcgccca ccatcgcgtc gcagcccctg     60

tccctgcgcc cagaggcgtg ccggccagcg gcggggggcg cagtgcacac gagggggctg    120

gacttcgcct gtgat                                                     135
```

<210> SEQ ID NO 6
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175
```

-continued

```
Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230


<210> SEQ ID NO 7
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

gagagcaagt acggccctcc ctgccccccct tgccctgccc ccgagttcct gggcggaccc      60

agcgtgttcc tgttcccccc caagcccaag gacaccctga tgatcagccg gacccccgag     120

gtgacctgtg tggtggtgga cgtgtcccag gaggaccccg aggtccagtt caactggtac     180

gtggacggcg tggaggtgca caacgccaag accaagcccc gggaggagca gttcaatagc     240

acctaccggg tggtgtccgt gctgaccgtg ctgcaccagg actggctgaa cggcaaggaa     300

tacaagtgta aggtgtccaa caagggcctg cccagcagca tcgagaaaac catcagcaag     360

gccaagggcc agcctcggga gccccaggtg tacaccctgc cccctagcca agaggagatg     420

accaagaacc aggtgtccct gacctgcctg gtgaagggct tctaccccag cgacatcgcc     480

gtggagtggg agagcaacgg ccagcccgag aacaactaca agaccacccc ccctgtgctg     540

gacagcgacg gcagcttctt cctgtacagc cggctgaccg tggacaagag ccggtggcag     600

gagggcaacg tctttagctg ctccgtgatg cacgaggccc tgcacaacca ctacacccag     660

aagagcctga gcctgtccct gggcaagatg                                      690


<210> SEQ ID NO 8
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
```

```
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280


<210> SEQ ID NO 9
<211> LENGTH: 847
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9

aggtggcccg aaagtcccaa ggcccaggca tctagtgttc ctactgcaca gccccaggca     60

gaaggcagcc tagccaaagc tactactgca cctgccacta cgcgcaatac tggccgtggc    120

ggggaggaga agaaaaagga gaaagagaaa gaagaacagg aagagaggga gaccaagacc    180

cctgaatgtc catcccatac ccagccgctg ggcgtctatc tcttgactcc cgcagtacag    240

gacttgtggc ttagagataa ggccaccttt acatgtttcg tcgtgggctc tgacctgaag    300

gatgcccatt tgacttggga ggttgccgga aaggtaccca caggggggt tgaggaaggg    360

ttgctggagc gccattccaa tggctctcag agccagcact caagactcac ccttccgaga    420

tccctgtgga acgccgggac ctctgtcaca tgtactctaa atcatcctag cctgcccccca    480

cagcgtctga tggcccttag agagccagcc gcccaggcac cagttaagct tagcctgaat    540

ctgctcgcca gtagtgatcc cccagaggcc gccagctggc tcttatgcga agtgtccggc    600

tttagcccgc ccaacatctt gctcatgtgg ctggaggacc agcgagaagt gaacaccagc    660

ggcttcgctc cagcccggcc cccaccccag ccgggttcta ccacattctg ggcctggagt    720

gtcttaaggg tcccagcacc acctagcccc cagccagcca catacacctg tgttgtgtcc    780

catgaagata gcaggaccct gctaaatgct tctaggagtc tggaggtttc ctacgtgact    840

gaccatt                                                              847


<210> SEQ ID NO 10
```

<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 10

Gly Gly Gly Gly Ser Gly Gly Gly Gly Ser
1 5 10

<210> SEQ ID NO 11
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 11
ggtggcggag gttctggagg tggaggttcc 30

<210> SEQ ID NO 12
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 12

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 13
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 13
atctacatct gggcgccctt ggccgggact tgtggggtcc ttctcctgtc actggttatc 60
accctttact gc 72

<210> SEQ ID NO 14
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

-continued

Pro Glu Glu Glu Glu Gly Gly Cys Glu Leu
35 40

<210> SEQ ID NO 15
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 16
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

Gln Arg Arg Lys Tyr Arg Ser Asn Lys Gly Glu Ser Pro Val Glu Pro
1 5 10 15

Ala Glu Pro Cys Arg Tyr Ser Cys Pro Arg Glu Glu Glu Gly Ser Thr
20 25 30

Ile Pro Ile Gln Glu Asp Tyr Arg Lys Pro Glu Pro Ala Cys Ser Pro
35 40 45

<210> SEQ ID NO 17
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 18
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys

```
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 19
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19

```
agagtgaagt tcagcaggag cgcagacgcc cccgcgtaca agcagggcca gaaccagctc      60

tataacgagc tcaatctagg acgaagagag gagtacgatg ttttggacaa gagacgtggc     120

cgggaccctg agatgggggg aaagccgaga aggaagaacc ctcaggaagg cctgtacaat     180

gaactgcaga aagataagat ggcggaggcc tacagtgaga ttgggatgaa aggcgagcgc     240

cggaggggca aggggcacga tggcctttac cagggtctca gtacagccac caaggacacc     300

tacgacgccc ttcacatgca ggccctgccc cctcgc                               336
```

<210> SEQ ID NO 20
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 21
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 21
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 22

Gly Gly Gly Gly Ser
1 5

<210> SEQ ID NO 23
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 23
ggtggcggag gttctggagg tggaggttcc 30

<210> SEQ ID NO 24
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

Pro Gly Trp Phe Leu Asp Ser Pro Asp Arg Pro Trp Asn Pro Pro Thr
1 5 10 15

Phe Ser Pro Ala Leu Leu Val Val Thr Glu Gly Asp Asn Ala Thr Phe
20 25 30

Thr Cys Ser Phe Ser Asn Thr Ser Glu Ser Phe Val Leu Asn Trp Tyr
35 40 45

Arg Met Ser Pro Ser Asn Gln Thr Asp Lys Leu Ala Ala Phe Pro Glu
50 55 60

Asp Arg Ser Gln Pro Gly Gln Asp Cys Arg Phe Arg Val Thr Gln Leu
65 70 75 80

Pro Asn Gly Arg Asp Phe His Met Ser Val Val Arg Ala Arg Arg Asn
85 90 95

Asp Ser Gly Thr Tyr Leu Cys Gly Ala Ile Ser Leu Ala Pro Lys Ala
100 105 110

Gln Ile Lys Glu Ser Leu Arg Ala Glu Leu Arg Val Thr Glu Arg Arg

```
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 25
<211> LENGTH: 450
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

```
cccggatggt ttctggactc tccggatcgc ccgtggaatc ccccaacctt ctcaccggca     60

ctcttggttg tgactgaggg cgataatgcg accttcacgt gctcgttctc caacacctcc    120

gaatcattcg tgctgaactg gtaccgcatg agcccgtcaa accagaccga caagctcgcc    180

gcgtttccgg aagatcggtc gcaaccggga caggattgtc ggttccgcgt gactcaactg    240

ccgaatggca gagacttcca catgagcgtg gtccgcgcta ggcgaaacga ctccgggacc    300

tacctgtgcg gagccatctc gctggcgcct aaggcccaaa tcaaagagag cttgagggcc    360

gaactgagag tgaccgagcg cagagctgag gtgccaactg cacatccatc cccatcgcct    420

cggcctgcgg ggcagtttca gaccctggtc                                     450
```

<210> SEQ ID NO 26
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Leu Cys Gly Ala Ile Ser
        115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
```

-continued

```
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205

Arg Gly Leu Asp Phe Ala Cys Asp Ile Tyr Ile Trp Ala Pro Leu Ala
    210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
            260                 265                 270

Pro Glu Glu Glu Glu Gly Gly Cys Glu Leu Arg Val Lys Phe Ser Arg
        275                 280                 285

Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390
```

<210> SEQ ID NO 27
<211> LENGTH: 1182
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27

```
atggccctcc ctgtcactgc cctgcttctc cccctcgcac tcctgctcca cgccgctaga     60

ccacccggat ggtttctgga ctctccggat cgcccgtgga atcccccaac cttctcaccg    120

gcactcttgg ttgtgactga gggcgataat gcgaccttca cgtgctcgtt ctccaacacc    180

tccgaatcat tcgtgctgaa ctggtaccgc atgagcccgt caaaccagac cgacaagctc    240

gccgcgtttc cggaagatcg gtcgcaaccg ggacaggatt gtcggttccg cgtgactcaa    300

ctgccgaatg gcagagactt ccacatgagc gtggtccgcg ctaggcgaaa cgactccggg    360

acctacctgt gcggagccat ctcgctggcg cctaaggccc aaatcaaaga gagcttgagg    420

gccgaactga gagtgaccga gcgcagagct gaggtgccaa ctgcacatcc atccccatcg    480

cctcggcctg cggggcagtt tcagaccctg gtcacgacca ctccggcgcc gcgcccaccg    540

actccggccc caactatcgc gagccagccc ctgtcgctga ggccggaagc atgccgccct    600

gccgccggag gtgctgtgca tacccgggga ttggacttcg catgcgacat ctacatttgg    660

gctcctctcg ccggaacttg tggcgtgctc cttctgtccc tggtcatcac cctgtactgc    720
```

```
aagcggggtc ggaaaaagct tctgtacatt ttcaagcagc ccttcatgag gcccgtgcaa    780

accacccagg aggaggacgg ttgctcctgc cggttccccg aagaggaaga aggaggttgc    840

gagctgcgcg tgaagttctc ccggagcgcc gacgcccccg cctataagca gggccagaac    900

cagctgtaca acgaactgaa cctgggacgg cgggaagagt acgatgtgct ggacaagcgg    960

cgcggccggg accccgaaat gggcgggaag cctagaagaa agaaccctca ggaaggcctg   1020

tataacgagc tgcagaagga caagatggcc gaggcctact ccgaaattgg gatgaaggga   1080

gagcggcgga ggggaaaggg gcacgacggc ctgtaccaag gactgtccac cgccaccaag   1140

gacacatacg atgccctgca catgcaggcc cttccccctc gc                      1182


<210> SEQ ID NO 28
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(40)
<223> OTHER INFORMATION: /note="This sequence may encompass 1-10 'Gly
      Gly Gly Ser' repeating units, wherein some positions may be
      absent"
<220> FEATURE:
<221> NAME/KEY: source
<223> OTHER INFORMATION: /note="See specification as filed for detailed
      description of substitutions and preferred embodiments"

<400> SEQUENCE: 28

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40


<210> SEQ ID NO 29
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Gly Gly Gly Ser Gly Gly Gly Gly Ser Gly Gly Gly Gly Ser Gly
1               5                   10                  15

Gly Gly Gly Ser
            20


<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Gly Gly Gly Ser Gly Gly Gly Gly Ser Gly Gly Gly Gly Ser
```

-continued 1 5 10 15

<210> SEQ ID NO 31
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 31

Gly Gly Gly Ser
1

<210> SEQ ID NO 32
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(2000)
<223> OTHER INFORMATION: /note="This sequence may encompass 50-2000 nucleotides"
<220> FEATURE:
<221> NAME/KEY: source
<223> OTHER INFORMATION: /note="See specification as filed for detailed description of substitutions and preferred embodiments"

<400> SEQUENCE: 32
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260

```
aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaaaaaaa aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaaaaaaaa aaaaaaaaaa aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaaaaaa aaaaaaaaaa   1800

aaaaaaaaaa aaaaaaaaaa aaaaaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaaaaa aaaaaaaaaa                                               2000


<210> SEQ ID NO 33
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa                                     150


<210> SEQ ID NO 34
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 50-5000
      nucleotides"
<220> FEATURE:
<221> NAME/KEY: source
<223> OTHER INFORMATION: /note="See specification as filed for detailed
      description of substitutions and preferred embodiments"

<400> SEQUENCE: 34

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa aaaaaaaaaa aaaaaaaaaa    420
```

-continued

```
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
```

-continued aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 35
<211> LENGTH: 100

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
tttttttttt tttttttttt tttttttttt tttttttttt tttttttttt tttttttttt 60
tttttttttt tttttttttt tttttttttt tttttttttt 100

<210> SEQ ID NO 36
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 50-5000
      nucleotides"
<220> FEATURE:
<221> NAME/KEY: source
<223> OTHER INFORMATION: /note="See specification as filed for detailed
      description of substitutions and preferred embodiments"

<400> SEQUENCE: 36
tttttttttt tttttttttt tttttttttt tttttttttt tttttttttt tttttttttt 60
tttttttttt tttttttttt tttttttttt tttttttttt tttttttttt tttttttttt 120
tttttttttt tttttttttt tttttttttt tttttttttt tttttttttt tttttttttt 180
tttttttttt tttttttttt tttttttttt tttttttttt tttttttttt tttttttttt 240
tttttttttt tttttttttt tttttttttt tttttttttt tttttttttt tttttttttt 300
tttttttttt tttttttttt tttttttttt tttttttttt tttttttttt tttttttttt 360
tttttttttt tttttttttt tttttttttt tttttttttt tttttttttt tttttttttt 420
tttttttttt tttttttttt tttttttttt tttttttttt tttttttttt tttttttttt 480
tttttttttt tttttttttt tttttttttt tttttttttt tttttttttt tttttttttt 540
tttttttttt tttttttttt tttttttttt tttttttttt tttttttttt tttttttttt 600
tttttttttt tttttttttt tttttttttt tttttttttt tttttttttt tttttttttt 660
tttttttttt tttttttttt tttttttttt tttttttttt tttttttttt tttttttttt 720
tttttttttt tttttttttt tttttttttt tttttttttt tttttttttt tttttttttt 780
tttttttttt tttttttttt tttttttttt tttttttttt tttttttttt tttttttttt 840
tttttttttt tttttttttt tttttttttt tttttttttt tttttttttt tttttttttt 900
tttttttttt tttttttttt tttttttttt tttttttttt tttttttttt tttttttttt 960
tttttttttt tttttttttt tttttttttt tttttttttt tttttttttt tttttttttt 1020
tttttttttt tttttttttt tttttttttt tttttttttt tttttttttt tttttttttt 1080
tttttttttt tttttttttt tttttttttt tttttttttt tttttttttt tttttttttt 1140
tttttttttt tttttttttt tttttttttt tttttttttt tttttttttt tttttttttt 1200
tttttttttt tttttttttt tttttttttt tttttttttt tttttttttt tttttttttt 1260
tttttttttt tttttttttt tttttttttt tttttttttt tttttttttt tttttttttt 1320
tttttttttt tttttttttt tttttttttt tttttttttt tttttttttt tttttttttt 1380

-continued tttttttttt tttttttttt tttttttttt tttttttttt tttttttttt tttttttttt 1440
tttttttttt tttttttttt tttttttttt tttttttttt tttttttttt tttttttttt 1500
tttttttttt tttttttttt tttttttttt tttttttttt tttttttttt tttttttttt 1560
tttttttttt tttttttttt tttttttttt tttttttttt tttttttttt tttttttttt 1620
tttttttttt tttttttttt tttttttttt tttttttttt tttttttttt tttttttttt 1680
tttttttttt tttttttttt tttttttttt tttttttttt tttttttttt tttttttttt 1740
tttttttttt tttttttttt tttttttttt tttttttttt tttttttttt tttttttttt 1800
tttttttttt tttttttttt tttttttttt tttttttttt tttttttttt tttttttttt 1860
tttttttttt tttttttttt tttttttttt tttttttttt tttttttttt tttttttttt 1920
tttttttttt tttttttttt tttttttttt tttttttttt tttttttttt tttttttttt 1980
tttttttttt tttttttttt tttttttttt tttttttttt tttttttttt tttttttttt 2040
tttttttttt tttttttttt tttttttttt tttttttttt tttttttttt tttttttttt 2100
tttttttttt tttttttttt tttttttttt tttttttttt tttttttttt tttttttttt 2160
tttttttttt tttttttttt tttttttttt tttttttttt tttttttttt tttttttttt 2220
tttttttttt tttttttttt tttttttttt tttttttttt tttttttttt tttttttttt 2280
tttttttttt tttttttttt tttttttttt tttttttttt tttttttttt tttttttttt 2340
tttttttttt tttttttttt tttttttttt tttttttttt tttttttttt tttttttttt 2400
tttttttttt tttttttttt tttttttttt tttttttttt tttttttttt tttttttttt 2460
tttttttttt tttttttttt tttttttttt tttttttttt tttttttttt tttttttttt 2520
tttttttttt tttttttttt tttttttttt tttttttttt tttttttttt tttttttttt 2580
tttttttttt tttttttttt tttttttttt tttttttttt tttttttttt tttttttttt 2640
tttttttttt tttttttttt tttttttttt tttttttttt tttttttttt tttttttttt 2700
tttttttttt tttttttttt tttttttttt tttttttttt tttttttttt tttttttttt 2760
tttttttttt tttttttttt tttttttttt tttttttttt tttttttttt tttttttttt 2820
tttttttttt tttttttttt tttttttttt tttttttttt tttttttttt tttttttttt 2880
tttttttttt tttttttttt tttttttttt tttttttttt tttttttttt tttttttttt 2940
tttttttttt tttttttttt tttttttttt tttttttttt tttttttttt tttttttttt 3000
tttttttttt tttttttttt tttttttttt tttttttttt tttttttttt tttttttttt 3060
tttttttttt tttttttttt tttttttttt tttttttttt tttttttttt tttttttttt 3120
tttttttttt tttttttttt tttttttttt tttttttttt tttttttttt tttttttttt 3180
tttttttttt tttttttttt tttttttttt tttttttttt tttttttttt tttttttttt 3240
tttttttttt tttttttttt tttttttttt tttttttttt tttttttttt tttttttttt 3300
tttttttttt tttttttttt tttttttttt tttttttttt tttttttttt tttttttttt 3360
tttttttttt tttttttttt tttttttttt tttttttttt tttttttttt tttttttttt 3420
tttttttttt tttttttttt tttttttttt tttttttttt tttttttttt tttttttttt 3480
tttttttttt tttttttttt tttttttttt tttttttttt tttttttttt tttttttttt 3540
tttttttttt tttttttttt tttttttttt tttttttttt tttttttttt tttttttttt 3600
tttttttttt tttttttttt tttttttttt tttttttttt tttttttttt tttttttttt 3660
tttttttttt tttttttttt tttttttttt tttttttttt tttttttttt tttttttttt 3720

-continued tttttttttt tttttttttt tttttttttt tttttttttt tttttttttt tttttttttt 3780
tttttttttt tttttttttt tttttttttt tttttttttt tttttttttt tttttttttt 3840
tttttttttt tttttttttt tttttttttt tttttttttt tttttttttt tttttttttt 3900
tttttttttt tttttttttt tttttttttt tttttttttt tttttttttt tttttttttt 3960
tttttttttt tttttttttt tttttttttt tttttttttt tttttttttt tttttttttt 4020
tttttttttt tttttttttt tttttttttt tttttttttt tttttttttt tttttttttt 4080
tttttttttt tttttttttt tttttttttt tttttttttt tttttttttt tttttttttt 4140
tttttttttt tttttttttt tttttttttt tttttttttt tttttttttt tttttttttt 4200
tttttttttt tttttttttt tttttttttt tttttttttt tttttttttt tttttttttt 4260
tttttttttt tttttttttt tttttttttt tttttttttt tttttttttt tttttttttt 4320
tttttttttt tttttttttt tttttttttt tttttttttt tttttttttt tttttttttt 4380
tttttttttt tttttttttt tttttttttt tttttttttt tttttttttt tttttttttt 4440
tttttttttt tttttttttt tttttttttt tttttttttt tttttttttt tttttttttt 4500
tttttttttt tttttttttt tttttttttt tttttttttt tttttttttt tttttttttt 4560
tttttttttt tttttttttt tttttttttt tttttttttt tttttttttt tttttttttt 4620
tttttttttt tttttttttt tttttttttt tttttttttt tttttttttt tttttttttt 4680
tttttttttt tttttttttt tttttttttt tttttttttt tttttttttt tttttttttt 4740
tttttttttt tttttttttt tttttttttt tttttttttt tttttttttt tttttttttt 4800
tttttttttt tttttttttt tttttttttt tttttttttt tttttttttt tttttttttt 4860
tttttttttt tttttttttt tttttttttt tttttttttt tttttttttt tttttttttt 4920
tttttttttt tttttttttt tttttttttt tttttttttt tttttttttt tttttttttt 4980
tttttttttt tttttttttt 5000

<210> SEQ ID NO 37
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: misc_feature
<222> LOCATION: (1)..(5000)
<223> OTHER INFORMATION: /note="This sequence may encompass 100-5000
nucleotides"
<220> FEATURE:
<221> NAME/KEY: source
<223> OTHER INFORMATION: /note="See specification as filed for detailed
description of substitutions and preferred embodiments"

<400> SEQUENCE: 37
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420

-continued

```
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
```

aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 38
<211> LENGTH: 400
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(400)
<223> OTHER INFORMATION: /note="This sequence may encompass 100-400 nucleotides"
<220> FEATURE:
<221> NAME/KEY: source
<223> OTHER INFORMATION: /note="See specification as filed for detailed description of substitutions and preferred embodiments"

<400> SEQUENCE: 38

```
aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa                          400
```

<210> SEQ ID NO 39
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190
```

```
Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370
```

<210> SEQ ID NO 40
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 40

```
atggacttcc aggttcagat cttttcgttc ctgctgatca gcgcctctgt tatcatgtcg     60

cgcggcgaca tccagatgac ccagtcccct tcctccctct ctgcctctgt gggagaccgc    120

gttaccatca catgccgagc ttcccaggac gtgaacacag ccgtggcctg gtaccagcag    180

aagcccggga aggcacccaa actcctcatc tactccgcct ccttcctata cagtggcgtg    240

ccttcccgat tctccggctc caggagtggc acggacttta cgctcaccat tagtagcctg    300

cagcccgaag acttcgcgac ctactattgt cagcaacact acacgacgcc accaactttc    360

ggccagggta ccaaggtcga gattaagcga accggcagta ccagtgggtc tggcaagccc    420

ggcagcggcg agggatccga ggtccagctg gtcgagtccg gcgggggcct ggtgcagccg    480

ggcggctcgc tgaggttatc ttgcgccgcc agtggcttca acatcaagga tacttacatc    540

cactgggtga ggcaggctcc gggcaagggc ctggaatggg tggctaggat ctaccctact    600

aacgggtaca cacgctacgc agattcggtg aaaggccgct tcactatctc cgccgacacc    660

tcgaagaaca ctgcttacct gcagatgaac tccctcaggg ccgaagatac tgcagtctac    720

tactgctccc gctggggtgg ggacggcttc tacgccatgg acgtgtgggg tcagggcact    780

ctagttacag tgtcatccac cacgacgcca gcgccgcgac caccaacacc ggcgcccacc    840

atcgcgtcgc agcccctgtc cctgcgccca gaggcgtgcc ggccagcggc ggggggcgca    900

gtgcacacga gggggctgga cttcgcctgt gatatctaca tctgggcgcc cttggccggg    960
```

```
acttgtgggg tccttctcct gtcactggtt atcacccttt actgcaaacg gggcagaaag   1020
aaactcctgt atatattcaa acaaccattt atgagaccag tacaaactac tcaagaggaa   1080
gatggctgta gctgccgatt tccagaagaa gaagaaggag gatgtgaact gagagtgaag   1140
ttcagcagga gcgcagacgc ccccgcgtac aagcagggcc agaaccagct ctataacgag   1200
ctcaatctag gacgaagaga ggagtacgac gttttggaca agagacgtgg ccgggaccct   1260
gagatggggg gaaagccgag aaggaagaac cctcaggaag gcctgtacaa tgaactgcag   1320
aaagataaga tggcggaggc ctacagtgag attgggatga aaggcgagcg ccggaggggc   1380
aaggggcacg atggccttta ccagggtctc agtacagcca ccaaggacac ctacgacgcc   1440
cttcacatgc aggccctgcc ccctcgctaa                                  1470
```

<210> SEQ ID NO 41
<211> LENGTH: 2268
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 41

```
atggacttcc aggttcagat cttttcgttc ctgctgatca gcgcctctgt tatcatgtcg     60
cgcggcgaca tccagatgac ccagtcccct tcctccctct ctgcctctgt gggagaccgc    120
gttaccatca catgccgagc ttcccaggac gtgaacacag ccgtggcctg gtaccagcag    180
aagcccggga aggcacccaa actcctcatc tactccgcct ccttcctaga gagtggcgtg    240
ccttcccgat tctccggctc cggcagtggc acggacttta cgctcaccat tagtagcctg    300
cagcccgaag acttcgcgac ctactattgt cagcaacact acacgacgcc accaactttc    360
ggccagggta ccaaggtcga gattaagcga accggcagta ccagtgggtc tggcaagccc    420
ggcagcggcg agggatccga ggtccagctg gtcgagtccg gcgggggcct ggtgcagccg    480
ggcggctcgc tgaggttatc ttgcgccgcc agtggcttca acatcaagga tacttacatc    540
cactgggtga ggcaggctcc gggcaagggc ctggaatggg tggctaggat ctaccctact    600
aacgggtaca cacgctacgc agattcggtg aaaggccgct tcactatctc cagggacgac    660
tcgaagaaca ctctgtacct gcagatgaac tccctcaggg ccgaagatac tgcagtctac    720
tactgcgccc gctggggtgg ggacggcttc gtagccatgg acgtgtgggg tcagggcact    780
ctagttacag tgtcatccac cacgacgcca gcgccgcgac caccaacacc ggcgcccacc    840
atcgcgtcgc agcccctgtc cctgcgccca gaggcgtgcc ggccagcggc ggggggcgca    900
gtgcacacga gggggctgga cttcgcctgt gatatctaca tctgggcgcc cttggccggg    960
acttgtgggg tccttctcct gtcactggtt atcacccttt actgcaaacg gggcagaaag   1020
aaactcctgt atatattcaa acaaccattt atgagaccag tacaaactac tcaagaggaa   1080
gatggctgta gctgccgatt tccagaagaa gaagaaggag gatgtgaact gagaatggac   1140
ttccaggttc agatcttttc gttcctgctg atcagcgcct ctgttatcat gtcgcgcggc   1200
gacatccaga tgacccagtc cccttcctcc ctctctgcct ctgtgggaga ccgcgttacc   1260
atcacatgcc gagcttccca ggacgtgaac acagccgtgg cctggtacca gcagaagccc   1320
gggaaggcac ccaaactcct catctactcc gcctccttcc tagagagtgg cgtgccttcc   1380
cgattctccg gctccggcag tggcacggac tttacgctca ccattagtag cctgcagccc   1440
```

gaagacttcg cgacctacta ttgtcagcaa cactacacga cgccaccaac tttcggccag 1500
ggtaccaagg tcgagattaa gcgaaccggc agtaccagtg ggtctggcaa gcccggcagc 1560
ggcgagggat ccgaggtcca gctggtcgag tccggcgggg gcctggtgca gccgggcggc 1620
tcgctgaggt tatcttgcgc cgccagtggc ttcaacatca aggatactta catccactgg 1680
gtgaggcagg ctccgggcaa gggcctggaa tgggtggcta ggatctaccc tactaacggg 1740
tacacacgct acgcagattc ggtgaaaggc cgcttcacta tctccaggga cgactcgaag 1800
aacactctgt acctgcagat gaactccctc agggccgaag atactgcagt ctactactgc 1860
gcccgctggg gtggggacgg cttcgtagcc atggacgtgt ggggtcaggg cactctagtt 1920
acagtgtcat ccgtgaagtt cagcaggagc gcagacgccc ccgcgtacaa gcagggccag 1980
aaccagctct ataacgagct caatctagga cgaagagagg agtacgacgt tttggacaag 2040
agacgtggcc gggaccctga gatgggggga aagccgagaa ggaagaaccc tcaggaaggc 2100
ctgtacaatg aactgcagaa agataagatg gcggaggcct acagtgagat tgggatgaaa 2160
ggcgagcgcc ggaggggcaa ggggcacgat ggcctttacc agggtctcag tacagccacc 2220
aaggacacct acgacgccct tcacatgcag gccctgcccc ctcgctaa 2268

<210> SEQ ID NO 42
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 42
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgatatcta catctgggcg cccttggccg ggacttgtgg ggtccttctc 180
ctgtcactgg ttatcaccct ttactgcaaa cggggcagaa agaaactcct gtatatattc 240
aaacaaccat ttatgagacc agtacaaact actcaagagg aagatggctg tagctgccga 300
tttccagaag aagaaatgga cttccaggtt cagatctttt cgttcctgct gatcagcgcc 360
tctgttatca tgtcgcgcgg cgacatccag atgacccagt ccccttcctc cctctctgcc 420
tctgtgggag accgcgttac catcacatgc cgagcttccc aggacgtgaa cacagccgtg 480
gcctggtacc agcagaagcc cgggaaggca cccaaactcc tcatctactc cgcctccttc 540
ctagagagtg gcgtgccttc ccgattctcc ggctccggca gtggcacgga ctttacgctc 600
accattagta gcctgcagcc cgaagacttc gcgacctact attgtcagca acactacacg 660
acgccaccaa ctttcggcca gggtaccaag gtcgagatta agcgaaccgg cagtaccagt 720
gggtctggca agcccggcag cggcgaggga tccgaggtcc agctggtcga gtccggcggg 780
ggcctggtgc agccgggcgg ctcgctgagg ttatcttgcg ccgccagtgg cttcaacatc 840
aaggatactt acatccactg ggtgaggcag gctccgggca agggcctgga atgggtggct 900
aggatctacc ctactaacgg gtacacacgc tacgcagatt cggtgaaagg ccgcttcact 960
atctccgccg acacctcgaa gaacactgct tacctgcaga tgaactccct cagggccgaa 1020
gatactgcag tctactactg ctcccgctgg ggtggggacg gcttcgtagc catggacgtg 1080
tggggtcagg gcactctagt tacagtgtca tccgaaggag gatgtgaact gagagtgaag 1140
ttcagcagga gcgcagacgc ccccgcgtac aagcagggcc agaaccagct ctataacgag 1200
ctcaatctag gacgaagaga ggagtacgac gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgctaa 1470

<210> SEQ ID NO 43
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43
atggacttcc aggttcagat cttttcgttc ctgctgatca gcgcctctgt tatcatgtcg 60
cgcggcgaca tccagatgac ccagtcccct tcctccctct ctgcctctgt gggagaccgc 120
gttaccatca catgccgagc ttcccaggac gtgaacacag ccgtggcctg gtaccagcag 180
aagcccggga aggcacccaa actcctcatc tactccgcct ccttcctaga gagtggcgtg 240
ccttcccgat tctccggctc caggagtggc acggacttta cgctcaccat tagtagcctg 300
cagcccgaag acttcgcgac ctactattgt cagcaacact acacgacgcc accaactttc 360
ggccagggta ccaaggtcga gattaagcga accggcagta ccagtgggtc tggcaagccc 420
ggcagcggcg agggatccga ggtccagctg gtcgagtccg gcgggggcct ggtgcagccg 480
ggcggctcgc tgaggttatc ttgcgccgcc agtggcttca acatcaagga tacttacatc 540
cactgggtga ggcaggctcc gggcaagggc ctggaatggg tggctaggat ctaccctact 600
aacgggtaca cacgctacgc agattcggtg aaaggccgct tcactatctc cgccgacacc 660
tcgaagaaca ctgcttacct gcagatgaac tccctcaggg ccgaagatac tgcagtctac 720
tactgctccc gctggggtgg ggacggcttc gtagccatgg acgtgtgggg tcagggcact 780
ctagttacag tgtcatccac cacgacgcca gcgccgcgac caccaacacc ggcgcccacc 840
atcgcgtcgc agcccctgtc cctgcgccca gaggcgtgcc ggccagcggc ggggggcgca 900
gtgcacacga gggggctgga cttcgcctgt gatatctaca tctgggcgcc cttggccggg 960
acttgtgggg tccttctcct gtcactggtt atcacccttt actgcaaacg gggcagaaag 1020
aaactcctgt atatattcaa acaaccattt atgagaccag tacaaactac tcaagaggaa 1080
gatggctgta gctgccgatt tccagaagaa gaagaaggag gatgtgaact gagagtgaag 1140
ttcagcagga gcgcagacgc ccccgcgtac aagcagggcc agaaccagct ctataacgag 1200
ctcaatctag gacgaagaga ggagtacgac gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgctaa 1470

<210> SEQ ID NO 44
<211> LENGTH: 1392
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 44

```
atggacttcc aggttcagat cttttcgttc ctgctgatca gcgcctctgt tatcatgtcg     60

cgcggcgaca tccagatgac ccagtcccct tcctccctct ctgcctctgt gggagaccgc    120

gttaccatca catgccgagc ttcccaggac gtgaacacag ccgtggcctg gtaccagcag    180

aagcccggga aggcacccaa actcctcatc tactccgcct ccttcctaga gagtggcgtg    240

ccttcccgat tctccggctc caggagtggc acggacttta cgctcaccat tagtagcctg    300

cagcccgaag acttcgcgac ctactattgt cagcaacact acacgacgcc accaactttc    360

ggccagggta ccaaggtcga gattaagcga accggcagta ccagtgggtc tggcaagccc    420

ggcagcggcg agggatccga ggtccagctg gtcgagtccg gcgggggcct ggtgcagccg    480

ggcggctcgc tgaggttatc ttgcgccgcc agtggcttca acatcaagga tacttacatc    540

cactgggtga ggcaggctcc gggcaagggc ctggaatggg tggctaggat ctaccctact    600

aacgggtaca cacgctacgc agattcggtg aaaggccgct tcactatctc cgccgacacc    660

tcgaagaaca ctgcttacct gcagatgaac tccctcaggg ccgaagatac tgcagtctac    720

accacgacgc cagcgccgcg accaccaaca ccggcgccca ccatcgcgtc gcagcccctg    780

tccctgcgcc cagaggcgtg ccggccagcg gcggggggcg cagtgcacac gagggggctg    840

gacttcgcct gtgatatcta catctgggcg cccttggccg ggacttgtgg ggtccttctc    900

ctgtcactgg ttatcaccct ttactgcaaa cggggcagaa agaaactcct gtatatattc    960

aaacaaccat ttatgagacc agtacaaact actcaagagg aagatggctg tagctgccga   1020

tttccagaag aagaagaagg aggatgtgaa ctgagagtga agttcagcag gagcgcagac   1080

gcccccgcgt acaagcaggg ccagaaccag ctctataacg agctcaatct aggacgaaga   1140

gaggagtacg acgttttgga caagagacgt ggccgggacc ctgagatggg gggaaagccg   1200

agaaggaaga accctcagga aggcctgtac aatgaactgc agaaagataa gatggcggag   1260

gcctacagtg agattgggat gaaaggcgag cgccggaggg gcaaggggca cgatggcctt   1320

taccagggtc tcagtacagc caccaaggac acctacgacg cccttcacat gcaggccctg   1380

ccccctcgct aa                                                       1392
```

<210> SEQ ID NO 45
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

```
atgggttggt cgtgcattat cctcttcctc gtcgcaaccg ctaccggcgt tcactcggat     60

tacaaggatg acgacgacaa agaggtacag ctggtgcaga gcggggccga ggttaagaag    120

cccgggtctt ccgtaaaggt gtcctgcaag gcctcggggg gcacattctc atcgtacgca    180

atatcgtggg tgcggcaggc ccccgggcag gggctggaat ggatgggcgg aattatccca    240

atcttcggga ccgccaacta tgcccagaag tttcagggtc gtgtgaccat tactgccgac    300

gagtccacca gtacggccta catggagctg agtagtctgc gtagcgagga tactgccgtt    360

tattattgcg cccgggaaga gggaccgtac tgctcgtcga cctcatgtta cggcgccttc    420
```

gacatctggg gccaaggcac cctggtgacg gtgtcctccg gtggtggcgg aagtggcggc 480
ggggggtccg gcgggggcgg ttcacagtcc gtcctgaccc aggatcccgc ggtgtcggtc 540
gcgctgggtc agacagtaaa gataacatgc cagggcgatt ctctgcgcag ttatttcgcc 600
tcgtggtacc agcagaaacc cggccaggct cctacccttg ttatgtacgc gcgcaatgac 660
agacccgcgg gcgtgcccga ccgcttctcc ggctcaaaga gcgggacctc cgcctccctg 720
gccatctccg ggctccagtc tgaggatgag gccgattact actgcgctgc ttgggacgac 780
tccctcaatg gctatctgtt tggcgcaggc acaaagctga ccgtgctcac cacgacgcca 840
gcgccgcgac caccaacacc ggcgcccacc atcgcgtcgc agcccctgtc cctgcgccca 900
gaggcgtgcc ggccagcggc ggggggcgca gtgcacacga gggggctgga cttcgcctgt 960
gatatctaca tctgggcgcc cttggccggg acttgtgggg tccttctcct gtcactggtt 1020
atcacccttt actgcaaacg gggcagaaag aaactcctgt atatattcaa acaaccattt 1080
atgagaccag tacaaactac tcaagaggaa gatggctgta gctgccgatt tccagaagaa 1140
gaagaaggag gatgtgaact gagagtgaag ttcagcagga gcgcagacgc ccccgcgtac 1200
aagcagggcc agaaccagct ctataacgag ctcaatctag gacgaagaga ggagtacgac 1260
gttttggaca agagacgtgg ccgggaccct gagatggggg gaaagccgag aaggaagaac 1320
cctcaggaag gcctgtacaa tgaactgcag aaagataaga tggcggaggc ctacagtgag 1380
attgggatga aaggcgagcg ccggaggggc aaggggcacg atggccttta ccagggtctc 1440
agtacagcca ccaaggacac ctacgacgcc cttcacatgc aggccctgcc ccctcgctaa 1500

<210> SEQ ID NO 46
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 46
atgggttggt cgtgcattat cctcttcctc gtcgcaaccg ctaccggcgt tcactcggat 60
tacaaggatg acgacgacaa agaggtacag ctggtgcaga gcggggccga ggttaagaag 120
cccgggtctt ccgtaaaggt gtcctgcaag gcctcggggg gcacattctc atcgtacgca 180
ataggttggg tgcggcaggc cccgggcag gggctggaat ggatgggcgg aattatccca 240
atcttcggga tcgccaacta tgcccagaag tttcagggtc gtgtgaccat tactgccgac 300
gagtccacca gtagtgccta catggagctg agtagtctgc gtagcgagga tactgccgtt 360
tattattgcg cccgggaaga gggaccgtac tgctcgtcga cctcatgtta cgcagccttc 420
gacatctggg gccaaggcac cctggtgacg gtgtcctccg gtggtggcgg aagtggcggc 480
ggggggtccg gcgggggcgg ttcacagtcc gtcctgaccc aggatcccgc ggtgtcggtc 540
gcgctgggtc agacagtaaa gataacatgc cagggcgatt ctctgcgcag ttatttcgcc 600
tcgtggtacc agcagaaacc cggccaggct cctacccttg ttatgtacgc gcgcaatgac 660
agacccgcgg gcgtgcccga ccgcttctcc ggctcaaaga gcgggacctc cgcctccctg 720
gccatctccg ggctccagcc cgaggatgag gccgattact actgcgctgc ttgggacgac 780
tccctcaatg gctatctgtt tggcgcaggc acaaagctga ccgtgctcac cacgacgcca 840
gcgccgcgac caccaacacc ggcgcccacc atcgcgtcgc agcccctgtc cctgcgccca 900

```
gaggcgtgcc ggccagcggc ggggggcgca gtgcacacga gggggctgga cttcgcctgt    960

gatatctaca tctgggcgcc cttggccggg acttgtgggg tccttctcct gtcactggtt   1020

atcacccttt actgcaaacg gggcagaaag aaactcctgt atatattcaa acaaccattt   1080

atgagaccag tacaaactac tcaagaggaa gatggctgta gctgccgatt tccagaagaa   1140

gaagaaggag gatgtgaact gagagtgaag ttcagcagga gcgcagacgc ccccgcgtac   1200

aagcagggcc agaaccagct ctataacgag ctcaatctag gacgaagaga ggagtacgac   1260

gttttggaca agagacgtgg ccgggaccct gagatggggg gaaagccgag aaggaagaac   1320

cctcaggaag gcctgtacaa tgaactgcag aaagataaga tggcggaggc ctacagtgag   1380

attgggatga aaggcgagcg ccggaggggc aaggggcacg atggccttta ccagggtctc   1440

agtacagcca ccaaggacac ctacgacgcc cttcacatgc aggccctgcc ccctcgctaa   1500


<210> SEQ ID NO 47
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47

atgggttggt cgtgcattat cctcttcctc gtcgcaaccg ctaccggcgt tcactcggat     60

tacaaggatg acgacgacaa agaggtacag ctggtgcaga gcggggccga ggttaagaag    120

cccgggtctt ccgtaaaggt gtcctgcaag gcctcggggg gcacattctc atcgtacgca    180

atatcgtggg tgcggcaggc ccccgggcag gggctggaat gggtcggcgg aattatccca    240

atcttcggga ccgccaacta tgcccagaag tttcagggtc gtgtgaagat tactgccgac    300

gagtccgcaa gtacggccta catggagctg agtagtctgc gtagcgagga tactgccgtt    360

tattattgcg cccgggaaga gggaccgtac tgctcgtcga cctcatgtta cgcagccttc    420

gacatctggg gccaaggcac cctggtgacg gtgtcctccg gtggtggcgg aagtggcggc    480

ggggggtccg gcgggggcgg ttcacagtcc gtcctgaccc aggatcccgc ggtgtcggtc    540

gcgctgggtc agacagtaaa gataacatgc cagggcgatt ctctgcgcag ttatctggcc    600

tcgtggtacc agcagaaacc cggccaggct cctacccttg ttacctacgc gcgcaatgac    660

agacccgcgg gcgtgcccga ccgcttctcc ggctcaaaga gcgggacctc cgcctccctg    720

gccatctccg ggctccagtc tgaggatgag gccgattact actgcgctgc ttgggacgac    780

tccctcaatg gctatctgtt tggcgcaggc acaaagctga ccgtgctcac cacgacgcca    840

gcgccgcgac caccaacacc ggcgcccacc atcgcgtcgc agcccctgtc cctgcgccca    900

gaggcgtgcc ggccagcggc ggggggcgca gtgcacacga gggggctgga cttcgcctgt    960

gatatctaca tctgggcgcc cttggccggg acttgtgggg tccttctcct gtcactggtt   1020

atcacccttt actgcaaacg gggcagaaag aaactcctgt atatattcaa acaaccattt   1080

atgagaccag tacaaactac tcaagaggaa gatggctgta gctgccgatt tccagaagaa   1140

gaagaaggag gatgtgaact gagagtgaag ttcagcagga gcgcagacgc ccccgcgtac   1200

aagcagggcc agaaccagct ctataacgag ctcaatctag gacgaagaga ggagtacgac   1260

gttttggaca agagacgtgg ccgggaccct gagatggggg gaaagccgag aaggaagaac   1320

cctcaggaag gcctgtacaa tgaactgcag aaagataaga tggcggaggc ctacagtgag   1380

attgggatga aaggcgagcg ccggaggggc aaggggcacg atggccttta ccagggtctc   1440
```

agtacagcca ccaaggacac ctacgacgcc cttcacatgc aggccctgcc ccctcgctaa 1500

<210> SEQ ID NO 48
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 48
atgggttggt cgtgcattat cctcttcctc gtcgcaaccg ctaccggcgt tcactcggat 60
tacaaggatg acgacgacaa agaggtacag ctggtgcaga gcggggccga ggttaagaag 120
cccgggtctt ccgtaaaggt gtcctgcaag gcctcggggg gcacattctc atcgtacgca 180
atatcgtggg tgcggcaggc ccccgggcag gggctggaat gggtcggcgg aattatccca 240
atcttcggga ccgccaacta tgcccagaag tttcagggtc gtgtgaagat tactgccgac 300
gagtccgcaa gtacggccta catggagctg agtagtctgc gtagcgagga tactgccgtt 360
tattattgcg cccgggaaga gggaccgtac tgctcgtcga cctcatgtta cggcgccttc 420
gacatctggg gccaaggcac cctggtgacg gtgtcctccg gtggtggcgg aagtggcggc 480
ggggggtccg gcgggggcgg ttcacagtcc gtcctgaccc aggatcccgc ggtgtcggtc 540
gcgctgggtc agacagtaaa gataacatgc cagggcgatt ctctgcgcag ttatctggcc 600
tcgtggtacc agcagaaacc cggccaggct cctacccttg ttacctacgc gcgcaatgac 660
agacccgcgg gcgtgcccga ccgcttctcc ggctcaaaga gcgggacctc cgcctccctg 720
gccatctccg ggctccagtc tgaggatgag gccgattact actgcgctgc ttgggacgac 780
tccctcaatg gctatctgtt tggcgcaggc acaaagctga ccgtgctcac cacgacgcca 840
gcgccgcgac caccaacacc ggcgcccacc atcgcgtcgc agcccctgtc cctgcgccca 900
gaggcgtgcc ggccagcggc gggggcgca gtgcacacga gggggctgga cttcgcctgt 960
gatatctaca tctgggcgcc cttggccggg acttgtgggg tccttctcct gtcactggtt 1020
atcacccttt actgcaaacg gggcagaaag aaactcctgt atatattcaa acaaccattt 1080
atgagaccag tacaaactac tcaagaggaa gatggctgta gctgccgatt tccagaagaa 1140
gaagaaggag gatgtgaact gagagtgaag ttcagcagga gcgcagacgc ccccgcgtac 1200
aagcagggcc agaaccagct ctataacgag ctcaatctag gacgaagaga ggagtacgac 1260
gttttggaca agagacgtgg ccgggaccct gagatggggg gaaagccgag aaggaagaac 1320
cctcaggaag gcctgtacaa tgaactgcag aaagataaga tggcggaggc ctacagtgag 1380
attgggatga aaggcgagcg ccggaggggc aaggggcacg atggccttta ccagggtctc 1440
agtacagcca ccaaggacac ctacgacgcc cttcacatgc aggccctgcc ccctcgctaa 1500

<210> SEQ ID NO 49
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 49
atgggttggt cgtgcattat cctcttcctc gtcgcaaccg ctaccggcgt tcactcggat 60

-continued

```
tacaaggatg acgacgacaa agaggtacag ctggtgcaga gcggggccga ggttaagaag    120

cccgggtctt ccgtaaaggt gtcctgcaag gcctcggggg gcacattctc atcgtacgca    180

atatcgtggg tgcggcaggc cccgggcag gggctggaat ggatgggcgg aattatccca    240

atcttcggga ccgccaacta tgcccagaag tttcagggtc gtgtgaccat tactgccgac    300

gagtccacca gtacggccta catggagctg agtagtctgc gtagcgagga tactgccgtt    360

tattattgcg cccgggaaga gggaccgtac tgctcgtcga cctcatgtta cgcagccttc    420

gacatctggg gccaaggcac cctggtgacg gtgtcctccg gtggtggcgg aagtggcggc    480

ggggggtccg gcgggggcgg ttcacagtcc gtcctgaccc aggatcccgc ggcatcggtc    540

gcgctgggtc agacagtaaa gataacatgc cagggcgatt ctctgcgcag ttatttcgcc    600

tcgtggtacc agcagaaacc cggccaggct cctacccttg ttatgtacgc gcgcaatgac    660

agacccgcgg gcgtgcccga ccgcttctcc ggctcaaaga gcgggacctc cgcctccctg    720

gccatctccg ggctccagtc tgaggatgag gccgattact actgcgctgc ttgggacgac    780

tccctcaatg gctatctgtt tggcgcaggc acaaagctga ccgtgctcac cacgacgcca    840

gcgccgcgac caccaacacc ggcgcccacc atcgcgtcgc agcccctgtc cctgcgccca    900

gaggcgtgcc ggccagcggc ggggggcgca gtgcacacga gggggctgga cttcgcctgt    960

gatatctaca tctgggcgcc cttggccggg acttgtgggg tccttctcct gtcactggtt   1020

atcacccttt actgcaaacg gggcagaaag aaactcctgt atatattcaa acaaccattt   1080

atgagaccag tacaaactac tcaagaggaa gatggctgta gctgccgatt tccagaagaa   1140

gaagaaggag gatgtgaact gagagtgaag ttcagcagga gcgcagacgc ccccgcgtac   1200

aagcagggcc agaaccagct ctataacgag ctcaatctag gacgaagaga ggagtacgac   1260

gttttggaca agagacgtgg ccgggaccct gagatggggg gaaagccgag aaggaagaac   1320

cctcaggaag gcctgtacaa tgaactgcag aaagataaga tggcggaggc ctacagtgag   1380

attgggatga aaggcgagcg ccggaggggc aaggggcacg atggccttta ccagggtctc   1440

agtacagcca ccaaggacac ctacgacgcc cttcacatgc aggccctgcc ccctcgctaa   1500
```

```
<210> SEQ ID NO 50
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50

ataggatccc agctggtgga gtctggggga ggc                                  33


<210> SEQ ID NO 51
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51

atagctagca cctaggacgg tcagcttggt ccc                                  33


<210> SEQ ID NO 52
<211> LENGTH: 132
```

<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 52

```
Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130
```

<210> SEQ ID NO 53
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 53

```
Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met
        35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
            100                 105
```

<210> SEQ ID NO 54
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 54

Ile Leu Trp His Glu Met Trp His Glu Gly Leu Glu Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Thr Gln Ala
65 70 75 80

Trp Asp Leu Tyr Tyr His Val Phe Arg Arg Ile Ser Lys
85 90

<210> SEQ ID NO 55
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

Ile Leu Trp His Glu Met Trp His Glu Gly Leu Ile Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Thr Gln Ala
65 70 75 80

Trp Asp Leu Tyr Tyr His Val Phe Arg Arg Ile Ser Lys Thr Ser
85 90 95

<210> SEQ ID NO 56
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

Ile Leu Trp His Glu Met Trp His Glu Gly Leu Leu Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Thr Gln Ala
65 70 75 80

Trp Asp Leu Tyr Tyr His Val Phe Arg Arg Ile Ser Lys Thr Ser
85 90 95

```
<210> SEQ ID NO 57
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95


<210> SEQ ID NO 58
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 58

Ile Leu Trp His Glu Met Trp His Glu Gly Leu Xaa Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Xaa Gln Ala
65                  70                  75                  80

Trp Asp Leu Tyr Tyr His Val Phe Arg Arg Ile Ser Lys Thr Ser
                85                  90                  95


<210> SEQ ID NO 59
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 59

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 60
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 61
<211> LENGTH: 1132
<212> TYPE: PRT
<213> ORGANISM: Homo sapiens

<400> SEQUENCE: 61

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

-continued

```
Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Gly Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
```

-continued

```
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960
```

```
Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                 1015                1020

Gln Val  Trp Lys Asn Pro Thr  Phe Phe Leu Arg Val  Ile Ser Asp
    1025                 1030                1035

Thr Ala  Ser Leu Cys Tyr Ser  Ile Leu Lys Ala Lys  Asn Ala Gly
    1040                 1045                1050

Met Ser  Leu Gly Ala Lys Gly  Ala Ala Gly Pro Leu  Pro Ser Glu
    1055                 1060                1065

Ala Val  Gln Trp Leu Cys His  Gln Ala Phe Leu Leu  Lys Leu Thr
    1070                 1075                1080

Arg His  Arg Val Thr Tyr Val  Pro Leu Leu Gly Ser  Leu Arg Thr
    1085                 1090                1095

Ala Gln  Thr Gln Leu Ser Arg  Lys Leu Pro Gly Thr  Thr Leu Thr
    1100                 1105                1110

Ala Leu  Glu Ala Ala Ala Asn  Pro Ala Leu Pro Ser  Asp Phe Lys
    1115                 1120                1125

Thr Ile  Leu Asp
    1130


<210> SEQ ID NO 62
<211> LENGTH: 4027
<212> TYPE: DNA
<213> ORGANISM: Homo sapiens

<400> SEQUENCE: 62

caggcagcgt ggtcctgctg cgcacgtggg aagccctggc cccggccacc cccgcgatgc     60

cgcgcgctcc ccgctgccga gccgtgcgct ccctgctgcg cagccactac cgcgaggtgc    120

tgccgctggc cacgttcgtg cggcgcctgg ggccccaggg ctggcggctg gtgcagcgcg    180

gggacccggc ggctttccgc gcgctggtgg cccagtgcct ggtgtgcgtg ccctgggacg    240

cacggccgcc ccccgccgcc ccctccttcc gccaggtgtc ctgcctgaag gagctggtgg    300

cccgagtgct gcagaggctg tgcgagcgcg gcgcgaagaa cgtgctggcc ttcggcttcg    360

cgctgctgga cggggcccgc gggggccccc ccgaggcctt caccaccagc gtgcgcagct    420

acctgcccaa cacggtgacc gacgcactgc gggggagcgg ggcgtggggg ctgctgttgc    480

gccgcgtggg cgacgacgtg ctggttcacc tgctggcacg ctgcgcgctc tttgtgctgg    540

tggctcccag ctgcgcctac caggtgtgcg ggccgccgct gtaccagctc ggcgctgcca    600

ctcaggcccg gcccccgcca cacgctagtg gaccccgaag gcgtctggga tgcgaacggg    660

cctggaacca tagcgtcagg gaggccgggg tcccccctggg cctgccagcc ccgggtgcga    720

ggaggcgcgg gggcagtgcc agccgaagtc tgccgttgcc caagaggccc aggcgtggcg    780

ctgcccctga gccggagcgg acgcccgttg ggcaggggtc ctgggcccac ccgggcagga    840

cgcgtggacc gagtgaccgt ggtttctgtg tggtgtcacc tgccagaccc gccgaagaag    900

ccacctcttt ggagggtgcg ctctctggca cgcgccactc ccacccatcc gtgggccgcc    960

agcaccacgc gggcccccca tccacatcgc ggccaccacg tccctgggac acgccttgtc   1020
```

-continued

```
ccccggtgta cgccgagacc aagcacttcc tctactcctc aggcgacaag gagcagctgc   1080
ggccctcctt cctactcagc tctctgaggc ccagcctgac tggcgctcgg aggctcgtgg   1140
agaccatctt tctgggttcc aggccctgga tgccagggac tccccgcagg ttgccccgcc   1200
tgccccagcg ctactggcaa atgcggcccc tgtttctgga gctgcttggg aaccacgcgc   1260
agtgccccta cggggtgctc ctcaagacgc actgcccgct gcgagctgcg gtcaccccag   1320
cagccggtgt ctgtgcccgg gagaagcccc agggctctgt ggcggccccc gaggaggagg   1380
acacagaccc ccgtcgcctg gtgcagctgc tccgccagca cagcagcccc tggcaggtgt   1440
acggcttcgt gcgggcctgc ctgcgccggc tggtgccccc aggcctctgg ggctccaggc   1500
acaacgaacg ccgcttcctc aggaacacca agaagttcat ctccctgggg aagcatgcca   1560
agctctcgct gcaggagctg acgtggaaga tgagcgtgcg gggctgcgct tggctgcgca   1620
ggagcccagg ggttggctgt gttccggccg cagagcaccg tctgcgtgag gagatcctgg   1680
ccaagttcct gcactggctg atgagtgtgt acgtcgtcga gctgctcagg tctttctttt   1740
atgtcacgga gaccacgttt caaaagaaca ggctcttttt ctaccggaag agtgtctgga   1800
gcaagttgca aagcattgga atcagacagc acttgaagag ggtgcagctg cgggagctgt   1860
cggaagcaga ggtcaggcag catcgggaag ccaggcccgc cctgctgacg tccagactcc   1920
gcttcatccc caagcctgac gggctgcggc cgattgtgaa catggactac gtcgtgggag   1980
ccagaacgtt ccgcagagaa aagagggccg agcgtctcac ctcgagggtg aaggcactgt   2040
tcagcgtgct caactacgag cgggcgcggc gccccggcct cctgggcgcc tctgtgctgg   2100
gcctggacga tatccacagg gcctggcgca ccttcgtgct gcgtgtgcgg gcccaggacc   2160
cgccgcctga gctgtacttt gtcaaggtgg atgtgacggg cgcgtacgac accatccccc   2220
aggacaggct cacggaggtc atcgccagca tcatcaaacc ccagaacacg tactgcgtgc   2280
gtcggtatgc cgtggtccag aaggccgccc atgggcacgt ccgcaaggcc ttcaagagcc   2340
acgtctctac cttgacagac ctccagccgt acatgcgaca gttcgtggct cacctgcagg   2400
agaccagccc gctgagggat gccgtcgtca tcgagcagag ctcctccctg aatgaggcca   2460
gcagtggcct cttcgacgtc ttcctacgct tcatgtgcca ccacgccgtg cgcatcaggg   2520
gcaagtccta cgtccagtgc caggggatcc cgcagggctc catcctctcc acgctgctct   2580
gcagcctgtg ctacggcgac atggagaaca agctgtttgc ggggattcgg cgggacgggc   2640
tgctcctgcg tttggtggat gatttcttgt tggtgacacc tcacctcacc cacgcgaaaa   2700
ccttcctcag gaccctggtc cgaggtgtcc ctgagtatgg ctgcgtggtg aacttgcgga   2760
agacagtggt gaacttccct gtagaagacg aggccctggg tggcacggct tttgttcaga   2820
tgccggccca cggcctattc ccctggtgcg gcctgctgct ggatacccgg accctggagg   2880
tgcagagcga ctactccagc tatgcccgga cctccatcag agccagtctc accttcaacc   2940
gcggcttcaa ggctgggagg aacatgcgtc gcaaactctt tggggtcttg cggctgaagt   3000
gtcacagcct gtttctggat ttgcaggtga acagcctcca gacggtgtgc accaacatct   3060
acaagatcct cctgctgcag gcgtacaggt ttcacgcatg tgtgctgcag ctcccatttc   3120
atcagcaagt ttggaagaac cccacatttt tcctgcgcgt catctctgac acggcctccc   3180
tctgctactc catcctgaaa gccaagaacg cagggatgtc gctgggggcc aagggcgccg   3240
ccggccctct gccctccgag gccgtgcagt ggctgtgcca ccaagcattc ctgctcaagc   3300
tgactcgaca ccgtgtcacc tacgtgccac tcctggggtc actcaggaca gcccagacgc   3360
agctgagtcg gaagctcccg gggacgacgc tgactgccct ggaggccgca gccaacccgg   3420
```

```
cactgccctc agacttcaag accatcctgg actgatggcc acccgcccac agccaggccg   3480

agagcagaca ccagcagccc tgtcacgccg ggctctacgt cccagggagg gaggggcggc   3540

ccacacccag gcccgcaccg ctgggagtct gaggcctgag tgagtgtttg gccgaggcct   3600

gcatgtccgg ctgaaggctg agtgtccggc tgaggcctga gcgagtgtcc agccaagggc   3660

tgagtgtcca gcacacctgc cgtcttcact tccccacagg ctggcgctcg gctccacccc   3720

agggccagct tttcctcacc aggagcccgg cttccactcc ccacatagga atagtccatc   3780

cccagattcg ccattgttca cccctcgccc tgccctcctt tgccttccac ccccaccatc   3840

caggtggaga ccctgagaag gaccctggga gctctgggaa tttggagtga ccaaaggtgt   3900

gccctgtaca caggcgagga ccctgcacct ggatgggggt ccctgtgggt caaattgggg   3960

ggaggtgctg tgggagtaaa atactgaata tatgagtttt tcagttttga aaaaaaaaaa   4020

aaaaaaa                                                             4027
```

```
<210> SEQ ID NO 63
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Leu Glu Gln Tyr Ala Asn Gln Leu Ala Asp Gln Ile Ile Lys Glu Ala
1               5                   10                  15

Thr Glu


<210> SEQ ID NO 64
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Glu Ser Lys Arg Arg Gln Glu Glu Ala Glu Gln Arg Lys
1               5                   10


<210> SEQ ID NO 65
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Glu Ser Lys Arg Arg Gln Glu Glu Ala Glu Gln Arg Lys Leu Glu Gln
1               5                   10                  15

Tyr Ala Asn Gln Leu Ala Asp Gln Ile Ile Lys Glu Ala Thr Glu
            20                  25                  30


<210> SEQ ID NO 66
<211> LENGTH: 68
<212> TYPE: PRT
<213> ORGANISM: Artificial Sequence
<220> FEATURE:
```

<221> NAME/KEY: source
<223> OTHER INFORMATION: /note="Description of Artificial Sequence: Synthetic polypeptide"

<400> SEQUENCE: 66

Leu Glu Gln Tyr Ala Asn Gln Leu Ala Asp Gln Ile Ile Lys Glu Ala
1 5 10 15

Thr Glu Thr Arg Thr Arg Pro Leu Glu Gln Lys Leu Ile Ser Glu Glu
20 25 30

Asp Leu Ala Ala Asn Asp Ile Leu Asp Tyr Lys Asp Asp Asp Asp Lys
35 40 45

Gly Ser Gly Glu Gly Arg Gly Ser Leu Leu Thr Cys Gly Asp Val Glu
50 55 60

Glu Asn Pro Gly
65

<210> SEQ ID NO 67
<211> LENGTH: 81
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 67

Glu Ser Lys Arg Arg Gln Glu Glu Ala Glu Gln Arg Lys Leu Glu Gln
1 5 10 15

Tyr Ala Asn Gln Leu Ala Asp Gln Ile Ile Lys Glu Ala Thr Glu Thr
20 25 30

Arg Thr Arg Pro Leu Glu Gln Lys Leu Ile Ser Glu Glu Asp Leu Ala
35 40 45

Ala Asn Asp Ile Leu Asp Tyr Lys Asp Asp Asp Asp Lys Gly Ser Gly
50 55 60

Glu Gly Arg Gly Ser Leu Leu Thr Cys Gly Asp Val Glu Glu Asn Pro
65 70 75 80

Gly

<210> SEQ ID NO 68
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 68
ctggaacagt atgcgaacca gctggcggat cagattatta aagaagcgac cgaa 54

<210> SEQ ID NO 69
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 69
gaaagcaaac gccaggaaga agcggaacag cgcaaa 36

<210> SEQ ID NO 70
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 70
gaaagcaaac gccaggaaga agcggaacag cgcaaactgg aacagtatgc gaaccagctg 60
gcggatcaga ttattaaaga agcgaccgaa 90

<210> SEQ ID NO 71
<211> LENGTH: 204
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 71
ctggaacagt atgcgaacca gctggcggat cagattatta aagaagcgac cgaaacgcgt 60
acgcggccgc tcgagcagaa actcatctca gaagaggatc tggcagcaaa tgatatcctg 120
gattacaagg atgacgacga taagggcagc ggagagggca gaggaagtct tctaacatgc 180
ggtgacgtgg aggagaatcc cggc 204

<210> SEQ ID NO 72
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 72

Leu Lys Gln Tyr Ala Asn Gln Leu Ala Ser Gln Val Ile Lys Glu Ala
1 5 10 15

Thr Glu

<210> SEQ ID NO 73
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(21)
<223> OTHER INFORMATION: /note="Variant residues given in the sequence
have no preference with respect to those in the annotations for
variant positions"

<400> SEQUENCE: 73

Gly Ser Gly Glu Gly Arg Gly Ser Leu Leu Thr Cys Gly Asp Val Glu
1 5 10 15

Glu Asn Pro Gly Pro
20

```
<210> SEQ ID NO 74
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(22)
<223> OTHER INFORMATION: /note="Variant residues given in the sequence
      have no preference with respect to those in the annotations for
      variant positions"

<400> SEQUENCE: 74

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 75
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(23)
<223> OTHER INFORMATION: /note="Variant residues given in the sequence
      have no preference with respect to those in the annotations for
      variant positions"

<400> SEQUENCE: 75

Gly Ser Gly Gln Cys Thr Asn Tyr Ala Leu Leu Lys Leu Ala Gly Asp
1               5                   10                  15

Val Glu Ser Asn Pro Gly Pro
            20


<210> SEQ ID NO 76
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(25)
<223> OTHER INFORMATION: /note="Variant residues given in the sequence
      have no preference with respect to those in the annotations for
      variant positions"

<400> SEQUENCE: 76
```

-continued

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25


<210> SEQ ID NO 77
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="C" or "I" or "Y" or "V" or "W" or "F"
<220> FEATURE:
<221> NAME/KEY: VARIANT
<222> LOCATION: (2)..(2)
<223> OTHER INFORMATION: /replace="R" or "H" or "E" or "D" or "C" or "V"
      or "A" or "I" or "Q" or "S" or "T" or "L"
<220> FEATURE:
<221> NAME/KEY: VARIANT
<222> LOCATION: (3)..(3)
<223> OTHER INFORMATION: /replace="D" or "E" or "A" or "S" or "I" or "F"
      or "K" or "R" or "L" or "M" or "T" or "G"
      or "N" or "W" or "V"
<220> FEATURE:
<221> NAME/KEY: VARIANT
<222> LOCATION: (6)..(6)
<223> OTHER INFORMATION: /replace="D" or "E" or "S" or "A" or "M" or "K"
      or "R" or "G" or "T" or "W" or "Q"
<220> FEATURE:
<221> NAME/KEY: VARIANT
<222> LOCATION: (7)..(7)
<223> OTHER INFORMATION: /replace="D" or "E" or "M" or "F" or "I" or "S"
      or "K" or "R" or "C" or "W" or "Y"
<220> FEATURE:
<221> NAME/KEY: VARIANT
<222> LOCATION: (10)..(10)
<223> OTHER INFORMATION: /replace="D" or "M" or "N" or "E" or "I" or "A"
      or "R" or "F" or "H" or "W" or "K" or "L"
      or "Y" or "Q" or "G"
<220> FEATURE:
<221> NAME/KEY: VARIANT
<222> LOCATION: (11)..(11)
<223> OTHER INFORMATION: /replace="D" or "E" or "I" or "K" or "R" or "T"
      or "V" or "F" or "N" or "S" or "L" or "W"
      or "M"
<220> FEATURE:
<221> NAME/KEY: VARIANT
<222> LOCATION: (12)..(12)
<223> OTHER INFORMATION: /replace="A" or "S" or "L" or "D" or "B" or "V"
<220> FEATURE:
<221> NAME/KEY: VARIANT
<222> LOCATION: (14)..(14)
<223> OTHER INFORMATION: /replace="C" or "D" or "E" or "R" or "A" or "M"
      or "T" or "W" or "H" or "Q" or "Y"
<220> FEATURE:
<221> NAME/KEY: VARIANT
<222> LOCATION: (15)..(15)
<223> OTHER INFORMATION: /replace="D" or "R" or "Q" or "K"
<220> FEATURE:
<221> NAME/KEY: VARIANT
<222> LOCATION: (16)..(16)
<223> OTHER INFORMATION: /replace="C" or "I" or "F" or "L" or "G" or "H"
      or "V"
<220> FEATURE:
<221> NAME/KEY: VARIANT
<222> LOCATION: (17)..(17)
<223> OTHER INFORMATION: /replace="C" or "L" or "F" or "I" or "V" or "M"
      or "K" or "R" or "W"
<220> FEATURE:
<221> NAME/KEY: VARIANT
<222> LOCATION: (18)..(18)
<223> OTHER INFORMATION: /replace="D" or "N" or "V" or "Y" or "K" or "A"
```

```
      or "F" or "G" or "H" or "I" or "Q" or "L"
      or "M" or "R" or "S" or "T" or "W"
<220> FEATURE:
<221> NAME/KEY: MISC_FEATURE
<222> LOCATION: (1)..(18)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 77

Leu Lys Gln Tyr Ala Asn Gln Leu Ala Ser Gln Ile Ile Lys Glu Ala
1               5                   10                  15

Thr Glu


<210> SEQ ID NO 78
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(30)
<223> OTHER INFORMATION: /note="This sequence may encompass 1-6 'Gly Gly
      Gly Gly Ser' repeating units"
<220> FEATURE:
<223> OTHER INFORMATION: /note="See specification as filed for detailed
      description of substitutions and preferred embodiments"

<400> SEQUENCE: 78

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 79
<211> LENGTH: 251
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79

ccaccatgga aagcaaacgc cgccaggaag aagcggaaca gcgcaaactg gaacagtatg     60

cgaaccagct ggcggatcag attattaaag aagcgaccga aacgcgtacg cggccgctcg    120

agcagaaact catctcagaa gaggatctgg cagcaaatga tatcctggat tacaaggatg    180

acgacgataa gggcagcgga gagggcagag gaagtcttct aacatgcggt gacgtggagg    240

agaatcccgg c                                                         251


<210> SEQ ID NO 80
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80
```

Leu Val Gln Tyr Ala Glu Gln Leu Ala Ser Gln Val Ile Lys Glu Ala
1 5 10 15

Thr

<210> SEQ ID NO 81
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 81

Leu Glu Ser Tyr Ala Asn Gln Leu Ala Ser Gln Val Ile Lys Glu Ala
1 5 10 15

Thr

<210> SEQ ID NO 82
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 82

Leu Glu Ser Tyr Ala Ser Gln Leu Ala Ser Gln Val Ile Lys Glu Ala
1 5 10 15

Thr

<210> SEQ ID NO 83
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 83

Leu Glu Gln Tyr Ala Glu Gln Leu Ala Ser Gln Val Ile Lys Glu Ala
1 5 10 15

Thr

<210> SEQ ID NO 84
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 84

Leu Glu Gln Tyr Ala Glu Gln Leu Ala Ser Gln Val Ile Lys Glu Ala
1 5 10 15

<210> SEQ ID NO 85
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 85

Leu Val Gln Tyr Ala Glu Glu Leu Ala Ser Gln Val Ile Lys Glu Ala
1 5 10 15

Thr

<210> SEQ ID NO 86
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 86

Leu Val Gln Tyr Ala Glu Glu Leu Ala Ser Gln Val Ile Lys Glu Ala
1 5 10 15

<210> SEQ ID NO 87
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 87

Leu Glu Ser Tyr Ala Asn Glu Leu Ala Ser Gln Val Ile Lys Glu Ala
1 5 10 15

Thr

<210> SEQ ID NO 88
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 88

Leu Glu Ser Tyr Ala Asn Glu Leu Ala Ser Gln Val Ile Lys Glu Ala
1 5 10 15

<210> SEQ ID NO 89
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 89

Leu Glu Gln Tyr Ala Ser Glu Leu Ala Ser Gln Val Ile Lys Glu Ala
1 5 10 15

Thr

<210> SEQ ID NO 90
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 90

Leu Glu Gln Tyr Ala Glu Glu Leu Ala Ser Gln Val Ile Lys Glu Ala
1 5 10 15

Thr

<210> SEQ ID NO 91
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 91

Leu Glu Gln Tyr Ala Glu Glu Leu Ala Ser Gln Val Ile Lys Glu Ala
1 5 10 15

<210> SEQ ID NO 92
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 92

Leu Glu Gln Tyr Ala Asn Glu Leu Ala Ser Gln Ile Ile Lys Glu Ala
1 5 10 15

Thr

<210> SEQ ID NO 93
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 93

Leu Glu Gln Tyr Ala Asn Glu Leu Ala Ser Gln Ile Ile Lys Glu Ala
1 5 10 15

<210> SEQ ID NO 94
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 94

Leu Glu Gln Tyr Ala Asn Glu Leu Ala Ser Gln Val Ile Lys Glu Ala
1 5 10 15

Leu

<210> SEQ ID NO 95
<211> LENGTH: 16

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 95

Leu Glu Gln Tyr Ala Asn Glu Leu Ala Ser Gln Val Ile Lys Glu Ala
1 5 10 15

<210> SEQ ID NO 96
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 96

Leu Glu Gln Tyr Ala Asn Gln Leu Ala Ser Gln Ile Ile Lys Glu Ala
1 5 10 15

Thr

<210> SEQ ID NO 97
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 97

Leu Glu Gln Tyr Ala Asn Gln Leu Ala Ser Gln Ile Ile Lys Glu Ala
1 5 10 15

<210> SEQ ID NO 98
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 98

Leu Glu Gln Tyr Ala Asn Gln Leu Ala Ser Gln Val Ile Lys Glu Ala
1 5 10 15

Leu

<210> SEQ ID NO 99
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 99

Leu Glu Gln Tyr Ala Asn Gln Leu Ala Ser Gln Val Ile Lys Glu Ala
1 5 10 15

<210> SEQ ID NO 100
<211> LENGTH: 17

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 100

Leu Glu Gln Tyr Ala Asn Gln Leu Ala Asp Gln Ile Ile Lys Glu Ala
1 5 10 15

Thr

<210> SEQ ID NO 101
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 101

Leu Glu Gln Tyr Ala Asn Gln Leu Ala Asp Gln Ile Ile Lys Glu Ala
1 5 10 15

<210> SEQ ID NO 102
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 102

Leu Glu Gln Tyr Ala Asn Gln Leu Ala Asp Asp Val Ile Lys Glu Ala
1 5 10 15

Leu

<210> SEQ ID NO 103
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 103

Leu Glu Gln Tyr Ala Asn Gln Leu Ala Asp Asp Val Ile Lys Glu Ala
1 5 10 15

<210> SEQ ID NO 104
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 104

Leu Glu Gln Tyr Ala Asn Gln Leu Ala Asp Asp Ile Ile Lys Glu Ala
1 5 10 15

Thr

```
<210> SEQ ID NO 105
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Leu Glu Gln Tyr Ala Asn Gln Leu Ala Asp Asp Ile Ile Lys Glu Ala
1               5                   10                  15


<210> SEQ ID NO 106
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Leu Glu Gln Tyr Ala Asn Gln Leu Ala Asp Asp Val Ile Lys Glu Ala
1               5                   10                  15

Leu


<210> SEQ ID NO 107
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Leu Glu Gln Tyr Ala Asn Gln Leu Ala Asp Asp Val Ile Lys Glu Ala
1               5                   10                  15


<210> SEQ ID NO 108
<211> LENGTH: 20
<212> TYPE: PRT
<213> ORGANISM: Homo sapiens

<400> SEQUENCE: 108

Lys Ser Gln Glu Gln Leu Ala Ala Glu Leu Ala Glu Tyr Thr Ala Lys
1               5                   10                  15

Ile Ala Leu Leu
            20


<210> SEQ ID NO 109
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Met Gln Met Met Arg Glu Lys Glu Glu Leu Met Leu Arg Leu Gln Asp
1               5                   10                  15

Tyr Glu Glu Lys Thr Lys Lys Ala Glu Arg Glu Leu Ser Glu Gln Ile
            20                  25                  30

Gln Arg Ala Leu Gln Leu Glu Glu Glu Arg Lys Arg Ala Gln Glu Glu
```

```
        35                  40                  45

Ala Glu Arg Leu Glu Ala Asp Arg Met Ala Ala Leu Arg Ala Lys Glu
    50                  55                  60

Glu Leu Glu Arg Gln Ala Val Asp Gln Ile
65                  70


<210> SEQ ID NO 110
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Met Gln Met Met Arg Glu Lys Glu Glu Leu Met Leu Arg Leu Gln Asp
1               5                   10                  15

Tyr Glu Glu Lys Thr Lys Lys Ala Glu Arg Glu Leu Ser Glu Gln Ile
            20                  25                  30

Gln Arg Ala Leu Gln Leu Glu Glu Glu Arg Lys Arg Ala Gln Glu Glu
        35                  40                  45

Ala Glu Arg Leu Glu Ala Asp Arg Met Ala Ala Leu Arg Ala Lys Glu
    50                  55                  60

Glu Leu Glu Arg Gln Ala Val Asp Gln Ile Lys Ser Gln Glu Gln Leu
65                  70                  75                  80

Ala Ala Glu Leu Ala Glu Tyr Thr Ala Lys Ile Ala Leu Leu
                85                  90


<210> SEQ ID NO 111
<211> LENGTH: 282
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 111

atgcagatga tgcgcgaaaa agaagaactg atgctgcgcc tgcaggatta tgaagaaaaa      60

accaaaaaag cggaacgcga actgagcgaa cagattcagc gcgcgctgca gctggaagaa     120

gaacgcaaac gcgcgcagga agaagcggaa cgcctggaag cggatcgcat ggcggcgctg     180

cgcgcgaaag aagaactgga acgccaggcg gtggatcaga ttaaaagcca ggaacagctg     240

gcggcggaac tggcggaata taccgcgaaa attgcgctgc tg                        282


<210> SEQ ID NO 112
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Arg Gly Asp Ser
1
```